US012405287B2

(12) United States Patent
Sudo et al.

(10) Patent No.: US 12,405,287 B2
(45) Date of Patent: Sep. 2, 2025

(54) LUNG CANCER DETECTION KIT OR DEVICE, AND DETECTION METHOD

(71) Applicants: TORAY INDUSTRIES, INC., Tokyo (JP); NATIONAL CANCER CENTER, Tokyo (JP)

(72) Inventors: Hiroko Sudo, Kamakura (JP); Hitoshi Nobumasa, Kamakura (JP); Satoko Kozono, Kamakura (JP); Satoshi Kondou, Kamakura (JP); Junpei Kawauchi, Kamakura (JP); Atsushi Ochiai, Kashiwa (JP); Motohiro Kojima, Kashiwa (JP)

(73) Assignees: TORAY INDUSTRIES, INC., Tokyo (JP); NATIONAL CANCER CENTER, Tokyo (JP)

( * ) Notice: Subject to any disclaimer, the term of this patent is extended or adjusted under 35 U.S.C. 154(b) by 57 days.

(21) Appl. No.: 18/405,371

(22) Filed: Jan. 5, 2024

(65) Prior Publication Data

US 2024/0183875 A1 Jun. 6, 2024

Related U.S. Application Data

(62) Division of application No. 17/977,377, filed on Oct. 31, 2022, now Pat. No. 12,117,462, which is a division of application No. 16/800,755, filed on Feb. 25, 2020, now Pat. No. 11,519,927, which is a division of application No. 15/319,695, filed as application No. PCT/JP2015/067533 on Jun. 18, 2015, now Pat. No. 10,620,228.

(30) Foreign Application Priority Data

Jun. 18, 2014 (JP) .................................. 2014-125561

(51) Int. Cl.
C12Q 1/68 (2018.01)
C12M 1/00 (2006.01)
C12N 15/09 (2006.01)
C12P 19/34 (2006.01)
G01N 37/00 (2006.01)

(52) U.S. Cl.
CPC ............... G01N 37/00 (2013.01); C12M 1/00 (2013.01); C12N 15/09 (2013.01); C12Q 1/68 (2013.01); C12Q 2600/118 (2013.01); C12Q 2600/158 (2013.01); C12Q 2600/178 (2013.01)

(58) Field of Classification Search
CPC ........ C12Q 2600/118; C12Q 2600/158; C12Q 2600/178
See application file for complete search history.

(56) References Cited

U.S. PATENT DOCUMENTS

| | | |
|---|---|---|
| 2001/0053519 A1 | 12/2001 | Fodor et al. |
| 2010/0233704 A1 | 9/2010 | Michot et al. |
| 2011/0053158 A1 | 3/2011 | Mambo et al. |
| 2011/0117565 A1 | 5/2011 | Zhang et al. |
| 2012/0108462 A1 | 5/2012 | Keller et al. |
| 2015/0080243 A1 | 3/2015 | Whitney |
| 2015/0337332 A1 | 11/2015 | Baker et al. |
| 2017/0107581 A1 | 4/2017 | Kawauchi et al. |
| 2017/0121778 A1 | 5/2017 | Kondou et al. |
| 2017/0130273 A1 | 5/2017 | Sudo et al. |
| 2017/0130275 A1 | 5/2017 | Kondou et al. |
| 2017/0130278 A1 | 5/2017 | Sudo et al. |
| 2017/0166976 A1 | 6/2017 | Kondou et al. |

FOREIGN PATENT DOCUMENTS

| | | |
|---|---|---|
| CN | 103173448 A | 6/2013 |
| CN | 106488986 A | 3/2017 |
| CN | 108471132 A | 3/2017 |
| EP | 3156500 A1 | 4/2017 |
| JP | 2011-505143 A | 2/2011 |
| JP | 2013-502931 A | 1/2013 |
| WO | WO 2007/081720 A2 | 7/2007 |
| WO | WO 2009/070653 A1 | 6/2009 |
| WO | WO 2010/139810 A1 | 12/2010 |
| WO | WO 2011/025919 A1 | 3/2011 |
| WO | WO 2011/076144 A1 | 6/2011 |
| WO | WO 2011/146937 A1 | 11/2011 |
| WO | WO 2014/013258 A1 | 1/2014 |
| WO | WO 2014/192907 A1 | 12/2014 |
| WO | WO 2015/012175 A1 | 1/2015 |
| WO | WO 2015/115923 A2 | 8/2015 |
| WO | WO 2015/190542 A1 | 12/2015 |
| WO | WO 2015/190584 A1 | 12/2015 |
| WO | WO 2015/194610 A1 | 12/2015 |
| WO | WO 2015/194615 A1 | 12/2015 |

OTHER PUBLICATIONS

N.P. Hessvik et al. "Profiling of microRNAs in exosomes released from PC-3 prostate cancer cells" Biochimica et Biophysica Acta 1819 (2010) 1154-1163 (Year: 2012).*
American Cancer Society, "Lung Cancer (Non-Small Cell)", 2013, total 77 pages, pp. 2-7 and 37-56.
Bai et al., "MIR-296-3p regulates cell growth and multi-drug resistance of human glioblastoma by targeting ether-á-go-go (EAG1)," European Journal of Cancer, vol. 49, No. 3, 2013 (available online Sep. 18, 2012), pp. 710-724.
Chen et al., "Identification of ten serum microRNAs from a genome-wide serum microRNA expression profile as novel noninvasive biomarkers for nonsmall cell lung cancer diagnosis", International Journal Cancer, vol. 130, May 9, 2011, pp. 1620-1628.

(Continued)

Primary Examiner — Stephen T Kapushoc
(74) Attorney, Agent, or Firm — Birch, Stewart, Kolasch & Birch, LLP

(57) ABSTRACT

It is intended to provide a kit or a device for the detection of lung cancer and a method for detecting lung cancer. The present invention provides a kit or a device for the detection of lung cancer, comprising a nucleic acid capable of specifically binding to a miRNA in a sample from a subject, and a method for detecting lung cancer, comprising measuring the miRNA in vitro.

6 Claims, 4 Drawing Sheets
Specification includes a Sequence Listing.

(56) References Cited

OTHER PUBLICATIONS

Cheung et al., "Natural variation in human gene expression assessed in lymphoblastoid cells", Nature Genetics, vol. 33, Mar. 2003, pp. 422-425.
Chinese Office Action and Search Report dated May 19, 2023 for Application No. 202010875727.X.
Chinese Office Action and Search Report dated Sep. 27, 2023 for Application No. 201880042985.0.
Cobb et al., "Sepsis gene expression profiling: Murine splenic compared with hepatic responses determined by using complementary DNA microarrays", Critical Care Medicine, vol. 30, No. 12, 2002, pp. 2711-2721.
Dissertation of Xin Wang, "Micro RNA: Profiling and Functional Implications in Cancer and Metabolism" from University of Houston, Dec. 2012, available online at https://uh-ir.tdl.org/bitstream/handle/10657/540/Diss_XinWang_20121.pdf?sequence=1&isAllowed=y (Year. 2012).
Enard et al., "Intra- and Interspecific Variation in Primate Gene Expression Patterns," Science, vol. 296, No. 340, Apr. 12, 2002, pp. 339-343.
Eto et al., "Prospect of microRNA toward laboratory medicine Gastrointestinal Cancer and microRNA", Clinical Chemistry, 2014, vol. 43, pp. 99-105.
Foss et al., "miR-1254 and miR-574-5p Serum-Based microRNA Biomarkers for Early-Stage Non-small Cell Lung Cancer", Journal of Thoracic Oncology, Mar. 2011, vol. 6, No. 3, pp. 482-488.
GenBank Locus NR_106826, "*Homo sapiens* micro RNA 6768 (MIR6768), micro RNA", (Apr. 3, 2014) from /www.ncbi.nlm.nih.gov, printed pp. 1-3.
Hoshikawa et al., "Hypoxia induces different genes in the lungs of rats compared with mice", Physiological Genomics, vol. 12, 2003, pp. 209-219.
International Search Report, issued in PCT/JP2015/067533, dated Sep. 15, 2015.
International Search Report, issued in PCT/JP2018/024834, dated Oct. 2, 2018.
Jin et al., "Circulating microRNA: a novel potential biomarker for early diagnosis of Intracranial Aneurysm Rupture a case control study," Journal of Translational Medicine (2013), vol. 11, No. 296, pp. 1-9.
Keller et al., "Stable serum miRNA profiles as potential tool for non-invasive lung cancer diagnosis", RNA Biology, May 1, 2011, vol. 8, No. 3, pp. 506-516, Supplemental Content.
Kozomara et al., "miRBase: annotating high confidence microRNAs using deep sequencing data", Nucleic Acids Research, Nov. 25, 2013, vol. 42, Database issue, pp. D68-D73.
Leidinger et al., "What makes a blood cell based miRNA expression pattern disease specific?—A miRNome analysis of blood cell subsets in lung cancer patients and healthy controls", Oncotarget, Sep. 19, 2014, vol. 5, No. 19, pp. 9484-9497.
Liu et al., "MicroRNA expression profile of gastric cancer stem cells in the MKN-45 cancer cell line", Acta Biochim Biophys Sin, 2014, vol. 46, pp. 92-99.
Markou et al., "Clinical evaluation of microRNA expression profiling in non small cell lung cancer", Lung Cancer, Sep. 2013, vol. 81, Issue No. 3, pp. 388-396.
MiScript™ miRNA PCR Array (384-well, 384HC) Human miRBase Profiler HC Plate 5, Qiagen, 2012, 10 pages, from https://b2b.qiagen.com/-/media/genetable/mi/hs/34/mihs-3403z.
Office Action issued Aug. 23, 2021, in Republic of Korea Patent Application No. 10-2017-7000867.
Office Action issued Jun. 7, 2022, in Japanese Patent Application No. 2019-527064.
Okamura et al., "Diagnostic value of CEA and CYFRA 21-1 tumor markers in primary lung cancer", Lung Cancer, 2013, vol. 80, pp. 45-49.

Ondracek et al., "Global MicroRNA Expression Profiling Identifies Unique MicroRNA Pattern of Radioresistant Glioblastoma Cells", Anticancer Research 37, pp. 1099-1104, 2017.
Partial Supplementary European Search Report, dated Dec. 14, 2017, for European Application No. 15809623.0.
Persson et al., "Identification of New MicroRNAs in Paired Normal and Tumor Breast Tissue Suggests a Dual Role for the ERBB2/Her2 Gene", Cancer Research 71(1), pp. 78-86, 2011.
Oiagen Product Description "mi Script™ miRNA PCR Array (384-well, 384HC) Human miRBase Profiler HC Plate 3" document 1073798, Aug. 2012, from https://b2b.qiagen.com/-/media/genetable/mi/hs/34/mihs-3403z (Year: 2012).
Rani et al., "Global analysis of serum microR NAs as potential biomarkers for lung adenocarcinoma", Cancer Biology & Therapy, 2013, vol. 14, Issue 12, pp. 1104-1112.
Roth et al., "Low Levels of Cell-Free Circulating miR-361-3p and miR-625* as Blood-Based Markers for Discriminating Malignant from Benign Lung Tumors", PLoS ONE, Jun. 2012, vol. 7, Issue 6, e38248, pp. 1-10.
Schmidt et al., "Liquid Profiling in Lung Cancer—Quantification of Extracellular miRNAs in Bronchial Lavage", Adv Exp Med Biol. 2016, vol. 924, pp. 33-37.
Shen et al., "Applications of MicroRNAs in the Diagnosis and Prognosis of Lung Cancer," Expert Opin. Med. Diagn. (2012), vol. 6, No. 3, pp. 197-207.
Sobin et al., "TNM Classification of Malignant Tumours, the 7th edition", International Union Against Cancer, 2010, pp. 129-134.
Song et al., "The role of deregulated microRNAs in high metastatic hepatocellular carcinoma", Chinese Journal Clinicians (Electronic Edition), vol. 7, No. 22, Nov. 15, 2013, pp. 10092-10097 with an English abstract.
Supplementary Partial European Search Report issued in Application No. 18823484.3 dated Mar. 12, 2021.
Tai et al., "Blood-borne miRNA profile-based diagnostic classifier for lung adenocarcinoma", Scientific Reports, Aug. 10, 2016, 6: 31389, total 9 pages.
Takizawa et al., "miRNA Profiling in Serum Samples Using DNA Chip 3D-Gene®", BIO Clinica, Jun. 10, 2014, vol. 29, No. 6, pp. 588-589.
U.S. Office Action for U.S. Appl. No. 16/626,781, dated Apr. 15, 2021.
U.S. Office Action for U.S. Appl. No. 16/626,781, dated Feb. 18, 2022.
U.S. Office Action for U.S. Appl. No. 16/626,781, dated Jun. 17, 2022.
U.S. Office Action for U.S. Appl. No. 16/626,781, dated May 25, 2022.
U.S. Office Action for U.S. Appl. No. 16/626,781, dated Sep. 14, 2021.
Volinia et al., "A microRNA expression signature of human solid tumors defines cancer gene targets", Proc Natl Acad Sci U S A, Feb. 14, 2006, vol. 103, No. 7, pp. 2257-2261.
Written Opinion of the International Searching Authority, issued in PCT/JP2015/067533, dated Sep. 15, 2015.
Written Opinion of the International Searching Authority, issued in PCT/JP2018/024834, dated Oct. 2, 2018.
Yanaihara et al., "Unique microRNA molecular profiles in lung cancer diagnosis and prognosis," Cancer Cell, vol. 9, No. 3, Mar. 13, 2006, pp. 189-198.
Zhai et al., "Differential expressions of microRNAs in the CD138+ cells of multiple myeloma patients with deletion of Chromosome 13", Journal of Shandong University (Health Sciences), vol. 51, No. 5, May 2013, pp. 80-84 with an English abstract.
Extended European Search Report for European Application No. 24182689.0, dated Jan. 28, 2025.
Korean Office Action for Korean Application No. 10-2019-7033142, dated Jan. 22, 2024.

* cited by examiner

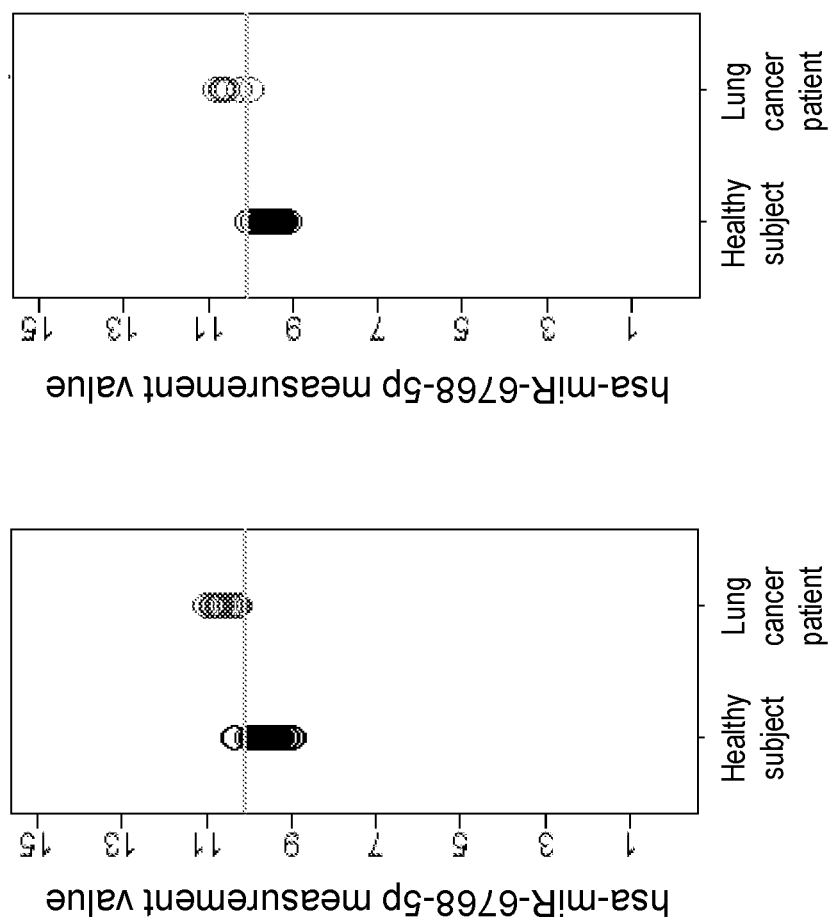

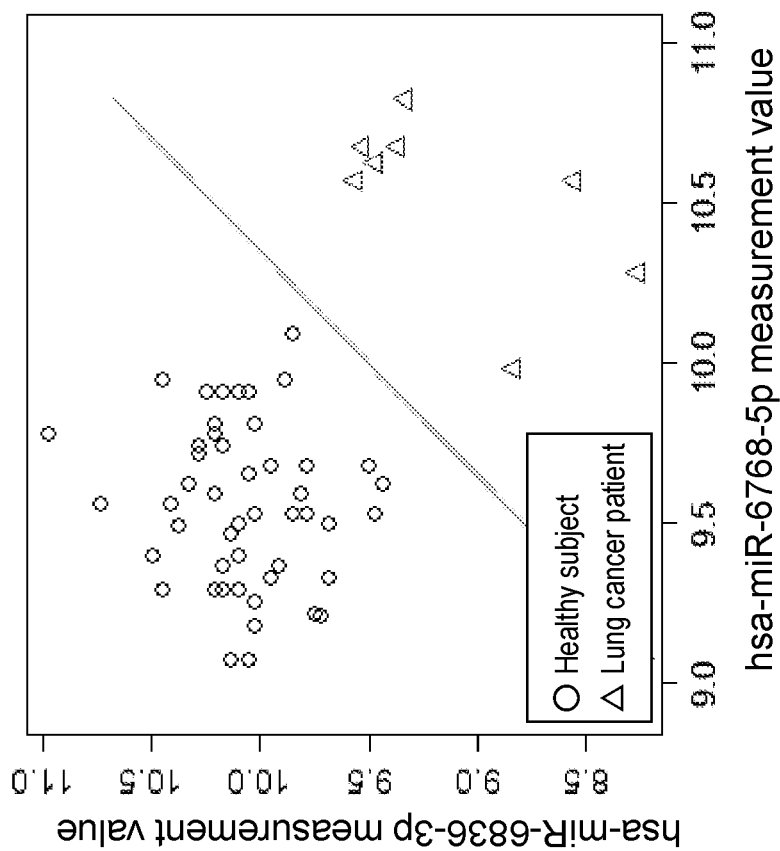
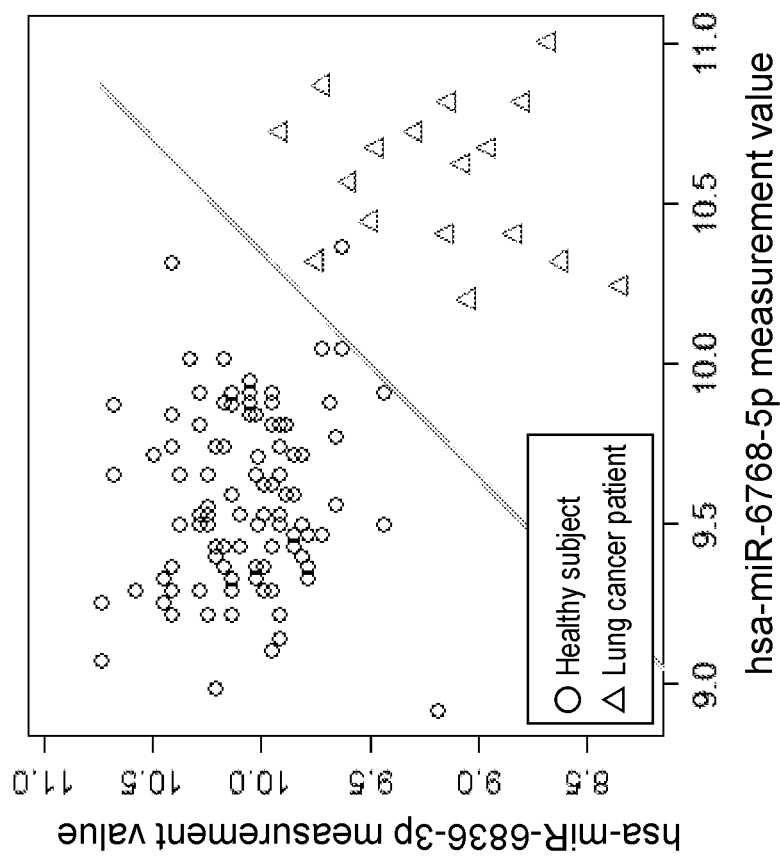

```
                           SEQUENCE LISTING

Sequence total quantity: 618
SEQ ID NO: 1            moltype = RNA   length = 23
FEATURE                 Location/Qualifiers
source                  1..23
                        mol_type = transcribed RNA
                        organism = Homo sapiens
SEQUENCE: 1
cacacaggaa aagcggggcc ctg                                            23

SEQ ID NO: 2            moltype = RNA   length = 21
FEATURE                 Location/Qualifiers
source                  1..21
                        mol_type = transcribed RNA
                        organism = Homo sapiens
SEQUENCE: 2
atgcctcccc cggccccgca g                                              21

SEQ ID NO: 3            moltype = RNA   length = 25
FEATURE                 Location/Qualifiers
source                  1..25
                        mol_type = transcribed RNA
                        organism = Homo sapiens
SEQUENCE: 3
tagggtggg ggaattcagg ggtgt                                           25

SEQ ID NO: 4            moltype = RNA   length = 23
FEATURE                 Location/Qualifiers
source                  1..23
                        mol_type = transcribed RNA
                        organism = Homo sapiens
SEQUENCE: 4
tgagcaccac acaggccggg cgc                                            23

SEQ ID NO: 5            moltype = RNA   length = 21
FEATURE                 Location/Qualifiers
source                  1..21
                        mol_type = transcribed RNA
                        organism = Homo sapiens
SEQUENCE: 5
ccggccgccg gctccgcccc g                                              21

SEQ ID NO: 6            moltype = RNA   length = 21
FEATURE                 Location/Qualifiers
source                  1..21
                        mol_type = transcribed RNA
                        organism = Homo sapiens
SEQUENCE: 6
cgggagctgg ggtctgcagg t                                              21

SEQ ID NO: 7            moltype = RNA   length = 17
FEATURE                 Location/Qualifiers
source                  1..17
                        mol_type = transcribed RNA
                        organism = Homo sapiens
SEQUENCE: 7
ccccgccacc gccttgg                                                   17

SEQ ID NO: 8            moltype = RNA   length = 22
FEATURE                 Location/Qualifiers
source                  1..22
                        mol_type = transcribed RNA
                        organism = Homo sapiens
SEQUENCE: 8
ctcctggggc ccgcactctc gc                                             22

SEQ ID NO: 9            moltype = RNA   length = 17
FEATURE                 Location/Qualifiers
source                  1..17
                        mol_type = transcribed RNA
                        organism = Homo sapiens
```

-continued

| | | |
|---|---|---|
| SEQUENCE: 9 gggagaaggg tcggggc | | 17 |
| SEQ ID NO: 10 FEATURE source | moltype = RNA length = 21 Location/Qualifiers 1..21 mol_type = transcribed RNA organism = Homo sapiens | |
| SEQUENCE: 10 tgagggaccc aggacaggag a | | 21 |
| SEQ ID NO: 11 FEATURE source | moltype = RNA length = 20 Location/Qualifiers 1..20 mol_type = transcribed RNA organism = Homo sapiens | |
| SEQUENCE: 11 cggggtgggt gaggtcgggc | | 20 |
| SEQ ID NO: 12 FEATURE source | moltype = RNA length = 22 Location/Qualifiers 1..22 mol_type = transcribed RNA organism = Homo sapiens | |
| SEQUENCE: 12 tggggaggtg tggagtcagc at | | 22 |
| SEQ ID NO: 13 FEATURE source | moltype = RNA length = 22 Location/Qualifiers 1..22 mol_type = transcribed RNA organism = Homo sapiens | |
| SEQUENCE: 13 gcccaggact ttgtgcgggg tg | | 22 |
| SEQ ID NO: 14 FEATURE source | moltype = RNA length = 23 Location/Qualifiers 1..23 mol_type = transcribed RNA organism = Homo sapiens | |
| SEQUENCE: 14 tggggaaggc ttggcaggga aga | | 23 |
| SEQ ID NO: 15 FEATURE source | moltype = RNA length = 22 Location/Qualifiers 1..22 mol_type = transcribed RNA organism = Homo sapiens | |
| SEQUENCE: 15 tcgggcctgg ggttggggga gc | | 22 |
| SEQ ID NO: 16 FEATURE source | moltype = RNA length = 22 Location/Qualifiers 1..22 mol_type = transcribed RNA organism = Homo sapiens | |
| SEQUENCE: 16 tcaaaatcag gagtcgggc tt | | 22 |
| SEQ ID NO: 17 FEATURE source | moltype = RNA length = 20 Location/Qualifiers 1..20 mol_type = transcribed RNA organism = Homo sapiens | |
| SEQUENCE: 17 gccggggctt tgggtgaggg | | 20 |
| SEQ ID NO: 18 FEATURE source | moltype = RNA length = 23 Location/Qualifiers 1..23 mol_type = transcribed RNA organism = Homo sapiens | |
| SEQUENCE: 18 tgaggatatg gcagggaagg gga | | 23 |
| SEQ ID NO: 19 FEATURE source | moltype = RNA length = 24 Location/Qualifiers 1..24 mol_type = transcribed RNA | |

```
                        organism = Homo sapiens
SEQUENCE: 19
tgagggcct cagaccgagc tttt                                                  24

SEQ ID NO: 20           moltype = RNA   length = 22
FEATURE                 Location/Qualifiers
source                  1..22
                        mol_type = transcribed RNA
                        organism = Homo sapiens
SEQUENCE: 20
ggtggcccgg ccgtgcctga gg                                                   22

SEQ ID NO: 21           moltype = RNA   length = 22
FEATURE                 Location/Qualifiers
source                  1..22
                        mol_type = transcribed RNA
                        organism = Homo sapiens
SEQUENCE: 21
tggtggagga agagggcagc tc                                                   22

SEQ ID NO: 22           moltype = RNA   length = 21
FEATURE                 Location/Qualifiers
source                  1..21
                        mol_type = transcribed RNA
                        organism = Homo sapiens
SEQUENCE: 22
cggcggggac ggcgattggt c                                                    21

SEQ ID NO: 23           moltype = RNA   length = 22
FEATURE                 Location/Qualifiers
source                  1..22
                        mol_type = transcribed RNA
                        organism = Homo sapiens
SEQUENCE: 23
gggtggggat tgttgcatt ac                                                    22

SEQ ID NO: 24           moltype = RNA   length = 18
FEATURE                 Location/Qualifiers
source                  1..18
                        mol_type = transcribed RNA
                        organism = Homo sapiens
SEQUENCE: 24
atcctagtca cggcacca                                                        18

SEQ ID NO: 25           moltype = RNA   length = 21
FEATURE                 Location/Qualifiers
source                  1..21
                        mol_type = transcribed RNA
                        organism = Homo sapiens
SEQUENCE: 25
tgggggtgtg gggagagaga g                                                    21

SEQ ID NO: 26           moltype = RNA   length = 22
FEATURE                 Location/Qualifiers
source                  1..22
                        mol_type = transcribed RNA
                        organism = Homo sapiens
SEQUENCE: 26
tggggggtggt ctctagccaa gg                                                  22

SEQ ID NO: 27           moltype = RNA   length = 22
FEATURE                 Location/Qualifiers
source                  1..22
                        mol_type = transcribed RNA
                        organism = Homo sapiens
SEQUENCE: 27
ttggggattg ggtcaggcca gt                                                   22

SEQ ID NO: 28           moltype = RNA   length = 21
FEATURE                 Location/Qualifiers
source                  1..21
                        mol_type = transcribed RNA
                        organism = Homo sapiens
SEQUENCE: 28
gttggggtgc agggggtctgc t                                                   21

SEQ ID NO: 29           moltype = RNA   length = 23
FEATURE                 Location/Qualifiers
source                  1..23
```

| | | |
|---|---|---|
| | mol_type = transcribed RNA | |
| | organism = Homo sapiens | |
| SEQUENCE: 29 | | |
| ggaggcgcag gctcggaaag gcg | | 23 |
| | | |
| SEQ ID NO: 30 | moltype = RNA   length = 19 | |
| FEATURE | Location/Qualifiers | |
| source | 1..19 | |
| | mol_type = transcribed RNA | |
| | organism = Homo sapiens | |
| SEQUENCE: 30 | | |
| ggctggtcag atgggagtg | | 19 |
| | | |
| SEQ ID NO: 31 | moltype = RNA   length = 23 | |
| FEATURE | Location/Qualifiers | |
| source | 1..23 | |
| | mol_type = transcribed RNA | |
| | organism = Homo sapiens | |
| SEQUENCE: 31 | | |
| tcggggagtc tggggtccgg aat | | 23 |
| | | |
| SEQ ID NO: 32 | moltype = RNA   length = 20 | |
| FEATURE | Location/Qualifiers | |
| source | 1..20 | |
| | mol_type = transcribed RNA | |
| | organism = Homo sapiens | |
| SEQUENCE: 32 | | |
| ggatccgagt cacggcacca | | 20 |
| | | |
| SEQ ID NO: 33 | moltype = RNA   length = 20 | |
| FEATURE | Location/Qualifiers | |
| source | 1..20 | |
| | mol_type = transcribed RNA | |
| | organism = Homo sapiens | |
| SEQUENCE: 33 | | |
| cctgagcccg ggccgcgcag | | 20 |
| | | |
| SEQ ID NO: 34 | moltype = RNA   length = 24 | |
| FEATURE | Location/Qualifiers | |
| source | 1..24 | |
| | mol_type = transcribed RNA | |
| | organism = Homo sapiens | |
| SEQUENCE: 34 | | |
| ccccgggaac gtcgagactg gagc | | 24 |
| | | |
| SEQ ID NO: 35 | moltype = RNA   length = 21 | |
| FEATURE | Location/Qualifiers | |
| source | 1..21 | |
| | mol_type = transcribed RNA | |
| | organism = Homo sapiens | |
| SEQUENCE: 35 | | |
| gtaggtgaca gtcaggggcg g | | 21 |
| | | |
| SEQ ID NO: 36 | moltype = RNA   length = 21 | |
| FEATURE | Location/Qualifiers | |
| source | 1..21 | |
| | mol_type = transcribed RNA | |
| | organism = Homo sapiens | |
| SEQUENCE: 36 | | |
| cccatgcctc ctgccgcggt c | | 21 |
| | | |
| SEQ ID NO: 37 | moltype = RNA   length = 24 | |
| FEATURE | Location/Qualifiers | |
| source | 1..24 | |
| | mol_type = transcribed RNA | |
| | organism = Homo sapiens | |
| SEQUENCE: 37 | | |
| tgggcgaggg gtgggctctc agag | | 24 |
| | | |
| SEQ ID NO: 38 | moltype = RNA   length = 22 | |
| FEATURE | Location/Qualifiers | |
| source | 1..22 | |
| | mol_type = transcribed RNA | |
| | organism = Homo sapiens | |
| SEQUENCE: 38 | | |
| cccctggggc tgggcaggcg ga | | 22 |
| | | |
| SEQ ID NO: 39 | moltype = RNA   length = 21 | |
| FEATURE | Location/Qualifiers | |

```
source                  1..21
                        mol_type = transcribed RNA
                        organism = Homo sapiens
SEQUENCE: 39
caggagtggg gggtgggacg t                                               21

SEQ ID NO: 40           moltype = RNA   length = 22
FEATURE                 Location/Qualifiers
source                  1..22
                        mol_type = transcribed RNA
                        organism = Homo sapiens
SEQUENCE: 40
ggctggagcg agtgcagtgg tg                                              22

SEQ ID NO: 41           moltype = RNA   length = 23
FEATURE                 Location/Qualifiers
source                  1..23
                        mol_type = transcribed RNA
                        organism = Homo sapiens
SEQUENCE: 41
gggggccgat acactgtacg aga                                             23

SEQ ID NO: 42           moltype = RNA   length = 22
FEATURE                 Location/Qualifiers
source                  1..22
                        mol_type = transcribed RNA
                        organism = Homo sapiens
SEQUENCE: 42
ggggctgtga ttgaccagca gg                                              22

SEQ ID NO: 43           moltype = RNA   length = 18
FEATURE                 Location/Qualifiers
source                  1..18
                        mol_type = transcribed RNA
                        organism = Homo sapiens
SEQUENCE: 43
ggtgggggt gttgtttt                                                    18

SEQ ID NO: 44           moltype = RNA   length = 22
FEATURE                 Location/Qualifiers
source                  1..22
                        mol_type = transcribed RNA
                        organism = Homo sapiens
SEQUENCE: 44
tgggagggcg tggatgatgg tg                                              22

SEQ ID NO: 45           moltype = RNA   length = 22
FEATURE                 Location/Qualifiers
source                  1..22
                        mol_type = transcribed RNA
                        organism = Homo sapiens
SEQUENCE: 45
gtgggtgctg gtgggagccg tg                                              22

SEQ ID NO: 46           moltype = RNA   length = 18
FEATURE                 Location/Qualifiers
source                  1..18
                        mol_type = transcribed RNA
                        organism = Homo sapiens
SEQUENCE: 46
ttcccagcca acgcacca                                                   18

SEQ ID NO: 47           moltype = RNA   length = 18
FEATURE                 Location/Qualifiers
source                  1..18
                        mol_type = transcribed RNA
                        organism = Homo sapiens
SEQUENCE: 47
agcaggtgcg gggcggcg                                                   18

SEQ ID NO: 48           moltype = RNA   length = 23
FEATURE                 Location/Qualifiers
source                  1..23
                        mol_type = transcribed RNA
                        organism = Homo sapiens
SEQUENCE: 48
cggggccgta gcactgtctg aga                                             23

SEQ ID NO: 49           moltype = RNA   length = 17
```

```
FEATURE                 Location/Qualifiers
source                  1..17
                        mol_type = transcribed RNA
                        organism = Homo sapiens
SEQUENCE: 49
accccactcc tggtacc                                                    17

SEQ ID NO: 50           moltype = RNA   length = 21
FEATURE                 Location/Qualifiers
source                  1..21
                        mol_type = transcribed RNA
                        organism = Homo sapiens
SEQUENCE: 50
tcacctggct ggcccgccca g                                               21

SEQ ID NO: 51           moltype = RNA   length = 23
FEATURE                 Location/Qualifiers
source                  1..23
                        mol_type = transcribed RNA
                        organism = Homo sapiens
SEQUENCE: 51
gagggcagcg tgggtgtggc gga                                             23

SEQ ID NO: 52           moltype = RNA   length = 23
FEATURE                 Location/Qualifiers
source                  1..23
                        mol_type = transcribed RNA
                        organism = Homo sapiens
SEQUENCE: 52
agggactttt gggggcagat gtg                                             23

SEQ ID NO: 53           moltype = RNA   length = 20
FEATURE                 Location/Qualifiers
source                  1..20
                        mol_type = transcribed RNA
                        organism = Homo sapiens
SEQUENCE: 53
agagatgaag cggggggggcg                                                20

SEQ ID NO: 54           moltype = RNA   length = 21
FEATURE                 Location/Qualifiers
source                  1..21
                        mol_type = transcribed RNA
                        organism = Homo sapiens
SEQUENCE: 54
tggggcgggg caggtccctg c                                               21

SEQ ID NO: 55           moltype = RNA   length = 25
FEATURE                 Location/Qualifiers
source                  1..25
                        mol_type = transcribed RNA
                        organism = Homo sapiens
SEQUENCE: 55
aggggggcac tgcgcaagca aagcc                                           25

SEQ ID NO: 56           moltype = RNA   length = 22
FEATURE                 Location/Qualifiers
source                  1..22
                        mol_type = transcribed RNA
                        organism = Homo sapiens
SEQUENCE: 56
gggacccagg gagagacgta ag                                              22

SEQ ID NO: 57           moltype = RNA   length = 25
FEATURE                 Location/Qualifiers
source                  1..25
                        mol_type = transcribed RNA
                        organism = Homo sapiens
SEQUENCE: 57
gtgaggcggg gccaggaggg tgtgt                                           25

SEQ ID NO: 58           moltype = RNA   length = 19
FEATURE                 Location/Qualifiers
source                  1..19
                        mol_type = transcribed RNA
                        organism = Homo sapiens
SEQUENCE: 58
tggggcggag cttccggag                                                  19
```

```
SEQ ID NO: 59          moltype = RNA  length = 17
FEATURE                Location/Qualifiers
source                 1..17
                       mol_type = transcribed RNA
                       organism = Homo sapiens
SEQUENCE: 59
gccggacaag agggagg                                                        17

SEQ ID NO: 60          moltype = RNA  length = 18
FEATURE                Location/Qualifiers
source                 1..18
                       mol_type = transcribed RNA
                       organism = Homo sapiens
SEQUENCE: 60
cggtgagcgc tcgctggc                                                       18

SEQ ID NO: 61          moltype = RNA  length = 23
FEATURE                Location/Qualifiers
source                 1..23
                       mol_type = transcribed RNA
                       organism = Homo sapiens
SEQUENCE: 61
tgggcagggg cttattgtag gag                                                 23

SEQ ID NO: 62          moltype = RNA  length = 23
FEATURE                Location/Qualifiers
source                 1..23
                       mol_type = transcribed RNA
                       organism = Homo sapiens
SEQUENCE: 62
ccaggggat gggcgagctt ggg                                                  23

SEQ ID NO: 63          moltype = RNA  length = 23
FEATURE                Location/Qualifiers
source                 1..23
                       mol_type = transcribed RNA
                       organism = Homo sapiens
SEQUENCE: 63
ttagggagta gaagggtggg gag                                                 23

SEQ ID NO: 64          moltype = RNA  length = 18
FEATURE                Location/Qualifiers
source                 1..18
                       mol_type = transcribed RNA
                       organism = Homo sapiens
SEQUENCE: 64
gtgaaggccc ggcggaga                                                       18

SEQ ID NO: 65          moltype = RNA  length = 23
FEATURE                Location/Qualifiers
source                 1..23
                       mol_type = transcribed RNA
                       organism = Homo sapiens
SEQUENCE: 65
gtgagtggga gccggtgggg ctg                                                 23

SEQ ID NO: 66          moltype = RNA  length = 20
FEATURE                Location/Qualifiers
source                 1..20
                       mol_type = transcribed RNA
                       organism = Homo sapiens
SEQUENCE: 66
taggatgggg gtgagaggtg                                                     20

SEQ ID NO: 67          moltype = RNA  length = 21
FEATURE                Location/Qualifiers
source                 1..21
                       mol_type = transcribed RNA
                       organism = Homo sapiens
SEQUENCE: 67
cggggcagct cagtacagga t                                                   21

SEQ ID NO: 68          moltype = RNA  length = 23
FEATURE                Location/Qualifiers
source                 1..23
                       mol_type = transcribed RNA
                       organism = Homo sapiens
SEQUENCE: 68
ctcggggcag gcggctggga gcg                                                 23
```

```
SEQ ID NO: 69          moltype = RNA  length = 23
FEATURE                Location/Qualifiers
source                 1..23
                       mol_type = transcribed RNA
                       organism = Homo sapiens
SEQUENCE: 69
tgggagggga gaggcagcaa gca                                              23

SEQ ID NO: 70          moltype = RNA  length = 22
FEATURE                Location/Qualifiers
source                 1..22
                       mol_type = transcribed RNA
                       organism = Homo sapiens
SEQUENCE: 70
ccgggagaag gaggtggcct gg                                               22

SEQ ID NO: 71          moltype = RNA  length = 20
FEATURE                Location/Qualifiers
source                 1..20
                       mol_type = transcribed RNA
                       organism = Homo sapiens
SEQUENCE: 71
tcagggagtc aggggagggc                                                  20

SEQ ID NO: 72          moltype = RNA  length = 20
FEATURE                Location/Qualifiers
source                 1..20
                       mol_type = transcribed RNA
                       organism = Homo sapiens
SEQUENCE: 72
gtgggttggg gcgggctctg                                                  20

SEQ ID NO: 73          moltype = RNA  length = 22
FEATURE                Location/Qualifiers
source                 1..22
                       mol_type = transcribed RNA
                       organism = Homo sapiens
SEQUENCE: 73
tggggaaggc gtcagtgtcg gg                                               22

SEQ ID NO: 74          moltype = RNA  length = 21
FEATURE                Location/Qualifiers
source                 1..21
                       mol_type = transcribed RNA
                       organism = Homo sapiens
SEQUENCE: 74
gtgtggccgg caggcgggtg g                                                21

SEQ ID NO: 75          moltype = RNA  length = 17
FEATURE                Location/Qualifiers
source                 1..17
                       mol_type = transcribed RNA
                       organism = Homo sapiens
SEQUENCE: 75
ggcgggtgcg ggggtgg                                                     17

SEQ ID NO: 76          moltype = RNA  length = 22
FEATURE                Location/Qualifiers
source                 1..22
                       mol_type = transcribed RNA
                       organism = Homo sapiens
SEQUENCE: 76
cagggcaggg aaggtgggag ag                                               22

SEQ ID NO: 77          moltype = RNA  length = 23
FEATURE                Location/Qualifiers
source                 1..23
                       mol_type = transcribed RNA
                       organism = Homo sapiens
SEQUENCE: 77
cgaggggtag aagagcacag ggg                                              23

SEQ ID NO: 78          moltype = RNA  length = 18
FEATURE                Location/Qualifiers
source                 1..18
                       mol_type = transcribed RNA
                       organism = Homo sapiens
SEQUENCE: 78
```
atcccacctc tgccacca                                                              18

SEQ ID NO: 79          moltype = RNA   length = 22
FEATURE                Location/Qualifiers
source                 1..22
                       mol_type = transcribed RNA
                       organism = Homo sapiens
SEQUENCE: 79
cagggctggc agtgacatgg gt                                                         22

SEQ ID NO: 80          moltype = RNA   length = 23
FEATURE                Location/Qualifiers
source                 1..23
                       mol_type = transcribed RNA
                       organism = Homo sapiens
SEQUENCE: 80
tcgaggactg gtggaagggc ctt                                                        23

SEQ ID NO: 81          moltype = RNA   length = 17
FEATURE                Location/Qualifiers
source                 1..17
                       mol_type = transcribed RNA
                       organism = Homo sapiens
SEQUENCE: 81
gagactgggg tggggcc                                                               17

SEQ ID NO: 82          moltype = RNA   length = 23
FEATURE                Location/Qualifiers
source                 1..23
                       mol_type = transcribed RNA
                       organism = Homo sapiens
SEQUENCE: 82
agaagaaggc ggtcggtctg cgg                                                        23

SEQ ID NO: 83          moltype = RNA   length = 19
FEATURE                Location/Qualifiers
source                 1..19
                       mol_type = transcribed RNA
                       organism = Homo sapiens
SEQUENCE: 83
tgggggagat gggggttga                                                             19

SEQ ID NO: 84          moltype = RNA   length = 21
FEATURE                Location/Qualifiers
source                 1..21
                       mol_type = transcribed RNA
                       organism = Homo sapiens
SEQUENCE: 84
ctgggagggg ctgggtttgg c                                                          21

SEQ ID NO: 85          moltype = RNA   length = 21
FEATURE                Location/Qualifiers
source                 1..21
                       mol_type = transcribed RNA
                       organism = Homo sapiens
SEQUENCE: 85
accactgcac tccagcctga g                                                          21

SEQ ID NO: 86          moltype = RNA   length = 22
FEATURE                Location/Qualifiers
source                 1..22
                       mol_type = transcribed RNA
                       organism = Homo sapiens
SEQUENCE: 86
ggggaactgt agatgaaaag gc                                                         22

SEQ ID NO: 87          moltype = RNA   length = 22
FEATURE                Location/Qualifiers
source                 1..22
                       mol_type = transcribed RNA
                       organism = Homo sapiens
SEQUENCE: 87
aggggggcgca gtcactgacg tg                                                        22

SEQ ID NO: 88          moltype = RNA   length = 21
FEATURE                Location/Qualifiers
source                 1..21
                       mol_type = transcribed RNA
                       organism = Homo sapiens

```
SEQUENCE: 88
ctgggctcgg gacgcgcggc t                                                    21

SEQ ID NO: 89           moltype = RNA   length = 21
FEATURE                 Location/Qualifiers
source                  1..21
                        mol_type = transcribed RNA
                        organism = Homo sapiens
SEQUENCE: 89
acaggagtgg gggtgggaca t                                                    21

SEQ ID NO: 90           moltype = RNA   length = 18
FEATURE                 Location/Qualifiers
source                  1..18
                        mol_type = transcribed RNA
                        organism = Homo sapiens
SEQUENCE: 90
ccagaggtgg ggactgag                                                        18

SEQ ID NO: 91           moltype = RNA   length = 22
FEATURE                 Location/Qualifiers
source                  1..22
                        mol_type = transcribed RNA
                        organism = Homo sapiens
SEQUENCE: 91
accttgcctt gctgcccggg cc                                                   22

SEQ ID NO: 92           moltype = RNA   length = 18
FEATURE                 Location/Qualifiers
source                  1..18
                        mol_type = transcribed RNA
                        organism = Homo sapiens
SEQUENCE: 92
ggtgggcttc ccggaggg                                                        18

SEQ ID NO: 93           moltype = RNA   length = 22
FEATURE                 Location/Qualifiers
source                  1..22
                        mol_type = transcribed RNA
                        organism = Homo sapiens
SEQUENCE: 93
tggggagcgg cccccgggtg gg                                                   22

SEQ ID NO: 94           moltype = RNA   length = 21
FEATURE                 Location/Qualifiers
source                  1..21
                        mol_type = transcribed RNA
                        organism = Homo sapiens
SEQUENCE: 94
cgggccggag gtcaagggcg t                                                    21

SEQ ID NO: 95           moltype = RNA   length = 22
FEATURE                 Location/Qualifiers
source                  1..22
                        mol_type = transcribed RNA
                        organism = Homo sapiens
SEQUENCE: 95
caggaggcag tgggcgagca gg                                                   22

SEQ ID NO: 96           moltype = RNA   length = 21
FEATURE                 Location/Qualifiers
source                  1..21
                        mol_type = transcribed RNA
                        organism = Homo sapiens
SEQUENCE: 96
cgggggcggg gccgaagcgc g                                                    21

SEQ ID NO: 97           moltype = RNA   length = 25
FEATURE                 Location/Qualifiers
source                  1..25
                        mol_type = transcribed RNA
                        organism = Homo sapiens
SEQUENCE: 97
tcggggcatg ggggagggag gctgg                                                25

SEQ ID NO: 98           moltype = RNA   length = 21
FEATURE                 Location/Qualifiers
source                  1..21
                        mol_type = transcribed RNA
```

```
                                       organism = Homo sapiens
SEQUENCE: 98
aagggacagg gagggtcgtg g                                                  21

SEQ ID NO: 99            moltype = RNA   length = 21
FEATURE                  Location/Qualifiers
source                   1..21
                         mol_type = transcribed RNA
                         organism = Homo sapiens
SEQUENCE: 99
agcggtgctc ctgcgggccg a                                                  21

SEQ ID NO: 100           moltype = RNA   length = 19
FEATURE                  Location/Qualifiers
source                   1..19
                         mol_type = transcribed RNA
                         organism = Homo sapiens
SEQUENCE: 100
ttgatctcgg aagctaagc                                                     19

SEQ ID NO: 101           moltype = RNA   length = 21
FEATURE                  Location/Qualifiers
source                   1..21
                         mol_type = transcribed RNA
                         organism = Homo sapiens
SEQUENCE: 101
cgtggaggac gaggaggagg c                                                  21

SEQ ID NO: 102           moltype = RNA   length = 24
FEATURE                  Location/Qualifiers
source                   1..24
                         mol_type = transcribed RNA
                         organism = Homo sapiens
SEQUENCE: 102
tgtaggcatg aggcagggcc cagg                                               24

SEQ ID NO: 103           moltype = RNA   length = 22
FEATURE                  Location/Qualifiers
source                   1..22
                         mol_type = transcribed RNA
                         organism = Homo sapiens
SEQUENCE: 103
tggcggcggt agttatgggc tt                                                 22

SEQ ID NO: 104           moltype = RNA   length = 23
FEATURE                  Location/Qualifiers
source                   1..23
                         mol_type = transcribed RNA
                         organism = Homo sapiens
SEQUENCE: 104
agggccagag gagcctggag tgg                                                23

SEQ ID NO: 105           moltype = RNA   length = 20
FEATURE                  Location/Qualifiers
source                   1..20
                         mol_type = transcribed RNA
                         organism = Homo sapiens
SEQUENCE: 105
tgtgggactg caaatgggag                                                    20

SEQ ID NO: 106           moltype = RNA   length = 24
FEATURE                  Location/Qualifiers
source                   1..24
                         mol_type = transcribed RNA
                         organism = Homo sapiens
SEQUENCE: 106
ggaggccggg gtgggcggg gcgg                                                24

SEQ ID NO: 107           moltype = RNA   length = 19
FEATURE                  Location/Qualifiers
source                   1..19
                         mol_type = transcribed RNA
                         organism = Homo sapiens
SEQUENCE: 107
atcccaccac tgccaccat                                                     19

SEQ ID NO: 108           moltype = RNA   length = 17
FEATURE                  Location/Qualifiers
source                   1..17
```

-continued

```
                          mol_type = transcribed RNA
                          organism = Homo sapiens
SEQUENCE: 108
ccccggggag cccggcg                                                     17

SEQ ID NO: 109           moltype = RNA   length = 21
FEATURE                  Location/Qualifiers
source                   1..21
                         mol_type = transcribed RNA
                         organism = Homo sapiens
SEQUENCE: 109
atccagttct ctgagggggc t                                                21

SEQ ID NO: 110           moltype = RNA   length = 23
FEATURE                  Location/Qualifiers
source                   1..23
                         mol_type = transcribed RNA
                         organism = Homo sapiens
SEQUENCE: 110
agaggctttg tgcggatacg ggg                                              23

SEQ ID NO: 111           moltype = RNA   length = 23
FEATURE                  Location/Qualifiers
source                   1..23
                         mol_type = transcribed RNA
                         organism = Homo sapiens
SEQUENCE: 111
tgggggctgg gatgggccat ggt                                              23

SEQ ID NO: 112           moltype = RNA   length = 22
FEATURE                  Location/Qualifiers
source                   1..22
                         mol_type = transcribed RNA
                         organism = Homo sapiens
SEQUENCE: 112
agtgggaggc cagggcacgg ca                                               22

SEQ ID NO: 113           moltype = RNA   length = 22
FEATURE                  Location/Qualifiers
source                   1..22
                         mol_type = transcribed RNA
                         organism = Homo sapiens
SEQUENCE: 113
aggcgatgtg gggatgtaga ga                                               22

SEQ ID NO: 114           moltype = RNA   length = 17
FEATURE                  Location/Qualifiers
source                   1..17
                         mol_type = transcribed RNA
                         organism = Homo sapiens
SEQUENCE: 114
cgcgccgggc ccgggtt                                                     17

SEQ ID NO: 115           moltype = RNA   length = 22
FEATURE                  Location/Qualifiers
source                   1..22
                         mol_type = transcribed RNA
                         organism = Homo sapiens
SEQUENCE: 115
tagggatggg aggccaggat ga                                               22

SEQ ID NO: 116           moltype = RNA   length = 20
FEATURE                  Location/Qualifiers
source                   1..20
                         mol_type = transcribed RNA
                         organism = Homo sapiens
SEQUENCE: 116
ggcggcgggg aggtaggcag                                                  20

SEQ ID NO: 117           moltype = RNA   length = 23
FEATURE                  Location/Qualifiers
source                   1..23
                         mol_type = transcribed RNA
                         organism = Homo sapiens
SEQUENCE: 117
tgagtggggc tcccgggacg gcg                                              23

SEQ ID NO: 118           moltype = RNA   length = 23
FEATURE                  Location/Qualifiers
```

```
source                       1..23
                             mol_type = transcribed RNA
                             organism = Homo sapiens
SEQUENCE: 118
caggcagaag tggggctgac agg                                              23

SEQ ID NO: 119               moltype = RNA   length = 19
FEATURE                      Location/Qualifiers
source                       1..19
                             mol_type = transcribed RNA
                             organism = Homo sapiens
SEQUENCE: 119
tctgggtgca gtgggggtt                                                   19

SEQ ID NO: 120               moltype = RNA   length = 20
FEATURE                      Location/Qualifiers
source                       1..20
                             mol_type = transcribed RNA
                             organism = Homo sapiens
SEQUENCE: 120
actcaaactg tgggggcact                                                  20

SEQ ID NO: 121               moltype = RNA   length = 17
FEATURE                      Location/Qualifiers
source                       1..17
                             mol_type = transcribed RNA
                             organism = Homo sapiens
SEQUENCE: 121
gtggggccag gcggtgg                                                     17

SEQ ID NO: 122               moltype = RNA   length = 18
FEATURE                      Location/Qualifiers
source                       1..18
                             mol_type = transcribed RNA
                             organism = Homo sapiens
SEQUENCE: 122
ctggcagggg gagaggta                                                    18

SEQ ID NO: 123               moltype = RNA   length = 20
FEATURE                      Location/Qualifiers
source                       1..20
                             mol_type = transcribed RNA
                             organism = Homo sapiens
SEQUENCE: 123
ccccagggcg acgcggcggg                                                  20

SEQ ID NO: 124               moltype = RNA   length = 22
FEATURE                      Location/Qualifiers
source                       1..22
                             mol_type = transcribed RNA
                             organism = Homo sapiens
SEQUENCE: 124
ggctacaaca caggacccgg gc                                               22

SEQ ID NO: 125               moltype = RNA   length = 23
FEATURE                      Location/Qualifiers
source                       1..23
                             mol_type = transcribed RNA
                             organism = Homo sapiens
SEQUENCE: 125
gaacgcctgt tcttgccagg tgg                                              23

SEQ ID NO: 126               moltype = RNA   length = 23
FEATURE                      Location/Qualifiers
source                       1..23
                             mol_type = transcribed RNA
                             organism = Homo sapiens
SEQUENCE: 126
tgtgcaaatc catgcaaaac tga                                              23

SEQ ID NO: 127               moltype = RNA   length = 22
FEATURE                      Location/Qualifiers
source                       1..22
                             mol_type = transcribed RNA
                             organism = Homo sapiens
SEQUENCE: 127
gtgggtacgg cccagtgggg gg                                               22

SEQ ID NO: 128               moltype = RNA   length = 22
```

```
                        -continued

FEATURE                 Location/Qualifiers
source                  1..22
                        mol_type = transcribed RNA
                        organism = Homo sapiens
SEQUENCE: 128
aaaccgttac cattactgag tt                                              22

SEQ ID NO: 129          moltype = RNA   length = 24
FEATURE                 Location/Qualifiers
source                  1..24
                        mol_type = transcribed RNA
                        organism = Homo sapiens
SEQUENCE: 129
tggggagctg aggctctggg ggtg                                            24

SEQ ID NO: 130          moltype = RNA   length = 22
FEATURE                 Location/Qualifiers
source                  1..22
                        mol_type = transcribed RNA
                        organism = Homo sapiens
SEQUENCE: 130
tgtcagtttg tcaaataccc ca                                              22

SEQ ID NO: 131          moltype = RNA   length = 21
FEATURE                 Location/Qualifiers
source                  1..21
                        mol_type = transcribed RNA
                        organism = Homo sapiens
SEQUENCE: 131
gtgggcgggg gcaggtgtgt g                                               21

SEQ ID NO: 132          moltype = RNA   length = 22
FEATURE                 Location/Qualifiers
source                  1..22
                        mol_type = transcribed RNA
                        organism = Homo sapiens
SEQUENCE: 132
acaggtgagg ttcttgggag cc                                              22

SEQ ID NO: 133          moltype = RNA   length = 22
FEATURE                 Location/Qualifiers
source                  1..22
                        mol_type = transcribed RNA
                        organism = Homo sapiens
SEQUENCE: 133
agggacggga cgcggtgcag tg                                              22

SEQ ID NO: 134          moltype = RNA   length = 22
FEATURE                 Location/Qualifiers
source                  1..22
                        mol_type = transcribed RNA
                        organism = Homo sapiens
SEQUENCE: 134
aagctgccag ttgaagaact gt                                              22

SEQ ID NO: 135          moltype = RNA   length = 19
FEATURE                 Location/Qualifiers
source                  1..19
                        mol_type = transcribed RNA
                        organism = Homo sapiens
SEQUENCE: 135
gggggaagaa aaggtgggg                                                  19

SEQ ID NO: 136          moltype = RNA   length = 22
FEATURE                 Location/Qualifiers
source                  1..22
                        mol_type = transcribed RNA
                        organism = Homo sapiens
SEQUENCE: 136
agacacattt ggagagggac cc                                              22

SEQ ID NO: 137          moltype = RNA   length = 21
FEATURE                 Location/Qualifiers
source                  1..21
                        mol_type = transcribed RNA
                        organism = Homo sapiens
SEQUENCE: 137
acggcccagg cggcattggt g                                               21
```

```
SEQ ID NO: 138          moltype = RNA   length = 20
FEATURE                 Location/Qualifiers
source                  1..20
                        mol_type = transcribed RNA
                        organism = Homo sapiens
SEQUENCE: 138
gcggaaggcg gagcggcgga                                                      20

SEQ ID NO: 139          moltype = RNA   length = 22
FEATURE                 Location/Qualifiers
source                  1..22
                        mol_type = transcribed RNA
                        organism = Homo sapiens
SEQUENCE: 139
gtgaacgggc gccatcccga gg                                                   22

SEQ ID NO: 140          moltype = RNA   length = 23
FEATURE                 Location/Qualifiers
source                  1..23
                        mol_type = transcribed RNA
                        organism = Homo sapiens
SEQUENCE: 140
aggaggtggt actagggcc agc                                                   23

SEQ ID NO: 141          moltype = RNA   length = 19
FEATURE                 Location/Qualifiers
source                  1..19
                        mol_type = transcribed RNA
                        organism = Homo sapiens
SEQUENCE: 141
ctggggagtg gctggggag                                                       19

SEQ ID NO: 142          moltype = RNA   length = 22
FEATURE                 Location/Qualifiers
source                  1..22
                        mol_type = transcribed RNA
                        organism = Homo sapiens
SEQUENCE: 142
ggaggaacct tggagcttcg gc                                                   22

SEQ ID NO: 143          moltype = RNA   length = 17
FEATURE                 Location/Qualifiers
source                  1..17
                        mol_type = transcribed RNA
                        organism = Homo sapiens
SEQUENCE: 143
ttggaggcgt gggtttt                                                         17

SEQ ID NO: 144          moltype = RNA   length = 21
FEATURE                 Location/Qualifiers
source                  1..21
                        mol_type = transcribed RNA
                        organism = Homo sapiens
SEQUENCE: 144
agccgcgggg atcgccgagg g                                                    21

SEQ ID NO: 145          moltype = RNA   length = 21
FEATURE                 Location/Qualifiers
source                  1..21
                        mol_type = transcribed RNA
                        organism = Homo sapiens
SEQUENCE: 145
agggagggac gggggctgtg c                                                    21

SEQ ID NO: 146          moltype = RNA   length = 22
FEATURE                 Location/Qualifiers
source                  1..22
                        mol_type = transcribed RNA
                        organism = Homo sapiens
SEQUENCE: 146
ttgaggagac atggtggggg cc                                                   22

SEQ ID NO: 147          moltype = RNA   length = 24
FEATURE                 Location/Qualifiers
source                  1..24
                        mol_type = transcribed RNA
                        organism = Homo sapiens
SEQUENCE: 147
aggcaggggc tggtgctggg cggg                                                 24
```

```
SEQ ID NO: 148        moltype = RNA  length = 22
FEATURE               Location/Qualifiers
source                1..22
                      mol_type = transcribed RNA
                      organism = Homo sapiens
SEQUENCE: 148
tgggcgaggg cggctgagcg gc                                                22

SEQ ID NO: 149        moltype = RNA  length = 18
FEATURE               Location/Qualifiers
source                1..18
                      mol_type = transcribed RNA
                      organism = Homo sapiens
SEQUENCE: 149
cggggcggca ggggcctc                                                     18

SEQ ID NO: 150        moltype = RNA  length = 23
FEATURE               Location/Qualifiers
source                1..23
                      mol_type = transcribed RNA
                      organism = Homo sapiens
SEQUENCE: 150
ggatggttgg gggcggtcgg cgt                                               23

SEQ ID NO: 151        moltype = RNA  length = 18
FEATURE               Location/Qualifiers
source                1..18
                      mol_type = transcribed RNA
                      organism = Homo sapiens
SEQUENCE: 151
cgggcgtggt ggtgggggg                                                    18

SEQ ID NO: 152        moltype = RNA  length = 25
FEATURE               Location/Qualifiers
source                1..25
                      mol_type = transcribed RNA
                      organism = Homo sapiens
SEQUENCE: 152
aagggaggag gagcggaggg gccct                                             25

SEQ ID NO: 153        moltype = RNA  length = 20
FEATURE               Location/Qualifiers
source                1..20
                      mol_type = transcribed RNA
                      organism = Homo sapiens
SEQUENCE: 153
cgggcgtggt ggtgggggtg                                                   20

SEQ ID NO: 154        moltype = RNA  length = 22
FEATURE               Location/Qualifiers
source                1..22
                      mol_type = transcribed RNA
                      organism = Homo sapiens
SEQUENCE: 154
tgggggagtg cagtgattgt gg                                                22

SEQ ID NO: 155        moltype = RNA  length = 22
FEATURE               Location/Qualifiers
source                1..22
                      mol_type = transcribed RNA
                      organism = Homo sapiens
SEQUENCE: 155
gggggtgtg gagccagggg gc                                                 22

SEQ ID NO: 156        moltype = RNA  length = 20
FEATURE               Location/Qualifiers
source                1..20
                      mol_type = transcribed RNA
                      organism = Homo sapiens
SEQUENCE: 156
ctgggttggg ctgggctggg                                                   20

SEQ ID NO: 157        moltype = RNA  length = 19
FEATURE               Location/Qualifiers
source                1..19
                      mol_type = transcribed RNA
                      organism = Homo sapiens
SEQUENCE: 157
```

```
aggcacggtg tcagcaggc                                                      19

SEQ ID NO: 158          moltype = RNA   length = 17
FEATURE                 Location/Qualifiers
source                  1..17
                        mol_type = transcribed RNA
                        organism = Homo sapiens
SEQUENCE: 158
ctccgggacg gctgggc                                                        17

SEQ ID NO: 159          moltype = RNA   length = 22
FEATURE                 Location/Qualifiers
source                  1..22
                        mol_type = transcribed RNA
                        organism = Homo sapiens
SEQUENCE: 159
agggccgaag ggtggaagct gc                                                  22

SEQ ID NO: 160          moltype = RNA   length = 18
FEATURE                 Location/Qualifiers
source                  1..18
                        mol_type = transcribed RNA
                        organism = Homo sapiens
SEQUENCE: 160
tgaggcgggg gggcgagc                                                       18

SEQ ID NO: 161          moltype = RNA   length = 22
FEATURE                 Location/Qualifiers
source                  1..22
                        mol_type = transcribed RNA
                        organism = Homo sapiens
SEQUENCE: 161
tgctgggggc cacatgagtg tg                                                  22

SEQ ID NO: 162          moltype = RNA   length = 22
FEATURE                 Location/Qualifiers
source                  1..22
                        mol_type = transcribed RNA
                        organism = Homo sapiens
SEQUENCE: 162
gggggtcccc ggtgctcgga tc                                                  22

SEQ ID NO: 163          moltype = RNA   length = 20
FEATURE                 Location/Qualifiers
source                  1..20
                        mol_type = transcribed RNA
                        organism = Homo sapiens
SEQUENCE: 163
cggctctggg tctgtgggga                                                     20

SEQ ID NO: 164          moltype = RNA   length = 19
FEATURE                 Location/Qualifiers
source                  1..19
                        mol_type = transcribed RNA
                        organism = Homo sapiens
SEQUENCE: 164
taaggagggg gatgagggg                                                      19

SEQ ID NO: 165          moltype = RNA   length = 23
FEATURE                 Location/Qualifiers
source                  1..23
                        mol_type = transcribed RNA
                        organism = Homo sapiens
SEQUENCE: 165
tgggggaca gatggagagg aca                                                  23

SEQ ID NO: 166          moltype = RNA   length = 21
FEATURE                 Location/Qualifiers
source                  1..21
                        mol_type = transcribed RNA
                        organism = Homo sapiens
SEQUENCE: 166
gggggatgt gcatgctggt t                                                    21

SEQ ID NO: 167          moltype = RNA   length = 22
FEATURE                 Location/Qualifiers
source                  1..22
                        mol_type = transcribed RNA
                        organism = Homo sapiens
```

```
SEQUENCE: 167
ggagggtcc cgcactggga gg                                                  22

SEQ ID NO: 168          moltype = RNA  length = 22
FEATURE                 Location/Qualifiers
source                  1..22
                        mol_type = transcribed RNA
                        organism = Homo sapiens
SEQUENCE: 168
gctgggatta caggcatgag cc                                                 22

SEQ ID NO: 169          moltype = RNA  length = 24
FEATURE                 Location/Qualifiers
source                  1..24
                        mol_type = transcribed RNA
                        organism = Homo sapiens
SEQUENCE: 169
agggctggac tcagcggcgg agct                                               24

SEQ ID NO: 170          moltype = RNA  length = 22
FEATURE                 Location/Qualifiers
source                  1..22
                        mol_type = transcribed RNA
                        organism = Homo sapiens
SEQUENCE: 170
tgcagggtc gggtgggcca gg                                                  22

SEQ ID NO: 171          moltype = RNA  length = 20
FEATURE                 Location/Qualifiers
source                  1..20
                        mol_type = transcribed RNA
                        organism = Homo sapiens
SEQUENCE: 171
cgcgggtcgg ggtctgcagg                                                    20

SEQ ID NO: 172          moltype = RNA  length = 22
FEATURE                 Location/Qualifiers
source                  1..22
                        mol_type = transcribed RNA
                        organism = Homo sapiens
SEQUENCE: 172
ctgggacagg aggaggaggc ag                                                 22

SEQ ID NO: 173          moltype = RNA  length = 23
FEATURE                 Location/Qualifiers
source                  1..23
                        mol_type = transcribed RNA
                        organism = Homo sapiens
SEQUENCE: 173
tggtgcggag agggcccaca gtg                                                23

SEQ ID NO: 174          moltype = RNA  length = 22
FEATURE                 Location/Qualifiers
source                  1..22
                        mol_type = transcribed RNA
                        organism = Homo sapiens
SEQUENCE: 174
caccggggat ggcagagggt cg                                                 22

SEQ ID NO: 175          moltype = RNA  length = 72
FEATURE                 Location/Qualifiers
source                  1..72
                        mol_type = transcribed RNA
                        organism = Homo sapiens
SEQUENCE: 175
ccaggcacac aggaaaagcg gggccctggg ttcggctgct accccaaagg ccacattctc        60
ctgtgcacac ag                                                            72

SEQ ID NO: 176          moltype = RNA  length = 63
FEATURE                 Location/Qualifiers
source                  1..63
                        mol_type = transcribed RNA
                        organism = Homo sapiens
SEQUENCE: 176
ggctccgcag ggccctggcg caggcatcca gacagcgggc gaatgcctcc cccggccccg        60
cag                                                                      63

SEQ ID NO: 177          moltype = RNA  length = 69
FEATURE                 Location/Qualifiers
```

```
                              source          1..69
                                              mol_type = transcribed RNA
                                              organism = Homo sapiens
SEQUENCE: 177
tggggtaggg gtgggggaat tcagggggtgt cgaactcatg gctgccacct ttgtgtcccc       60
atcctgcag                                                                69

SEQ ID NO: 178                  moltype = RNA   length = 97
FEATURE                         Location/Qualifiers
source                          1..97
                                mol_type = transcribed RNA
                                organism = Homo sapiens
SEQUENCE: 178
cccgggacct tggtccaggc gctggtctgc gtggtgctcg ggtggataag tctgatctga       60
gcaccacaca ggccgggcgc cgggaccaag ggggctc                                 97

SEQ ID NO: 179                  moltype = RNA   length = 80
FEATURE                         Location/Qualifiers
source                          1..80
                                mol_type = transcribed RNA
                                organism = Homo sapiens
SEQUENCE: 179
cgggaatgcc gcggcgggga cggcgattgg tccgtatgtg tggtgccacc ggccgccggc       60
tccgccccgg cccccgcccc                                                    80

SEQ ID NO: 180                  moltype = RNA   length = 61
FEATURE                         Location/Qualifiers
source                          1..61
                                mol_type = transcribed RNA
                                organism = Homo sapiens
SEQUENCE: 180
gggggcggga gctggggtct gcaggttcgc actgatgcct gctcgccctg tctcccgcta       60
g                                                                        61

SEQ ID NO: 181                  moltype = RNA   length = 91
FEATURE                         Location/Qualifiers
source                          1..91
                                mol_type = transcribed RNA
                                organism = Homo sapiens
SEQUENCE: 181
acgccccccg ccccgccacc gccttggagg ctgacctctt actttcggtc ggtcttcttc       60
cctgggcttg gtttgggggc gggggagtgt c                                       91

SEQ ID NO: 182                  moltype = RNA   length = 84
FEATURE                         Location/Qualifiers
source                          1..84
                                mol_type = transcribed RNA
                                organism = Homo sapiens
SEQUENCE: 182
gctggcgtcg gtgctgggga gcggcccccg ggtgggcctc tgctctggcc cctcctgggg       60
cccgcactct cgctctgggc ccgc                                               84

SEQ ID NO: 183                  moltype = RNA   length = 86
FEATURE                         Location/Qualifiers
source                          1..86
                                mol_type = transcribed RNA
                                organism = Homo sapiens
SEQUENCE: 183
agggagaagg gtcgggggcag ggagggcagg gcaggctctg gggtggggggg tctgtgagtc     60
agccacggct ctgcccacgt ctcccc                                             86

SEQ ID NO: 184                  moltype = RNA   length = 72
FEATURE                         Location/Qualifiers
source                          1..72
                                mol_type = transcribed RNA
                                organism = Homo sapiens
SEQUENCE: 184
gagtctgagg gacccaggac aggagaaggc ctatggtgat ttgcattctt cctgccctgg       60
ctccatcctc ag                                                            72

SEQ ID NO: 185                  moltype = RNA   length = 73
FEATURE                         Location/Qualifiers
source                          1..73
                                mol_type = transcribed RNA
                                organism = Homo sapiens
SEQUENCE: 185
cggcgacggc ggggtgggtg aggtcgggcc ccaagactcg gggtttgccg ggcgcctcag       60
ttcaccgcgg ccg                                                           73
```

```
SEQ ID NO: 186            moltype = RNA   length = 66
FEATURE                   Location/Qualifiers
source                    1..66
                          mol_type = transcribed RNA
                          organism = Homo sapiens
SEQUENCE: 186
gggcatgggg aggtgtggag tcagcatggg gctaggaggc cccgcgctga cccgccttct    60
ccgcag                                                               66

SEQ ID NO: 187            moltype = RNA   length = 71
FEATURE                   Location/Qualifiers
source                    1..71
                          mol_type = transcribed RNA
                          organism = Homo sapiens
SEQUENCE: 187
tgaccacccc cgggcaaaga cctgcagatc ccctgttaga gacgggccca ggactttgtg    60
cggggtgccc a                                                         71

SEQ ID NO: 188            moltype = RNA   length = 79
FEATURE                   Location/Qualifiers
source                    1..79
                          mol_type = transcribed RNA
                          organism = Homo sapiens
SEQUENCE: 188
cagcctgggg aaggcttggc agggaagaca catgagcagt gcctccactt cacgcctctc    60
ccttgtctcc tttccctag                                                 79

SEQ ID NO: 189            moltype = RNA   length = 69
FEATURE                   Location/Qualifiers
source                    1..69
                          mol_type = transcribed RNA
                          organism = Homo sapiens
SEQUENCE: 189
ggccctcggg cctggggttg ggggagctct gtcctgtctc actcattgct cctcccctgc    60
ctggcccag                                                            69

SEQ ID NO: 190            moltype = RNA   length = 81
FEATURE                   Location/Qualifiers
source                    1..81
                          mol_type = transcribed RNA
                          organism = Homo sapiens
SEQUENCE: 190
tagaggcagt ttcaacagat gtgtagactt ttgatatgag aaattggttt caaaatcagg    60
agtcggggct ttactgcttt t                                              81

SEQ ID NO: 191            moltype = RNA   length = 67
FEATURE                   Location/Qualifiers
source                    1..67
                          mol_type = transcribed RNA
                          organism = Homo sapiens
SEQUENCE: 191
tacaggccgg ggctttgggt gagggacccc cggagtctgt cacggtctca ccccaactct    60
gccccag                                                              67

SEQ ID NO: 192            moltype = RNA   length = 68
FEATURE                   Location/Qualifiers
source                    1..68
                          mol_type = transcribed RNA
                          organism = Homo sapiens
SEQUENCE: 192
cgtggtgagg atatggcagg gaagggagt ttccctctat tcccttcccc ccagtaatct    60
tcatcatg                                                             68

SEQ ID NO: 193            moltype = RNA   length = 75
FEATURE                   Location/Qualifiers
source                    1..75
                          mol_type = transcribed RNA
                          organism = Homo sapiens
SEQUENCE: 193
aagcaagact gaggggcctc agaccgagct tttggaaaat agaaaagtct cgctctctgc    60
ccctcagcct aactt                                                     75

SEQ ID NO: 194            moltype = RNA   length = 115
FEATURE                   Location/Qualifiers
source                    1..115
                          mol_type = transcribed RNA
                          organism = Homo sapiens
SEQUENCE: 194
ggtgccgagg gccgtccggc atcctaggcg ggtcgctgcg gtacctccct cctgtctgtg    60
```

```
gcggtgggat cccgtggccg tgttttcctg gtggcccggc cgtgcctgag gtttc          115

SEQ ID NO: 195            moltype = RNA   length = 62
FEATURE                   Location/Qualifiers
source                    1..62
                          mol_type = transcribed RNA
                          organism = Homo sapiens
SEQUENCE: 195
gagggtggtg gaggaagagg gcagctccca tgactgcctg accgccttct ctcctccccc      60
ag                                                                     62

SEQ ID NO: 196            moltype = RNA   length = 75
FEATURE                   Location/Qualifiers
source                    1..75
                          mol_type = transcribed RNA
                          organism = Homo sapiens
SEQUENCE: 196
tcatccctgg gtggggattt gttgcattac ttgtgttcta tataaagtat tgcacttgtc      60
ccggcctgtg gaaga                                                       75

SEQ ID NO: 197            moltype = RNA   length = 68
FEATURE                   Location/Qualifiers
source                    1..68
                          mol_type = transcribed RNA
                          organism = Homo sapiens
SEQUENCE: 197
gtgcaaagag caggaggaca ggggatttat ctcccaaggg aggtcccctg atcctagtca      60
cggcacca                                                               68

SEQ ID NO: 198            moltype = RNA   length = 86
FEATURE                   Location/Qualifiers
source                    1..86
                          mol_type = transcribed RNA
                          organism = Homo sapiens
SEQUENCE: 198
ggggctgggg gtgtggggag agagagtgca cagccagctc agggattaaa gctctttctc      60
tctctctctc tcccacttcc ctgcag                                           86

SEQ ID NO: 199            moltype = RNA   length = 65
FEATURE                   Location/Qualifiers
source                    1..65
                          mol_type = transcribed RNA
                          organism = Homo sapiens
SEQUENCE: 199
agccctgggg gtggtctcta gccaaggctc tggggtctca cccttggctg gtctctgctc      60
cgcag                                                                  65

SEQ ID NO: 200            moltype = RNA   length = 93
FEATURE                   Location/Qualifiers
source                    1..93
                          mol_type = transcribed RNA
                          organism = Homo sapiens
SEQUENCE: 200
gcttgttggg gattgggtca ggccagtgtt caagggcccc tcctctagta ctccctgttt      60
gtgttctgcc actgactgag cttctcccca cag                                   93

SEQ ID NO: 201            moltype = RNA   length = 137
FEATURE                   Location/Qualifiers
source                    1..137
                          mol_type = transcribed RNA
                          organism = Homo sapiens
SEQUENCE: 201
agccagacaa gagggtcatg gggagtcact gtcaacccag agcaggcact gcccctgcga      60
ccagcctggg gcatcggttg gggtgcaggg gtctgctggt gatgctttcc atctctttgc     120
tttgtcctga ttgtagc                                                    137

SEQ ID NO: 202            moltype = RNA   length = 73
FEATURE                   Location/Qualifiers
source                    1..73
                          mol_type = transcribed RNA
                          organism = Homo sapiens
SEQUENCE: 202
ggcgagggga ggcgcaggct cggaaaggcg cgcgaggctc caggctcctt cccgatccac      60
cgctctcctc gct                                                         73

SEQ ID NO: 203            moltype = RNA   length = 109
FEATURE                   Location/Qualifiers
source                    1..109
                          mol_type = transcribed RNA
```

```
                                organism = Homo sapiens
SEQUENCE: 203
tcccgcattc cctctgcttt ggtcaggtgg tgccctcctt ccatgggtag agccagagat    60
ggtgggttct ggctggtcag atgggagtgg acagagaccc ggggtcctc               109

SEQ ID NO: 204          moltype = RNA   length = 59
FEATURE                 Location/Qualifiers
source                  1..59
                        mol_type = transcribed RNA
                        organism = Homo sapiens
SEQUENCE: 204
ctgtgtcggg gagtctgggg tccggaattc tccagagcct ctgtgcccct acttcccag    59

SEQ ID NO: 205          moltype = RNA   length = 55
FEATURE                 Location/Qualifiers
source                  1..55
                        mol_type = transcribed RNA
                        organism = Homo sapiens
SEQUENCE: 205
ccggatccga gtcacggcac caaatttcat gcgtgtccgt gtgaagagac cacca        55

SEQ ID NO: 206          moltype = RNA   length = 119
FEATURE                 Location/Qualifiers
source                  1..119
                        mol_type = transcribed RNA
                        organism = Homo sapiens
SEQUENCE: 206
agcctgcgcc ggagccgggg cctgagcccg ggccgcgcag gccgtgaact cgtcgagctg    60
cgcgtgcggc cggtgctcaa cctgccgggt cctggccccg cgctcccgcg cgccctgga    119

SEQ ID NO: 207          moltype = RNA   length = 136
FEATURE                 Location/Qualifiers
source                  1..136
                        mol_type = transcribed RNA
                        organism = Homo sapiens
SEQUENCE: 207
ccgcttgcct cgcccagcgc agccccggcc gctgggcgca cccgtcccgt tcgtcccgg    60
acgttgctct ctaccccggg aacgtcgaga ctggagcgcc cgaactgagc caccttcgcg    120
gaccccgaga gcggcg                                                   136

SEQ ID NO: 208          moltype = RNA   length = 82
FEATURE                 Location/Qualifiers
source                  1..82
                        mol_type = transcribed RNA
                        organism = Homo sapiens
SEQUENCE: 208
acctgtaggt gacagtcagg ggcggggtgt ggtggggctg gggctggccc cctcctcaca    60
cctctcctgg catcgccccc ag                                            82

SEQ ID NO: 209          moltype = RNA   length = 62
FEATURE                 Location/Qualifiers
source                  1..62
                        mol_type = transcribed RNA
                        organism = Homo sapiens
SEQUENCE: 209
gtgggtctcg catcaggagg caaggccagg acccgctgac ccatgcctcc tgccgcggtc    60
ag                                                                  62

SEQ ID NO: 210          moltype = RNA   length = 64
FEATURE                 Location/Qualifiers
source                  1..64
                        mol_type = transcribed RNA
                        organism = Homo sapiens
SEQUENCE: 210
tctgggcgag gggtgggctc tcagaggggc tggcagtact gctctgaggc ctgcctctcc    60
ccag                                                                64

SEQ ID NO: 211          moltype = RNA   length = 67
FEATURE                 Location/Qualifiers
source                  1..67
                        mol_type = transcribed RNA
                        organism = Homo sapiens
SEQUENCE: 211
ccagaccct ggggctgggc aggcggaaag aggtctgaac tgcctctgcc tccttggtct    60
ccggcag                                                             67

SEQ ID NO: 212          moltype = RNA   length = 102
FEATURE                 Location/Qualifiers
source                  1..102
```

```
                              mol_type = transcribed RNA
                              organism = Homo sapiens
SEQUENCE: 212
tgtgttccct atcctcctta tgtcccaccc ccactcctgt ttgaatattt caccagaaac      60
aggagtgggg ggtgggacgt aaggaggatg ggggaaagaa ca                        102

SEQ ID NO: 213                moltype = RNA   length = 68
FEATURE                       Location/Qualifiers
source                        1..68
                              mol_type = transcribed RNA
                              organism = Homo sapiens
SEQUENCE: 213
tgcccaggct ggagcgagtg cagtggtgca gtcagtccta gctcactgca gcctcgaact      60
cctgggct                                                              68

SEQ ID NO: 214                moltype = RNA   length = 84
FEATURE                       Location/Qualifiers
source                        1..84
                              mol_type = transcribed RNA
                              organism = Homo sapiens
SEQUENCE: 214
tgtgcagtgg aaggggggc cgatacactg tacgagagtg agtagcaggt ctcacagtga       60
accggtctct ttccctactg tgtc                                            84

SEQ ID NO: 215                moltype = RNA   length = 77
FEATURE                       Location/Qualifiers
source                        1..77
                              mol_type = transcribed RNA
                              organism = Homo sapiens
SEQUENCE: 215
catgagaaat cctgctggtc aaccatagcc ctggtcagac tctccggggc tgtgattgac      60
cagcaggact tctcatg                                                    77

SEQ ID NO: 216                moltype = RNA   length = 80
FEATURE                       Location/Qualifiers
source                        1..80
                              mol_type = transcribed RNA
                              organism = Homo sapiens
SEQUENCE: 216
tggcagaccc ttgctctctc actctcccta atggggctga agacagctca ggggcagggt      60
gggggtgtt gttttgttt                                                   80

SEQ ID NO: 217                moltype = RNA   length = 67
FEATURE                       Location/Qualifiers
source                        1..67
                              mol_type = transcribed RNA
                              organism = Homo sapiens
SEQUENCE: 217
tggtgggggt gggggtgtt gttttgttt ttgagacaga gtcttgctcc gtcgcccagg        60
ccggagt                                                               67

SEQ ID NO: 218                moltype = RNA   length = 81
FEATURE                       Location/Qualifiers
source                        1..81
                              mol_type = transcribed RNA
                              organism = Homo sapiens
SEQUENCE: 218
ctccctggga gggcgtggat gatggtggga gaggagcccc actgtggaag tctgaccccc      60
acatcgcccc accttcccca g                                               81

SEQ ID NO: 219                moltype = RNA   length = 63
FEATURE                       Location/Qualifiers
source                        1..63
                              mol_type = transcribed RNA
                              organism = Homo sapiens
SEQUENCE: 219
aatgggtggg tgctggtggg agccgtgccc tggccactca ttcggctctc tccctcaccc      60
tag                                                                   63

SEQ ID NO: 220                moltype = RNA   length = 49
FEATURE                       Location/Qualifiers
source                        1..49
                              mol_type = transcribed RNA
                              organism = Homo sapiens
SEQUENCE: 220
ttcccagcca acgcaccaaa aatgatatgg gtctgttgtc tggagaaac                  49

SEQ ID NO: 221                moltype = RNA   length = 105
FEATURE                       Location/Qualifiers
```

```
source                  1..105
                        mol_type = transcribed RNA
                        organism = Homo sapiens
SEQUENCE: 221
gcgggcggcg gcggcggcag cagcagcagg tgcggggcgg cggccgcgct ggccgctcga   60
ctccgcagct gctcgttctg cttctccagc ttgcgcacca gctcc                  105

SEQ ID NO: 222          moltype = RNA   length = 82
FEATURE                 Location/Qualifiers
source                  1..82
                        mol_type = transcribed RNA
                        organism = Homo sapiens
SEQUENCE: 222
tgagctgttg gattcggggc cgtagcactg tctgagaggt ttacatttct cacagtgaac   60
cggtctcttt ttcagctgct tc                                           82

SEQ ID NO: 223          moltype = RNA   length = 93
FEATURE                 Location/Qualifiers
source                  1..93
                        mol_type = transcribed RNA
                        organism = Homo sapiens
SEQUENCE: 223
tacttatggc accccactcc tggtaccata gtcataagtt aggagatgtt agagctgtga   60
gtaccatgac ttaagtgtgg tggcttaaac atg                               93

SEQ ID NO: 224          moltype = RNA   length = 87
FEATURE                 Location/Qualifiers
source                  1..87
                        mol_type = transcribed RNA
                        organism = Homo sapiens
SEQUENCE: 224
gtgaggcggg gccaggaggg tgtgtggcgt gggtgctgcg gggccgtcag ggtgcctgcg   60
ggacgctcac ctggctggcc cgcccag                                      87

SEQ ID NO: 225          moltype = RNA   length = 61
FEATURE                 Location/Qualifiers
source                  1..61
                        mol_type = transcribed RNA
                        organism = Homo sapiens
SEQUENCE: 225
gagggcagcg tgggtgtggc ggaggcaggc gtgaccgttt ccgccctct cgctgctcta    60
g                                                                  61

SEQ ID NO: 226          moltype = RNA   length = 87
FEATURE                 Location/Qualifiers
source                  1..87
                        mol_type = transcribed RNA
                        organism = Homo sapiens
SEQUENCE: 226
accgcaggga aaatgaggga cttttggggg cagatgtgtt tccattccac tatcataatg   60
cccctaaaaa tccttattgc tcttgca                                      87

SEQ ID NO: 227          moltype = RNA   length = 51
FEATURE                 Location/Qualifiers
source                  1..51
                        mol_type = transcribed RNA
                        organism = Homo sapiens
SEQUENCE: 227
agagatgaag cggggggggcg gggtcttgct ctattgccta cgctgatctc a           51

SEQ ID NO: 228          moltype = RNA   length = 66
FEATURE                 Location/Qualifiers
source                  1..66
                        mol_type = transcribed RNA
                        organism = Homo sapiens
SEQUENCE: 228
ccgagtgggg cggggcaggt ccctgcaggg actgtgacac tgaaggacct gcaccttcgc   60
ccacag                                                             66

SEQ ID NO: 229          moltype = RNA   length = 66
FEATURE                 Location/Qualifiers
source                  1..66
                        mol_type = transcribed RNA
                        organism = Homo sapiens
SEQUENCE: 229
cctggagggg ggcactgcgc aagcaaagcc agggaccctg agaggctttg cttcctgctc   60
ccctag                                                             66

SEQ ID NO: 230          moltype = RNA   length = 76
```

| FEATURE | Location/Qualifiers |
|---|---|
| source | 1..76<br>mol_type = transcribed RNA<br>organism = Homo sapiens |

SEQUENCE: 230
```
actgactttg agtctctcct cagggtgctg caggcaaagc tggggaccca gggagagacg   60
taagtgaggg gagatg                                                   76
```

| SEQ ID NO: 231 | moltype = RNA  length = 153 |
|---|---|
| FEATURE | Location/Qualifiers |
| source | 1..153<br>mol_type = transcribed RNA<br>organism = Homo sapiens |

SEQUENCE: 231
```
gctccgcccc acgtcgcatg cgccccggga acgcgtgggg cggagcttcc ggaggccccg   60
ctctgctgcc gaccctgtgg agcggagggt gaagcctccg gatgccagtc cctcatcgct  120
ggcctggtcg cgctgtggcg aaggggggcgg agc                              153
```

| SEQ ID NO: 232 | moltype = RNA  length = 153 |
|---|---|
| FEATURE | Location/Qualifiers |
| source | 1..153<br>mol_type = transcribed RNA<br>organism = Homo sapiens |

SEQUENCE: 232
```
gctccgcccc acgtcgcatg cgccccggga acgcgtgggg cggagcttcc ggaggccccg   60
ccctgctgcc gaccctgtgg agcggagggt gaagcctccg gatgccagtc cctcatcgct  120
ggcccggtcg cgctgtggcg aaggggggcgg agc                              153
```

| SEQ ID NO: 233 | moltype = RNA  length = 67 |
|---|---|
| FEATURE | Location/Qualifiers |
| source | 1..67<br>mol_type = transcribed RNA<br>organism = Homo sapiens |

SEQUENCE: 233
```
gcgccctccc tctctccccg gtgtgcaaat gtgtgtgtgc ggtgttatgc cggacaagag   60
ggaggtg                                                             67
```

| SEQ ID NO: 234 | moltype = RNA  length = 74 |
|---|---|
| FEATURE | Location/Qualifiers |
| source | 1..74<br>mol_type = transcribed RNA<br>organism = Homo sapiens |

SEQUENCE: 234
```
gcagcccggt gagcgctcgc tggcctggca gtgcgtcgga agaacagggc gggtggggcc   60
gcgcacatct ctgc                                                     74
```

| SEQ ID NO: 235 | moltype = RNA  length = 87 |
|---|---|
| FEATURE | Location/Qualifiers |
| source | 1..87<br>mol_type = transcribed RNA<br>organism = Homo sapiens |

SEQUENCE: 235
```
ccctcatctc tgggcagggg cttattgtag gagtctctga agagagctgt ggactgacct   60
gctttaaccc ttccccaggt tcccatt                                       87
```

| SEQ ID NO: 236 | moltype = RNA  length = 67 |
|---|---|
| FEATURE | Location/Qualifiers |
| source | 1..67<br>mol_type = transcribed RNA<br>organism = Homo sapiens |

SEQUENCE: 236
```
ggcagccagg gggatgggcg agcttgggcc cattcctttc cttaccctac ccccatccc   60
cctgtag                                                             67
```

| SEQ ID NO: 237 | moltype = RNA  length = 82 |
|---|---|
| FEATURE | Location/Qualifiers |
| source | 1..82<br>mol_type = transcribed RNA<br>organism = Homo sapiens |

SEQUENCE: 237
```
ctgactttt tagggagtag aagggtgggg agcatgaaca atgtttctca ctccctaccc   60
ctccactccc caaaaaagtc ag                                            82
```

| SEQ ID NO: 238 | moltype = RNA  length = 89 |
|---|---|
| FEATURE | Location/Qualifiers |
| source | 1..89<br>mol_type = transcribed RNA<br>organism = Homo sapiens |

SEQUENCE: 238

```
agcctgtggg aaagagaaga gcagggcagg gtgaaggccc ggcggagaca ctctgcccac    60
cccacaccct gcctatgggc cacacagct                                      89

SEQ ID NO: 239          moltype = RNA  length = 71
FEATURE                 Location/Qualifiers
source                  1..71
                        mol_type = transcribed RNA
                        organism = Homo sapiens
SEQUENCE: 239
ggtgagtggg agccggtggg gctggagtaa gggcacgccc ggggctgccc cacctgctga    60
ccaccctccc c                                                         71

SEQ ID NO: 240          moltype = RNA  length = 84
FEATURE                 Location/Qualifiers
source                  1..84
                        mol_type = transcribed RNA
                        organism = Homo sapiens
SEQUENCE: 240
atggtccctc ccaatccagc cattcctcag accaggtggc tcccgagcca ccccaggctg    60
taggatgggg gtgagaggtg ctag                                           84

SEQ ID NO: 241          moltype = RNA  length = 68
FEATURE                 Location/Qualifiers
source                  1..68
                        mol_type = transcribed RNA
                        organism = Homo sapiens
SEQUENCE: 241
gcatcctgta ctgagctgcc ccgaggccct tcatgctgcc cagctcgggg cagctcagta    60
caggatac                                                             68

SEQ ID NO: 242          moltype = RNA  length = 64
FEATURE                 Location/Qualifiers
source                  1..64
                        mol_type = transcribed RNA
                        organism = Homo sapiens
SEQUENCE: 242
tcctgtactg agctgccccg agctgggcag catgaagggc ctcggggcag ctcagtacag    60
gatg                                                                 64

SEQ ID NO: 243          moltype = RNA  length = 65
FEATURE                 Location/Qualifiers
source                  1..65
                        mol_type = transcribed RNA
                        organism = Homo sapiens
SEQUENCE: 243
gggtgctcgg ggcaggcggc tgggagcggc cctcacattg atggctcctg ccacctcctc    60
cgcag                                                                65

SEQ ID NO: 244          moltype = RNA  length = 67
FEATURE                 Location/Qualifiers
source                  1..67
                        mol_type = transcribed RNA
                        organism = Homo sapiens
SEQUENCE: 244
gtgggagggg agaggcagca agcacacagg gcctgggact agcatgctga cctccctcct    60
gccccag                                                              67

SEQ ID NO: 245          moltype = RNA  length = 63
FEATURE                 Location/Qualifiers
source                  1..63
                        mol_type = transcribed RNA
                        organism = Homo sapiens
SEQUENCE: 245
cttgcccggg agaaggaggt ggcctggaga gctgctgtct ccagccgccg cctgtctcca    60
cag                                                                  63

SEQ ID NO: 246          moltype = RNA  length = 70
FEATURE                 Location/Qualifiers
source                  1..70
                        mol_type = transcribed RNA
                        organism = Homo sapiens
SEQUENCE: 246
acaaatagct tcagggagtc aggggagggc agaaatagat ggccttcccc tgctgggaag    60
aaagtgggtc                                                           70

SEQ ID NO: 247          moltype = RNA  length = 102
FEATURE                 Location/Qualifiers
source                  1..102
                        mol_type = transcribed RNA
```

```
                        organism = Homo sapiens
SEQUENCE: 247
gcttatcgag gaaaagatcg aggtgggttg gggcgggctc tgggattttg gtctcacagc    60
ccggatccca gcccacttac cttggttact ctccttcctt ct                      102

SEQ ID NO: 248          moltype = RNA   length = 90
FEATURE                 Location/Qualifiers
source                  1..90
                        mol_type = transcribed RNA
                        organism = Homo sapiens
SEQUENCE: 248
gtgtctctct ggagaccctg cagccttccc acccaccagg gagctttcca tgggctgtgg    60
ggaaggcgtc agtgtcgggt gagggaacac                                    90

SEQ ID NO: 249          moltype = RNA   length = 87
FEATURE                 Location/Qualifiers
source                  1..87
                        mol_type = transcribed RNA
                        organism = Homo sapiens
SEQUENCE: 249
gtgtggccgg caggcgggtg ggcggggggcg gccggtggga accccgcccc gccccgcgcc    60
cgcactcacc cgcccgtctc cccacag                                       87

SEQ ID NO: 250          moltype = RNA   length = 69
FEATURE                 Location/Qualifiers
source                  1..69
                        mol_type = transcribed RNA
                        organism = Homo sapiens
SEQUENCE: 250
cttcggcca gcgggacggc atccgaggtg ggctaggctc gggcccgtgg cgggtgcggg     60
ggtgggagg                                                           69

SEQ ID NO: 251          moltype = RNA   length = 66
FEATURE                 Location/Qualifiers
source                  1..66
                        mol_type = transcribed RNA
                        organism = Homo sapiens
SEQUENCE: 251
cagagcaggg cagggaaggt gggagagggg cccagctgac cctcctgtca cccgctcctt    60
gcccag                                                              66

SEQ ID NO: 252          moltype = RNA   length = 64
FEATURE                 Location/Qualifiers
source                  1..64
                        mol_type = transcribed RNA
                        organism = Homo sapiens
SEQUENCE: 252
gaaggcgagg ggtagaagag cacaggggtt ctgataaacc cttctgcctg cattctactc    60
ccag                                                                64

SEQ ID NO: 253          moltype = RNA   length = 73
FEATURE                 Location/Qualifiers
source                  1..73
                        mol_type = transcribed RNA
                        organism = Homo sapiens
SEQUENCE: 253
acctttccag ctcatcccac ctctgccacc aaaacactca tcgcggggtc agagggagtg    60
ccaaaaaagg taa                                                      73

SEQ ID NO: 254          moltype = RNA   length = 67
FEATURE                 Location/Qualifiers
source                  1..67
                        mol_type = transcribed RNA
                        organism = Homo sapiens
SEQUENCE: 254
ctggtccatt tccctgccat tcccttggct tcaatttact cccagggctg gcagtgacat    60
gggtcaa                                                             67

SEQ ID NO: 255          moltype = RNA   length = 63
FEATURE                 Location/Qualifiers
source                  1..63
                        mol_type = transcribed RNA
                        organism = Homo sapiens
SEQUENCE: 255
gagtcgagga ctggtggaag ggcctttccc ctcagaccaa ggccctggcc ccagcttctt    60
ctc                                                                 63

SEQ ID NO: 256          moltype = RNA   length = 67
FEATURE                 Location/Qualifiers
```

| | |
|---|---|
| source | 1..67 |
| | mol_type = transcribed RNA |
| | organism = Homo sapiens |

SEQUENCE: 256
aatagattat tggtcaccac ctccagtttc tgaatttgtg agactggggt ggggcctgag 60
aatttgc 67

| SEQ ID NO: 257 | moltype = RNA length = 68 |
|---|---|
| FEATURE | Location/Qualifiers |
| source | 1..68 |
| | mol_type = transcribed RNA |
| | organism = Homo sapiens |

SEQUENCE: 257
gaatggaaga agaaggcggt cggtctgcgg gagccaggcc gcagagccat ccgccttctg 60
tccatgtc 68

| SEQ ID NO: 258 | moltype = RNA length = 60 |
|---|---|
| FEATURE | Location/Qualifiers |
| source | 1..60 |
| | mol_type = transcribed RNA |
| | organism = Homo sapiens |

SEQUENCE: 258
caaggtgggg gagatggggg ttgaacttca tttctcatgc tcatcccat ctcctttcag 60

| SEQ ID NO: 259 | moltype = RNA length = 64 |
|---|---|
| FEATURE | Location/Qualifiers |
| source | 1..64 |
| | mol_type = transcribed RNA |
| | organism = Homo sapiens |

SEQUENCE: 259
gagctctggg aggggctggg tttggcagga cagtttccaa gccctgtctc ctcccatctt 60
ccag 64

| SEQ ID NO: 260 | moltype = RNA length = 100 |
|---|---|
| FEATURE | Location/Qualifiers |
| source | 1..100 |
| | mol_type = transcribed RNA |
| | organism = Homo sapiens |

SEQUENCE: 260
gaggtgggag gattgcttga gtcagggtgg ttgaggctgc agtaagttgt gatcatacca 60
ctgcactcca gcctgagtga cagagcaaga ccttgtctca 100

| SEQ ID NO: 261 | moltype = RNA length = 81 |
|---|---|
| FEATURE | Location/Qualifiers |
| source | 1..81 |
| | mol_type = transcribed RNA |
| | organism = Homo sapiens |

SEQUENCE: 261
tacaggtgca ggggaactgt agatgaaaag gcttggcact tgagggaaag cctcagttca 60
ttctcatttt gctcacctgt t 81

| SEQ ID NO: 262 | moltype = RNA length = 78 |
|---|---|
| FEATURE | Location/Qualifiers |
| source | 1..78 |
| | mol_type = transcribed RNA |
| | organism = Homo sapiens |

SEQUENCE: 262
gggcccagaa gggggcgcag tcactgacgt gaagggacca catcccgctt catgtcagtg 60
actcctgccc cttggtct 78

| SEQ ID NO: 263 | moltype = RNA length = 87 |
|---|---|
| FEATURE | Location/Qualifiers |
| source | 1..87 |
| | mol_type = transcribed RNA |
| | organism = Homo sapiens |

SEQUENCE: 263
cccaggcgcc cgctcccgac ccacgccgcg ccgccgggtc cctcctcccc ggagaggctg 60
ggctcggac gcgcggctca gctcggg 87

| SEQ ID NO: 264 | moltype = RNA length = 81 |
|---|---|
| FEATURE | Location/Qualifiers |
| source | 1..81 |
| | mol_type = transcribed RNA |
| | organism = Homo sapiens |

SEQUENCE: 264
catcctcctt acgtcccacc ccccactcct gtttctggtg aaatattcaa acaggagtgg 60
gggtgggaca taaggaggat a 81

| SEQ ID NO: 265 | moltype = RNA length = 86 |
|---|---|

```
FEATURE                 Location/Qualifiers
source                  1..86
                        mol_type = transcribed RNA
                        organism = Homo sapiens
SEQUENCE: 265
ggcttagaaa cagtccctag gtaggatttg gggaggagct aagaagcccc tacagggccc    60
agaggtgggg actgagcctt agttgg                                         86

SEQ ID NO: 266          moltype = RNA   length = 80
FEATURE                 Location/Qualifiers
source                  1..80
                        mol_type = transcribed RNA
                        organism = Homo sapiens
SEQUENCE: 266
tgagaggccg caccttgcct tgctgcccgg gccgtgcacc cgtgggcccc agggcgacgc    60
ggcgggggcg gccctagcga                                                80

SEQ ID NO: 267          moltype = RNA   length = 73
FEATURE                 Location/Qualifiers
source                  1..73
                        mol_type = transcribed RNA
                        organism = Homo sapiens
SEQUENCE: 267
gaaaacaacc aggtgggctt cccggagggc ggaacaccca gccccagcat ccagggctca    60
cctaccacgt ttg                                                       73

SEQ ID NO: 268          moltype = RNA   length = 64
FEATURE                 Location/Qualifiers
source                  1..64
                        mol_type = transcribed RNA
                        organism = Homo sapiens
SEQUENCE: 268
aaccccgggc cggaggtcaa gggcgtcgct tctccctaat gttgcctctt ttccacggcc    60
tcag                                                                 64

SEQ ID NO: 269          moltype = RNA   length = 74
FEATURE                 Location/Qualifiers
source                  1..74
                        mol_type = transcribed RNA
                        organism = Homo sapiens
SEQUENCE: 269
cctgcaggag gcagtgggcg agcaggcggg gcagcccaat gccatgggcc tgatctcacc    60
gctgcctcct tccc                                                      74

SEQ ID NO: 270          moltype = RNA   length = 102
FEATURE                 Location/Qualifiers
source                  1..102
                        mol_type = transcribed RNA
                        organism = Homo sapiens
SEQUENCE: 270
gtgggagggc ccaggcgcgg gcaggggtgg gggtggcaga gcgctgtccc gggggcgggg    60
ccgaagcgcg gcgaccgtaa ctccttctgc tccgtccccc ag                      102

SEQ ID NO: 271          moltype = RNA   length = 69
FEATURE                 Location/Qualifiers
source                  1..69
                        mol_type = transcribed RNA
                        organism = Homo sapiens
SEQUENCE: 271
gaacctcggg gcatggggga gggaggctgg acaggagagg gctcacccag gccctgtcct    60
ctgccccag                                                            69

SEQ ID NO: 272          moltype = RNA   length = 99
FEATURE                 Location/Qualifiers
source                  1..99
                        mol_type = transcribed RNA
                        organism = Homo sapiens
SEQUENCE: 272
gcaagggaca gggagggtcg tggcgacact cgcgccagct cccgggacgg ctgggctcgg    60
gctggtcgcc gacctccgac cctccactag atgcctggc                           99

SEQ ID NO: 273          moltype = RNA   length = 71
FEATURE                 Location/Qualifiers
source                  1..71
                        mol_type = transcribed RNA
                        organism = Homo sapiens
SEQUENCE: 273
gtgtctgtgc cggtcccagg agaacctgca gaggcatcgg gtcagcggtg ctcctgcggg    60
ccgacactca c                                                         71
```

```
SEQ ID NO: 274         moltype = RNA   length = 61
FEATURE                Location/Qualifiers
source                 1..61
                       mol_type = transcribed RNA
                       organism = Homo sapiens
SEQUENCE: 274
tctcgtttga tctcggaagc taagcagggt tgggcctggt tagtacttgg atgggaaact   60
t                                                                  61

SEQ ID NO: 275         moltype = RNA   length = 53
FEATURE                Location/Qualifiers
source                 1..53
                       mol_type = transcribed RNA
                       organism = Homo sapiens
SEQUENCE: 275
gtttgatctc ggaagctaag cagggtcggg cctggttagt acttggatgg gag          53

SEQ ID NO: 276         moltype = RNA   length = 103
FEATURE                Location/Qualifiers
source                 1..103
                       mol_type = transcribed RNA
                       organism = Homo sapiens
SEQUENCE: 276
gtgtcggctg tggcgtgact gtccctctgt gtcccccact aggcccactg ctcagtggag   60
cgtggaggac gaggaggagg ccgtccacga gcaatgccag cat                    103

SEQ ID NO: 277         moltype = RNA   length = 64
FEATURE                Location/Qualifiers
source                 1..64
                       mol_type = transcribed RNA
                       organism = Homo sapiens
SEQUENCE: 277
tgctctgtag gcatgaggca gggcccaggt tccatgtgat gctgaagctc tgacattcct   60
gcag                                                               64

SEQ ID NO: 278         moltype = RNA   length = 63
FEATURE                Location/Qualifiers
source                 1..63
                       mol_type = transcribed RNA
                       organism = Homo sapiens
SEQUENCE: 278
tggtggcggc ggtagttatg ggcttctctt tctcaccagc agccctggg ccgccgcctc    60
cct                                                                63

SEQ ID NO: 279         moltype = RNA   length = 58
FEATURE                Location/Qualifiers
source                 1..58
                       mol_type = transcribed RNA
                       organism = Homo sapiens
SEQUENCE: 279
agggccagag gagcctggag tggtcgggtc gactgaaccc aggttccctc tggccgca     58

SEQ ID NO: 280         moltype = RNA   length = 72
FEATURE                Location/Qualifiers
source                 1..72
                       mol_type = transcribed RNA
                       organism = Homo sapiens
SEQUENCE: 280
tgtgggactg caaatgggag ctcagcacct gcctgccacc cacgcagacc agccctgct    60
ctgttcccac ag                                                      72

SEQ ID NO: 281         moltype = RNA   length = 64
FEATURE                Location/Qualifiers
source                 1..64
                       mol_type = transcribed RNA
                       organism = Homo sapiens
SEQUENCE: 281
ccccgggccc ggcgttccct cccttccgt gcgccagtgg aggccggggt ggggcgggc     60
gggg                                                               64

SEQ ID NO: 282         moltype = RNA   length = 64
FEATURE                Location/Qualifiers
source                 1..64
                       mol_type = transcribed RNA
                       organism = Homo sapiens
SEQUENCE: 282
ccccgggccc ggcgttccct cccttccgt gcgccagtgg aggccggggt ggggcgggc     60
gggg                                                               64
```

```
SEQ ID NO: 283          moltype = RNA   length = 89
FEATURE                 Location/Qualifiers
source                  1..89
                        mol_type = transcribed RNA
                        organism = Homo sapiens
SEQUENCE: 283
tctccgttta tcccaccact gccaccatta ttgctactgt tcagcaggtg ctgctggtgg    60
tgatggtgat agtctggtgg gggcggtgg                                      89

SEQ ID NO: 284          moltype = RNA   length = 51
FEATURE                 Location/Qualifiers
source                  1..51
                        mol_type = transcribed RNA
                        organism = Homo sapiens
SEQUENCE: 284
acagaccccg gggagcccgg cggtgaagct cctggtatcc tgggtgtctg a              51

SEQ ID NO: 285          moltype = RNA   length = 115
FEATURE                 Location/Qualifiers
source                  1..115
                        mol_type = transcribed RNA
                        organism = Homo sapiens
SEQUENCE: 285
gagcaaaaac cagagaacaa catgggagcg ttcctaaccc ctaaggcaac tggatgggag    60
acctgaccca tccagttctc tgagggggct cttgtgtgtt ctacaaggtt gttca        115

SEQ ID NO: 286          moltype = RNA   length = 85
FEATURE                 Location/Qualifiers
source                  1..85
                        mol_type = transcribed RNA
                        organism = Homo sapiens
SEQUENCE: 286
ggcgcctcct gctctgctgt gccgccaggg cctcccctag cgcgccttct ggagaggctt    60
tgtgcggata cggggctgga ggcct                                          85

SEQ ID NO: 287          moltype = RNA   length = 70
FEATURE                 Location/Qualifiers
source                  1..70
                        mol_type = transcribed RNA
                        organism = Homo sapiens
SEQUENCE: 287
gtccctgggg gctgggatgg gccatggtgt gctctgatcc ccctgtggtc tcttggcccc    60
caggaactcc                                                           70

SEQ ID NO: 288          moltype = RNA   length = 82
FEATURE                 Location/Qualifiers
source                  1..82
                        mol_type = transcribed RNA
                        organism = Homo sapiens
SEQUENCE: 288
gtgagtggga ggccagggca cggcaggggg agctgcaggg ctatgggagg ggccccagcg    60
tctgagccct gtcctcccgc ag                                             82

SEQ ID NO: 289          moltype = RNA   length = 82
FEATURE                 Location/Qualifiers
source                  1..82
                        mol_type = transcribed RNA
                        organism = Homo sapiens
SEQUENCE: 289
gtgagtggga ggccagggca cggcaggggg agctgcaggg ctatgggagg ggccccagcg    60
tctgagccct gtcctcccgc ag                                             82

SEQ ID NO: 290          moltype = RNA   length = 73
FEATURE                 Location/Qualifiers
source                  1..73
                        mol_type = transcribed RNA
                        organism = Homo sapiens
SEQUENCE: 290
ctggtgtttg aggcgatgtg gggatgtaga gacaacttcc cagtctcatt tcctcatcct    60
gccaggccac cat                                                       73

SEQ ID NO: 291          moltype = RNA   length = 84
FEATURE                 Location/Qualifiers
source                  1..84
                        mol_type = transcribed RNA
                        organism = Homo sapiens
SEQUENCE: 291
ccgcagccgc cgcgccgggc ccgggttggc cgctgacccc cgcggggccc ccggcggccg    60
```

```
gggcgggggc gggggctgcc ccgg                                              84

SEQ ID NO: 292          moltype = RNA   length = 69
FEATURE                 Location/Qualifiers
source                  1..69
                        mol_type = transcribed RNA
                        organism = Homo sapiens
SEQUENCE: 292
gggcttaggg atgggaggcc aggatgaaga ttaatcccta atccccaaca ctggccttgc       60
tatccccag                                                               69

SEQ ID NO: 293          moltype = RNA   length = 80
FEATURE                 Location/Qualifiers
source                  1..80
                        mol_type = transcribed RNA
                        organism = Homo sapiens
SEQUENCE: 293
gcgtcaagat ggcggcgggg aggtaggcag agcaggacgc cgctgctgcc gccgccaccg       60
ccgcctccgc tccagtcgcc                                                   80

SEQ ID NO: 294          moltype = RNA   length = 62
FEATURE                 Location/Qualifiers
source                  1..62
                        mol_type = transcribed RNA
                        organism = Homo sapiens
SEQUENCE: 294
gtgagtgggg ctcccgggac ggcgcccgcc ctggccctgg cccggcgacg tctcacggtc       60
cc                                                                      62

SEQ ID NO: 295          moltype = RNA   length = 67
FEATURE                 Location/Qualifiers
source                  1..67
                        mol_type = transcribed RNA
                        organism = Homo sapiens
SEQUENCE: 295
cctgcaggca gaagtggggc tgacagggca gagggttgcg cccccctcacc atcccttctg      60
cctgcag                                                                 67

SEQ ID NO: 296          moltype = RNA   length = 67
FEATURE                 Location/Qualifiers
source                  1..67
                        mol_type = transcribed RNA
                        organism = Homo sapiens
SEQUENCE: 296
cctgcaggca gaagtggggc tgacagggca gagggttgcg cccccctcacc atcccttctg      60
cctgcag                                                                 67

SEQ ID NO: 297          moltype = RNA   length = 67
FEATURE                 Location/Qualifiers
source                  1..67
                        mol_type = transcribed RNA
                        organism = Homo sapiens
SEQUENCE: 297
cctgcaggca gaagtggggc tgacagggca gagggttgcg cccccctcacc atcccttctg      60
cctgcag                                                                 67

SEQ ID NO: 298          moltype = RNA   length = 67
FEATURE                 Location/Qualifiers
source                  1..67
                        mol_type = transcribed RNA
                        organism = Homo sapiens
SEQUENCE: 298
cctgcaggca gaagtggggc tgacagggca gagggttgcg cccccctcacc atcccttctg      60
cctgcag                                                                 67

SEQ ID NO: 299          moltype = RNA   length = 59
FEATURE                 Location/Qualifiers
source                  1..59
                        mol_type = transcribed RNA
                        organism = Homo sapiens
SEQUENCE: 299
cgggctctgg gtgcagtggg ggttcccacg ccgcggcaac caccactgtc tctccccag        59

SEQ ID NO: 300          moltype = RNA   length = 67
FEATURE                 Location/Qualifiers
source                  1..67
                        mol_type = transcribed RNA
                        organism = Homo sapiens
SEQUENCE: 300
```

```
gtggcactca aactgtgggg gcactttctg ctctctggtg aaagtgccgc catcttttga    60
gtgttac                                                              67

SEQ ID NO: 301          moltype = RNA  length = 88
FEATURE                 Location/Qualifiers
source                  1..88
                        mol_type = transcribed RNA
                        organism = Homo sapiens
SEQUENCE: 301
gtggggccag gcggtggtgg gcactgctgg ggtgggcaca gcagccatgc agagcgggca    60
tttgaccccg tgccaccctt ttccccag                                       88

SEQ ID NO: 302          moltype = RNA  length = 94
FEATURE                 Location/Qualifiers
source                  1..94
                        mol_type = transcribed RNA
                        organism = Homo sapiens
SEQUENCE: 302
cacggtgtcc cctggtggaa cctggcaggg ggagaggtaa ggtctttcag cctctccaaa    60
gcccatggtc aggtactcag gtgggggagc cctg                                94

SEQ ID NO: 303          moltype = RNA  length = 109
FEATURE                 Location/Qualifiers
source                  1..109
                        mol_type = transcribed RNA
                        organism = Homo sapiens
SEQUENCE: 303
ggtcgggctc accatgacac agtgtgagac ctcgggctac aacacaggac ccgggcgctg    60
ctctgacccc tcgtgtcttg tgttgcagcc ggagggacgc aggtccgca               109

SEQ ID NO: 304          moltype = RNA  length = 90
FEATURE                 Location/Qualifiers
source                  1..90
                        mol_type = transcribed RNA
                        organism = Homo sapiens
SEQUENCE: 304
tctaagaaac gcagtggtct ctgaagcctg caggggcagg ccagccctgc actgaacgcc    60
tgttcttgcc aggtggcaga aggttgctgc                                     90

SEQ ID NO: 305          moltype = RNA  length = 87
FEATURE                 Location/Qualifiers
source                  1..87
                        mol_type = transcribed RNA
                        organism = Homo sapiens
SEQUENCE: 305
cactgttcta tggttagttt tgcaggtttg catccagctg tgtgatattc tgctgtgcaa    60
atccatgcaa aactgactgt ggtagtg                                        87

SEQ ID NO: 306          moltype = RNA  length = 96
FEATURE                 Location/Qualifiers
source                  1..96
                        mol_type = transcribed RNA
                        organism = Homo sapiens
SEQUENCE: 306
acattgctac ttacaattag ttttgcaggt ttgcatttca gcgtatatat gtatatgtgg    60
ctgtgcaaat ccatgcaaaa ctgattgtga taatgt                              96

SEQ ID NO: 307          moltype = RNA  length = 90
FEATURE                 Location/Qualifiers
source                  1..90
                        mol_type = transcribed RNA
                        organism = Homo sapiens
SEQUENCE: 307
gtgggtacgg cccagtgggg gggagaggga cacgccctgg gctctgccca gggtgcagcc    60
ggactgactg agcccctgtg ccgcccccag                                     90

SEQ ID NO: 308          moltype = RNA  length = 72
FEATURE                 Location/Qualifiers
source                  1..72
                        mol_type = transcribed RNA
                        organism = Homo sapiens
SEQUENCE: 308
cttgggaatg gcaaggaaac cgttaccatt actgagttta gtaatggtaa tggttctctt    60
gctataccca ga                                                        72

SEQ ID NO: 309          moltype = RNA  length = 82
FEATURE                 Location/Qualifiers
source                  1..82
                        mol_type = transcribed RNA
```

```
                        organism = Homo sapiens
SEQUENCE: 309
tgtgggcagg gccctgggga gctgaggctc tggggtggc cggggctgac cctgggcctc    60
tgctccccag tgtctgaccg cg                                            82

SEQ ID NO: 310          moltype = RNA   length = 110
FEATURE                 Location/Qualifiers
source                  1..110
                        mol_type = transcribed RNA
                        organism = Homo sapiens
SEQUENCE: 310
cctggcctcc tgcagtgcca cgctccgtgt atttgacaag ctgagttgga cactccatgt   60
ggtagagtgt cagtttgtca aatacccaa gtgcggcaca tgcttaccag              110

SEQ ID NO: 311          moltype = RNA   length = 73
FEATURE                 Location/Qualifiers
source                  1..73
                        mol_type = transcribed RNA
                        organism = Homo sapiens
SEQUENCE: 311
gtgggcgggg gcaggtgtgt ggtgggtggt ggcctgcggt gagcagggcc ctcacacctg   60
cctcgccccc cag                                                      73

SEQ ID NO: 312          moltype = RNA   length = 86
FEATURE                 Location/Qualifiers
source                  1..86
                        mol_type = transcribed RNA
                        organism = Homo sapiens
SEQUENCE: 312
tgccagtctc taggtccctg agacccttta acctgtgagg acatccaggg tcacaggtga   60
ggttcttggg agcctggcgt ctggcc                                        86

SEQ ID NO: 313          moltype = RNA   length = 96
FEATURE                 Location/Qualifiers
source                  1..96
                        mol_type = transcribed RNA
                        organism = Homo sapiens
SEQUENCE: 313
cgggcccgg gcgggcggga gggacgggac gcggtgcagt gttgtttttt cccccgccaa    60
tattgcactc gtcccggcct ccggcccccc cggccc                             96

SEQ ID NO: 314          moltype = RNA   length = 85
FEATURE                 Location/Qualifiers
source                  1..85
                        mol_type = transcribed RNA
                        organism = Homo sapiens
SEQUENCE: 314
ggctgagccg cagtagttct tcagtggcaa gctttatgtc ctgacccagc taaagctgcc   60
agttgaagaa ctgttgccct ctgcc                                         85

SEQ ID NO: 315          moltype = RNA   length = 67
FEATURE                 Location/Qualifiers
source                  1..67
                        mol_type = transcribed RNA
                        organism = Homo sapiens
SEQUENCE: 315
aaatctctct ccatatcttt cctgcagccc ccaggtgggg gggaagaaaa ggtggggaat   60
tagattc                                                             67

SEQ ID NO: 316          moltype = RNA   length = 77
FEATURE                 Location/Qualifiers
source                  1..77
                        mol_type = transcribed RNA
                        organism = Homo sapiens
SEQUENCE: 316
gagttgggag gttccctctc caaatgtgtc ttgatccccc accccaagac acatttggag   60
agggaccctc ccaactc                                                  77

SEQ ID NO: 317          moltype = RNA   length = 95
FEATURE                 Location/Qualifiers
source                  1..95
                        mol_type = transcribed RNA
                        organism = Homo sapiens
SEQUENCE: 317
gacaccacat gctcctccag gcctgcctgc cctccaggtc atgttccagt gtcccacaga   60
tgcagcacca cggcccaggc ggcattggtg tcacc                              95

SEQ ID NO: 318          moltype = RNA   length = 96
FEATURE                 Location/Qualifiers
```

```
source                  1..96
                        mol_type = transcribed RNA
                        organism = Homo sapiens
SEQUENCE: 318
gctctggggc gtgccgccgc cgtcgctgcc acctccccta ccgctagtgg aagaagatgg    60
cggaaggcgg agcggcggat ctggacaccc agcggt                              96

SEQ ID NO: 319          moltype = RNA  length = 79
FEATURE                 Location/Qualifiers
source                  1..79
                        mol_type = transcribed RNA
                        organism = Homo sapiens
SEQUENCE: 319
gtgcagatcc ttgggagccc tgttagactc tggattttac acttggagtg aacgggcgcc    60
atcccgaggc tttgcacag                                                 79

SEQ ID NO: 320          moltype = RNA  length = 67
FEATURE                 Location/Qualifiers
source                  1..67
                        mol_type = transcribed RNA
                        organism = Homo sapiens
SEQUENCE: 320
cagggaggag gtggtactag gggccagcaa cctgattacc cctctttggc cctttgtacc    60
cctccag                                                              67

SEQ ID NO: 321          moltype = RNA  length = 65
FEATURE                 Location/Qualifiers
source                  1..65
                        mol_type = transcribed RNA
                        organism = Homo sapiens
SEQUENCE: 321
ttctcctggg gagtggctgg ggagcagaca gacccaacct catgctcccc ggcctctgcc    60
cccag                                                                65

SEQ ID NO: 322          moltype = RNA  length = 58
FEATURE                 Location/Qualifiers
source                  1..58
                        mol_type = transcribed RNA
                        organism = Homo sapiens
SEQUENCE: 322
gctgaagctc taaggttccg cctgcgggca ggaagcggag gaaccttgga gcttcggc      58

SEQ ID NO: 323          moltype = RNA  length = 53
FEATURE                 Location/Qualifiers
source                  1..53
                        mol_type = transcribed RNA
                        organism = Homo sapiens
SEQUENCE: 323
ggtgggggtt ggaggcgtgg gttttagaac ctatcccttt ctagccctga gca           53

SEQ ID NO: 324          moltype = RNA  length = 180
FEATURE                 Location/Qualifiers
source                  1..180
                        mol_type = transcribed RNA
                        organism = Homo sapiens
SEQUENCE: 324
cgcgactgcg gcggcggtgg tgggggagc cgcggggatc gccgagggcc ggtcggccgc     60
cccgggtgcc gcgcggtgcc gccgcggcg gtgaggcccc gcgcgtgtgt cccggctgcg    120
gtcggccgcg ctcgaggggt ccccgtggcg tccccttccc cgccggccgc ctttctcgcg   180

SEQ ID NO: 325          moltype = RNA  length = 89
FEATURE                 Location/Qualifiers
source                  1..89
                        mol_type = transcribed RNA
                        organism = Homo sapiens
SEQUENCE: 325
gccggcgccc gagctctggc tccgtgtctt cactcccgtg cttgtccgag gagggaggga    60
gggacggggg ctgtgctggg gcagctgga                                      89

SEQ ID NO: 326          moltype = RNA  length = 70
FEATURE                 Location/Qualifiers
source                  1..70
                        mol_type = transcribed RNA
                        organism = Homo sapiens
SEQUENCE: 326
ggtttctcct tgaggagaca tggtgggggc cggtcaggca gcccatgcca tgtgtcctca    60
tggagaggcc                                                           70

SEQ ID NO: 327          moltype = RNA  length = 92
```

```
FEATURE                 Location/Qualifiers
source                  1..92
                        mol_type = transcribed RNA
                        organism = Homo sapiens
SEQUENCE: 327
cctgtccctc ctgccctgcg cctgcccagc cctcctgctc tggtgactga ggaccgccag    60
gcaggggctg gtgctgggcg gggggcggcg gg                                  92

SEQ ID NO: 328          moltype = RNA  length = 65
FEATURE                 Location/Qualifiers
source                  1..65
                        mol_type = transcribed RNA
                        organism = Homo sapiens
SEQUENCE: 328
gagggtgggc gagggcggct gagcggctcc atccccggc ctgctcatcc ccctcgccct     60
ctcag                                                                65

SEQ ID NO: 329          moltype = RNA  length = 64
FEATURE                 Location/Qualifiers
source                  1..64
                        mol_type = transcribed RNA
                        organism = Homo sapiens
SEQUENCE: 329
gggtggggc gggcggcag gggcctcccc cagtgccagg ccccattctg cttctctccc      60
agct                                                                 64

SEQ ID NO: 330          moltype = RNA  length = 86
FEATURE                 Location/Qualifiers
source                  1..86
                        mol_type = transcribed RNA
                        organism = Homo sapiens
SEQUENCE: 330
cgcctgagcg tgcagcagga catcttcctg acctggtaat aattaggtga gaaggatggt    60
tgggggcggt cggcgtaact caggga                                         86

SEQ ID NO: 331          moltype = RNA  length = 52
FEATURE                 Location/Qualifiers
source                  1..52
                        mol_type = transcribed RNA
                        organism = Homo sapiens
SEQUENCE: 331
tagccgggcg tggtggtggg ggcctgtggt cccagctact ttggaggctg ag            52

SEQ ID NO: 332          moltype = RNA  length = 74
FEATURE                 Location/Qualifiers
source                  1..74
                        mol_type = transcribed RNA
                        organism = Homo sapiens
SEQUENCE: 332
gggaggaaga agggaggagg agcggagggg cccttgtctt cccagagcct ctcccttcct    60
cccctccccc tccc                                                      74

SEQ ID NO: 333          moltype = RNA  length = 50
FEATURE                 Location/Qualifiers
source                  1..50
                        mol_type = transcribed RNA
                        organism = Homo sapiens
SEQUENCE: 333
acccgggcgt ggtggtgggg gtgggtgcct gtaattccag ctagttggga              50

SEQ ID NO: 334          moltype = RNA  length = 72
FEATURE                 Location/Qualifiers
source                  1..72
                        mol_type = transcribed RNA
                        organism = Homo sapiens
SEQUENCE: 334
ctgtgcacct gggggagtgc agtgattgtg gaatgcaaag tcccacaatc actgtactcc    60
ccaggtgcac ag                                                        72

SEQ ID NO: 335          moltype = RNA  length = 71
FEATURE                 Location/Qualifiers
source                  1..71
                        mol_type = transcribed RNA
                        organism = Homo sapiens
SEQUENCE: 335
atggagggg gtgtggagcc aggggcccca ggtctacagc ttctccccgc tccctgcccc     60
catactccca g                                                         71

SEQ ID NO: 336          moltype = RNA  length = 52
```

```
FEATURE                 Location/Qualifiers
source                  1..52
                        mol_type = transcribed RNA
                        organism = Homo sapiens
SEQUENCE: 336
tctgggctga gccgagctgg gttaagccga gctgggttgg gctgggctgg gt            52

SEQ ID NO: 337          moltype = RNA   length = 94
FEATURE                 Location/Qualifiers
source                  1..94
                        mol_type = transcribed RNA
                        organism = Homo sapiens
SEQUENCE: 337
cgggcagcgg gtgccaggca cggtgtcagc aggcaacatg gccgagaggc cggggcctcc    60
gggcggcgcc gtgtccgcga ccgcgtaccc tgac                                94

SEQ ID NO: 338          moltype = RNA   length = 89
FEATURE                 Location/Qualifiers
source                  1..89
                        mol_type = transcribed RNA
                        organism = Homo sapiens
SEQUENCE: 338
acctccggga cggctgggcg ccggcggccg ggagatccgc gcttcctgaa tcccggccgg    60
cccgccggc gcccgtccgc ccgcgggtc                                       89

SEQ ID NO: 339          moltype = RNA   length = 64
FEATURE                 Location/Qualifiers
source                  1..64
                        mol_type = transcribed RNA
                        organism = Homo sapiens
SEQUENCE: 339
agttcagggc cgaagggtgg aagctgctgg tgctcatctc agcctctgcc cttggcctcc    60
ccag                                                                 64

SEQ ID NO: 340          moltype = RNA   length = 49
FEATURE                 Location/Qualifiers
source                  1..49
                        mol_type = transcribed RNA
                        organism = Homo sapiens
SEQUENCE: 340
ggtgaggcgg gggggcgagc cctgaggggc tctcgcttct ggcgccaag               49

SEQ ID NO: 341          moltype = RNA   length = 70
FEATURE                 Location/Qualifiers
source                  1..70
                        mol_type = transcribed RNA
                        organism = Homo sapiens
SEQUENCE: 341
ccctgccagt gctgggggcc acatgagtgt gcagtcatcc acacacaagt ggcccccaac    60
actggcaggg                                                           70

SEQ ID NO: 342          moltype = RNA   length = 96
FEATURE                 Location/Qualifiers
source                  1..96
                        mol_type = transcribed RNA
                        organism = Homo sapiens
SEQUENCE: 342
ctcgggaggg gcgggagggg ggtccccggt gctcggatct cgagggtgct tattgttcgg    60
tccgagcctg ggtctccctc ttcccccaa cccccc                              96

SEQ ID NO: 343          moltype = RNA   length = 80
FEATURE                 Location/Qualifiers
source                  1..80
                        mol_type = transcribed RNA
                        organism = Homo sapiens
SEQUENCE: 343
ggcgcgtcgc ccccctcagt ccaccagagc ccggatacct cagaaattcg gctctgggtc    60
tgtggggagc gaaatgcaac                                                80

SEQ ID NO: 344          moltype = RNA   length = 93
FEATURE                 Location/Qualifiers
source                  1..93
                        mol_type = transcribed RNA
                        organism = Homo sapiens
SEQUENCE: 344
gtaaggaggg ggatgagggg tcatatctct tctcagggaa agcaggagcc cttcagcagg    60
gtcagggccc ctcatcttcc cctcctttcc cag                                 93

SEQ ID NO: 345          moltype = RNA   length = 65
```

```
FEATURE                 Location/Qualifiers
source                  1..65
                        mol_type = transcribed RNA
                        organism = Homo sapiens
SEQUENCE: 345
gagaatgggg ggacagatgg agaggacaca ggctggcact gaggtccccct ccactttcct   60
cctag                                                                65

SEQ ID NO: 346          moltype = RNA   length = 75
FEATURE                 Location/Qualifiers
source                  1..75
                        mol_type = transcribed RNA
                        organism = Homo sapiens
SEQUENCE: 346
gtcagagggg ggatgtgcat gctggttggg gtgggctgcc tgtggaccaa tcagcgtgca   60
cttccccacc ctgaa                                                    75

SEQ ID NO: 347          moltype = RNA   length = 80
FEATURE                 Location/Qualifiers
source                  1..80
                        mol_type = transcribed RNA
                        organism = Homo sapiens
SEQUENCE: 347
cgtgtgagcc cgccctgtgc ccggcccact tctgcttcct cttagcgcag gaggggtccc   60
gcactgggag gggccctcac                                               80

SEQ ID NO: 348          moltype = RNA   length = 99
FEATURE                 Location/Qualifiers
source                  1..99
                        mol_type = transcribed RNA
                        organism = Homo sapiens
SEQUENCE: 348
cgcccacctc agcctcccaa aatgctggga ttacaggcat gagccactgc ggtcgaccat   60
gacctggaca tgtttgtgcc cagtactgtc agtttgcag                          99

SEQ ID NO: 349          moltype = RNA   length = 100
FEATURE                 Location/Qualifiers
source                  1..100
                        mol_type = transcribed RNA
                        organism = Homo sapiens
SEQUENCE: 349
agctcagggc ggctgcgcag agggctggac tcagcggcgg agctggctgc tggcctcagt   60
tctgcctctg tccaggtcct tgtgacccgc ccgctctcct                        100

SEQ ID NO: 350          moltype = RNA   length = 78
FEATURE                 Location/Qualifiers
source                  1..78
                        mol_type = transcribed RNA
                        organism = Homo sapiens
SEQUENCE: 350
ggcctcaggc aggcgcaccc gaccacatgc atggctggtg gcggcgtgca ggggtcgggt   60
gggccaggct gtggggcg                                                 78

SEQ ID NO: 351          moltype = RNA   length = 85
FEATURE                 Location/Qualifiers
source                  1..85
                        mol_type = transcribed RNA
                        organism = Homo sapiens
SEQUENCE: 351
gtgagctgct ggggacgcgg gtcggggtct gcagggcggt gcggcagccg ccacctgacg   60
ccgcgccttt gtctgtgtcc cacag                                         85

SEQ ID NO: 352          moltype = RNA   length = 73
FEATURE                 Location/Qualifiers
source                  1..73
                        mol_type = transcribed RNA
                        organism = Homo sapiens
SEQUENCE: 352
ggggaggtac ctgggacagg aggaggaggc agccttgcct cagaaaccaa actgtcaaaa   60
gtgtaggttc cac                                                      73

SEQ ID NO: 353          moltype = RNA   length = 73
FEATURE                 Location/Qualifiers
source                  1..73
                        mol_type = transcribed RNA
                        organism = Homo sapiens
SEQUENCE: 353
cccagggtct ggtgcggaga gggcccacag tggacttggt gacgctgtat gccctcaccg   60
ctcagcccct ggg                                                      73
```

```
SEQ ID NO: 354          moltype = RNA   length = 74
FEATURE                 Location/Qualifiers
source                  1..74
                        mol_type = transcribed RNA
                        organism = Homo sapiens
SEQUENCE: 354
ccaagggcac accgggatg gcagagggtc gtgggaaagt gttgaccctc gtcaggtccc        60
cggggagccc ctgg                                                        74

SEQ ID NO: 355          moltype = RNA   length = 21
FEATURE                 Location/Qualifiers
source                  1..21
                        mol_type = transcribed RNA
                        organism = Homo sapiens
SEQUENCE: 355
ccggccgccg gctccgcccc g                                                21

SEQ ID NO: 356          moltype = RNA   length = 17
FEATURE                 Location/Qualifiers
source                  1..17
                        mol_type = transcribed RNA
                        organism = Homo sapiens
SEQUENCE: 356
ccggccgccg gctccgc                                                     17

SEQ ID NO: 357          moltype = RNA   length = 23
FEATURE                 Location/Qualifiers
source                  1..23
                        mol_type = transcribed RNA
                        organism = Homo sapiens
SEQUENCE: 357
ctcctggggc ccgcactctc gct                                              23

SEQ ID NO: 358          moltype = RNA   length = 18
FEATURE                 Location/Qualifiers
source                  1..18
                        mol_type = transcribed RNA
                        organism = Homo sapiens
SEQUENCE: 358
ctcctggggc ccgcactc                                                    18

SEQ ID NO: 359          moltype = RNA   length = 23
FEATURE                 Location/Qualifiers
source                  1..23
                        mol_type = transcribed RNA
                        organism = Homo sapiens
SEQUENCE: 359
agggtcgggg cagggagggc agg                                              23

SEQ ID NO: 360          moltype = RNA   length = 15
FEATURE                 Location/Qualifiers
source                  1..15
                        mol_type = transcribed RNA
                        organism = Homo sapiens
SEQUENCE: 360
gggagaaggg tcggg                                                       15

SEQ ID NO: 361          moltype = RNA   length = 23
FEATURE                 Location/Qualifiers
source                  1..23
                        mol_type = transcribed RNA
                        organism = Homo sapiens
SEQUENCE: 361
ggtgggtgag gtcgggcccc aag                                              23

SEQ ID NO: 362          moltype = RNA   length = 20
FEATURE                 Location/Qualifiers
source                  1..20
                        mol_type = transcribed RNA
                        organism = Homo sapiens
SEQUENCE: 362
cggggtgggt gaggtcgggc                                                  20

SEQ ID NO: 363          moltype = RNA   length = 23
FEATURE                 Location/Qualifiers
source                  1..23
                        mol_type = transcribed RNA
                        organism = Homo sapiens
```

| | | |
|---|---|---|
| SEQUENCE: 363 tgaggatatg gcagggaagg gga | | 23 |
| SEQ ID NO: 364 FEATURE source | moltype = RNA   length = 19 Location/Qualifiers 1..19 mol_type = transcribed RNA organism = Homo sapiens | |
| SEQUENCE: 364 tgaggatatg gcagggaag | | 19 |
| SEQ ID NO: 365 FEATURE source | moltype = RNA   length = 23 Location/Qualifiers 1..23 mol_type = transcribed RNA organism = Homo sapiens | |
| SEQUENCE: 365 ggcccggccg tgcctgaggt ttc | | 23 |
| SEQ ID NO: 366 FEATURE source | moltype = RNA   length = 15 Location/Qualifiers 1..15 mol_type = transcribed RNA organism = Homo sapiens | |
| SEQUENCE: 366 ggcggtggga tcccg | | 15 |
| SEQ ID NO: 367 FEATURE source | moltype = RNA   length = 22 Location/Qualifiers 1..22 mol_type = transcribed RNA organism = Homo sapiens | |
| SEQUENCE: 367 cgcggcgggg acggcgattg gt | | 22 |
| SEQ ID NO: 368 FEATURE source | moltype = RNA   length = 17 Location/Qualifiers 1..17 mol_type = transcribed RNA organism = Homo sapiens | |
| SEQUENCE: 368 cggcggggac ggcgatt | | 17 |
| SEQ ID NO: 369 FEATURE source | moltype = RNA   length = 25 Location/Qualifiers 1..25 mol_type = transcribed RNA organism = Homo sapiens | |
| SEQUENCE: 369 gggtggggat ttgttgcatt acttg | | 25 |
| SEQ ID NO: 370 FEATURE source | moltype = RNA   length = 20 Location/Qualifiers 1..20 mol_type = transcribed RNA organism = Homo sapiens | |
| SEQUENCE: 370 gggtggggat ttgttgcatt | | 20 |
| SEQ ID NO: 371 FEATURE source | moltype = RNA   length = 17 Location/Qualifiers 1..17 mol_type = transcribed RNA organism = Homo sapiens | |
| SEQUENCE: 371 tcctagtcac ggcacca | | 17 |
| SEQ ID NO: 372 FEATURE source | moltype = RNA   length = 17 Location/Qualifiers 1..17 mol_type = transcribed RNA organism = Homo sapiens | |
| SEQUENCE: 372 tcctagtcac ggcacca | | 17 |
| SEQ ID NO: 373 FEATURE source | moltype = RNA   length = 16 Location/Qualifiers 1..16 mol_type = transcribed RNA | |

```
                              organism = Homo sapiens
SEQUENCE: 373
tgctggtgat gctttc                                                          16

SEQ ID NO: 374          moltype = RNA  length = 16
FEATURE                 Location/Qualifiers
source                  1..16
                        mol_type = transcribed RNA
                        organism = Homo sapiens
SEQUENCE: 374
tgctggtgat gctttc                                                          16

SEQ ID NO: 375          moltype = RNA  length = 23
FEATURE                 Location/Qualifiers
source                  1..23
                        mol_type = transcribed RNA
                        organism = Homo sapiens
SEQUENCE: 375
ggaggcgcag gctcggaaag gcg                                                  23

SEQ ID NO: 376          moltype = RNA  length = 15
FEATURE                 Location/Qualifiers
source                  1..15
                        mol_type = transcribed RNA
                        organism = Homo sapiens
SEQUENCE: 376
gcaggctcgg aaagg                                                           15

SEQ ID NO: 377          moltype = RNA  length = 20
FEATURE                 Location/Qualifiers
source                  1..20
                        mol_type = transcribed RNA
                        organism = Homo sapiens
SEQUENCE: 377
ggctggtcag atgggagtgg                                                      20

SEQ ID NO: 378          moltype = RNA  length = 20
FEATURE                 Location/Qualifiers
source                  1..20
                        mol_type = transcribed RNA
                        organism = Homo sapiens
SEQUENCE: 378
ggctggtcag atgggagtgg                                                      20

SEQ ID NO: 379          moltype = RNA  length = 21
FEATURE                 Location/Qualifiers
source                  1..21
                        mol_type = transcribed RNA
                        organism = Homo sapiens
SEQUENCE: 379
cggatccgag tcacggcacc a                                                    21

SEQ ID NO: 380          moltype = RNA  length = 15
FEATURE                 Location/Qualifiers
source                  1..15
                        mol_type = transcribed RNA
                        organism = Homo sapiens
SEQUENCE: 380
ggatccgagt cacgg                                                           15

SEQ ID NO: 381          moltype = RNA  length = 22
FEATURE                 Location/Qualifiers
source                  1..22
                        mol_type = transcribed RNA
                        organism = Homo sapiens
SEQUENCE: 381
ccgggaacgt cgagactgga gc                                                   22

SEQ ID NO: 382          moltype = RNA  length = 15
FEATURE                 Location/Qualifiers
source                  1..15
                        mol_type = transcribed RNA
                        organism = Homo sapiens
SEQUENCE: 382
cgggaacgtc gagac                                                           15

SEQ ID NO: 383          moltype = RNA  length = 15
FEATURE                 Location/Qualifiers
source                  1..15
```

-continued

```
                           mol_type = transcribed RNA
                           organism = Homo sapiens
SEQUENCE: 383
tctgggcgag gggtg                                                        15

SEQ ID NO: 384            moltype = RNA  length = 15
FEATURE                   Location/Qualifiers
source                    1..15
                           mol_type = transcribed RNA
                           organism = Homo sapiens
SEQUENCE: 384
tctgggcgag gggtg                                                        15

SEQ ID NO: 385            moltype = RNA  length = 21
FEATURE                   Location/Qualifiers
source                    1..21
                           mol_type = transcribed RNA
                           organism = Homo sapiens
SEQUENCE: 385
cccaggctgg agcgagtgca g                                                 21

SEQ ID NO: 386            moltype = RNA  length = 15
FEATURE                   Location/Qualifiers
source                    1..15
                           mol_type = transcribed RNA
                           organism = Homo sapiens
SEQUENCE: 386
agctcactgc agcct                                                        15

SEQ ID NO: 387            moltype = RNA  length = 23
FEATURE                   Location/Qualifiers
source                    1..23
                           mol_type = transcribed RNA
                           organism = Homo sapiens
SEQUENCE: 387
gggggccgat acactgtacg aga                                               23

SEQ ID NO: 388            moltype = RNA  length = 20
FEATURE                   Location/Qualifiers
source                    1..20
                           mol_type = transcribed RNA
                           organism = Homo sapiens
SEQUENCE: 388
gggggccgat acactgtacg                                                   20

SEQ ID NO: 389            moltype = RNA  length = 18
FEATURE                   Location/Qualifiers
source                    1..18
                           mol_type = transcribed RNA
                           organism = Homo sapiens
SEQUENCE: 389
gcggcggcgg cggcagca                                                     18

SEQ ID NO: 390            moltype = RNA  length = 15
FEATURE                   Location/Qualifiers
source                    1..15
                           mol_type = transcribed RNA
                           organism = Homo sapiens
SEQUENCE: 390
gcgggcggcg gcggc                                                        15

SEQ ID NO: 391            moltype = RNA  length = 23
FEATURE                   Location/Qualifiers
source                    1..23
                           mol_type = transcribed RNA
                           organism = Homo sapiens
SEQUENCE: 391
cggggccgta gcactgtctg aga                                               23

SEQ ID NO: 392            moltype = RNA  length = 20
FEATURE                   Location/Qualifiers
source                    1..20
                           mol_type = transcribed RNA
                           organism = Homo sapiens
SEQUENCE: 392
cggggccgta gcactgtctg                                                   20

SEQ ID NO: 393            moltype = RNA  length = 22
FEATURE                   Location/Qualifiers
```

```
                            source               1..22
                                                 mol_type = transcribed RNA
                                                 organism = Homo sapiens
                            SEQUENCE: 393
                            accccactcc tggtaccata gt                                     22

SEQ ID NO: 394       moltype = RNA   length = 15
                            FEATURE              Location/Qualifiers
                            source               1..15
                                                 mol_type = transcribed RNA
                                                 organism = Homo sapiens
                            SEQUENCE: 394
                            accccactcc tggta                                             15

SEQ ID NO: 395       moltype = RNA   length = 21
                            FEATURE              Location/Qualifiers
                            source               1..21
                                                 mol_type = transcribed RNA
                                                 organism = Homo sapiens
                            SEQUENCE: 395
                            gagggcagcg tgggtgtggc g                                      21

SEQ ID NO: 396       moltype = RNA   length = 21
                            FEATURE              Location/Qualifiers
                            source               1..21
                                                 mol_type = transcribed RNA
                                                 organism = Homo sapiens
                            SEQUENCE: 396
                            gagggcagcg tgggtgtggc g                                      21

SEQ ID NO: 397       moltype = RNA   length = 27
                            FEATURE              Location/Qualifiers
                            source               1..27
                                                 mol_type = transcribed RNA
                                                 organism = Homo sapiens
                            SEQUENCE: 397
                            tgagggactt ttgggggcag atgtgtt                                27

SEQ ID NO: 398       moltype = RNA   length = 17
                            FEATURE              Location/Qualifiers
                            source               1..17
                                                 mol_type = transcribed RNA
                                                 organism = Homo sapiens
                            SEQUENCE: 398
                            ggactttttgg gggcaga                                          17

SEQ ID NO: 399       moltype = RNA   length = 15
                            FEATURE              Location/Qualifiers
                            source               1..15
                                                 mol_type = transcribed RNA
                                                 organism = Homo sapiens
                            SEQUENCE: 399
                            tgaagcgggg gggcg                                             15

SEQ ID NO: 400       moltype = RNA   length = 15
                            FEATURE              Location/Qualifiers
                            source               1..15
                                                 mol_type = transcribed RNA
                                                 organism = Homo sapiens
                            SEQUENCE: 400
                            tgaagcgggg gggcg                                             15

SEQ ID NO: 401       moltype = RNA   length = 16
                            FEATURE              Location/Qualifiers
                            source               1..16
                                                 mol_type = transcribed RNA
                                                 organism = Homo sapiens
                            SEQUENCE: 401
                            ggacccaggg agagac                                            16

SEQ ID NO: 402       moltype = RNA   length = 16
                            FEATURE              Location/Qualifiers
                            source               1..16
                                                 mol_type = transcribed RNA
                                                 organism = Homo sapiens
                            SEQUENCE: 402
                            ggacccaggg agagac                                            16

SEQ ID NO: 403       moltype = RNA   length = 23
```

```
FEATURE              Location/Qualifiers
source               1..23
                     mol_type = transcribed RNA
                     organism = Homo sapiens
SEQUENCE: 403
tgggcggag cttccggagg ccc                                            23

SEQ ID NO: 404       moltype = RNA   length = 16
FEATURE              Location/Qualifiers
source               1..16
                     mol_type = transcribed RNA
                     organism = Homo sapiens
SEQUENCE: 404
atcgctggcc tggtcg                                                   16

SEQ ID NO: 405       moltype = RNA   length = 20
FEATURE              Location/Qualifiers
source               1..20
                     mol_type = transcribed RNA
                     organism = Homo sapiens
SEQUENCE: 405
ctccccggtg tgcaaatgtg                                               20

SEQ ID NO: 406       moltype = RNA   length = 15
FEATURE              Location/Qualifiers
source               1..15
                     mol_type = transcribed RNA
                     organism = Homo sapiens
SEQUENCE: 406
gtgtgcggtg ttatg                                                    15

SEQ ID NO: 407       moltype = RNA   length = 17
FEATURE              Location/Qualifiers
source               1..17
                     mol_type = transcribed RNA
                     organism = Homo sapiens
SEQUENCE: 407
ggtgagcgct cgctggc                                                  17

SEQ ID NO: 408       moltype = RNA   length = 15
FEATURE              Location/Qualifiers
source               1..15
                     mol_type = transcribed RNA
                     organism = Homo sapiens
SEQUENCE: 408
cggtgagcgc tcgct                                                    15

SEQ ID NO: 409       moltype = RNA   length = 25
FEATURE              Location/Qualifiers
source               1..25
                     mol_type = transcribed RNA
                     organism = Homo sapiens
SEQUENCE: 409
tgggcagggg cttattgtag gagtc                                         25

SEQ ID NO: 410       moltype = RNA   length = 19
FEATURE              Location/Qualifiers
source               1..19
                     mol_type = transcribed RNA
                     organism = Homo sapiens
SEQUENCE: 410
tgggcagggg cttattgta                                                19

SEQ ID NO: 411       moltype = RNA   length = 23
FEATURE              Location/Qualifiers
source               1..23
                     mol_type = transcribed RNA
                     organism = Homo sapiens
SEQUENCE: 411
agggagtaga agggtgggga gca                                           23

SEQ ID NO: 412       moltype = RNA   length = 16
FEATURE              Location/Qualifiers
source               1..16
                     mol_type = transcribed RNA
                     organism = Homo sapiens
SEQUENCE: 412
tagggagtag aagggt                                                   16
```

-continued

| | | |
|---|---|---|
| SEQ ID NO: 413 | moltype = RNA length = 16 | |
| FEATURE | Location/Qualifiers | |
| source | 1..16 | |
| | mol_type = transcribed RNA | |
| | organism = Homo sapiens | |
| SEQUENCE: 413 | | |
| gtgaaggccc ggcgga | | 16 |
| | | |
| SEQ ID NO: 414 | moltype = RNA length = 15 | |
| FEATURE | Location/Qualifiers | |
| source | 1..15 | |
| | mol_type = transcribed RNA | |
| | organism = Homo sapiens | |
| SEQUENCE: 414 | | |
| gtgaaggccc ggcgg | | 15 |
| | | |
| SEQ ID NO: 415 | moltype = RNA length = 24 | |
| FEATURE | Location/Qualifiers | |
| source | 1..24 | |
| | mol_type = transcribed RNA | |
| | organism = Homo sapiens | |
| SEQUENCE: 415 | | |
| gtgagtggga gccggtgggg ctgg | | 24 |
| | | |
| SEQ ID NO: 416 | moltype = RNA length = 15 | |
| FEATURE | Location/Qualifiers | |
| source | 1..15 | |
| | mol_type = transcribed RNA | |
| | organism = Homo sapiens | |
| SEQUENCE: 416 | | |
| ggggctggag taagg | | 15 |
| | | |
| SEQ ID NO: 417 | moltype = RNA length = 20 | |
| FEATURE | Location/Qualifiers | |
| source | 1..20 | |
| | mol_type = transcribed RNA | |
| | organism = Homo sapiens | |
| SEQUENCE: 417 | | |
| taggatgggg gtgagaggtg | | 20 |
| | | |
| SEQ ID NO: 418 | moltype = RNA length = 18 | |
| FEATURE | Location/Qualifiers | |
| source | 1..18 | |
| | mol_type = transcribed RNA | |
| | organism = Homo sapiens | |
| SEQUENCE: 418 | | |
| taggatgggg gtgagagg | | 18 |
| | | |
| SEQ ID NO: 419 | moltype = RNA length = 23 | |
| FEATURE | Location/Qualifiers | |
| source | 1..23 | |
| | mol_type = transcribed RNA | |
| | organism = Homo sapiens | |
| SEQUENCE: 419 | | |
| cggggcagct cagtacagga tac | | 23 |
| | | |
| SEQ ID NO: 420 | moltype = RNA length = 15 | |
| FEATURE | Location/Qualifiers | |
| source | 1..15 | |
| | mol_type = transcribed RNA | |
| | organism = Homo sapiens | |
| SEQUENCE: 420 | | |
| agctcagtac aggat | | 15 |
| | | |
| SEQ ID NO: 421 | moltype = RNA length = 22 | |
| FEATURE | Location/Qualifiers | |
| source | 1..22 | |
| | mol_type = transcribed RNA | |
| | organism = Homo sapiens | |
| SEQUENCE: 421 | | |
| tgggagggga gaggcagcaa gc | | 22 |
| | | |
| SEQ ID NO: 422 | moltype = RNA length = 22 | |
| FEATURE | Location/Qualifiers | |
| source | 1..22 | |
| | mol_type = transcribed RNA | |
| | organism = Homo sapiens | |
| SEQUENCE: 422 | | |
| tgggagggga gaggcagcaa gc | | 22 |

```
SEQ ID NO: 423              moltype = RNA   length = 19
FEATURE                     Location/Qualifiers
source                      1..19
                            mol_type = transcribed RNA
                            organism = Homo sapiens
SEQUENCE: 423
gtgggttggg gcgggctct                                                              19

SEQ ID NO: 424              moltype = RNA   length = 19
FEATURE                     Location/Qualifiers
source                      1..19
                            mol_type = transcribed RNA
                            organism = Homo sapiens
SEQUENCE: 424
gtgggttggg gcgggctct                                                              19

SEQ ID NO: 425              moltype = RNA   length = 23
FEATURE                     Location/Qualifiers
source                      1..23
                            mol_type = transcribed RNA
                            organism = Homo sapiens
SEQUENCE: 425
tggggaaggc gtcagtgtcg ggt                                                         23

SEQ ID NO: 426              moltype = RNA   length = 16
FEATURE                     Location/Qualifiers
source                      1..16
                            mol_type = transcribed RNA
                            organism = Homo sapiens
SEQUENCE: 426
tggggaaggc gtcagt                                                                 16

SEQ ID NO: 427              moltype = RNA   length = 19
FEATURE                     Location/Qualifiers
source                      1..19
                            mol_type = transcribed RNA
                            organism = Homo sapiens
SEQUENCE: 427
tggcgggtgc gggggtggg                                                              19

SEQ ID NO: 428              moltype = RNA   length = 15
FEATURE                     Location/Qualifiers
source                      1..15
                            mol_type = transcribed RNA
                            organism = Homo sapiens
SEQUENCE: 428
tggcgggtgc ggggg                                                                  15

SEQ ID NO: 429              moltype = RNA   length = 20
FEATURE                     Location/Qualifiers
source                      1..20
                            mol_type = transcribed RNA
                            organism = Homo sapiens
SEQUENCE: 429
atcccacctc tgccaccaaa                                                             20

SEQ ID NO: 430              moltype = RNA   length = 15
FEATURE                     Location/Qualifiers
source                      1..15
                            mol_type = transcribed RNA
                            organism = Homo sapiens
SEQUENCE: 430
atcccacctc tgcca                                                                  15

SEQ ID NO: 431              moltype = RNA   length = 23
FEATURE                     Location/Qualifiers
source                      1..23
                            mol_type = transcribed RNA
                            organism = Homo sapiens
SEQUENCE: 431
ccagggctgg cagtgacatg ggt                                                         23

SEQ ID NO: 432              moltype = RNA   length = 19
FEATURE                     Location/Qualifiers
source                      1..19
                            mol_type = transcribed RNA
                            organism = Homo sapiens
SEQUENCE: 432
```

-continued

```
cagggctggc agtgacatg                                                   19

SEQ ID NO: 433          moltype = RNA   length = 24
FEATURE                 Location/Qualifiers
source                  1..24
                        mol_type = transcribed RNA
                        organism = Homo sapiens
SEQUENCE: 433
tcgaggactg gtggaagggc cttt                                             24

SEQ ID NO: 434          moltype = RNA   length = 16
FEATURE                 Location/Qualifiers
source                  1..16
                        mol_type = transcribed RNA
                        organism = Homo sapiens
SEQUENCE: 434
tcgaggactg gtggaa                                                      16

SEQ ID NO: 435          moltype = RNA   length = 18
FEATURE                 Location/Qualifiers
source                  1..18
                        mol_type = transcribed RNA
                        organism = Homo sapiens
SEQUENCE: 435
gagactgggg tggggcct                                                    18

SEQ ID NO: 436          moltype = RNA   length = 16
FEATURE                 Location/Qualifiers
source                  1..16
                        mol_type = transcribed RNA
                        organism = Homo sapiens
SEQUENCE: 436
agactggggt ggggcc                                                      16

SEQ ID NO: 437          moltype = RNA   length = 23
FEATURE                 Location/Qualifiers
source                  1..23
                        mol_type = transcribed RNA
                        organism = Homo sapiens
SEQUENCE: 437
agaagaaggc ggtcggtctg cgg                                              23

SEQ ID NO: 438          moltype = RNA   length = 21
FEATURE                 Location/Qualifiers
source                  1..21
                        mol_type = transcribed RNA
                        organism = Homo sapiens
SEQUENCE: 438
aagaaggcgg tcggtctgcg g                                                21

SEQ ID NO: 439          moltype = RNA   length = 21
FEATURE                 Location/Qualifiers
source                  1..21
                        mol_type = transcribed RNA
                        organism = Homo sapiens
SEQUENCE: 439
cagcctgagt gacagagcaa g                                                21

SEQ ID NO: 440          moltype = RNA   length = 15
FEATURE                 Location/Qualifiers
source                  1..15
                        mol_type = transcribed RNA
                        organism = Homo sapiens
SEQUENCE: 440
actgcactcc agcct                                                       15

SEQ ID NO: 441          moltype = RNA   length = 22
FEATURE                 Location/Qualifiers
source                  1..22
                        mol_type = transcribed RNA
                        organism = Homo sapiens
SEQUENCE: 441
ctgggctcgg gacgcgcggc tc                                               22

SEQ ID NO: 442          moltype = RNA   length = 19
FEATURE                 Location/Qualifiers
source                  1..19
                        mol_type = transcribed RNA
                        organism = Homo sapiens
```

```
SEQUENCE: 442
ctgggctcgg gacgcgcgg                                                 19

SEQ ID NO: 443            moltype = RNA   length = 23
FEATURE                   Location/Qualifiers
source                    1..23
                          mol_type = transcribed RNA
                          organism = Homo sapiens
SEQUENCE: 443
acaggagtgg gggtgggaca taa                                            23

SEQ ID NO: 444            moltype = RNA   length = 20
FEATURE                   Location/Qualifiers
source                    1..20
                          mol_type = transcribed RNA
                          organism = Homo sapiens
SEQUENCE: 444
acaggagtgg gggtgggaca                                                20

SEQ ID NO: 445            moltype = RNA   length = 23
FEATURE                   Location/Qualifiers
source                    1..23
                          mol_type = transcribed RNA
                          organism = Homo sapiens
SEQUENCE: 445
caccttgcct tgctgcccgg gcc                                            23

SEQ ID NO: 446            moltype = RNA   length = 22
FEATURE                   Location/Qualifiers
source                    1..22
                          mol_type = transcribed RNA
                          organism = Homo sapiens
SEQUENCE: 446
caccttgcct tgctgcccgg gc                                             22

SEQ ID NO: 447            moltype = RNA   length = 18
FEATURE                   Location/Qualifiers
source                    1..18
                          mol_type = transcribed RNA
                          organism = Homo sapiens
SEQUENCE: 447
ggtgggcttc ccggaggg                                                  18

SEQ ID NO: 448            moltype = RNA   length = 15
FEATURE                   Location/Qualifiers
source                    1..15
                          mol_type = transcribed RNA
                          organism = Homo sapiens
SEQUENCE: 448
ggtgggcttc ccgga                                                     15

SEQ ID NO: 449            moltype = RNA   length = 21
FEATURE                   Location/Qualifiers
source                    1..21
                          mol_type = transcribed RNA
                          organism = Homo sapiens
SEQUENCE: 449
aggaggcagt gggcgagcag g                                              21

SEQ ID NO: 450            moltype = RNA   length = 21
FEATURE                   Location/Qualifiers
source                    1..21
                          mol_type = transcribed RNA
                          organism = Homo sapiens
SEQUENCE: 450
aggaggcagt gggcgagcag g                                              21

SEQ ID NO: 451            moltype = RNA   length = 15
FEATURE                   Location/Qualifiers
source                    1..15
                          mol_type = transcribed RNA
                          organism = Homo sapiens
SEQUENCE: 451
tggcagagcg ctgtc                                                     15

SEQ ID NO: 452            moltype = RNA   length = 15
FEATURE                   Location/Qualifiers
source                    1..15
                          mol_type = transcribed RNA
```

```
                                organism = Homo sapiens
SEQUENCE: 452
tggcagagcg ctgtc                                                            15

SEQ ID NO: 453          moltype = RNA   length = 25
FEATURE                 Location/Qualifiers
source                  1..25
                        mol_type = transcribed RNA
                        organism = Homo sapiens
SEQUENCE: 453
tggcggcggt agttatgggc ttctc                                                 25

SEQ ID NO: 454          moltype = RNA   length = 25
FEATURE                 Location/Qualifiers
source                  1..25
                        mol_type = transcribed RNA
                        organism = Homo sapiens
SEQUENCE: 454
tggcggcggt agttatgggc ttctc                                                 25

SEQ ID NO: 455          moltype = RNA   length = 27
FEATURE                 Location/Qualifiers
source                  1..27
                        mol_type = transcribed RNA
                        organism = Homo sapiens
SEQUENCE: 455
agggccagag gagcctggag tggtcgg                                               27

SEQ ID NO: 456          moltype = RNA   length = 23
FEATURE                 Location/Qualifiers
source                  1..23
                        mol_type = transcribed RNA
                        organism = Homo sapiens
SEQUENCE: 456
agggccagag gagcctggag tgg                                                   23

SEQ ID NO: 457          moltype = RNA   length = 22
FEATURE                 Location/Qualifiers
source                  1..22
                        mol_type = transcribed RNA
                        organism = Homo sapiens
SEQUENCE: 457
tgtgggactg caaatgggag ct                                                    22

SEQ ID NO: 458          moltype = RNA   length = 22
FEATURE                 Location/Qualifiers
source                  1..22
                        mol_type = transcribed RNA
                        organism = Homo sapiens
SEQUENCE: 458
tgtgggactg caaatgggag ct                                                    22

SEQ ID NO: 459          moltype = RNA   length = 16
FEATURE                 Location/Qualifiers
source                  1..16
                        mol_type = transcribed RNA
                        organism = Homo sapiens
SEQUENCE: 459
cgggcccggc gttccc                                                           16

SEQ ID NO: 460          moltype = RNA   length = 15
FEATURE                 Location/Qualifiers
source                  1..15
                        mol_type = transcribed RNA
                        organism = Homo sapiens
SEQUENCE: 460
ccgggcccgg cgttc                                                            15

SEQ ID NO: 461          moltype = RNA   length = 20
FEATURE                 Location/Qualifiers
source                  1..20
                        mol_type = transcribed RNA
                        organism = Homo sapiens
SEQUENCE: 461
atcccaccac tgccaccatt                                                       20

SEQ ID NO: 462          moltype = RNA   length = 15
FEATURE                 Location/Qualifiers
source                  1..15
```

```
                           mol_type = transcribed RNA
                           organism = Homo sapiens
SEQUENCE: 462
atcccaccac tgcca                                                    15

SEQ ID NO: 463             moltype = RNA   length = 20
FEATURE                    Location/Qualifiers
source                     1..20
                           mol_type = transcribed RNA
                           organism = Homo sapiens
SEQUENCE: 463
ccccggggag cccggcggtg                                               20

SEQ ID NO: 464             moltype = RNA   length = 15
FEATURE                    Location/Qualifiers
source                     1..15
                           mol_type = transcribed RNA
                           organism = Homo sapiens
SEQUENCE: 464
accccgggga gcccg                                                    15

SEQ ID NO: 465             moltype = RNA   length = 21
FEATURE                    Location/Qualifiers
source                     1..21
                           mol_type = transcribed RNA
                           organism = Homo sapiens
SEQUENCE: 465
atccagttct ctgaggggc t                                              21

SEQ ID NO: 466             moltype = RNA   length = 21
FEATURE                    Location/Qualifiers
source                     1..21
                           mol_type = transcribed RNA
                           organism = Homo sapiens
SEQUENCE: 466
atccagttct ctgaggggc t                                              21

SEQ ID NO: 467             moltype = RNA   length = 26
FEATURE                    Location/Qualifiers
source                     1..26
                           mol_type = transcribed RNA
                           organism = Homo sapiens
SEQUENCE: 467
ccttctggag aggctttgtg cggata                                        26

SEQ ID NO: 468             moltype = RNA   length = 15
FEATURE                    Location/Qualifiers
source                     1..15
                           mol_type = transcribed RNA
                           organism = Homo sapiens
SEQUENCE: 468
ccttctggag aggct                                                    15

SEQ ID NO: 469             moltype = RNA   length = 19
FEATURE                    Location/Qualifiers
source                     1..19
                           mol_type = transcribed RNA
                           organism = Homo sapiens
SEQUENCE: 469
agtgggaggc cagggcacg                                                19

SEQ ID NO: 470             moltype = RNA   length = 15
FEATURE                    Location/Qualifiers
source                     1..15
                           mol_type = transcribed RNA
                           organism = Homo sapiens
SEQUENCE: 470
aggggagct gcagg                                                     15

SEQ ID NO: 471             moltype = RNA   length = 21
FEATURE                    Location/Qualifiers
source                     1..21
                           mol_type = transcribed RNA
                           organism = Homo sapiens
SEQUENCE: 471
gaggcgatgt ggggatgtag a                                             21

SEQ ID NO: 472             moltype = RNA   length = 20
FEATURE                    Location/Qualifiers
```

```
source                  1..20
                        mol_type = transcribed RNA
                        organism = Homo sapiens
SEQUENCE: 472
cccagtctca tttcctcatc                                                     20

SEQ ID NO: 473          moltype = RNA   length = 17
FEATURE                 Location/Qualifiers
source                  1..17
                        mol_type = transcribed RNA
                        organism = Homo sapiens
SEQUENCE: 473
ggggcggggg cgggggc                                                        17

SEQ ID NO: 474          moltype = RNA   length = 15
FEATURE                 Location/Qualifiers
source                  1..15
                        mol_type = transcribed RNA
                        organism = Homo sapiens
SEQUENCE: 474
cgcgccgggc ccggg                                                          15

SEQ ID NO: 475          moltype = RNA   length = 20
FEATURE                 Location/Qualifiers
source                  1..20
                        mol_type = transcribed RNA
                        organism = Homo sapiens
SEQUENCE: 475
tgagtgtgggc tcccgggacg                                                    20

SEQ ID NO: 476          moltype = RNA   length = 20
FEATURE                 Location/Qualifiers
source                  1..20
                        mol_type = transcribed RNA
                        organism = Homo sapiens
SEQUENCE: 476
tgagtgtgggc tcccgggacg                                                    20

SEQ ID NO: 477          moltype = RNA   length = 25
FEATURE                 Location/Qualifiers
source                  1..25
                        mol_type = transcribed RNA
                        organism = Homo sapiens
SEQUENCE: 477
tgcaggcaga agtggggctg acagg                                               25

SEQ ID NO: 478          moltype = RNA   length = 20
FEATURE                 Location/Qualifiers
source                  1..20
                        mol_type = transcribed RNA
                        organism = Homo sapiens
SEQUENCE: 478
ctgcaggcag aagtggggct                                                     20

SEQ ID NO: 479          moltype = RNA   length = 22
FEATURE                 Location/Qualifiers
source                  1..22
                        mol_type = transcribed RNA
                        organism = Homo sapiens
SEQUENCE: 479
actcaaactg tgggggcact tt                                                  22

SEQ ID NO: 480          moltype = RNA   length = 19
FEATURE                 Location/Qualifiers
source                  1..19
                        mol_type = transcribed RNA
                        organism = Homo sapiens
SEQUENCE: 480
actcaaactg tgggggcac                                                      19

SEQ ID NO: 481          moltype = RNA   length = 20
FEATURE                 Location/Qualifiers
source                  1..20
                        mol_type = transcribed RNA
                        organism = Homo sapiens
SEQUENCE: 481
ccccagggcg acgcggcggg                                                     20

SEQ ID NO: 482          moltype = RNA   length = 15
```

```
FEATURE              Location/Qualifiers
source               1..15
                     mol_type = transcribed RNA
                     organism = Homo sapiens
SEQUENCE: 482
cgcggcgggg gcggc                                                    15

SEQ ID NO: 483       moltype = RNA   length = 23
FEATURE              Location/Qualifiers
source               1..23
                     mol_type = transcribed RNA
                     organism = Homo sapiens
SEQUENCE: 483
ggctacaaca caggacccgg gcg                                           23

SEQ ID NO: 484       moltype = RNA   length = 21
FEATURE              Location/Qualifiers
source               1..21
                     mol_type = transcribed RNA
                     organism = Homo sapiens
SEQUENCE: 484
ggctacaaca caggacccgg g                                             21

SEQ ID NO: 485       moltype = RNA   length = 17
FEATURE              Location/Qualifiers
source               1..17
                     mol_type = transcribed RNA
                     organism = Homo sapiens
SEQUENCE: 485
tgcaggggca ggccagc                                                  17

SEQ ID NO: 486       moltype = RNA   length = 17
FEATURE              Location/Qualifiers
source               1..17
                     mol_type = transcribed RNA
                     organism = Homo sapiens
SEQUENCE: 486
tgcaggggca ggccagc                                                  17

SEQ ID NO: 487       moltype = RNA   length = 24
FEATURE              Location/Qualifiers
source               1..24
                     mol_type = transcribed RNA
                     organism = Homo sapiens
SEQUENCE: 487
ctgtgcaaat ccatgcaaaa ctga                                          24

SEQ ID NO: 488       moltype = RNA   length = 15
FEATURE              Location/Qualifiers
source               1..15
                     mol_type = transcribed RNA
                     organism = Homo sapiens
SEQUENCE: 488
tgtgcaaatc catgc                                                    15

SEQ ID NO: 489       moltype = RNA   length = 27
FEATURE              Location/Qualifiers
source               1..27
                     mol_type = transcribed RNA
                     organism = Homo sapiens
SEQUENCE: 489
aaaccgttac cattactgag tttagta                                       27

SEQ ID NO: 490       moltype = RNA   length = 15
FEATURE              Location/Qualifiers
source               1..15
                     mol_type = transcribed RNA
                     organism = Homo sapiens
SEQUENCE: 490
gaaaccgtta ccatt                                                    15

SEQ ID NO: 491       moltype = RNA   length = 24
FEATURE              Location/Qualifiers
source               1..24
                     mol_type = transcribed RNA
                     organism = Homo sapiens
SEQUENCE: 491
tggggagctg aggctctggg ggtg                                          24
```

| | | |
|---|---|---|
| SEQ ID NO: 492<br>FEATURE<br>source | moltype = RNA   length = 15<br>Location/Qualifiers<br>1..15<br>mol_type = transcribed RNA<br>organism = Homo sapiens | |
| SEQUENCE: 492<br>ggccctgggg agctg | | 15 |
| SEQ ID NO: 493<br>FEATURE<br>source | moltype = RNA   length = 25<br>Location/Qualifiers<br>1..25<br>mol_type = transcribed RNA<br>organism = Homo sapiens | |
| SEQUENCE: 493<br>tgtcagtttg tcaaataccc caagt | | 25 |
| SEQ ID NO: 494<br>FEATURE<br>source | moltype = RNA   length = 15<br>Location/Qualifiers<br>1..15<br>mol_type = transcribed RNA<br>organism = Homo sapiens | |
| SEQUENCE: 494<br>tccatgtggt agagt | | 15 |
| SEQ ID NO: 495<br>FEATURE<br>source | moltype = RNA   length = 22<br>Location/Qualifiers<br>1..22<br>mol_type = transcribed RNA<br>organism = Homo sapiens | |
| SEQUENCE: 495<br>gtgggcgggg gcaggtgtgt gg | | 22 |
| SEQ ID NO: 496<br>FEATURE<br>source | moltype = RNA   length = 15<br>Location/Qualifiers<br>1..15<br>mol_type = transcribed RNA<br>organism = Homo sapiens | |
| SEQUENCE: 496<br>cgggggcagg tgtgt | | 15 |
| SEQ ID NO: 497<br>FEATURE<br>source | moltype = RNA   length = 23<br>Location/Qualifiers<br>1..23<br>mol_type = transcribed RNA<br>organism = Homo sapiens | |
| SEQUENCE: 497<br>cacaggtgag gttcttggga gcc | | 23 |
| SEQ ID NO: 498<br>FEATURE<br>source | moltype = RNA   length = 15<br>Location/Qualifiers<br>1..15<br>mol_type = transcribed RNA<br>organism = Homo sapiens | |
| SEQUENCE: 498<br>acaggtgagg ttctt | | 15 |
| SEQ ID NO: 499<br>FEATURE<br>source | moltype = RNA   length = 26<br>Location/Qualifiers<br>1..26<br>mol_type = transcribed RNA<br>organism = Homo sapiens | |
| SEQUENCE: 499<br>agggacggga cgcggtgcag tgttgt | | 26 |
| SEQ ID NO: 500<br>FEATURE<br>source | moltype = RNA   length = 15<br>Location/Qualifiers<br>1..15<br>mol_type = transcribed RNA<br>organism = Homo sapiens | |
| SEQUENCE: 500<br>ggcgggcggg aggga | | 15 |
| SEQ ID NO: 501<br>FEATURE<br>source | moltype = RNA   length = 25<br>Location/Qualifiers<br>1..25<br>mol_type = transcribed RNA<br>organism = Homo sapiens | |
| SEQUENCE: 501<br>aagctgccag ttgaagaact gttgc | | 25 |

| | | |
|---|---|---|
| SEQ ID NO: 502<br>FEATURE<br>source | moltype = RNA   length = 15<br>Location/Qualifiers<br>1..15<br>mol_type = transcribed RNA<br>organism = Homo sapiens | |
| SEQUENCE: 502<br>aagctgccag ttgaa | | 15 |
| SEQ ID NO: 503<br>FEATURE<br>source | moltype = RNA   length = 16<br>Location/Qualifiers<br>1..16<br>mol_type = transcribed RNA<br>organism = Homo sapiens | |
| SEQUENCE: 503<br>tgggggggaa gaaaag | | 16 |
| SEQ ID NO: 504<br>FEATURE<br>source | moltype = RNA   length = 16<br>Location/Qualifiers<br>1..16<br>mol_type = transcribed RNA<br>organism = Homo sapiens | |
| SEQUENCE: 504<br>tgggggggaa gaaaag | | 16 |
| SEQ ID NO: 505<br>FEATURE<br>source | moltype = RNA   length = 20<br>Location/Qualifiers<br>1..20<br>mol_type = transcribed RNA<br>organism = Homo sapiens | |
| SEQUENCE: 505<br>aagacacatt tggagaggga | | 20 |
| SEQ ID NO: 506<br>FEATURE<br>source | moltype = RNA   length = 16<br>Location/Qualifiers<br>1..16<br>mol_type = transcribed RNA<br>organism = Homo sapiens | |
| SEQUENCE: 506<br>agacacattt ggagag | | 16 |
| SEQ ID NO: 507<br>FEATURE<br>source | moltype = RNA   length = 23<br>Location/Qualifiers<br>1..23<br>mol_type = transcribed RNA<br>organism = Homo sapiens | |
| SEQUENCE: 507<br>ctagtggaag aagatggcgg aag | | 23 |
| SEQ ID NO: 508<br>FEATURE<br>source | moltype = RNA   length = 15<br>Location/Qualifiers<br>1..15<br>mol_type = transcribed RNA<br>organism = Homo sapiens | |
| SEQUENCE: 508<br>tagtggaaga agatg | | 15 |
| SEQ ID NO: 509<br>FEATURE<br>source | moltype = RNA   length = 27<br>Location/Qualifiers<br>1..27<br>mol_type = transcribed RNA<br>organism = Homo sapiens | |
| SEQUENCE: 509<br>gtgaacgggc gccatcccga ggctttg | | 27 |
| SEQ ID NO: 510<br>FEATURE<br>source | moltype = RNA   length = 16<br>Location/Qualifiers<br>1..16<br>mol_type = transcribed RNA<br>organism = Homo sapiens | |
| SEQUENCE: 510<br>gtgaacgggc gccatc | | 16 |
| SEQ ID NO: 511<br>FEATURE<br>source | moltype = RNA   length = 22<br>Location/Qualifiers<br>1..22<br>mol_type = transcribed RNA<br>organism = Homo sapiens | |
| SEQUENCE: 511 | | |

```
ggcaggaagc ggaggaacct tg                                              22

SEQ ID NO: 512          moltype = RNA   length = 17
FEATURE                 Location/Qualifiers
source                  1..17
                        mol_type = transcribed RNA
                        organism = Homo sapiens
SEQUENCE: 512
ggaggaacct tggagct                                                    17

SEQ ID NO: 513          moltype = RNA   length = 21
FEATURE                 Location/Qualifiers
source                  1..21
                        mol_type = transcribed RNA
                        organism = Homo sapiens
SEQUENCE: 513
gttggaggcg tgggttttag a                                               21

SEQ ID NO: 514          moltype = RNA   length = 15
FEATURE                 Location/Qualifiers
source                  1..15
                        mol_type = transcribed RNA
                        organism = Homo sapiens
SEQUENCE: 514
gttggaggcg tgggt                                                      15

SEQ ID NO: 515          moltype = RNA   length = 29
FEATURE                 Location/Qualifiers
source                  1..29
                        mol_type = transcribed RNA
                        organism = Homo sapiens
SEQUENCE: 515
gggagccgcg gggatcgccg agggccggt                                       29

SEQ ID NO: 516          moltype = RNA   length = 15
FEATURE                 Location/Qualifiers
source                  1..15
                        mol_type = transcribed RNA
                        organism = Homo sapiens
SEQUENCE: 516
ggcggcggtg gtggg                                                      15

SEQ ID NO: 517          moltype = RNA   length = 23
FEATURE                 Location/Qualifiers
source                  1..23
                        mol_type = transcribed RNA
                        organism = Homo sapiens
SEQUENCE: 517
gagggaggga cggggctgt gct                                              23

SEQ ID NO: 518          moltype = RNA   length = 15
FEATURE                 Location/Qualifiers
source                  1..15
                        mol_type = transcribed RNA
                        organism = Homo sapiens
SEQUENCE: 518
gaggagggag ggagg                                                      15

SEQ ID NO: 519          moltype = RNA   length = 21
FEATURE                 Location/Qualifiers
source                  1..21
                        mol_type = transcribed RNA
                        organism = Homo sapiens
SEQUENCE: 519
ttgaggagac atggtggggg c                                               21

SEQ ID NO: 520          moltype = RNA   length = 15
FEATURE                 Location/Qualifiers
source                  1..15
                        mol_type = transcribed RNA
                        organism = Homo sapiens
SEQUENCE: 520
ttgaggagac atggt                                                      15

SEQ ID NO: 521          moltype = RNA   length = 24
FEATURE                 Location/Qualifiers
source                  1..24
                        mol_type = transcribed RNA
                        organism = Homo sapiens
```

```
SEQUENCE: 521
aggcaggggc tggtgctggg cggg                                                    24

SEQ ID NO: 522          moltype = RNA   length = 15
FEATURE                 Location/Qualifiers
source                  1..15
                        mol_type = transcribed RNA
                        organism = Homo sapiens
SEQUENCE: 522
gggcgggggg cggcg                                                              15

SEQ ID NO: 523          moltype = RNA   length = 17
FEATURE                 Location/Qualifiers
source                  1..17
                        mol_type = transcribed RNA
                        organism = Homo sapiens
SEQUENCE: 523
gcggggcggc aggggcc                                                            17

SEQ ID NO: 524          moltype = RNA   length = 15
FEATURE                 Location/Qualifiers
source                  1..15
                        mol_type = transcribed RNA
                        organism = Homo sapiens
SEQUENCE: 524
gggggcgggg cggca                                                              15

SEQ ID NO: 525          moltype = RNA   length = 21
FEATURE                 Location/Qualifiers
source                  1..21
                        mol_type = transcribed RNA
                        organism = Homo sapiens
SEQUENCE: 525
gccgggcgtg gtggtggggg c                                                       21

SEQ ID NO: 526          moltype = RNA   length = 15
FEATURE                 Location/Qualifiers
source                  1..15
                        mol_type = transcribed RNA
                        organism = Homo sapiens
SEQUENCE: 526
tagccgggcg tggtg                                                              15

SEQ ID NO: 527          moltype = RNA   length = 23
FEATURE                 Location/Qualifiers
source                  1..23
                        mol_type = transcribed RNA
                        organism = Homo sapiens
SEQUENCE: 527
aagggaggag gagcggaggg gcc                                                     23

SEQ ID NO: 528          moltype = RNA   length = 15
FEATURE                 Location/Qualifiers
source                  1..15
                        mol_type = transcribed RNA
                        organism = Homo sapiens
SEQUENCE: 528
gggaggagga gcgga                                                              15

SEQ ID NO: 529          moltype = RNA   length = 24
FEATURE                 Location/Qualifiers
source                  1..24
                        mol_type = transcribed RNA
                        organism = Homo sapiens
SEQUENCE: 529
cgggcgtggt ggtggggtg ggtg                                                     24

SEQ ID NO: 530          moltype = RNA   length = 15
FEATURE                 Location/Qualifiers
source                  1..15
                        mol_type = transcribed RNA
                        organism = Homo sapiens
SEQUENCE: 530
cgggcgtggt ggtgg                                                              15

SEQ ID NO: 531          moltype = RNA   length = 24
FEATURE                 Location/Qualifiers
source                  1..24
                        mol_type = transcribed RNA
```

```
                              organism = Homo sapiens
SEQUENCE: 531
tgggggagtg cagtgattgt ggaa                                                    24

SEQ ID NO: 532          moltype = RNA   length = 19
FEATURE                 Location/Qualifiers
source                  1..19
                        mol_type = transcribed RNA
                        organism = Homo sapiens
SEQUENCE: 532
tgggggagtg cagtgattg                                                          19

SEQ ID NO: 533          moltype = RNA   length = 29
FEATURE                 Location/Qualifiers
source                  1..29
                        mol_type = transcribed RNA
                        organism = Homo sapiens
SEQUENCE: 533
gctgggttaa gccgagctgg gttgggctg                                               29

SEQ ID NO: 534          moltype = RNA   length = 19
FEATURE                 Location/Qualifiers
source                  1..19
                        mol_type = transcribed RNA
                        organism = Homo sapiens
SEQUENCE: 534
ctgggttggg ctgggctgg                                                          19

SEQ ID NO: 535          moltype = RNA   length = 18
FEATURE                 Location/Qualifiers
source                  1..18
                        mol_type = transcribed RNA
                        organism = Homo sapiens
SEQUENCE: 535
ctccgggcgg cgccgtgt                                                           18

SEQ ID NO: 536          moltype = RNA   length = 18
FEATURE                 Location/Qualifiers
source                  1..18
                        mol_type = transcribed RNA
                        organism = Homo sapiens
SEQUENCE: 536
ctccgggcgg cgccgtgt                                                           18

SEQ ID NO: 537          moltype = RNA   length = 17
FEATURE                 Location/Qualifiers
source                  1..17
                        mol_type = transcribed RNA
                        organism = Homo sapiens
SEQUENCE: 537
cctccgggac ggctggg                                                            17

SEQ ID NO: 538          moltype = RNA   length = 15
FEATURE                 Location/Qualifiers
source                  1..15
                        mol_type = transcribed RNA
                        organism = Homo sapiens
SEQUENCE: 538
ctccgggacg gctgg                                                              15

SEQ ID NO: 539          moltype = RNA   length = 26
FEATURE                 Location/Qualifiers
source                  1..26
                        mol_type = transcribed RNA
                        organism = Homo sapiens
SEQUENCE: 539
gaggggctct cgcttctggc gccaag                                                  26

SEQ ID NO: 540          moltype = RNA   length = 15
FEATURE                 Location/Qualifiers
source                  1..15
                        mol_type = transcribed RNA
                        organism = Homo sapiens
SEQUENCE: 540
ggtgaggcgg ggggg                                                              15

SEQ ID NO: 541          moltype = RNA   length = 21
FEATURE                 Location/Qualifiers
source                  1..21
```

```
                        mol_type = transcribed RNA
                        organism = Homo sapiens
SEQUENCE: 541
tgctgggggc cacatgagtg t                                              21

SEQ ID NO: 542          moltype = RNA    length = 20
FEATURE                 Location/Qualifiers
source                  1..20
                        mol_type = transcribed RNA
                        organism = Homo sapiens
SEQUENCE: 542
gctggggggcc acatgagtgt                                                20

SEQ ID NO: 543          moltype = RNA    length = 23
FEATURE                 Location/Qualifiers
source                  1..23
                        mol_type = transcribed RNA
                        organism = Homo sapiens
SEQUENCE: 543
gggggtcccc ggtgctcgga tct                                            23

SEQ ID NO: 544          moltype = RNA    length = 16
FEATURE                 Location/Qualifiers
source                  1..16
                        mol_type = transcribed RNA
                        organism = Homo sapiens
SEQUENCE: 544
tcgggagggg cgggag                                                    16

SEQ ID NO: 545          moltype = RNA    length = 23
FEATURE                 Location/Qualifiers
source                  1..23
                        mol_type = transcribed RNA
                        organism = Homo sapiens
SEQUENCE: 545
tcggctctgg gtctgtgggg agc                                            23

SEQ ID NO: 546          moltype = RNA    length = 15
FEATURE                 Location/Qualifiers
source                  1..15
                        mol_type = transcribed RNA
                        organism = Homo sapiens
SEQUENCE: 546
gcccggatac ctcag                                                     15

SEQ ID NO: 547          moltype = RNA    length = 23
FEATURE                 Location/Qualifiers
source                  1..23
                        mol_type = transcribed RNA
                        organism = Homo sapiens
SEQUENCE: 547
gggggggatgt gcatgctggt tgg                                           23

SEQ ID NO: 548          moltype = RNA    length = 15
FEATURE                 Location/Qualifiers
source                  1..15
                        mol_type = transcribed RNA
                        organism = Homo sapiens
SEQUENCE: 548
atcagcgtgc acttc                                                     15

SEQ ID NO: 549          moltype = RNA    length = 23
FEATURE                 Location/Qualifiers
source                  1..23
                        mol_type = transcribed RNA
                        organism = Homo sapiens
SEQUENCE: 549
aggagggtc ccgcactggg agg                                             23

SEQ ID NO: 550          moltype = RNA    length = 15
FEATURE                 Location/Qualifiers
source                  1..15
                        mol_type = transcribed RNA
                        organism = Homo sapiens
SEQUENCE: 550
tgggaggggc cctca                                                     15

SEQ ID NO: 551          moltype = RNA    length = 24
FEATURE                 Location/Qualifiers
```

```
source                  1..24
                        mol_type = transcribed RNA
                        organism = Homo sapiens
SEQUENCE: 551
cccaaaatgc tgggattaca ggca                                          24

SEQ ID NO: 552          moltype = RNA   length = 15
FEATURE                 Location/Qualifiers
source                  1..15
                        mol_type = transcribed RNA
                        organism = Homo sapiens
SEQUENCE: 552
gcccacctca gcctc                                                    15

SEQ ID NO: 553          moltype = RNA   length = 26
FEATURE                 Location/Qualifiers
source                  1..26
                        mol_type = transcribed RNA
                        organism = Homo sapiens
SEQUENCE: 553
agggctggac tcagcggcgg agctgg                                        26

SEQ ID NO: 554          moltype = RNA   length = 17
FEATURE                 Location/Qualifiers
source                  1..17
                        mol_type = transcribed RNA
                        organism = Homo sapiens
SEQUENCE: 554
gcggcggagc tggctgc                                                  17

SEQ ID NO: 555          moltype = RNA   length = 15
FEATURE                 Location/Qualifiers
source                  1..15
                        mol_type = transcribed RNA
                        organism = Homo sapiens
SEQUENCE: 555
aggaggagga ggcag                                                    15

SEQ ID NO: 556          moltype = RNA   length = 15
FEATURE                 Location/Qualifiers
source                  1..15
                        mol_type = transcribed RNA
                        organism = Homo sapiens
SEQUENCE: 556
aggaggagga ggcag                                                    15

SEQ ID NO: 557          moltype = RNA   length = 23
FEATURE                 Location/Qualifiers
source                  1..23
                        mol_type = transcribed RNA
                        organism = Homo sapiens
SEQUENCE: 557
tggtgcggag agggcccaca gtg                                           23

SEQ ID NO: 558          moltype = RNA   length = 15
FEATURE                 Location/Qualifiers
source                  1..15
                        mol_type = transcribed RNA
                        organism = Homo sapiens
SEQUENCE: 558
gggtctggtg cggag                                                    15

SEQ ID NO: 559          moltype = RNA   length = 22
FEATURE                 Location/Qualifiers
source                  1..22
                        mol_type = transcribed RNA
                        organism = Homo sapiens
SEQUENCE: 559
acaccgggga tggcagaggg tc                                            22

SEQ ID NO: 560          moltype = RNA   length = 20
FEATURE                 Location/Qualifiers
source                  1..20
                        mol_type = transcribed RNA
                        organism = Homo sapiens
SEQUENCE: 560
caccggggat ggcagagggt                                               20

SEQ ID NO: 561          moltype = RNA   length = 20
```

| | | |
|---|---|---|
| FEATURE | Location/Qualifiers | |
| source | 1..20 | |
| | mol_type = transcribed RNA | |
| | organism = Homo sapiens | |
| SEQUENCE: 561 | | |
| ggtagtgagt tatcagctac | | 20 |
| | | |
| SEQ ID NO: 562 | moltype = RNA length = 19 | |
| FEATURE | Location/Qualifiers | |
| source | 1..19 | |
| | mol_type = transcribed RNA | |
| | organism = Homo sapiens | |
| SEQUENCE: 562 | | |
| cggggccaga gcagagagc | | 19 |
| | | |
| SEQ ID NO: 563 | moltype = RNA length = 23 | |
| FEATURE | Location/Qualifiers | |
| source | 1..23 | |
| | mol_type = transcribed RNA | |
| | organism = Homo sapiens | |
| SEQUENCE: 563 | | |
| tggtgggtgg ggaggagaag tgc | | 23 |
| | | |
| SEQ ID NO: 564 | moltype = RNA length = 26 | |
| FEATURE | Location/Qualifiers | |
| source | 1..26 | |
| | mol_type = transcribed RNA | |
| | organism = Homo sapiens | |
| SEQUENCE: 564 | | |
| ctcggccgcg gcgcgtagcc cccgcc | | 26 |
| | | |
| SEQ ID NO: 565 | moltype = RNA length = 22 | |
| FEATURE | Location/Qualifiers | |
| source | 1..22 | |
| | mol_type = transcribed RNA | |
| | organism = Homo sapiens | |
| SEQUENCE: 565 | | |
| tctgccccct ccgctgctgc ca | | 22 |
| | | |
| SEQ ID NO: 566 | moltype = RNA length = 20 | |
| FEATURE | Location/Qualifiers | |
| source | 1..20 | |
| | mol_type = transcribed RNA | |
| | organism = Homo sapiens | |
| SEQUENCE: 566 | | |
| tcacacctgc ctcgcccccc | | 20 |
| | | |
| SEQ ID NO: 567 | moltype = RNA length = 21 | |
| FEATURE | Location/Qualifiers | |
| source | 1..21 | |
| | mol_type = transcribed RNA | |
| | organism = Homo sapiens | |
| SEQUENCE: 567 | | |
| aaggcagggc ccccgctccc c | | 21 |
| | | |
| SEQ ID NO: 568 | moltype = RNA length = 22 | |
| FEATURE | Location/Qualifiers | |
| source | 1..22 | |
| | mol_type = transcribed RNA | |
| | organism = Homo sapiens | |
| SEQUENCE: 568 | | |
| gagggttggg tggaggctct cc | | 22 |
| | | |
| SEQ ID NO: 569 | moltype = RNA length = 22 | |
| FEATURE | Location/Qualifiers | |
| source | 1..22 | |
| | mol_type = transcribed RNA | |
| | organism = Homo sapiens | |
| SEQUENCE: 569 | | |
| gagcaggcga ggctgggctg aa | | 22 |
| | | |
| SEQ ID NO: 570 | moltype = RNA length = 22 | |
| FEATURE | Location/Qualifiers | |
| source | 1..22 | |
| | mol_type = transcribed RNA | |
| | organism = Homo sapiens | |
| SEQUENCE: 570 | | |
| gctggtgcaa aagtaatggc gg | | 22 |

-continued

```
SEQ ID NO: 571        moltype = RNA    length = 22
FEATURE               Location/Qualifiers
source                1..22
                      mol_type = transcribed RNA
                      organism = Homo sapiens
SEQUENCE: 571
aggcggggcg ccgcgggacc gc                                                  22

SEQ ID NO: 572        moltype = RNA    length = 22
FEATURE               Location/Qualifiers
source                1..22
                      mol_type = transcribed RNA
                      organism = Homo sapiens
SEQUENCE: 572
acgcccttcc ccccttcttt ca                                                  22

SEQ ID NO: 573        moltype = RNA    length = 21
FEATURE               Location/Qualifiers
source                1..21
                      mol_type = transcribed RNA
                      organism = Homo sapiens
SEQUENCE: 573
gtgccagctg cagtggggga g                                                   21

SEQ ID NO: 574        moltype = RNA    length = 23
FEATURE               Location/Qualifiers
source                1..23
                      mol_type = transcribed RNA
                      organism = Homo sapiens
SEQUENCE: 574
cctccctgcc cgcctctctg cag                                                 23

SEQ ID NO: 575        moltype = RNA    length = 22
FEATURE               Location/Qualifiers
source                1..22
                      mol_type = transcribed RNA
                      organism = Homo sapiens
SEQUENCE: 575
tgagcccctg tgccgcccc ag                                                   22

SEQ ID NO: 576        moltype = RNA    length = 23
FEATURE               Location/Qualifiers
source                1..23
                      mol_type = transcribed RNA
                      organism = Homo sapiens
SEQUENCE: 576
ccccggtgtt ggggcgcgtc tgc                                                 23

SEQ ID NO: 577        moltype = RNA    length = 20
FEATURE               Location/Qualifiers
source                1..20
                      mol_type = transcribed RNA
                      organism = Homo sapiens
SEQUENCE: 577
ggctccttgg tctaggggta                                                     20

SEQ ID NO: 578        moltype = RNA    length = 17
FEATURE               Location/Qualifiers
source                1..17
                      mol_type = transcribed RNA
                      organism = Homo sapiens
SEQUENCE: 578
ggatggagga ggggtct                                                        17

SEQ ID NO: 579        moltype = RNA    length = 22
FEATURE               Location/Qualifiers
source                1..22
                      mol_type = transcribed RNA
                      organism = Homo sapiens
SEQUENCE: 579
actcggcgtg gcgtcggtcg tg                                                  22

SEQ ID NO: 580        moltype = RNA    length = 89
FEATURE               Location/Qualifiers
source                1..89
                      mol_type = transcribed RNA
                      organism = Homo sapiens
SEQUENCE: 580
tagatgttgg tccaaactga aagttgatga gtcactgtgc ctctcggggt agtgagttat         60
```

```
cagctacagt gagagagcag tgtttggcc                                            89

SEQ ID NO: 581         moltype = RNA   length = 61
FEATURE                Location/Qualifiers
source                 1..61
                       mol_type = transcribed RNA
                       organism = Homo sapiens
SEQUENCE: 581
aactgcgggg ccagagcaga gagcccttgc acaccaccag cctctcctcc ctgtgcccca          60
g                                                                          61

SEQ ID NO: 582         moltype = RNA   length = 62
FEATURE                Location/Qualifiers
source                 1..62
                       mol_type = transcribed RNA
                       organism = Homo sapiens
SEQUENCE: 582
cttcctggtg ggtggggagg agaagtgccg tcctcatgag cccctctctg tcccacccat          60
ag                                                                         62

SEQ ID NO: 583         moltype = RNA   length = 79
FEATURE                Location/Qualifiers
source                 1..79
                       mol_type = transcribed RNA
                       organism = Homo sapiens
SEQUENCE: 583
ctcgaggtgc tgggggacgc gtgagcgcga gccgcttcct cacggctcgg ccgcggcgcg          60
tagccccgc cacatcggg                                                        79

SEQ ID NO: 584         moltype = RNA   length = 80
FEATURE                Location/Qualifiers
source                 1..80
                       mol_type = transcribed RNA
                       organism = Homo sapiens
SEQUENCE: 584
acctctacct cccggcagag gaggctgcag aggctggctt tccaaaactc tgccccctcc          60
gctgctgcca agtggctggt                                                      80

SEQ ID NO: 585         moltype = RNA   length = 94
FEATURE                Location/Qualifiers
source                 1..94
                       mol_type = transcribed RNA
                       organism = Homo sapiens
SEQUENCE: 585
gtgaggtgtg ggcccggccc caggagcggg gcctgggcag ccccgtgtgt tgaggaagga          60
aggcagggcc cccgctcccc gggcctgacc ccac                                      94

SEQ ID NO: 586         moltype = RNA   length = 80
FEATURE                Location/Qualifiers
source                 1..80
                       mol_type = transcribed RNA
                       organism = Homo sapiens
SEQUENCE: 586
aggacccttc cagagggccc ccctcaatc ctgttgtgcc taattcagag ggttgggtgg           60
aggctctcct gaagggctct                                                      80

SEQ ID NO: 587         moltype = RNA   length = 60
FEATURE                Location/Qualifiers
source                 1..60
                       mol_type = transcribed RNA
                       organism = Homo sapiens
SEQUENCE: 587
gagcaggcga ggctgggctg aacccgtggg tgaggagtgc agcccagctg aggcctctgc          60

SEQ ID NO: 588         moltype = RNA   length = 100
FEATURE                Location/Qualifiers
source                 1..100
                       mol_type = transcribed RNA
                       organism = Homo sapiens
SEQUENCE: 588
atattaggct ggtgcaaaag taatggcggt ttttgccatt actttcatt tttaccatta           60
aaagtaatgg caaaaagcat gattactttt tcaccaacct                                100

SEQ ID NO: 589         moltype = RNA   length = 93
FEATURE                Location/Qualifiers
source                 1..93
                       mol_type = transcribed RNA
                       organism = Homo sapiens
SEQUENCE: 589
```

```
ccttccggcg tcccaggcgg ggcgccgcgg gaccgccctc gtgtctgtgg cggtgggatc    60
ccgcggccgt gttttcctgg tggcccggcc atg                                 93

SEQ ID NO: 590        moltype = RNA   length = 66
FEATURE               Location/Qualifiers
source                1..66
                      mol_type = transcribed RNA
                      organism = Homo sapiens
SEQUENCE: 590
gggaggaggg aggagatggg ccaagttccc tctggctgga acgcccttcc ccccttctt     60
cacctg                                                               66

SEQ ID NO: 591        moltype = RNA   length = 83
FEATURE               Location/Qualifiers
source                1..83
                      mol_type = transcribed RNA
                      organism = Homo sapiens
SEQUENCE: 591
cctgctgcag aggtgccagc tgcagtgggg gaggcactgc cagggctgcc cactctgctt    60
agccagcagg tgccaagaac agg                                            83

SEQ ID NO: 592        moltype = RNA   length = 59
FEATURE               Location/Qualifiers
source                1..59
                      mol_type = transcribed RNA
                      organism = Homo sapiens
SEQUENCE: 592
ctccagggag acagtgtgtg aggcctcttg ccatggcctc cctgcccgcc tctctgcag     59

SEQ ID NO: 593        moltype = RNA   length = 82
FEATURE               Location/Qualifiers
source                1..82
                      mol_type = transcribed RNA
                      organism = Homo sapiens
SEQUENCE: 593
gggaaagcgg agggcgcgcc cagctcccgg gctgattgcg ctaacagtgg ccccggtgtt    60
ggggcgcgtc tgccgctgcc cc                                             82

SEQ ID NO: 594        moltype = RNA   length = 86
FEATURE               Location/Qualifiers
source                1..86
                      mol_type = transcribed RNA
                      organism = Homo sapiens
SEQUENCE: 594
aggagtgacc aaaagacaag agtgcgagcc ttctattatg cccagacagg gccaccagag    60
ggctccttgg tctaggggta atgcca                                         86

SEQ ID NO: 595        moltype = RNA   length = 60
FEATURE               Location/Qualifiers
source                1..60
                      mol_type = transcribed RNA
                      organism = Homo sapiens
SEQUENCE: 595
tgtgaatgac cccct tccag agccaaaatc accaggg atg gaggagg ggt cttgggtact  60

SEQ ID NO: 596        moltype = RNA   length = 149
FEATURE               Location/Qualifiers
source                1..149
                      mol_type = transcribed RNA
                      organism = Homo sapiens
SEQUENCE: 596
catcaagacc cagctgagtc actgtcactg cctaccaatc tcgaccggac ctcgaccggc    60
tcgtctgtgt tgccaatcga ctcggcgtgg cgtcggtcgt ggtagatagg cggtcatgca   120
tacgaatttt cagctcttgt tctggtgac                                     149

SEQ ID NO: 597        moltype = RNA   length = 22
FEATURE               Location/Qualifiers
source                1..22
                      mol_type = transcribed RNA
                      organism = Homo sapiens
SEQUENCE: 597
ccggcagagg aggctgcaga gg                                             22

SEQ ID NO: 598        moltype = RNA   length = 19
FEATURE               Location/Qualifiers
source                1..19
                      mol_type = transcribed RNA
                      organism = Homo sapiens
SEQUENCE: 598
```

-continued

```
ccggcagagg aggctgcag                                         19

SEQ ID NO: 599         moltype = RNA   length = 22
FEATURE                Location/Qualifiers
source                 1..22
                       mol_type = transcribed RNA
                       organism = Homo sapiens
SEQUENCE: 599
cctcacacct gcctcgcccc cc                                     22

SEQ ID NO: 600         moltype = RNA   length = 15
FEATURE                Location/Qualifiers
source                 1..15
                       mol_type = transcribed RNA
                       organism = Homo sapiens
SEQUENCE: 600
tcacacctgc ctcgc                                             15

SEQ ID NO: 601         moltype = RNA   length = 25
FEATURE                Location/Qualifiers
source                 1..25
                       mol_type = transcribed RNA
                       organism = Homo sapiens
SEQUENCE: 601
aaggcagggc ccccgctccc cgggc                                  25

SEQ ID NO: 602         moltype = RNA   length = 15
FEATURE                Location/Qualifiers
source                 1..15
                       mol_type = transcribed RNA
                       organism = Homo sapiens
SEQUENCE: 602
gtgtgttgag gaagg                                             15

SEQ ID NO: 603         moltype = RNA   length = 22
FEATURE                Location/Qualifiers
source                 1..22
                       mol_type = transcribed RNA
                       organism = Homo sapiens
SEQUENCE: 603
gagggttggg tggaggctct cc                                     22

SEQ ID NO: 604         moltype = RNA   length = 15
FEATURE                Location/Qualifiers
source                 1..15
                       mol_type = transcribed RNA
                       organism = Homo sapiens
SEQUENCE: 604
gagggttggg tggag                                             15

SEQ ID NO: 605         moltype = RNA   length = 19
FEATURE                Location/Qualifiers
source                 1..19
                       mol_type = transcribed RNA
                       organism = Homo sapiens
SEQUENCE: 605
gcaggcgagg ctgggctga                                         19

SEQ ID NO: 606         moltype = RNA   length = 16
FEATURE                Location/Qualifiers
source                 1..16
                       mol_type = transcribed RNA
                       organism = Homo sapiens
SEQUENCE: 606
aggcgaggct gggctg                                            16

SEQ ID NO: 607         moltype = RNA   length = 26
FEATURE                Location/Qualifiers
source                 1..26
                       mol_type = transcribed RNA
                       organism = Homo sapiens
SEQUENCE: 607
cggtgggatc ccgcggccgt gttttc                                 26

SEQ ID NO: 608         moltype = RNA   length = 15
FEATURE                Location/Qualifiers
source                 1..15
                       mol_type = transcribed RNA
                       organism = Homo sapiens
```

| | | |
|---|---|---|
| SEQUENCE: 608 ggggcgccgc gggac | | 15 |
| SEQ ID NO: 609 FEATURE source | moltype = RNA length = 26 Location/Qualifiers 1..26 mol_type = transcribed RNA organism = Homo sapiens | |
| SEQUENCE: 609 aggagggagg agatgggcca agttcc | | 26 |
| SEQ ID NO: 610 FEATURE source | moltype = RNA length = 15 Location/Qualifiers 1..15 mol_type = transcribed RNA organism = Homo sapiens | |
| SEQUENCE: 610 gggaggaggg aggag | | 15 |
| SEQ ID NO: 611 FEATURE source | moltype = RNA length = 16 Location/Qualifiers 1..16 mol_type = transcribed RNA organism = Homo sapiens | |
| SEQUENCE: 611 agctgcagtg gggag | | 16 |
| SEQ ID NO: 612 FEATURE source | moltype = RNA length = 15 Location/Qualifiers 1..15 mol_type = transcribed RNA organism = Homo sapiens | |
| SEQUENCE: 612 gctgcagtgg gggag | | 15 |
| SEQ ID NO: 613 FEATURE source | moltype = RNA length = 22 Location/Qualifiers 1..22 mol_type = transcribed RNA organism = Homo sapiens | |
| SEQUENCE: 613 ccccggtgtt ggggcgcgtc tg | | 22 |
| SEQ ID NO: 614 FEATURE source | moltype = RNA length = 21 Location/Qualifiers 1..21 mol_type = transcribed RNA organism = Homo sapiens | |
| SEQUENCE: 614 cccggtgttg gggcgcgtct g | | 21 |
| SEQ ID NO: 615 FEATURE source | moltype = RNA length = 20 Location/Qualifiers 1..20 mol_type = transcribed RNA organism = Homo sapiens | |
| SEQUENCE: 615 ggctccttgg tctagggta | | 20 |
| SEQ ID NO: 616 FEATURE source | moltype = RNA length = 15 Location/Qualifiers 1..15 mol_type = transcribed RNA organism = Homo sapiens | |
| SEQUENCE: 616 cttggtctag gggta | | 15 |
| SEQ ID NO: 617 FEATURE source | moltype = RNA length = 25 Location/Qualifiers 1..25 mol_type = transcribed RNA organism = Homo sapiens | |
| SEQUENCE: 617 actcggcgtg gcgtcggtcg tggta | | 25 |
| SEQ ID NO: 618 FEATURE source | moltype = RNA length = 15 Location/Qualifiers 1..15 mol_type = transcribed RNA | |

-continued organism = Homo sapiens
SEQUENCE: 618
actcggcgtg gcgtc                                                        15

LUNG CANCER DETECTION KIT OR DEVICE, AND DETECTION METHOD

CROSS-REFERENCE TO RELATED APPLICATIONS

This application is a Divisional of application Ser. No. 17/977,377, filed on Oct. 31, 2022, which is a Divisional of application Ser. No. 16/800,755 filed Feb. 25, 2020 (now U.S. Pat. No. 11,519,927), which is a Divisional of application Ser. No. 15/319,695, filed on Dec. 16, 2016 (now U.S. Pat. No. 10,620,228), which is the National Phase under 35 U.S.C. § 371 of International Application No. PCT/JP2015/067533, filed on Jun. 18, 2015, and claims the benefit under 35 U.S.C. § 119(a) to Patent Application No. 2014-125561, filed in Japan on Jun. 18, 2014, all of which are hereby expressly incorporated by reference into the present application.

REFERENCE TO ELECTRONIC SEQUENCE LISTING

The application contains a Sequence Listing which has been submitted electronically in .XML format and is hereby incorporated by reference in its entirety. Said .XML copy, created on Feb. 1, 2023, is named "PH-6239-PCT.xml" and is 557,029 bytes in size. The sequence listing contained in this .XML file is part of the specification and is hereby incorporated by reference herein in its entirety.

TECHNICAL FIELD

The present invention relates to a kit or a device for the detection of lung cancer, comprising a nucleic acid capable of specifically binding to a particular miRNA, which is used for examining the presence or absence of lung cancer in a subject, and a method for detecting lung cancer, comprising measuring an expression level of the miRNA using the nucleic acid.

BACKGROUND ART

The lungs have important functions of supplying oxygen into the body through respiration and eliminating carbon dioxide. Air taken up from the mouth or the nose passes through the trachea and the bronchus, then separately enters the left lung and the right lung, and spreads throughout the lung through the thinner bronchial tubes. Eventually, oxygen is taken up into blood in the alveoli while carbon dioxide is eliminated (Non Patent Literature 1).

According to the 2012 cancer type-specific statistics in Japan disclosed by the Center for Cancer Control and Information Services, National Cancer Center, the number of individuals affected by lung cancer was 107,241 people. Namely, it is estimated that one out of 10 males and one out of 22 females experience lung cancer. The number of incidences of this cancer among other cancer types takes the 3rd in place. Men are twice as likely as women to develop lung cancer. The number of lung cancer deaths in men and women together climbs to 71,518 people and takes the 1st in place among other cancer types. The estimated number of American individuals affected by lung cancer climbed to 224,210 people in 2014, among which approximately 159,260 people reportedly died (Non Patent Literature 1).

Lung cancer has multiple histological types. Small-cell lung cancer occupies approximately 15%, while the remaining histological types are called non-small cell lung cancer. The non-small cell lung cancer is further broadly classified into three subtypes; adenocarcinoma, squamous cell carcinoma, and large-cell carcinoma. These histological types differ largely in the site of origin, the manner and rate of progression, symptoms, etc., and therefore differ in treatment methods.

The stages of lung cancer progression are classified into stages 0 to 4 according to the degrees of tumor spread (T0, Tis, and T1 to T4), lymph node metastasis (N0 to N3), and distant metastasis (M0 and M1). Particularly, as for the tumor spread, T1 denotes tumor of 3 cm or less in greatest diameter; T2 denotes tumor of more than 3 cm but 7 cm or less across; T3 denotes tumor of more than 7 cm across or found to have invaded adjacent sites; and T4 denotes tumor that has invaded adjacent sites more widely regardless of its size.

The survival rate of lung cancer differs depending on the stages of progression. According to the report of Non Patent Literature 1, the 5-year relative survival rate of non-small cell lung cancer is 45 to 49% for stage 1, 30 to 31% for stage 2, 5 to 14% for stage 3, and 1% for stage 4. Thus, the detection and treatment of lung cancer at an early stage makes a significant contribution to improvement in the survival rate.

The treatment of lung cancer is mainly performed by surgical resection, radiotherapy, and anticancer drug treatment. Particularly, in early lung cancer, surgery is applicable and the cancer is likely to be completely cured (Non Patent Literature 1). For early lung cancer, there are some therapeutic options, and for example, treatment that places less burden on patients, such as thoracoscopic surgery, stereotactic body radiotherapy (SBRT), photo dynamic therapy, laser treatment, and brachytherapy, which delivers radiation from within the body, can also be applied to such lung cancer (Non Patent Literature 1).

As described in Non Patent Literature 1, diagnostic tests of lung cancer are medical history check and physical examination as well as chest X-ray examination which is most commonly conducted. When there are findings that suspects lung cancer by the chest X-ray examination, more precise diagnostic imaging such as CT, MRI, or PET is carried out. Alternatively, as tests using samples, sputum cytology, pleural fluid analysis, or pathological examination which involves inserting a needle into a lesion and collecting cells or tissues, which are then examined under a microscope is carried out. Furthermore, CEA and CYFRA21-1 are known as tumor markers for the detection of lung cancer.

As shown in Patent Literatures 1 and 2, there are reports, albeit at a research stage, on the detection of lung cancer using the expression levels of microRNAs (miRNAs) or combinations of the expression levels of miRNAs and the expression levels of additional protein markers in biological samples including blood.

Patent Literature 1 discloses a method for detecting lung cancer or other lung diseases using miR-19b (miR-19b-3p) and the like in serum.

Patent Literature 2 discloses a method for detecting lung cancer using miR-1268 and miR-1228 in serum or plasma.

Patent Literature 3 discloses a method for detecting lung cancer using miR-1307 and the like in blood cells.

CITATION LIST

Patent Literature

Patent Literature 1: JP Patent Publication (Kohyo) No. 2013-502931 A (2013)

Patent Literature 2: International Publication No. WO 2011/146937

Patent Literature 3: U.S. patent application Ser. No. 13/376,281

Non Patent Literature

Non Patent Literature 1: American Cancer Society, "Lung Cancer (Non-Small Cell)", 2013, p. 2 to 7 and 37 to 56

Non Patent Literature 2: Sobin, L. et al., "TNM Classification of Malignant Tumours, the 7th edition", 2010, p. 129-134

Non Patent Literature 3: Okamura, K. et al, Lung Cancer, 2013, Vol. 80 (1), p. 45-9

SUMMARY OF INVENTION

Technical Problem

An object of the present invention is to find a novel tumor marker for lung cancer and to provide a method that can effectively detect lung cancer using a nucleic acid capable of specifically binding to the marker. Chest X-ray examination is being commonly practiced as a test of lung cancer. Nonetheless, the number of lung cancer deaths is increasing yearly and takes the first place by cancer type. For these reasons, it is not always true that the X-ray examination works as a deterrent for lung cancer. Although CT and MRI are capable of detecting lung cancer with high performance, these tests are not suitable for widespread use as 1st tests because of the necessity of their special apparatuses and expensive examination cost.

For example, CEA and CYFRA21-1 are known as tumor markers in blood for the detection of lung cancer (Non Patent Literature 3). The usefulness thereof, however, has not yet been established. The lung cancer guidebook provided by the American Cancer Society makes no mention about these markers (Non Patent Literature 1). According to the report of Non Patent Literature 3, these tumor markers in blood have general lung cancer detection sensitivity of 69% (CEA) and 43% (CYFRA21-1). The tumor markers such as CEA and CYFRA21-1 may elevate for reasons other than lung cancer and therefore allegedly fail to determine the presence or absence of lung cancer. The false diagnosis of other cancers as lung cancer wastes appropriate therapeutic opportunity or places unnecessary economical and physical burdens on patients due to the application of wrong medicine.

As described below, there are reports, albeit at a research stage, on the determination of lung cancer using the expression levels of microRNAs (miRNAs) in biological samples including blood, none of which, however, have yet been brought into practical use.

Patent Literature 1 discloses a method for detecting lung cancer or other lung diseases using miR-19b (miR-19b-3p) and the like in serum. However, the number of samples from healthy subjects used as negative controls was as small as a dozen. Therefore, the universality of the marker for the difference among subjects is not insured. Thus, this method has low reliability as a method for detecting lung cancer.

Patent Literature 2 discloses a method for detecting lung cancer using miR-1268 and miR-1228 in serum or plasma. These markers, however, were validated in only 3 mesothelioma cases as a cancer other than lung cancer. Thus, the possibility that these markers have a high rate of false positives and detect cancers other than lung cancer cannot be excluded.

Patent Literature 3 discloses a method for detecting lung cancer using miR-1307 and the like in blood cells. However, a marker obtained using one case group was not validated in another independent case group. Thus, this method has low reliability as a method for testing lung cancer.

As mentioned above, the existing tumor markers exhibit low performance in the detection of lung cancer, or neither performance nor detection methods are specifically shown as to the markers at a research stage. Therefore, use of these markers might lead to carrying out needless extra examination due to the false detection of healthy subjects as being lung cancer patients, or might waste therapeutic opportunity because of overlooking lung cancer patients. In addition, the measurement of several dozens to several hundreds of miRNAs increases examination cost and is therefore difficult to use in large-scale screening such as medical checkup. Furthermore, the collection of lung tissues for measuring the tumor markers is highly invasive to patients and is not favorable. Hence, there is a demand for a highly accurate lung cancer marker that is detectable from blood, which can be collected with limited invasiveness, and is capable of correctly determining a lung cancer patient as a lung cancer patient and a healthy subject as a healthy subject. Particularly, the early detection of lung cancer can increase the applicability of surgery and drastically improve the survival rates. For early lung cancer, there are multiple therapeutic options. There is a possibility that treatment that places less burden on patients, such as thoracoscopic surgery or stereotactic body radiotherapy, can also be applied to such lung cancer. Therefore, a highly sensitive lung cancer marker that can detect lung cancer even at an early stage of progression is desired.

Solution to Problem

The present inventors have conducted diligent studies to attain the object and consequently completed the present invention by finding multiple genes usable as markers for the detection of lung cancer from blood, which can be collected with limited invasiveness, and finding that lung cancer can be significantly detected by using a nucleic acid capable of specifically binding to any of these markers.

SUMMARY OF INVENTION

Specifically, the present invention has the following features:

(1) A kit for the detection of lung cancer, comprising a nucleic acid capable of specifically binding to at least one or more polynucleotide(s) selected from the group consisting of lung cancer markers miR-6768-5p, miR-6836-3p, miR-6782-5p, miR-3663-3p, miR-1908-3p, miR-6726-5p, miR-4258, miR-1343-3p, miR-4516, miR-6875-5p, miR-4651, miR-6825-5p, miR-6840-3p, miR-6780b-5p, miR-6749-5p, miR-8063, miR-6784-5p, miR-3679-5p, miR-3184-5p, miR-663b, miR-6880-5p, miR-1908-5p, miR-92a-2-5p, miR-7975, miR-7110-5p, miR-6842-5p, miR-6857-5p, miR-5572, miR-3197, miR-6131, miR-6889-5p, miR-4454, miR-1199-5p, miR-1247-3p, miR-6800-5p, miR-6872-3p, miR-4649-5p, miR-6791-5p, miR-4433b-3p, miR-3135b, miR-128-2-5p, miR-4675, miR-4472, miR-6785-5p, miR-6741-5p, miR-7977, miR-3665, miR-128-1-5p, miR-4286, miR-6765-3p, miR-4632-5p, miR-365a-5p, miR-6088, miR-6816-5p, miR-6885-5p, miR-711, miR-6765-5p, miR-3180, miR-4442, miR-4792, miR-6721-5p, miR-6798-5p, miR-3162-5p, miR-6126, miR-4758-5p, miR-2392, miR-486-3p, miR-6727-5p, miR-4728-5p, miR-6746-5p, miR- 4270, miR-3940-5p, miR-4725-3p, miR-7108-5p, miR-3656, miR-6879-5p, miR-6738-5p, miR-1260a, miR-4446-3p, miR-3131, miR-4463, miR-3185, miR-6870-5p, miR-6779-5p, miR-1273g-3p, miR-8059, miR-4697-5p, miR-4674, miR-4433-3p, miR-4257, miR-1915-5p, miR-4417, miR-1343-5p, miR-6781-5p, miR-4695-5p, miR-1237-5p, miR-6775-5p, miR-7845-5p, miR-4746-3p, miR-7641, miR-7847-3p, miR-6806-5p, miR-4467, miR-4726-5p, miR-4648, miR-6089, miR-1260b, miR-4532, miR-5195-3p, miR-3188, miR-6848-5p, miR-1233-5p, miR-6717-5p, miR-3195, miR-6757-5p, miR-8072, miR-4745-5p, miR-6511a-5p, miR-6776-5p, miR-371a-5p, miR-1227-5p, miR-7150, miR-1915-3p, miR-187-5p, miR-614, miR-1225-5p, miR-451a, miR-939-5p, miR-223-3p, miR-125a-3p, miR-92b-5p, miR-22-3p, miR-6073, miR-6845-5p, miR-6769b-5p, miR-4665-3p, miR-1913, miR-1228-3p, miR-940, miR-296-3p, miR-4690-5p, miR-548q, miR-663a, miR-1249, miR-1202, miR-7113-3p, miR-1225-3p, miR-4783-3p, miR-4448 and miR-4534.

(2) The kit according to (1), wherein miR-6768-5p is hsa-miR-6768-5p, miR-6836-3p is hsa-miR-6836-3p, miR-6782-5p is hsa-miR-6782-5p, miR-3663-3p is hsa-miR-3663-3p, miR-1908-3p is hsa-miR-1908-3p, miR-6726-5p is hsa-miR-6726-5p, miR-4258 is hsa-miR-4258, miR-1343-3p is hsa-miR-1343-3p, miR-4516 is hsa-miR-4516, miR-6875-5p is hsa-miR-6875-5p, miR-4651 is hsa-miR-4651, miR-6825-5p is hsa-miR-6825-5p, miR-6840-3p is hsa-miR-6840-3p, miR-6780b-5p is hsa-miR-6780b-5p, miR-6749-5p is hsa-miR-6749-5p, miR-8063 is hsa-miR-8063, miR-6784-5p is hsa-miR-6784-5p, miR-3679-5p is hsa-miR-3679-5p, miR-3184-5p is hsa-miR-3184-5p, miR-663b is hsa-miR-663b, miR-6880-5p is hsa-miR-6880-5p, miR-1908-5p is hsa-miR-1908-5p, miR-92a-2-5p is hsa-miR-92a-2-5p, miR-7975 is hsa-miR-7975, miR-7110-5p is hsa-miR-7110-5p, miR-6842-5p is hsa-miR-6842-5p, miR-6857-5p is hsa-miR-6857-5p, miR-5572 is hsa-miR-5572, miR-3197 is hsa-miR-3197, miR-6131 is hsa-miR-6131, miR-6889-5p is hsa-miR-6889-5p, miR-4454 is hsa-miR-4454, miR-1199-5p is hsa-miR-1199-5p, miR-1247-3p is hsa-miR-1247-3p, miR-6800-5p is hsa-miR-6800-5p, miR-6872-3p is hsa-miR-6872-3p, miR-4649-5p is hsa-miR-4649-5p, miR-6791-5p is hsa-miR-6791-5p, miR-4433b-3p is hsa-miR-4433b-3p, miR-3135b is hsa-miR-3135b, miR-128-2-5p is hsa-miR-128-2-5p, miR-4675 is hsa-miR-4675, miR-4472 is hsa-miR-4472, miR-6785-5p is hsa-miR-6785-5p, miR-6741-5p is hsa-miR-6741-5p, miR-7977 is hsa-miR-7977, miR-3665 is hsa-miR-3665, miR-128-1-5p is hsa-miR-128-1-5p, miR-4286 is hsa-miR-4286, miR-6765-3p is hsa-miR-6765-3p, miR-4632-5p is hsa-miR-4632-5p, miR-365a-5p is hsa-miR-365a-5p, miR-6088 is hsa-miR-6088, miR-6816-5p is hsa-miR-6816-5p, miR-6885-5p is hsa-miR-6885-5p, miR-711 is hsa-miR-711, miR-6765-5p is hsa-miR-6765-5p, miR-3180 is hsa-miR-3180, miR-4442 is hsa-miR-4442, miR-4792 is hsa-miR-4792, miR-6721-5p is hsa-miR-6721-5p, miR-6798-5p is hsa-miR-6798-5p, miR-3162-5p is hsa-miR-3162-5p, miR-6126 is hsa-miR-6126, miR-4758-5p is hsa-miR-4758-5p, miR-2392 is hsa-miR-2392, miR-486-3p is hsa-miR-486-3p, miR-6727-5p is hsa-miR-6727-5p, miR-4728-5p is hsa-miR-4728-5p, miR-6746-5p is hsa-miR-6746-5p, miR-4270 is hsa-miR-4270, miR-3940-5p is hsa-miR-3940-5p, miR-4725-3p is hsa-miR-4725-3p, miR-7108-5p is hsa-miR-7108-5p, miR-3656 is hsa-miR-3656, miR-6879-5p is hsa-miR-6879-5p, miR-6738-5p is hsa-miR-6738-5p, miR-1260a is hsa-miR-1260a, miR-4446-3p is hsa-miR-4446-3p, miR-3131 is hsa-miR-3131, miR-4463 is hsa-miR-4463, miR-3185 is hsa-miR-3185, miR-6870-5p is hsa-miR-6870-5p, miR-6779-5p is hsa-miR-6779-5p, miR-1273g-3p is hsa-miR-1273g-3p, miR-8059 is hsa-miR-8059, miR-4697-5p is hsa-miR-4697-5p, miR-4674 is hsa-miR-4674, miR-4433-3p is hsa-miR-4433-3p, miR-4257 is hsa-miR-4257, miR-1915-5p is hsa-miR-1915-5p, miR-4417 is hsa-miR-4417, miR-1343-5p is hsa-miR-1343-5p, miR-6781-5p is hsa-miR-6781-5p, miR-4695-5p is hsa-miR-4695-5p, miR-1237-5p is hsa-miR-1237-5p, miR-6775-5p is hsa-miR-6775-5p, miR-7845-5p is hsa-miR-7845-5p, miR-4746-3p is hsa-miR-4746-3p, miR-7641 is hsa-miR-7641, miR-7847-3p is hsa-miR-7847-3p, miR-6806-5p is hsa-miR-6806-5p, miR-4467 is hsa-miR-4467, miR-4726-5p is hsa-miR-4726-5p, miR-4648 is hsa-miR-4648, miR-6089 is hsa-miR-6089, miR-1260b is hsa-miR-1260b, miR-4532 is hsa-miR-4532, miR-5195-3p is hsa-miR-5195-3p, miR-3188 is hsa-miR-3188, miR-6848-5p is hsa-miR-6848-5p, miR-1233-5p is hsa-miR-1233-5p, miR-6717-5p is hsa-miR-6717-5p, miR-3195 is hsa-miR-3195, miR-6757-5p is hsa-miR-6757-5p, miR-8072 is hsa-miR-8072, miR-4745-5p is hsa-miR-4745-5p, miR-6511a-5p is hsa-miR-6511a-5p, miR-6776-5p is hsa-miR-6776-5p, miR-371a-5p is hsa-miR-371a-5p, miR-1227-5p is hsa-miR-1227-5p, miR-7150 is hsa-miR-7150, miR-1915-3p is hsa-miR-1915-3p, miR-187-5p is hsa-miR-187-5p, miR-614 is hsa-miR-614, miR-1225-5p is hsa-miR-1225-5p, miR-451a is hsa-miR-451a, miR-939-5p is hsa-miR-939-5p, miR-223-3p is hsa-miR-223-3p, miR-125a-3p is hsa-miR-125a-3p, miR-92b-5p is hsa-miR-92b-5p, miR-22-3p is hsa-miR-22-3p, miR-6073 is hsa-miR-6073, miR-6845-5p is hsa-miR-6845-5p, miR-6769b-5p is hsa-miR-6769b-5p, miR-4665-3p is hsa-miR-4665-3p, miR-1913 is hsa-miR-1913, miR-1228-3p is hsa-miR-1228-3p, miR-940 is hsa-miR-940, miR-296-3p is hsa-miR-296-3p, miR-4690-5p is hsa-miR-4690-5p, miR-548q is hsa-miR-548q, miR-663a is hsa-miR-663a, miR-1249 is hsa-miR-1249, miR-1202 is hsa-miR-1202, miR-7113-3p is hsa-miR-7113-3p, miR-1225-3p is hsa-miR-1225-3p, miR-4783-3p is hsa-miR-4783-3p, miR-4448 is hsa-miR-4448, and miR-4534 is hsa-miR-4534.

(3) The kit according to (1) or (2), wherein the nucleic acid is a polynucleotide selected from the group consisting of the following polynucleotides (a) to (e):

(a) a polynucleotide consisting of a nucleotide sequence represented by any of SEQ ID NOs: 1 to 125, 127 to 130, 132 to 134, and 561 to 578 or a nucleotide sequence derived from the nucleotide sequence by the replacement of u with t, a variant thereof, a derivative thereof, or a fragment thereof comprising 15 or more consecutive nucleotides, (b) a polynucleotide comprising a nucleotide sequence represented by any of SEQ ID NOs: 1 to 125, 127 to 130, 132 to 134, and 561 to 578, (c) a polynucleotide consisting of a nucleotide sequence complementary to a nucleotide sequence represented by any of SEQ ID NOs: 1 to 125, 127 to 130, 132 to 134, and 561 to 578 or a nucleotide sequence derived from the nucleotide sequence by the replacement of u with t, a variant thereof, a derivative thereof, or a fragment thereof comprising 15 or more consecutive nucleotides, (d) a polynucleotide comprising a nucleotide sequence complementary to a nucleotide sequence represented by any of SEQ ID NOs: 1 to 125, 127 to 130, 132 to 134, and 561 to 578 or a nucleotide sequence derived from the nucleotide sequence by the replacement of u with t, and (e) a polynucleotide hybridizing under stringent conditions to any of the polynucleotides (a) to (d).

(4) The kit according to any of (1) to (3), wherein the kit further comprises a nucleic acid capable of specifically binding to at least one or more polynucleotide(s) selected from the group consisting of other lung cancer markers miR-19b-3p, miR-1228-5p, and miR-1307-3p.

(5) The kit according to (4), wherein miR-19b-3p is hsa-miR-19b-3p, miR-1228-5p is hsa-miR-1228-5p, and miR-1307-3p is hsa-miR-1307-3p.

(6) The kit according to (4) or (5), wherein the nucleic acid is a polynucleotide selected from the group consisting of the following polynucleotides (f) to (j):
(f) a polynucleotide consisting of a nucleotide sequence represented by any of SEQ ID NOs: 126, 131, and 579 or a nucleotide sequence derived from the nucleotide sequence by the replacement of u with t, a variant thereof, a derivative thereof, or a fragment thereof comprising 15 or more consecutive nucleotides,
(g) a polynucleotide comprising a nucleotide sequence represented by any of SEQ ID NOs: 126, 131, and 579,
(h) a polynucleotide consisting of a nucleotide sequence complementary to a nucleotide sequence represented by any of SEQ ID NOs: 126, 131, and 579 or a nucleotide sequence derived from the nucleotide sequence by the replacement of u with t, a variant thereof, a derivative thereof, or a fragment thereof comprising 15 or more consecutive nucleotides, (i) a polynucleotide comprising a nucleotide sequence complementary to a nucleotide sequence represented by any of SEQ ID NOs: 126, 131, and 579 or a nucleotide sequence derived from the nucleotide sequence by the replacement of u with t, and
(j) a polynucleotide hybridizing under stringent conditions to any of the polynucleotides (f) to (i).

(7) The kit according to any of (1) to (6), wherein the kit further comprises a nucleic acid capable of specifically binding to at least one or more polynucleotide(s) selected from the group consisting of other lung cancer markers miR-4271, miR-642b-3p, miR-6075, miR-6125, miR-887-3p, miR-6851-5p, miR-6763-5p, miR-3928-3p, miR-4443, miR-3648, miR-149-3p, miR-4689, miR-4763-3p, miR-6729-5p, miR-3196, miR-8069, miR-1268a, miR-4739, miR-1268b, miR-5698, miR-6752-5p, miR-4507, miR-564, miR-4497, miR-6877-5p, miR-6087, miR-4731-5p, miR-615-5p, miR-760, miR-6891-5p, miR-6887-5p, miR-4525, miR-1914-3p, miR-619-5p, miR-5001-5p, miR-6722-3p, miR-3621, miR-4298, miR-675-5p and miR-4655-5p.

(8) The kit according to (7), wherein miR-4271 is hsa-miR-4271, miR-642b-3p is hsa-miR-642b-3p, miR-6075 is hsa-miR-6075, miR-6125 is hsa-miR-6125, miR-887-3p is hsa-miR-887-3p, miR-6851-5p is hsa-miR-6851-5p, miR-6763-5p is hsa-miR-6763-5p, miR-3928-3p is hsa-miR-3928-3p, miR-4443 is hsa-miR-4443, miR-3648 is hsa-miR-3648, miR-149-3p is hsa-miR-149-3p, miR-4689 is hsa-miR-4689, miR-4763-3p is hsa-miR-4763-3p, miR-6729-5p is hsa-miR-6729-5p, miR-3196 is hsa-miR-3196, miR-8069 is hsa-miR-8069, miR-1268a is hsa-miR-1268a, miR-4739 is hsa-miR-4739, miR-1268b is hsa-miR-1268b, miR-5698 is hsa-miR-5698, miR-6752-5p is hsa-miR-6752-5p, miR-4507 is hsa-miR-4507, miR-564 is hsa-miR-564, miR-4497 is hsa-miR-4497, miR-6877-5p is hsa-miR-6877-5p, miR-6087 is hsa-miR-6087, miR-4731-5p is hsa-miR-4731-5p, miR-615-5p is hsa-miR-615-5p, miR-760 is hsa-miR-760, miR-6891-5p is hsa-miR-6891-5p, miR-6887-5p is hsa-miR-6887-5p, miR-4525 is hsa-miR-4525, miR-1914-3p is hsa-miR-1914-3p, miR-619-5p is hsa-miR-619-5p, miR-5001-5p is hsa-miR-5001-5p, miR-6722-3p is hsa-miR-6722-3p, miR-3621 is hsa-miR-3621, miR-4298 is hsa-miR-4298, miR-675-5p is hsa-miR-675-5p, and miR-4655-5p is hsa-miR-4655-5p.

(9) The kit according to (7) or (8), wherein the nucleic acid is a polynucleotide selected from the group consisting of the following polynucleotides (k) to (o):
(k) a polynucleotide consisting of a nucleotide sequence represented by any of SEQ ID NOs: 135 to 174 or a nucleotide sequence derived from the nucleotide sequence by the replacement of u with t, a variant thereof, a derivative thereof, or a fragment thereof comprising 15 or more consecutive nucleotides,
(l) a polynucleotide comprising a nucleotide sequence represented by any of SEQ ID NOs: 135 to 174,
(m) a polynucleotide consisting of a nucleotide sequence complementary to a nucleotide sequence represented by any of SEQ ID NOs: 135 to 174 or a nucleotide sequence derived from the nucleotide sequence by the replacement of u with t, a variant thereof, a derivative thereof, or a fragment thereof comprising 15 or more consecutive nucleotides,
(n) a polynucleotide comprising a nucleotide sequence complementary to a nucleotide sequence represented by any of SEQ ID NOs: 135 to 174 or a nucleotide sequence derived from the nucleotide sequence by the replacement of u with t, and
(o) a polynucleotide hybridizing under stringent conditions to any of the polynucleotides (k) to (n).

(10) The kit according to any one of (1) to (9), wherein the kit comprises at least two or more nucleic acids capable of specifically binding to at least two or more polynucleotides, respectively, selected from the group consisting of all of the lung cancer markers according to (1) or (2).

(11) A device for the detection of lung cancer, comprising a nucleic acid capable of specifically binding to at least one or more polynucleotide(s) selected from the group consisting of lung cancer markers miR-6768-5p, miR-6836-3p, miR-6782-5p, miR-3663-3p, miR-1908-3p, miR-6726-5p, miR-4258, miR-1343-3p, miR-4516, miR-6875-5p, miR-4651, miR-6825-5p, miR-6840-3p, miR-6780b-5p, miR-6749-5p, miR-8063, miR-6784-5p, miR-3679-5p, miR-3184-5p, miR-663b, miR-6880-5p, miR-1908-5p, miR-92a-2-5p, miR-7975, miR-7110-5p, miR-6842-5p, miR-6857-5p, miR-5572, miR-3197, miR-6131, miR-6889-5p, miR-4454, miR-1199-5p, miR-1247-3p, miR-6800-5p, miR-6872-3p, miR-4649-5p, miR-6791-5p, miR-4433b-3p, miR-3135b, miR-128-2-5p, miR-4675, miR-4472, miR-6785-5p, miR-6741-5p, miR-7977, miR-3665, miR-128-1-5p, miR-4286, miR-6765-3p, miR-4632-5p, miR-365a-5p, miR-6088, miR-6816-5p, miR-6885-5p, miR-711, miR-6765-5p, miR-3180, miR-4442, miR-4792, miR-6721-5p, miR-6798-5p, miR-3162-5p, miR-6126, miR-4758-5p, miR-2392, miR-486-3p, miR-6727-5p, miR-4728-5p, miR-6746-5p, miR-4270, miR-3940-5p, miR-4725-3p, miR-7108-5p, miR-3656, miR-6879-5p, miR-6738-5p, miR-1260a, miR-4446-3p, miR-3131, miR-4463, miR-3185, miR-6870-5p, miR-6779-5p, miR-1273g-3p, miR-8059, miR-4697-5p, miR-4674, miR-4433-3p, miR-4257, miR-1915-5p, miR-4417, miR-1343-5p, miR-6781-5p, miR-4695-5p, miR-1237-5p, miR-6775-5p, miR-7845-5p, miR-4746-3p, miR-7641, miR-7847-3p, miR-6806-5p, miR-4467, miR-4726-5p, miR-4648, miR-6089, miR-1260b, miR-4532, miR-5195-3p, miR-3188, miR-6848-5p, miR-1233-5p, miR-6717-5p, miR-3195, miR-6757-5p, miR-8072, miR-4745-5p, miR-6511a-5p, miR-6776-5p, miR-371a-5p, miR-1227-5p, miR-7150, miR-1915-3p, miR-187-5p, miR-614, miR-1225-5p, miR-451a, miR-939-5p, miR-223-3p, miR-125a-

3p, miR-92b-5p, miR-22-3p, miR-6073, miR-6845-5p, miR-6769b-5p, miR-4665-3p, miR-1913, miR-1228-3p, miR-940, miR-296-3p, miR-4690-5p, miR-548q, miR-663a, miR-1249, miR-1202, miR-7113-3p, miR-1225-3p, miR-4783-3p, miR-4448 and miR-4534.

(12) The device according to (11), wherein miR-6768-5p is hsa-miR-6768-5p, miR-6836-3p is hsa-miR-6836-3p, miR-6782-5p is hsa-miR-6782-5p, miR-3663-3p is hsa-miR-3663-3p, miR-1908-3p is hsa-miR-1908-3p, miR-6726-5p is hsa-miR-6726-5p, miR-4258 is hsa-miR-4258, miR-1343-3p is hsa-miR-1343-3p, miR-4516 is hsa-miR-4516, miR-6875-5p is hsa-miR-6875-5p, miR-4651 is hsa-miR-4651, miR-6825-5p is hsa-miR-6825-5p, miR-6840-3p is hsa-miR-6840-3p, miR-6780b-5p is hsa-miR-6780b-5p, miR-6749-5p is hsa-miR-6749-5p, miR-8063 is hsa-miR-8063, miR-6784-5p is hsa-miR-6784-5p, miR-3679-5p is hsa-miR-3679-5p, miR-3184-5p is hsa-miR-3184-5p, miR-663b is hsa-miR-663b, miR-6880-5p is hsa-miR-6880-5p, miR-1908-5p is hsa-miR-1908-5p, miR-92a-2-5p is hsa-miR-92a-2-5p, miR-7975 is hsa-miR-7975, miR-7110-5p is hsa-miR-7110-5p, miR-6842-5p is hsa-miR-6842-5p, miR-6857-5p is hsa-miR-6857-5p, miR-5572 is hsa-miR-5572, miR-3197 is hsa-miR-3197, miR-6131 is hsa-miR-6131, miR-6889-5p is hsa-miR-6889-5p, miR-4454 is hsa-miR-4454, miR-1199-5p is hsa-miR-1199-5p, miR-1247-3p is hsa-miR-1247-3p, miR-6800-5p is hsa-miR-6800-5p, miR-6872-3p is hsa-miR-6872-3p, miR-4649-5p is hsa-miR-4649-5p, miR-6791-5p is hsa-miR-6791-5p, miR-4433b-3p is hsa-miR-4433b-3p, miR-3135b is hsa-miR-3135b, miR-128-2-5p is hsa-miR-128-2-5p, miR-4675 is hsa-miR-4675, miR-4472 is hsa-miR-4472, miR-6785-5p is hsa-miR-6785-5p, miR-6741-5p is hsa-miR-6741-5p, miR-7977 is hsa-miR-7977, miR-3665 is hsa-miR-3665, miR-128-1-5p is hsa-miR-128-1-5p, miR-4286 is hsa-miR-4286, miR-6765-3p is hsa-miR-6765-3p, miR-4632-5p is hsa-miR-4632-5p, miR-365a-5p is hsa-miR-365a-5p, miR-6088 is hsa-miR-6088, miR-6816-5p is hsa-miR-6816-5p, miR-6885-5p is hsa-miR-6885-5p, miR-711 is hsa-miR-711, miR-6765-5p is hsa-miR-6765-5p, miR-3180 is hsa-miR-3180, miR-4442 is hsa-miR-4442, miR-4792 is hsa-miR-4792, miR-6721-5p is hsa-miR-6721-5p, miR-6798-5p is hsa-miR-6798-5p, miR-3162-5p is hsa-miR-3162-5p, miR-6126 is hsa-miR-6126, miR-4758-5p is hsa-miR-4758-5p, miR-2392 is hsa-miR-2392, miR-486-3p is hsa-miR-486-3p, miR-6727-5p is hsa-miR-6727-5p, miR-4728-5p is hsa-miR-4728-5p, miR-6746-5p is hsa-miR-6746-5p, miR-4270 is hsa-miR-4270, miR-3940-5p is hsa-miR-3940-5p, miR-4725-3p is hsa-miR-4725-3p, miR-7108-5p is hsa-miR-7108-5p, miR-3656 is hsa-miR-3656, miR-6879-5p is hsa-miR-6879-5p, miR-6738-5p is hsa-miR-6738-5p, miR-1260a is hsa-miR-1260a, miR-4446-3p is hsa-miR-4446-3p, miR-3131 is hsa-miR-3131, miR-4463 is hsa-miR-4463, miR-3185 is hsa-miR-3185, miR-6870-5p is hsa-miR-6870-5p, miR-6779-5p is hsa-miR-6779-5p, miR-1273g-3p is hsa-miR-1273g-3p, miR-8059 is hsa-miR-8059, miR-4697-5p is hsa-miR-4697-5p, miR-4674 is hsa-miR-4674, miR-4433-3p is hsa-miR-4433-3p, miR-4257 is hsa-miR-4257, miR-1915-5p is hsa-miR-1915-5p, miR-4417 is hsa-miR-4417, miR-1343-5p is hsa-miR-1343-5p, miR-6781-5p is hsa-miR-6781-5p, miR-4695-5p is hsa-miR-4695-5p, miR-1237-5p is hsa-miR-1237-5p, miR-6775-5p is hsa-miR-6775-5p, miR-7845-5p is hsa-miR-7845-5p, miR-4746-3p is hsa-miR-4746-3p, miR-7641 is hsa-miR-7641, miR-7847-3p is hsa-miR-7847-3p, miR-6806-5p is hsa-miR-6806-5p, miR-4467 is hsa-miR-4467, miR-4726-5p is hsa-miR-4726-5p, miR-4648 is hsa-miR-4648, miR-6089 is hsa-miR-6089, miR-1260b is hsa-miR-1260b, miR-4532 is hsa-miR-4532, miR-5195-3p is hsa-miR-5195-3p, miR-3188 is hsa-miR-3188, miR-6848-5p is hsa-miR-6848-5p, miR-1233-5p is hsa-miR-1233-5p, miR-6717-5p is hsa-miR-6717-5p, miR-3195 is hsa-miR-3195, miR-6757-5p is hsa-miR-6757-5p, miR-8072 is hsa-miR-8072, miR-4745-5p is hsa-miR-4745-5p, miR-6511a-5p is hsa-miR-6511a-5p, miR-6776-5p is hsa-miR-6776-5p, miR-371a-5p is hsa-miR-371a-5p, miR-1227-5p is hsa-miR-1227-5p, miR-7150 is hsa-miR-7150, miR-1915-3p is hsa-miR-1915-3p, miR-187-5p is hsa-miR-187-5p, miR-614 is hsa-miR-614, miR-1225-5p is hsa-miR-1225-5p, miR-451a is hsa-miR-451a, miR-939-5p is hsa-miR-939-5p, miR-223-3p is hsa-miR-223-3p, miR-125a-3p is hsa-miR-125a-3p, miR-92b-5p is hsa-miR-92b-5p, miR-22-3p is hsa-miR-22-3p, miR-6073 is hsa-miR-6073, miR-6845-5p is hsa-miR-6845-5p, miR-6769b-5p is hsa-miR-6769b-5p, miR-4665-3p is hsa-miR-4665-3p, miR-1913 is hsa-miR-1913, miR-1228-3p is hsa-miR-1228-3p, miR-940 is hsa-miR-940, miR-296-3p is hsa-miR-296-3p, miR-4690-5p is hsa-miR-4690-5p, miR-548q is hsa-miR-548q, miR-663a is hsa-miR-663a, miR-1249 is hsa-miR-1249, miR-1202 is hsa-miR-1202, miR-7113-3p is hsa-miR-7113-3p, miR-1225-3p is hsa-miR-1225-3p, miR-4783-3p is hsa-miR-4783-3p, miR-4448 is hsa-miR-4448, and miR-4534 is hsa-miR-4534.

(13) The device according to (11) or (12), wherein the nucleic acid is a polynucleotide selected from the group consisting of the following polynucleotides (a) to (e):
 (a) a polynucleotide consisting of a nucleotide sequence represented by any of SEQ ID NOs: 1 to 125, 127 to 130, 132 to 134, and 561 to 578 or a nucleotide sequence derived from the nucleotide sequence by the replacement of u with t, a variant thereof, a derivative thereof, or a fragment thereof comprising 15 or more consecutive nucleotides,
 (b) a polynucleotide comprising a nucleotide sequence represented by any of SEQ ID NOs: 1 to 125, 127 to 130, 132 to 134, and 561 to 578,
 (c) a polynucleotide consisting of a nucleotide sequence complementary to a nucleotide sequence represented by any of SEQ ID NOs: 1 to 125, 127 to 130, 132 to 134, and 561 to 578 or a nucleotide sequence derived from the nucleotide sequence by the replacement of u with t, a variant thereof, a derivative thereof, or a fragment thereof comprising 15 or more consecutive nucleotides,
 (d) a polynucleotide comprising a nucleotide sequence complementary to a nucleotide sequence represented by any of SEQ ID NOs: 1 to 125, 127 to 130, 132 to 134, and 561 to 578 or a nucleotide sequence derived from the nucleotide sequence by the replacement of u with t, and (e) a polynucleotide hybridizing under stringent conditions to any of the polynucleotides (a) to (d).

(14) The device according to any of (11) to (13), wherein the device further comprises a nucleic acid capable of specifically binding to at least one or more polynucleotide(s) selected from the group consisting of other lung cancer markers miR-19b-3p, miR-1228-5p, and miR-1307-3p.

(15) The device according to (14), wherein miR-19b-3p is hsa-miR-19b-3p, miR-1228-5p is hsa-miR-1228-5p, and miR-1307-3p is hsa-miR-1307-3p.

(16) The device according to (14) or (15), wherein the nucleic acid is a polynucleotide selected from the group consisting of the following polynucleotides (f) to (j):
 (f) a polynucleotide consisting of a nucleotide sequence represented by any of SEQ ID NOs: 126, 131, and 579 or a nucleotide sequence derived from the nucleotide sequence by the replacement of u with t, a variant thereof, a derivative thereof, or a fragment thereof comprising 15 or more consecutive nucleotides, (g) a polynucleotide comprising a nucleotide sequence represented by any of SEQ ID NOs: 126, 131, and 579, (h) a polynucleotide consisting of a nucleotide sequence complementary to a nucleotide sequence represented by any of SEQ ID NOs: 126, 131, and 579 or a nucleotide sequence derived from the nucleotide sequence by the replacement of u with t, a variant thereof, a derivative thereof, or a fragment thereof comprising 15 or more consecutive nucleotides, (i) a polynucleotide comprising a nucleotide sequence complementary to a nucleotide sequence represented by any of SEQ ID NOs: 126, 131, and 579 or a nucleotide sequence derived from the nucleotide sequence by the replacement of u with t, and (j) a polynucleotide hybridizing under stringent conditions to any of the polynucleotides (f) to (i).

(17) The device according to any of (11) to (16), wherein the device further comprises a nucleic acid capable of specifically binding to at least one or more polynucleotide(s) selected from the group consisting of other lung cancer markers miR-4271, miR-642b-3p, miR-6075, miR-6125, miR-887-3p, miR-6851-5p, miR-6763-5p, miR-3928-3p, miR-4443, miR-3648, miR-149-3p, miR-4689, miR-4763-3p, miR-6729-5p, miR-3196, miR-8069, miR-1268a, miR-4739, miR-1268b, miR-5698, miR-6752-5p, miR-4507, miR-564, miR-4497, miR-6877-5p, miR-6087, miR-4731-5p, miR-615-5p, miR-760, miR-6891-5p, miR-6887-5p, miR-4525, miR-1914-3p, miR-619-5p, miR-5001-5p, miR-6722-3p, miR-3621, miR-4298, miR-675-5p and miR-4655-5p.

(18) The device according to (17), wherein miR-4271 is hsa-miR-4271, miR-642b-3p is hsa-miR-642b-3p, miR-6075 is hsa-miR-6075, miR-6125 is hsa-miR-6125, miR-887-3p is hsa-miR-887-3p, miR-6851-5p is hsa-miR-6851-5p, miR-6763-5p is hsa-miR-6763-5p, miR-3928-3p is hsa-miR-3928-3p, miR-4443 is hsa-miR-4443, miR-3648 is hsa-miR-3648, miR-149-3p is hsa-miR-149-3p, miR-4689 is hsa-miR-4689, miR-4763-3p is hsa-miR-4763-3p, miR-6729-5p is hsa-miR-6729-5p, miR-3196 is hsa-miR-3196, miR-8069 is hsa-miR-8069, miR-1268a is hsa-miR-1268a, miR-4739 is hsa-miR-4739, miR-1268b is hsa-miR-1268b, miR-5698 is hsa-miR-5698, miR-6752-5p is hsa-miR-6752-5p, miR-4507 is hsa-miR-4507, miR-564 is hsa-miR-564, miR-4497 is hsa-miR-4497, miR-6877-5p is hsa-miR-6877-5p, miR-6087 is hsa-miR-6087, miR-4731-5p is hsa-miR-4731-5p, miR-615-5p is hsa-miR-615-5p, miR-760 is hsa-miR-760, miR-6891-5p is hsa-miR-6891-5p, miR-6887-5p is hsa-miR-6887-5p, miR-4525 is hsa-miR-4525, miR-1914-3p is hsa-miR-1914-3p, miR-619-5p is hsa-miR-619-5p, miR-5001-5p is hsa-miR-5001-5p, miR-6722-3p is hsa-miR-6722-3p, miR-3621 is hsa-miR-3621, miR-4298 is hsa-miR-4298, miR-675-5p is hsa-miR-675-5p, and miR-4655-5p is hsa-miR-4655-5p.

(19) The device according to (17) or (18), wherein the nucleic acid is a polynucleotide selected from the group consisting of the following polynucleotides (k) to (o):

(k) a polynucleotide consisting of a nucleotide sequence represented by any of SEQ ID NOs: 135 to 174 or a nucleotide sequence derived from the nucleotide sequence by the replacement of u with t, a variant thereof, a derivative thereof, or a fragment thereof comprising 15 or more consecutive nucleotides, (l) a polynucleotide comprising a nucleotide sequence represented by any of SEQ ID NOs: 135 to 174, (m) a polynucleotide consisting of a nucleotide sequence complementary to a nucleotide sequence represented by any of SEQ ID NOs: 135 to 174 or a nucleotide sequence derived from the nucleotide sequence by the replacement of u with t, a variant thereof, a derivative thereof, or a fragment thereof comprising 15 or more consecutive nucleotides, (n) a polynucleotide comprising a nucleotide sequence complementary to a nucleotide sequence represented by any of SEQ ID NOs: 135 to 174 or a nucleotide sequence derived from the nucleotide sequence by the replacement of u with t, and (o) a polynucleotide hybridizing under stringent conditions to any of the polynucleotides (k) to (n).

(20) The device according to any one of (11) to (19), wherein the device is a device for measurement by a hybridization technique.

(21) The device according to (20), wherein the hybridization technique is a nucleic acid array technique.

(22) The device according to any one of (11) to (21), wherein the device comprises at least two or more nucleic acids capable of specifically binding to at least two or more polynucleotides, respectively, selected from all of the lung cancer markers according to (11) or (12).

(23) A method for detecting lung cancer, comprising measuring an expression level of a target nucleic acid in a sample from a subject using a kit according to any one of (1) to (10) or a device according to any one of (11) to (22), and evaluating in vitro whether or not the subject has lung cancer using both of the measured expression level and a control expression level in a sample from a healthy subject measured in the same way.

(24) The method according to (23), wherein the subject is a human.

(25) The method according to (23) or (24), wherein the sample is blood, serum, or plasma.

Definition of Terms

The terms used herein are defined as follows.

Abbreviations or terms such as nucleotide, polynucleotide, DNA, and RNA abide by "Guidelines for the preparation of specification which contain nucleotide and/or amino acid sequences" (edited by Japan Patent Office) and common use in the art.

The term "polynucleotide" used herein is used for a nucleic acid including any of RNA, DNA, and RNA/DNA (chimera). The DNA includes any of cDNA, genomic DNA, and synthetic DNA. The RNA includes any of total RNA, mRNA, rRNA, miRNA, siRNA, snoRNA, snRNA, non-coding RNA and synthetic RNA. Here the "synthetic DNA" and the "synthetic RNA" refer to DNA and RNA artificially prepared using, for example, an automatic nucleic acid synthesizer, on the basis of predetermined nucleotide sequences (which may be any of natural and non-natural sequences). The "non-natural sequence" is intended to be used in a broad sense and includes, for example, a sequence comprising substitution, deletion, insertion, and/or addition of one or more nucleotide(s) (i.e., a variant sequence) and a sequence comprising one or more modified nucleotide(s) (i.e., a modified sequence), which are different from the natural sequence. Herein, the term "polynucleotide" is used interchangeably with the term "nucleic acid".

The term "fragment" used herein is a polynucleotide having a nucleotide sequence that consists of a consecutive portion of a polynucleotide and desirably has a length of 15 or more nucleotides, preferably 17 or more nucleotides, more preferably 19 or more nucleotides.

The term "gene" used herein is intended to include not only RNA and double-stranded DNA but each single-stranded DNA such as a plus strand (or a sense strand) or a complementary strand (or an antisense strand) constituting the duplex. The gene is not particularly limited by its length.

Thus, the "gene" used herein includes any of double-stranded DNA including human genomic DNA, single-stranded DNA (plus strand), single-stranded DNA having a sequence complementary to the plus strand (complementary strand) including cDNA, microRNA (miRNA), and their fragments, and transcripts, unless otherwise specified. The "gene" includes not only a "gene" represented by a particular nucleotide sequence (or SEQ ID NO) but "nucleic acids" encoding RNAs having biological functions equivalent to an RNA encoded by the gene, for example, a congener (i.e., a homolog or an ortholog), a variant (e.g., a genetic polymorph), and a derivative. Specific examples of such a "nucleic acid" encoding a congener, a variant, or a derivative can include a "nucleic acid" having a nucleotide sequence hybridizing under stringent conditions described later to a complementary sequence of a nucleotide sequence represented by any of SEQ ID NOs: 1 to 618, or a nucleotide sequence derived from the nucleotide sequence by the replacement of u with t. The "gene" is not particularly limited by its functional region and can contain, for example, an expression regulatory region, a coding region, an exon, or an intron. The "gene" may be contained in a cell or may exist alone after being released into the outside of a cell. Alternatively, the "gene" may be in a state enclosed in a vesicle called exosome.

The term "exosome" used herein is a vesicle that is encapsulated by a lipid bilayer and secreted from a cell. The exosome is derived from a multivesicular endosome and may incorporate biomaterials such as a "gene" (e.g., RNA or DNA) or a protein when released into an extracellular environment. The exosome is known to be contained in a body fluid such as blood, serum, plasma, or lymph.

The term "transcript" used herein refers to an RNA synthesized with the DNA sequence of a gene as a template. RNA polymerase binds to a site called a promoter located upstream of the gene and adds ribonucleotides complementary to the nucleotide sequence of the DNA to the 3' end to synthesize RNA. This RNA contains not only the gene itself but also the whole sequence from a transcription initiation site to the end of a polyA sequence, including an expression regulatory region, a coding region, an exon, or an intron.

The term "microRNA (miRNA)" used herein is intended to mean a 15- to 25-nucleotide non-coding RNA that is involved in the suppression of translation of mRNA, and that transcribed as an RNA precursor having a hairpin-like structure, cleaved by a dsRNA-cleaving enzyme which has RNase III cleavage activity, and integrated into a protein complex called RISC, unless otherwise specified. The term "miRNA" used herein includes not only a "miRNA" represented by a particular nucleotide sequence (or SEQ ID NO) but a precursor of the "miRNA" (pre-miRNA or pri-miRNA), and miRNAs having biological functions equivalent thereto, for example, a congener (i.e., a homolog or an ortholog), a variant (e.g., a genetic polymorph), and a derivative. Such a precursor, a congener, a variant, or a derivative can be specifically identified using miRBase Release 20 (http://www.mirbase.org/), and examples thereof can include a "miRNA" having a nucleotide sequence hybridizing under stringent conditions described later to a complementary sequence of any particular nucleotide sequence represented by any of SEQ ID NOs: 1 to 618. The term "miRNA" used herein may be a gene product of a miR gene. Such a gene product includes a mature miRNA (e.g., a 15- to 25-nucleotide or 19- to 25-nucleotide non-coding RNA involved in the suppression of translation of mRNA as described above) or a miRNA precursor (e.g., pre-miRNA or pri-miRNA as described above).

The term "probe" used herein includes a polynucleotide that is used for specifically detecting RNA resulting from the expression of a gene or a polynucleotide derived from the RNA, and/or a polynucleotide complementary thereto.

The term "primer" used herein includes a polynucleotide that specifically recognizes and amplifies RNA resulting from the expression of a gene or a polynucleotide derived from the RNA, and/or a polynucleotide complementary thereto.

In this context, the complementary polynucleotide (complementary strand or reverse strand) means a polynucleotide in a complementary base relationship of A:T (U) and G:C base pairs with the full-length sequence of a polynucleotide consisting of a nucleotide sequence defined by any of SEQ ID NOs: 1 to 618 or a nucleotide sequence derived from the nucleotide sequence by the replacement of u with t, or a partial sequence thereof (here, this full-length or partial sequence is referred to as a plus strand for the sake of convenience). However, such a complementary strand is not limited to a sequence completely complementary to the nucleotide sequence of the target plus strand and may have a complementary relationship to an extent that permits hybridization under stringent conditions to the target plus strand.

The term "stringent conditions" used herein refers to conditions under which a nucleic acid probe hybridizes to its target sequence to a larger extent (e.g., a measurement value equal to or larger than a mean of background measurement values+a standard deviation of the background measurement values×2) than that for other sequences. The stringent conditions are dependent on a sequence and differ depending on an environment where hybridization is performed. A target sequence that is 100% complementary to the nucleic acid probe can be identified by controlling the stringency of hybridization and/or washing conditions. Specific examples of the "stringent conditions" will be mentioned later.

The term "Tm value" used herein means a temperature at which the double-stranded moiety of a polynucleotide is denatured into single strands so that the double strands and the single strands exist at a ratio of 1:1.

The term "variant" used herein means, in the case of a nucleic acid, a natural variant attributed to polymorphism, mutation, or the like; a variant containing the deletion, substitution, addition, or insertion of 1, 2, or 3 or more nucleotides in a nucleotide sequence represented by any of SEQ ID NOs: 1 to 618 or a nucleotide sequence derived from the nucleotide sequence by the replacement of u with t, or a partial sequence thereof; a variant containing the deletion, substitution, addition, or insertion of 1 or 2 or more nucleotides in a nucleotide sequence of a premature miRNA of a sequence represented by any of SEQ ID NOs: 1 to 618 or a nucleotide sequence derived from the nucleotide sequence by the replacement of u with t, or a partial sequence thereof; a variant that exhibits identity of approximately 90% or higher, approximately 95% or higher, approximately 97% or higher, approximately 98% or higher, approximately 99% or higher to each of these nucleotide sequences or the partial sequence thereof; or a nucleic acid hybridizing under the stringent conditions defined above to a polynucleotide or an oligonucleotide comprising each of these nucleotide sequences or the partial sequence thereof.

The term "several" used herein means an integer of approximately 10, 9, 8, 7, 6, 5, 4, 3, or 2.

The variant used herein can be prepared by use of a well-known technique such as site-directed mutagenesis or PCR-based mutagenesis.

The term "identity" used herein can be determined with or without an introduced gap, using a protein or gene search system based on BLAST or FASTA described above (Zheng Zhang et al., 2000, J. Comput. Biol., Vol. 7, p. 203-214; Altschul, S. F. et al., 1990, Journal of Molecular Biology, Vol. 215, p. 403-410; and Pearson, W. R. et al., 1988, Proc. Natl. Acad. Sci. U.S.A., Vol. 85, p. 2444-2448).

The term "derivative" used herein is meant to include a modified nucleic acid, for example, a derivative labeled with a fluorophore or the like, a derivative containing a modified nucleotide (e.g., a nucleotide containing a group such as halogen, alkyl such as methyl, alkoxy such as methoxy, thio, or carboxymethyl, and a nucleotide that has undergone base rearrangement, double bond saturation, deamination, replacement of an oxygen molecule with a sulfur atom, etc.), PNA (peptide nucleic acid; Nielsen, P. E. et al., 1991, Science, Vol. 254, p. 1497-500), and LNA (locked nucleic acid; Obika, S. et al., 1998, Tetrahedron Lett., Vol. 39, p. 5401-5404) without any limitation.

As used herein, the "nucleic acid" capable of specifically binding to a polynucleotide selected from the lung cancer marker miRNAs described above is a synthesized or prepared nucleic acid and specifically includes a "nucleic acid probe" or a "primer". The "nucleic acid" is utilized directly or indirectly for detecting the presence or absence of lung cancer in a subject, for diagnosing the presence or absence of lung cancer, the severity of lung cancer, the presence or absence of amelioration or the degree of amelioration of lung cancer, or the sensitivity of lung cancer for treatment, or for screening for a candidate substance useful in the prevention, amelioration, or treatment of lung cancer. The "nucleic acid" includes a nucleotide, an oligonucleotide, and a polynucleotide capable of specifically recognizing and binding to a transcript represented by any of SEQ ID NOs: 1 to 618 or a synthetic cDNA nucleic acid thereof in vivo, particularly, in a sample such as a body fluid (e.g., blood or urine), in relation to the development of lung cancer. The nucleotide, the oligonucleotide, and the polynucleotide can be effectively used as probes for detecting the aforementioned gene expressed in vivo, in tissues, in cells, or the like on the basis of the properties described above, or as primers for amplifying the aforementioned gene expressed in vivo.

The term "detection" used herein is interchangeable with the term "examination", "measurement", "detection", or "decision support". As used herein, the term "evaluation" is meant to include diagnosing or evaluation-supporting on the basis of examination results or measurement results.

The term "subject" used herein means a mammal such as a primate including a human and a chimpanzee, a pet animal including a dog and a cat, a livestock animal including cattle, a horse, sheep, and a goat, and a rodent including a mouse and a rat. The term "healthy subject" also means such a mammal without the cancer to be detected.

The term "P" or "P value" used herein refers to a probability at which a more extreme statistic than that actually calculated from data under null hypothesis is observed in a statistical test. Thus, smaller "P" or "P value" means more significant difference between subjects to be compared.

The term "sensitivity" used herein means a value of (the number of true positives)/(the number of true positives+the number of false negatives). High sensitivity allows lung cancer to be detected early, leading to the complete resection of cancer sites and reduction in the rate of recurrence.

The term "specificity" used herein means a value of (the number of true negatives)/(the number of true negatives+the number of false positives). High specificity prevents needless extra examination for healthy subjects misjudged as being lung cancer patients, leading to reduction in burden on patients and reduction in medical expense.

The term "accuracy" used herein means a value of (the number of true positives+the number of true negatives)/(the total number of cases). The accuracy indicates the ratio of samples that correctly identified in the discriminant results to all samples, and serves as a primary index for evaluating detection performance.

As used herein, the "sample" that is subject to determination, detection, or diagnosis refers to a tissue and a biological material in which the expression of the gene of the present invention varies as lung cancer develops, lung cancer progresses, and therapeutic effects on lung cancer are exerted. Specifically, the "sample" refers to a lung tissue, a peripulmonary vascular channel, lymph node, and organ, an organ suspected of having metastasis, the skin, a body fluid such as blood, urine, saliva, sweat, or tissue exudates, serum or plasma prepared from blood, feces, hair, and the like. The "sample" further refers to a biological sample extracted therefrom, specifically, a gene such as RNA or miRNA.

The term "hsa-miR-6768-5p gene" or "hsa-miR-6768-5p" used herein includes the hsa-miR-6768-5p gene (miRBase Accession No. MIMAT0027436) described in SEQ ID NO: 1, a homolog or an ortholog of a different organism species, and the like. The hsa-miR-6768-5p gene can be obtained by a method described in Ladewig E et al., 2012, Genome Res, Vol. 22, p. 1634-1645. Also, "hsa-mir-6768" (miRBase Accession No. MI0022613, SEQ ID NO: 175) having a hairpin-like structure is known as a precursor of "hsa-miR-6768-5p".

The term "hsa-miR-6836-3p gene" or "hsa-miR-6836-3p" used herein includes the hsa-miR-6836-3p gene (miRBase Accession No. MIMAT0027575) described in SEQ ID NO: 2, a homolog or an ortholog of a different organism species, and the like. The hsa-miR-6836-3p gene can be obtained by a method described in Ladewig E et al., 2012, Genome Res, Vol. 22, p. 1634-1645. Also, "hsa-mir-6836" (miRBase Accession No. MI0022682, SEQ ID NO: 176) having a hairpin-like structure is known as a precursor of "hsa-miR-6836-3p".

The term "hsa-miR-6782-5p gene" or "hsa-miR-6782-5p" used herein includes the hsa-miR-6782-5p gene (miRBase Accession No. MIMAT0027464) described in SEQ ID NO: 3, a homolog or an ortholog of a different organism species, and the like. The hsa-miR-6782-5p gene can be obtained by a method described in Ladewig E et al., 2012, Genome Res, Vol. 22, p. 1634-1645. Also, "hsa-mir-6782" (miRBase Accession No. MI0022627, SEQ ID NO: 177) having a hairpin-like structure is known as a precursor of "hsa-miR-6782-5p".

The term "hsa-miR-3663-3p gene" or "hsa-miR-3663-3p" used herein includes the hsa-miR-3663-3p gene (miRBase Accession No. MIMAT0018085) described in SEQ ID NO: 4, a homolog or an ortholog of a different organism species, and the like. The hsa-miR-3663-3p gene can be obtained by a method described in Liao J Y et al., 2010, PLoS One, Vol. 5, e10563. Also, "hsa-mir-3663" (miRBase Accession No.

MI0016064, SEQ ID NO: 178) having a hairpin-like structure is known as a precursor of "hsa-miR-3663-3p".

The term "hsa-miR-1908-3p gene" or "hsa-miR-1908-3p" used herein includes the hsa-miR-1908-3p gene (miRBase Accession No. MIMAT0026916) described in SEQ ID NO: 5, a homolog or an ortholog of a different organism species, and the like. The hsa-miR-1908-3p gene can be obtained by a method described in Bar M et al., 2008, Stem Cells, Vol. 26, p. 2496-2505. Also, "hsa-mir-1908" (miRBase Accession No. MI0008329, SEQ ID NO: 179) having a hairpin-like structure is known as a precursor of "hsa-miR-1908-3p".

The term "hsa-miR-6726-5p gene" or "hsa-miR-6726-5p" used herein includes the hsa-miR-6726-5p gene (miRBase Accession No. MIMAT0027353) described in SEQ ID NO: 6, a homolog or an ortholog of a different organism species, and the like. The hsa-miR-6726-5p gene can be obtained by a method described in Ladewig E et al., 2012, Genome Res, Vol. 22, p. 1634-1645. Also, "hsa-mir-6726" (miRBase Accession No. MI0022571, SEQ ID NO: 180) having a hairpin-like structure is known as a precursor of "hsa-miR-6726-5p".

The term "hsa-miR-4258 gene" or "hsa-miR-4258" used herein includes the hsa-miR-4258 gene (miRBase Accession No. MIMAT0016879) described in SEQ ID NO: 7, a homolog or an ortholog of a different organism species, and the like. The hsa-miR-4258 gene can be obtained by a method described in Goff L A et al., 2009, PLoS One, Vol. 4, e7192. Also, "hsa-mir-4258" (miRBase Accession No. MI0015857, SEQ ID NO: 181) having a hairpin-like structure is known as a precursor of "hsa-miR-4258".

The term "hsa-miR-1343-3p gene" or "hsa-miR-1343-3p" used herein includes the hsa-miR-1343-3p gene (miRBase Accession No. MIMAT0019776) described in SEQ ID NO: 8, a homolog or an ortholog of a different organism species, and the like. The hsa-miR-1343-3p gene can be obtained by a method described in Persson H et al., 2011, Cancer Res, Vol. 71, p. 78-86. Also, "hsa-mir-1343" (miRBase Accession No. MI0017320, SEQ ID NO: 182) having a hairpin-like structure is known as a precursor of "hsa-miR-1343-3p".

The term "hsa-miR-4516 gene" or "hsa-miR-4516" used herein includes the hsa-miR-4516 gene (miRBase Accession No. MIMAT0019053) described in SEQ ID NO: 9, a homolog or an ortholog of a different organism species, and the like. The hsa-miR-4516 gene can be obtained by a method described in Jima D D et al., 2010, Blood, Vol. 116, e118-e127. Also, "hsa-mir-4516" (miRBase Accession No. MI0016882, SEQ ID NO: 183) having a hairpin-like structure is known as a precursor of "hsa-miR-4516".

The term "hsa-miR-6875-5p gene" or "hsa-miR-6875-5p" used herein includes the hsa-miR-6875-5p gene (miRBase Accession No. MIMAT0027650) described in SEQ ID NO: 10, a homolog or an ortholog of a different organism species, and the like. The hsa-miR-6875-5p gene can be obtained by a method described in Ladewig E et al., 2012, Genome Res, Vol. 22, p. 1634-1645. Also, "hsa-mir-6875" (miRBase Accession No. MI0022722, SEQ ID NO: 184) having a hairpin-like structure is known as a precursor of "hsa-miR-6875-5p".

The term "hsa-miR-4651 gene" or "hsa-miR-4651" used herein includes the hsa-miR-4651 gene (miRBase Accession No. MIMAT0019715) described in SEQ ID NO: 11, a homolog or an ortholog of a different organism species, and the like. The hsa-miR-4651 gene can be obtained by a method described in Persson H et al., 2011, Cancer Res, Vol. 71, p. 78-86. Also, "hsa-mir-4651" (miRBase Accession No. MI0017279, SEQ ID NO: 185) having a hairpin-like structure is known as a precursor of "hsa-miR-4651".

The term "hsa-miR-6825-5p gene" or "hsa-miR-6825-5p" used herein includes the hsa-miR-6825-5p gene (miRBase Accession No. MIMAT0027550) described in SEQ ID NO: 12, a homolog or an ortholog of a different organism species, and the like. The hsa-miR-6825-5p gene can be obtained by a method described in Ladewig E et al., 2012, Genome Res, Vol. 22, p. 1634-1645. Also, "hsa-mir-6825" (miRBase Accession No. MI0022670, SEQ ID NO: 186) having a hairpin-like structure is known as a precursor of "hsa-miR-6825-5p".

The term "hsa-miR-6840-3p gene" or "hsa-miR-6840-3p" used herein includes the hsa-miR-6840-3p gene (miRBase Accession No. MIMAT0027583) described in SEQ ID NO: 13, a homolog or an ortholog of a different organism species, and the like. The hsa-miR-6840-3p gene can be obtained by a method described in Ladewig E et al., 2012, Genome Res, Vol. 22, p. 1634-1645. Also, "hsa-mir-6840" (miRBase Accession No. MI0022686, SEQ ID NO: 187) having a hairpin-like structure is known as a precursor of "hsa-miR-6840-3p".

The term "hsa-miR-6780b-5p gene" or "hsa-miR-6780b-5p" used herein includes the hsa-miR-6780b-5p gene (miRBase Accession No. MIMAT0027572) described in SEQ ID NO: 14, a homolog or an ortholog of a different organism species, and the like. The hsa-miR-6780b-5p gene can be obtained by a method described in Ladewig E et al., 2012, Genome Res, Vol. 22, p. 1634-1645. Also, "hsa-mir-6780b" (miRBase Accession No. MI0022681, SEQ ID NO: 188) having a hairpin-like structure is known as a precursor of "hsa-miR-6780b-5p".

The term "hsa-miR-6749-5p gene" or "hsa-miR-6749-5p" used herein includes the hsa-miR-6749-5p gene (miRBase Accession No. MIMAT0027398) described in SEQ ID NO: 15, a homolog or an ortholog of a different organism species, and the like. The hsa-miR-6749-5p gene can be obtained by a method described in Ladewig E et al., 2012, Genome Res, Vol. 22, p. 1634-1645. Also, "hsa-mir-6749" (miRBase Accession No. MI0022594, SEQ ID NO: 189) having a hairpin-like structure is known as a precursor of "hsa-miR-6749-5p".

The term "hsa-miR-8063 gene" or "hsa-miR-8063" used herein includes the hsa-miR-8063 gene (miRBase Accession No. MIMAT0030990) described in SEQ ID NO: 16, a homolog or an ortholog of a different organism species, and the like. The hsa-miR-8063 gene can be obtained by a method described in Wang H J et al., 2013, Shock, Vol. 39, p. 480-487. Also, "hsa-mir-8063" (miRBase Accession No. MI0025899, SEQ ID NO: 190) having a hairpin-like structure is known as a precursor of "hsa-miR-8063".

The term "hsa-miR-6784-5p gene" or "hsa-miR-6784-5p" used herein includes the hsa-miR-6784-5p gene (miRBase Accession No. MIMAT0027468) described in SEQ ID NO: 17, a homolog or an ortholog of a different organism species, and the like. The hsa-miR-6784-5p gene can be obtained by a method described in Ladewig E et al., 2012, Genome Res, Vol. 22, p. 1634-1645. Also, "hsa-mir-6784" (miRBase Accession No. MI0022629, SEQ ID NO: 191) having a hairpin-like structure is known as a precursor of "hsa-miR-6784-5p".

The term "hsa-miR-3679-5p gene" or "hsa-miR-3679-5p" used herein includes the hsa-miR-3679-5p gene (miRBase Accession No. MIMAT0018104) described in SEQ ID NO: 18, a homolog or an ortholog of a different organism species, and the like. The hsa-miR-3679-5p gene can be obtained by a method described in Creighton C J et al., 2010, PLoS One, Vol. 5, e9637. Also, "hsa-mir-3679" (miRBase Accession No. MI0016080, SEQ ID NO: 192) having a hairpin-like structure is known as a precursor of "hsa-miR-3679-5p".

The term "hsa-miR-3184-5p gene" or "hsa-miR-3184-5p" used herein includes the hsa-miR-3184-5p gene (miRBase Accession No. MIMAT0015064) described in SEQ ID NO: 19, a homolog or an ortholog of a different organism species, and the like. The hsa-miR-3184-5p gene can be obtained by a method described in Stark M S et al., 2010, PLoS One, Vol. 5, e9685. Also, "hsa-mir-3184" (miRBase Accession No. MI0014226, SEQ ID NO: 193) having a hairpin-like structure is known as a precursor of "hsa-miR-3184-5p".

The term "hsa-miR-663b gene" or "hsa-miR-663b" used herein includes the hsa-miR-663b gene (miRBase Accession No. MIMAT0005867) described in SEQ ID NO: 20, a homolog or an ortholog of a different organism species, and the like. The hsa-miR-663b gene can be obtained by a method described in Takada S et al., 2008, Leukemia, Vol. 22, p. 1274-1278. Also, "hsa-mir-663b" (miRBase Accession No. MI0006336, SEQ ID NO: 194) having a hairpin-like structure is known as a precursor of "hsa-miR-663b".

The term "hsa-miR-6880-5p gene" or "hsa-miR-6880-5p" used herein includes the hsa-miR-6880-5p gene (miRBase Accession No. MIMAT0027660) described in SEQ ID NO: 21, a homolog or an ortholog of a different organism species, and the like. The hsa-miR-6880-5p gene can be obtained by a method described in Ladewig E et al., 2012, Genome Res, Vol. 22, p. 1634-1645. Also, "hsa-mir-6880" (miRBase Accession No. MI0022727, SEQ ID NO: 195) having a hairpin-like structure is known as a precursor of "hsa-miR-6880-5p".

The term "hsa-miR-1908-5p gene" or "hsa-miR-1908-5p" used herein includes the hsa-miR-1908-5p gene (miRBase Accession No. MIMAT0007881) described in SEQ ID NO: 22, a homolog or an ortholog of a different organism species, and the like. The hsa-miR-1908-5p gene can be obtained by a method described in Bar M et al., 2008, Stem Cells, Vol. 26, p. 2496-2505. Also, "hsa-mir-1908" (miRBase Accession No. MI0008329, SEQ ID NO: 179) having a hairpin-like structure is known as a precursor of "hsa-miR-1908-5p".

The term "hsa-miR-92a-2-5p gene" or "hsa-miR-92a-2-5p" used herein includes the hsa-miR-92a-2-5p gene (miRBase Accession No. MIMAT0004508) described in SEQ ID NO: 23, a homolog or an ortholog of a different organism species, and the like. The hsa-miR-92a-2-5p gene can be obtained by a method described in Mourelatos Z et al., 2002, Genes Dev, Vol. 16, p. 720-728. Also, "hsa-mir-92a-2" (miRBase Accession No. MI0000094, SEQ ID NO: 196) having a hairpin-like structure is known as a precursor of "hsa-miR-92a-2-5p".

The term "hsa-miR-7975 gene" or "hsa-miR-7975" used herein includes the hsa-miR-7975 gene (miRBase Accession No. MIMAT0031178) described in SEQ ID NO: 24, a homolog or an ortholog of a different organism species, and the like. The hsa-miR-7975 gene can be obtained by a method described in Velthut-Meikas A et al., 2013, Mol Endocrinol, online. Also, "hsa-mir-7975" (miRBase Accession No. MI0025751, SEQ ID NO: 197) having a hairpin-like structure is known as a precursor of "hsa-miR-7975".

The term "hsa-miR-7110-5p gene" or "hsa-miR-7110-5p" used herein includes the hsa-miR-7110-5p gene (miRBase Accession No. MIMAT0028117) described in SEQ ID NO: 25, a homolog or an ortholog of a different organism species, and the like. The hsa-miR-7110-5p gene can be obtained by a method described in Ladewig E et al., 2012, Genome Res, Vol. 22, p. 1634-1645. Also, "hsa-mir-7110" (miRBase Accession No. MI0022961, SEQ ID NO: 198) having a hairpin-like structure is known as a precursor of "hsa-miR-7110-5p".

The term "hsa-miR-6842-5p gene" or "hsa-miR-6842-5p" used herein includes the hsa-miR-6842-5p gene (miRBase Accession No. MIMAT0027586) described in SEQ ID NO: 26, a homolog or an ortholog of a different organism species, and the like. The hsa-miR-6842-5p gene can be obtained by a method described in Ladewig E et al., 2012, Genome Res, Vol. 22, p. 1634-1645. Also, "hsa-mir-6842" (miRBase Accession No. MI0022688, SEQ ID NO: 199) having a hairpin-like structure is known as a precursor of "hsa-miR-6842-5p".

The term "hsa-miR-6857-5p gene" or "hsa-miR-6857-5p" used herein includes the hsa-miR-6857-5p gene (miRBase Accession No. MIMAT0027614) described in SEQ ID NO: 27, a homolog or an ortholog of a different organism species, and the like. The hsa-miR-6857-5p gene can be obtained by a method described in Ladewig E et al., 2012, Genome Res, Vol. 22, p. 1634-1645. Also, "hsa-mir-6857" (miRBase Accession No. MI0022703, SEQ ID NO: 200) having a hairpin-like structure is known as a precursor of "hsa-miR-6857-5p".

The term "hsa-miR-5572 gene" or "hsa-miR-5572" used herein includes the hsa-miR-5572 gene (miRBase Accession No. MIMAT0022260) described in SEQ ID NO: 28, a homolog or an ortholog of a different organism species, and the like. The hsa-miR-5572 gene can be obtained by a method described in Tandon M et al., 2012, Oral Dis, Vol. 18, p. 127-131. Also, "hsa-mir-5572" (miRBase Accession No. MI0019117, SEQ ID NO: 201) having a hairpin-like structure is known as a precursor of "hsa-miR-5572".

The term "hsa-miR-3197 gene" or "hsa-miR-3197" used herein includes the hsa-miR-3197 gene (miRBase Accession No. MIMAT0015082) described in SEQ ID NO: 29, a homolog or an ortholog of a different organism species, and the like. The hsa-miR-3197 gene can be obtained by a method described in Stark M S et al., 2010, PLoS One, Vol. 5, e9685. Also, "hsa-mir-3197" (miRBase Accession No. MI0014245, SEQ ID NO: 202) having a hairpin-like structure is known as a precursor of "hsa-miR-3197".

The term "hsa-miR-6131 gene" or "hsa-miR-6131" used herein includes the hsa-miR-6131 gene (miRBase Accession No. MIMAT0024615) described in SEQ ID NO: 30, a homolog or an ortholog of a different organism species, and the like. The hsa-miR-6131 gene can be obtained by a method described in Dannemann M et al., 2012, Genome Biol Evol, Vol. 4, p. 552-564. Also, "hsa-mir-6131" (miRBase Accession No. MI0021276, SEQ ID NO: 203) having a hairpin-like structure is known as a precursor of "hsa-miR-6131".

The term "hsa-miR-6889-5p gene" or "hsa-miR-6889-5p" used herein includes the hsa-miR-6889-5p gene (miRBase Accession No. MIMAT0027678) described in SEQ ID NO: 31, a homolog or an ortholog of a different organism species, and the like. The hsa-miR-6889-5p gene can be obtained by a method described in Ladewig E et al., 2012, Genome Res, Vol. 22, p. 1634-1645. Also, "hsa-mir-6889" (miRBase Accession No. MI0022736, SEQ ID NO: 204) having a hairpin-like structure is known as a precursor of "hsa-miR-6889-5p".

The term "hsa-miR-4454 gene" or "hsa-miR-4454" used herein includes the hsa-miR-4454 gene (miRBase Accession No. MIMAT0018976) described in SEQ ID NO: 32, a homolog or an ortholog of a different organism species, and the like. The hsa-miR-4454 gene can be obtained by a method described in Jima D D et al., 2010, Blood, Vol. 116, e118-e127. Also, "hsa-mir-4454" (miRBase Accession No. MI0016800, SEQ ID NO: 205) having a hairpin-like structure is known as a precursor of "hsa-miR-4454".

The term "hsa-miR-1199-5p gene" or "hsa-miR-1199-5p" used herein includes the hsa-miR-1199-5p gene (miRBase Accession No. MIMAT0031119) described in SEQ ID NO: 33, a homolog or an ortholog of a different organism species, and the like. The hsa-miR-1199-5p gene can be obtained by a method described in Salvi A et al., 2013, Int J Oncol, Vol. 42, p. 391-402. Also, "hsa-mir-1199" (miRBase Accession No. MI0020340, SEQ ID NO: 206) having a hairpin-like structure is known as a precursor of "hsa-miR-1199-5p".

The term "hsa-miR-1247-3p gene" or "hsa-miR-1247-3p" used herein includes the hsa-miR-1247-3p gene (miRBase Accession No. MIMAT0022721) described in SEQ ID NO: 34, a homolog or an ortholog of a different organism species, and the like. The hsa-miR-1247-3p gene can be obtained by a method described in Morin R D et al., 2008, Genome Res, Vol. 18, p. 610-621. Also, "hsa-mir-1247" (miRBase Accession No. MI0006382, SEQ ID NO: 207) having a hairpin-like structure is known as a precursor of "hsa-miR-1247-3p".

The term "hsa-miR-6800-5p gene" or "hsa-miR-6800-5p" used herein includes the hsa-miR-6800-5p gene (miRBase Accession No. MIMAT0027500) described in SEQ ID NO: 35, a homolog or an ortholog of a different organism species, and the like. The hsa-miR-6800-5p gene can be obtained by a method described in Ladewig E et al., 2012, Genome Res, Vol. 22, p. 1634-1645. Also, "hsa-mir-6800" (miRBase Accession No. MI0022645, SEQ ID NO: 208) having a hairpin-like structure is known as a precursor of "hsa-miR-6800-5p".

The term "hsa-miR-6872-3p gene" or "hsa-miR-6872-3p" used herein includes the hsa-miR-6872-3p gene (miRBase Accession No. MIMAT0027645) described in SEQ ID NO: 36, a homolog or an ortholog of a different organism species, and the like. The hsa-miR-6872-3p gene can be obtained by a method described in Ladewig E et al., 2012, Genome Res, Vol. 22, p. 1634-1645. Also, "hsa-mir-6872" (miRBase Accession No. MI0022719, SEQ ID NO: 209) having a hairpin-like structure is known as a precursor of "hsa-miR-6872-3p".

The term "hsa-miR-4649-5p gene" or "hsa-miR-4649-5p" used herein includes the hsa-miR-4649-5p gene (miRBase Accession No. MIMAT0019711) described in SEQ ID NO: 37, a homolog or an ortholog of a different organism species, and the like. The hsa-miR-4649-5p gene can be obtained by a method described in Persson H et al., 2011, Cancer Res, Vol. 71, p. 78-86. Also, "hsa-mir-4649" (miRBase Accession No. MI0017276, SEQ ID NO: 210) having a hairpin-like structure is known as a precursor of "hsa-miR-4649-5p".

The term "hsa-miR-6791-5p gene" or "hsa-miR-6791-5p" used herein includes the hsa-miR-6791-5p gene (miRBase Accession No. MIMAT0027482) described in SEQ ID NO: 38, a homolog or an ortholog of a different organism species, and the like. The hsa-miR-6791-5p gene can be obtained by a method described in Ladewig E et al., 2012, Genome Res, Vol. 22, p. 1634-1645. Also, "hsa-mir-6791" (miRBase Accession No. MI0022636, SEQ ID NO: 211) having a hairpin-like structure is known as a precursor of "hsa-miR-6791-5p".

The term "hsa-miR-4433b-3p gene" or "hsa-miR-4433b-3p" used herein includes the hsa-miR-4433b-3p gene (miRBase Accession No. MIMAT0030414) described in SEQ ID NO: 39, a homolog or an ortholog of a different organism species, and the like. The hsa-miR-4433b-3p gene can be obtained by a method described in Ple H et al., 2012, PLoS One, Vol. 7, e50746. Also, "hsa-mir-4433b" (miRBase Accession No. MI0025511, SEQ ID NO: 212) having a hairpin-like structure is known as a precursor of "hsa-miR-4433b-3p".

The term "hsa-miR-3135b gene" or "hsa-miR-3135b" used herein includes the hsa-miR-3135b gene (miRBase Accession No. MIMAT0018985) described in SEQ ID NO: 40, a homolog or an ortholog of a different organism species, and the like. The hsa-miR-3135b gene can be obtained by a method described in Jima D D et al., 2010, Blood, Vol. 116, e118-e127. Also, "hsa-mir-3135b" (miRBase Accession No. MI0016809, SEQ ID NO: 213) having a hairpin-like structure is known as a precursor of "hsa-miR-3135b".

The term "hsa-miR-128-2-5p gene" or "hsa-miR-128-2-5p" used herein includes the hsa-miR-128-2-5p gene (miRBase Accession No. MIMAT0031095) described in SEQ ID NO: 41, a homolog or an ortholog of a different organism species, and the like. The hsa-miR-128-2-5p gene can be obtained by a method described in Lagos-Quintana M et al., 2002, Curr Biol, Vol. 12, p. 735-739. Also, "hsa-mir-128-2" (miRBase Accession No. MI0000727, SEQ ID NO: 214) having a hairpin-like structure is known as a precursor of "hsa-miR-128-2-5p".

The term "hsa-miR-4675 gene" or "hsa-miR-4675" used herein includes the hsa-miR-4675 gene (miRBase Accession No. MIMAT0019757) described in SEQ ID NO: 42, a homolog or an ortholog of a different organism species, and the like. The hsa-miR-4675 gene can be obtained by a method described in Persson H et al., 2011, Cancer Res, Vol. 71, p. 78-86. Also, "hsa-mir-4675" (miRBase Accession No. MI0017306, SEQ ID NO: 215) having a hairpin-like structure is known as a precursor of "hsa-miR-4675".

The term "hsa-miR-4472 gene" or "hsa-miR-4472" used herein includes the hsa-miR-4472 gene (miRBase Accession No. MIMAT0018999) described in SEQ ID NO: 43, a homolog or an ortholog of a different organism species, and the like. The hsa-miR-4472 gene can be obtained by a method described in Jima D D et al., 2010, Blood, Vol. 116, e118-e127. Also, "hsa-mir-4472-1 and hsa-mir-4472-2" (miRBase Accession Nos. MI0016823 and MI0016824, SEQ ID NOs: 216 and 217) having a hairpin-like structure are known as precursors of "hsa-miR-4472".

The term "hsa-miR-6785-5p gene" or "hsa-miR-6785-5p" used herein includes the hsa-miR-6785-5p gene (miRBase Accession No. MIMAT0027470) described in SEQ ID NO: 44, a homolog or an ortholog of a different organism species, and the like. The hsa-miR-6785-5p gene can be obtained by a method described in Ladewig E et al., 2012, Genome Res, Vol. 22, p. 1634-1645. Also, "hsa-mir-6785" (miRBase Accession No. MI0022630, SEQ ID NO: 218) having a hairpin-like structure is known as a precursor of "hsa-miR-6785-5p".

The term "hsa-miR-6741-5p gene" or "hsa-miR-6741-5p" used herein includes the hsa-miR-6741-5p gene (miRBase Accession No. MIMAT0027383) described in SEQ ID NO: 45, a homolog or an ortholog of a different organism species, and the like. The hsa-miR-6741-5p gene can be obtained by a method described in Ladewig E et al., 2012, Genome Res, Vol. 22, p. 1634-1645. Also, "hsa-mir-6741" (miRBase Accession No. MI0022586, SEQ ID NO: 219) having a hairpin-like structure is known as a precursor of "hsa-miR-6741-5p".

The term "hsa-miR-7977 gene" or "hsa-miR-7977" used herein includes the hsa-miR-7977 gene (miRBase Accession No. MIMAT0031180) described in SEQ ID NO: 46, a homolog or an ortholog of a different organism species, and the like. The hsa-miR-7977 gene can be obtained by a method described in Velthut-Meikas A et al., 2013, Mol Endocrinol, online. Also, "hsa-mir-7977" (miRBase Accession No. MI0025753, SEQ ID NO: 220) having a hairpin-like structure is known as a precursor of "hsa-miR-7977".

The term "hsa-miR-3665 gene" or "hsa-miR-3665" used herein includes the hsa-miR-3665 gene (miRBase Accession No. MIMAT0018087) described in SEQ ID NO: 47, a homolog or an ortholog of a different organism species, and the like. The hsa-miR-3665 gene can be obtained by a method described in Xie X et al., 2005, Nature, Vol. 434, p. 338-345. Also, "hsa-mir-3665" (miRBase Accession No. MI0016066, SEQ ID NO: 221) having a hairpin-like structure is known as a precursor of "hsa-miR-3665".

The term "hsa-miR-128-1-5p gene" or "hsa-miR-128-1-5p" used herein includes the hsa-miR-128-1-5p gene (miRBase Accession No. MIMAT0026477) described in SEQ ID NO: 48, a homolog or an ortholog of a different organism species, and the like. The hsa-miR-128-1-5p gene can be obtained by a method described in Lagos-Quintana M et al., 2002, Curr Biol, Vol. 12, p. 735-739. Also, "hsa-mir-128-1" (miRBase Accession No. MI0000447, SEQ ID NO: 222) having a hairpin-like structure is known as a precursor of "hsa-miR-128-1-5p".

The term "hsa-miR-4286 gene" or "hsa-miR-4286" used herein includes the hsa-miR-4286 gene (miRBase Accession No. MIMAT0016916) described in SEQ ID NO: 49, a homolog or an ortholog of a different organism species, and the like. The hsa-miR-4286 gene can be obtained by a method described in Goff L A et al., 2009, PLoS One, Vol. 4, e7192. Also, "hsa-mir-4286" (miRBase Accession No. MI0015894, SEQ ID NO: 223) having a hairpin-like structure is known as a precursor of "hsa-miR-4286".

The term "hsa-miR-6765-3p gene" or "hsa-miR-6765-3p" used herein includes the hsa-miR-6765-3p gene (miRBase Accession No. MIMAT0027431) described in SEQ ID NO: 50, a homolog or an ortholog of a different organism species, and the like. The hsa-miR-6765-3p gene can be obtained by a method described in Ladewig E et al., 2012, Genome Res, Vol. 22, p. 1634-1645. Also, "hsa-mir-6765" (miRBase Accession No. MI0022610, SEQ ID NO: 224) having a hairpin-like structure is known as a precursor of "hsa-miR-6765-3p".

The term "hsa-miR-4632-5p gene" or "hsa-miR-4632-5p" used herein includes the hsa-miR-4632-5p gene (miRBase Accession No. MIMAT0022977) described in SEQ ID NO: 51, a homolog or an ortholog of a different organism species, and the like. The hsa-miR-4632-5p gene can be obtained by a method described in Persson H et al., 2011, Cancer Res, Vol. 71, p. 78-86. Also, "hsa-mir-4632" (miRBase Accession No. MI0017259, SEQ ID NO: 225) having a hairpin-like structure is known as a precursor of "hsa-miR-4632-5p".

The term "hsa-miR-365a-5p gene" or "hsa-miR-365a-5p" used herein includes the hsa-miR-365a-5p gene (miRBase Accession No. MIMAT0009199) described in SEQ ID NO: 52, a homolog or an ortholog of a different organism species, and the like. The hsa-miR-365a-5p gene can be obtained by a method described in Xie X et al., 2005, Nature, Vol. 434, p. 338-345. Also, "hsa-mir-365a" (miRBase Accession No. MI0000767, SEQ ID NO: 226) having a hairpin-like structure is known as a precursor of "hsa-miR-365a-5p".

The term "hsa-miR-6088 gene" or "hsa-miR-6088" used herein includes the hsa-miR-6088 gene (miRBase Accession No. MIMAT0023713) described in SEQ ID NO: 53, a homolog or an ortholog of a different organism species, and the like. The hsa-miR-6088 gene can be obtained by a method described in Yoo J K et al., 2012, Stem Cells Dev, Vol. 21, p. 2049-2057. Also, "hsa-mir-6088" (miRBase Accession No. MI0020365, SEQ ID NO: 227) having a hairpin-like structure is known as a precursor of "hsa-miR-6088".

The term "hsa-miR-6816-5p gene" or "hsa-miR-6816-5p" used herein includes the hsa-miR-6816-5p gene (miRBase Accession No. MIMAT0027532) described in SEQ ID NO: 54, a homolog or an ortholog of a different organism species, and the like. The hsa-miR-6816-5p gene can be obtained by a method described in Ladewig E et al., 2012, Genome Res, Vol. 22, p. 1634-1645. Also, "hsa-mir-6816" (miRBase Accession No. MI0022661, SEQ ID NO: 228) having a hairpin-like structure is known as a precursor of "hsa-miR-6816-5p".

The term "hsa-miR-6885-5p gene" or "hsa-miR-6885-5p" used herein includes the hsa-miR-6885-5p gene (miRBase Accession No. MIMAT0027670) described in SEQ ID NO: 55, a homolog or an ortholog of a different organism species, and the like. The hsa-miR-6885-5p gene can be obtained by a method described in Ladewig E et al., 2012, Genome Res, Vol. 22, p. 1634-1645. Also, "hsa-mir-6885" (miRBase Accession No. M10022732, SEQ ID NO: 229) having a hairpin-like structure is known as a precursor of "hsa-miR-6885-5p".

The term "hsa-miR-711 gene" or "hsa-miR-711" used herein includes the hsa-miR-711 gene (miRBase Accession No. MIMAT0012734) described in SEQ ID NO: 56, a homolog or an ortholog of a different organism species, and the like. The hsa-miR-711 gene can be obtained by a method described in Artzi S et al., 2008, BMC Bioinformatics, Vol. 9, p. 39. Also, "hsa-mir-711" (miRBase Accession No. M10012488, SEQ ID NO: 230) having a hairpin-like structure is known as a precursor of "hsa-miR-711".

The term "hsa-miR-6765-5p gene" or "hsa-miR-6765-5p" used herein includes the hsa-miR-6765-5p gene (miRBase Accession No. MIMAT0027430) described in SEQ ID NO: 57, a homolog or an ortholog of a different organism species, and the like. The hsa-miR-6765-5p gene can be obtained by a method described in Ladewig E et al., 2012, Genome Res, Vol. 22, p. 1634-1645. Also, "hsa-mir-6765" (miRBase Accession No. MI0022610, SEQ ID NO: 224) having a hairpin-like structure is known as a precursor of "hsa-miR-6765-5p".

The term "hsa-miR-3180 gene" or "hsa-miR-3180" used herein includes the hsa-miR-3180 gene (miRBase Accession No. MIMAT0018178) described in SEQ ID NO: 58, a homolog or an ortholog of a different organism species, and the like. The hsa-miR-3180 gene can be obtained by a method described in Creighton C J et al., 2010, PLoS One, Vol. 5, e9637. Also, "hsa-mir-3180-4 and hsa-mir-3180-5" (miRBase Accession Nos. MI0016408 and MI0016409, SEQ ID NOs: 231 and 232) having a hairpin-like structure are known as precursors of "hsa-miR-3180".

The term "hsa-miR-4442 gene" or "hsa-miR-4442" used herein includes the hsa-miR-4442 gene (miRBase Accession No. MIMAT0018960) described in SEQ ID NO: 59, a homolog or an ortholog of a different organism species, and the like. The hsa-miR-4442 gene can be obtained by a method described in Jima D D et al., 2010, Blood, Vol. 116, e118-e127. Also, "hsa-mir-4442" (miRBase Accession No. M10016785, SEQ ID NO: 233) having a hairpin-like structure is known as a precursor of "hsa-miR-4442".

The term "hsa-miR-4792 gene" or "hsa-miR-4792" used herein includes the hsa-miR-4792 gene (miRBase Accession No. MIMAT0019964) described in SEQ ID NO: 60, a homolog or an ortholog of a different organism species, and the like. The hsa-miR-4792 gene can be obtained by a method described in Persson H et al., 2011, Cancer Res, Vol.

71, p. 78-86. Also, "hsa-mir-4792" (miRBase Accession No. MI0017439, SEQ ID NO: 234) having a hairpin-like structure is known as a precursor of "hsa-miR-4792".

The term "hsa-miR-6721-5p gene" or "hsa-miR-6721-5p" used herein includes the hsa-miR-6721-5p gene (miRBase Accession No. MIMAT0025852) described in SEQ ID NO: 61, a homolog or an ortholog of a different organism species, and the like. The hsa-miR-6721-5p gene can be obtained by a method described in Li Y et al., 2012, Gene, Vol. 497, p. 330-335. Also, "hsa-mir-6721" (miRBase Accession No. MI0022556, SEQ ID NO: 235) having a hairpin-like structure is known as a precursor of "hsa-miR-6721-5p".

The term "hsa-miR-6798-5p gene" or "hsa-miR-6798-5p" used herein includes the hsa-miR-6798-5p gene (miRBase Accession No. MIMAT0027496) described in SEQ ID NO: 62, a homolog or an ortholog of a different organism species, and the like. The hsa-miR-6798-5p gene can be obtained by a method described in Ladewig E et al., 2012, Genome Res, Vol. 22, p. 1634-1645. Also, "hsa-mir-6798" (miRBase Accession No. MI0022643, SEQ ID NO: 236) having a hairpin-like structure is known as a precursor of "hsa-miR-6798-5p".

The term "hsa-miR-3162-5p gene" or "hsa-miR-3162-5p" used herein includes the hsa-miR-3162-5p gene (miRBase Accession No. MIMAT0015036) described in SEQ ID NO: 63, a homolog or an ortholog of a different organism species, and the like. The hsa-miR-3162-5p gene can be obtained by a method described in Stark M S et al., 2010, PLoS One, Vol. 5, e9685. Also, "hsa-mir-3162" (miRBase Accession No. MI0014192, SEQ ID NO: 237) having a hairpin-like structure is known as a precursor of "hsa-miR-3162-5p".

The term "hsa-miR-6126 gene" or "hsa-miR-6126" used herein includes the hsa-miR-6126 gene (miRBase Accession No. MIMAT0024599) described in SEQ ID NO: 64, a homolog or an ortholog of a different organism species, and the like. The hsa-miR-6126 gene can be obtained by a method described in Smith J L et al., 2012, J Virol, Vol. 86, p. 5278-5287. Also, "hsa-mir-6126" (miRBase Accession No. MI0021260, SEQ ID NO: 238) having a hairpin-like structure is known as a precursor of "hsa-miR-6126".

The term "hsa-miR-4758-5p gene" or "hsa-miR-4758-5p" used herein includes the hsa-miR-4758-5p gene (miRBase Accession No. MIMAT0019903) described in SEQ ID NO: 65, a homolog or an ortholog of a different organism species, and the like. The hsa-miR-4758-5p gene can be obtained by a method described in Persson H et al., 2011, Cancer Res, Vol. 71, p. 78-86. Also, "hsa-mir-4758" (miRBase Accession No. MI0017399, SEQ ID NO: 239) having a hairpin-like structure is known as a precursor of "hsa-miR-4758-5p".

The term "hsa-miR-2392 gene" or "hsa-miR-2392" used herein includes the hsa-miR-2392 gene (miRBase Accession No. MIMAT0019043) described in SEQ ID NO: 66, a homolog or an ortholog of a different organism species, and the like. The hsa-miR-2392 gene can be obtained by a method described in Jima D D et al., 2010, Blood, Vol. 116, e118-e127. Also, "hsa-mir-2392" (miRBase Accession No. MI0016870, SEQ ID NO: 240) having a hairpin-like structure is known as a precursor of "hsa-miR-2392".

The term "hsa-miR-486-3p gene" or "hsa-miR-486-3p" used herein includes the hsa-miR-486-3p gene (miRBase Accession No. MIMAT0004762) described in SEQ ID NO: 67, a homolog or an ortholog of a different organism species, and the like. The hsa-miR-486-3p gene can be obtained by a method described in Fu H et al., 2005, FEBS Lett, Vol. 579, p. 3849-3854. Also, "hsa-mir-486 and hsa-mir-486-2" (miRBase Accession Nos. MI0002470 and MI0023622, SEQ ID NOs: 241 and 242) having a hairpin-like structure are known as precursors of "hsa-miR-486-3p".

The term "hsa-miR-6727-5p gene" or "hsa-miR-6727-5p" used herein includes the hsa-miR-6727-5p gene (miRBase Accession No. MIMAT0027355) described in SEQ ID NO: 68, a homolog or an ortholog of a different organism species, and the like. The hsa-miR-6727-5p gene can be obtained by a method described in Ladewig E et al., 2012, Genome Res, Vol. 22, p. 1634-1645. Also, "hsa-mir-6727" (miRBase Accession No. MI0022572, SEQ ID NO: 243) having a hairpin-like structure is known as a precursor of "hsa-miR-6727-5p".

The term "hsa-miR-4728-5p gene" or "hsa-miR-4728-5p" used herein includes the hsa-miR-4728-5p gene (miRBase Accession No. MIMAT0019849) described in SEQ ID NO: 69, a homolog or an ortholog of a different organism species, and the like. The hsa-miR-4728-5p gene can be obtained by a method described in Persson H et al., 2011, Cancer Res, Vol. 71, p. 78-86. Also, "hsa-mir-4728" (miRBase Accession No. MI0017365, SEQ ID NO: 244) having a hairpin-like structure is known as a precursor of "hsa-miR-4728-5p".

The term "hsa-miR-6746-5p gene" or "hsa-miR-6746-5p" used herein includes the hsa-miR-6746-5p gene (miRBase Accession No. MIMAT0027392) described in SEQ ID NO: 70, a homolog or an ortholog of a different organism species, and the like. The hsa-miR-6746-5p gene can be obtained by a method described in Ladewig E et al., 2012, Genome Res, Vol. 22, p. 1634-1645. Also, "hsa-mir-6746" (miRBase Accession No. MI0022591, SEQ ID NO: 245) having a hairpin-like structure is known as a precursor of "hsa-miR-6746-5p".

The term "hsa-miR-4270 gene" or "hsa-miR-4270" used herein includes the hsa-miR-4270 gene (miRBase Accession No. MIMAT0016900) described in SEQ ID NO: 71, a homolog or an ortholog of a different organism species, and the like. The hsa-miR-4270 gene can be obtained by a method described in Goff L A et al., 2009, PLoS One, Vol. 4, e7192. Also, "hsa-mir-4270" (miRBase Accession No. MI0015878, SEQ ID NO: 246) having a hairpin-like structure is known as a precursor of "hsa-miR-4270".

The term "hsa-miR-3940-5p gene" or "hsa-miR-3940-5p" used herein includes the hsa-miR-3940-5p gene (miRBase Accession No. MIMAT0019229) described in SEQ ID NO: 72, a homolog or an ortholog of a different organism species, and the like. The hsa-miR-3940-5p gene can be obtained by a method described in Liao J Y et al., 2010, PLoS One, Vol. 5, e10563. Also, "hsa-mir-3940" (miRBase Accession No. MI0016597, SEQ ID NO: 247) having a hairpin-like structure is known as a precursor of "hsa-miR-3940-5p".

The term "hsa-miR-4725-3p gene" or "hsa-miR-4725-3p" used herein includes the hsa-miR-4725-3p gene (miRBase Accession No. MIMAT0019844) described in SEQ ID NO: 73, a homolog or an ortholog of a different organism species, and the like. The hsa-miR-4725-3p gene can be obtained by a method described in Persson H et al., 2011, Cancer Res, Vol. 71, p. 78-86. Also, "hsa-mir-4725" (miRBase Accession No. MI0017362, SEQ ID NO: 248) having a hairpin-like structure is known as a precursor of "hsa-miR-4725-3p".

The term "hsa-miR-7108-5p gene" or "hsa-miR-7108-5p" used herein includes the hsa-miR-7108-5p gene (miRBase Accession No. MIMAT0028113) described in SEQ ID NO: 74, a homolog or an ortholog of a different organism species, and the like. The hsa-miR-7108-5p gene can be obtained by a method described in Ladewig E et al., 2012, Genome Res, Vol. 22, p. 1634-1645. Also, "hsa-mir-7108" (miRBase Accession No. MI0022959, SEQ ID NO: 249) having a hairpin-like structure is known as a precursor of "hsa-miR-7108-5p".

The term "hsa-miR-3656 gene" or "hsa-miR-3656" used herein includes the hsa-miR-3656 gene (miRBase Accession No. MIMAT0018076) described in SEQ ID NO: 75, a homolog or an ortholog of a different organism species, and the like. The hsa-miR-3656 gene can be obtained by a method described in Meiri E et al., 2010, Nucleic Acids Res, Vol. 38, p. 6234-6246. Also, "hsa-mir-3656" (miRBase Accession No. MI0016056, SEQ ID NO: 250) having a hairpin-like structure is known as a precursor of "hsa-miR-3656".

The term "hsa-miR-6879-5p gene" or "hsa-miR-6879-5p" used herein includes the hsa-miR-6879-5p gene (miRBase Accession No. MIMAT0027658) described in SEQ ID NO: 76, a homolog or an ortholog of a different organism species, and the like. The hsa-miR-6879-5p gene can be obtained by a method described in Ladewig E et al., 2012, Genome Res, Vol. 22, p. 1634-1645. Also, "hsa-mir-6879" (miRBase Accession No. MI0022726, SEQ ID NO: 251) having a hairpin-like structure is known as a precursor of "hsa-miR-6879-5p".

The term "hsa-miR-6738-5p gene" or "hsa-miR-6738-5p" used herein includes the hsa-miR-6738-5p gene (miRBase Accession No. MIMAT0027377) described in SEQ ID NO: 77, a homolog or an ortholog of a different organism species, and the like. The hsa-miR-6738-5p gene can be obtained by a method described in Ladewig E et al., 2012, Genome Res, Vol. 22, p. 1634-1645. Also, "hsa-mir-6738" (miRBase Accession No. MI0022583, SEQ ID NO: 252) having a hairpin-like structure is known as a precursor of "hsa-miR-6738-5p".

The term "hsa-miR-1260a gene" or "hsa-miR-1260a" used herein includes the hsa-miR-1260a gene (miRBase Accession No. MIMAT0005911) described in SEQ ID NO: 78, a homolog or an ortholog of a different organism species, and the like. The hsa-miR-1260a gene can be obtained by a method described in Morin R D et al., 2008, Genome Res, Vol. 18, p. 610-621. Also, "hsa-mir-1260a" (miRBase Accession No. MI0006394, SEQ ID NO: 253) having a hairpin-like structure is known as a precursor of "hsa-miR-1260a".

The term "hsa-miR-4446-3p gene" or "hsa-miR-4446-3p" used herein includes the hsa-miR-4446-3p gene (miRBase Accession No. MIMAT0018965) described in SEQ ID NO: 79, a homolog or an ortholog of a different organism species, and the like. The hsa-miR-4446-3p gene can be obtained by a method described in Jima D D et al., 2010, Blood, Vol. 116, e118-e127. Also, "hsa-mir-4446" (miRBase Accession No. MI0016789, SEQ ID NO: 254) having a hairpin-like structure is known as a precursor of "hsa-miR-4446-3p".

The term "hsa-miR-3131 gene" or "hsa-miR-3131" used herein includes the hsa-miR-3131 gene (miRBase Accession No. MIMAT0014996) described in SEQ ID NO: 80, a homolog or an ortholog of a different organism species, and the like. The hsa-miR-3131 gene can be obtained by a method described in Stark M S et al., 2010, PLoS One, Vol. 5, e9685. Also, "hsa-mir-3131" (miRBase Accession No. MI0014151, SEQ ID NO: 255) having a hairpin-like structure is known as a precursor of "hsa-miR-3131".

The term "hsa-miR-4463 gene" or "hsa-miR-4463" used herein includes the hsa-miR-4463 gene (miRBase Accession No. MIMAT0018987) described in SEQ ID NO: 81, a homolog or an ortholog of a different organism species, and the like. The hsa-miR-4463 gene can be obtained by a method described in Jima D D et al., 2010, Blood, Vol. 116, e118-e127. Also, "hsa-mir-4463" (miRBase Accession No. MI0016811, SEQ ID NO: 256) having a hairpin-like structure is known as a precursor of "hsa-miR-4463".

The term "hsa-miR-3185 gene" or "hsa-miR-3185" used herein includes the hsa-miR-3185 gene (miRBase Accession No. MIMAT0015065) described in SEQ ID NO: 82, a homolog or an ortholog of a different organism species, and the like. The hsa-miR-3185 gene can be obtained by a method described in Stark M S et al., 2010, PLoS One, Vol. 5, e9685. Also, "hsa-mir-3185" (miRBase Accession No. MI0014227, SEQ ID NO: 257) having a hairpin-like structure is known as a precursor of "hsa-miR-3185".

The term "hsa-miR-6870-5p gene" or "hsa-miR-6870-5p" used herein includes the hsa-miR-6870-5p gene (miRBase Accession No. MIMAT0027640) described in SEQ ID NO: 83, a homolog or an ortholog of a different organism species, and the like. The hsa-miR-6870-5p gene can be obtained by a method described in Ladewig E et al., 2012, Genome Res, Vol. 22, p. 1634-1645. Also, "hsa-mir-6870" (miRBase Accession No. MI0022717, SEQ ID NO: 258) having a hairpin-like structure is known as a precursor of "hsa-miR-6870-5p".

The term "hsa-miR-6779-5p gene" or "hsa-miR-6779-5p" used herein includes the hsa-miR-6779-5p gene (miRBase Accession No. MIMAT0027458) described in SEQ ID NO: 84, a homolog or an ortholog of a different organism species, and the like. The hsa-miR-6779-5p gene can be obtained by a method described in Ladewig E et al., 2012, Genome Res, Vol. 22, p. 1634-1645. Also, "hsa-mir-6779" (miRBase Accession No. MI0022624, SEQ ID NO: 259) having a hairpin-like structure is known as a precursor of "hsa-miR-6779-5p".

The term "hsa-miR-1273g-3p gene" or "hsa-miR-1273g-3p" used herein includes the hsa-miR-1273g-3p gene (miRBase Accession No. MIMAT0022742) described in SEQ ID NO: 85, a homolog or an ortholog of a different organism species, and the like. The hsa-miR-1273g-3p gene can be obtained by a method described in Reshmi G et al., 2011, Genomics, Vol. 97, p. 333-340. Also, "hsa-mir-1273g" (miRBase Accession No. MI0018003, SEQ ID NO: 260) having a hairpin-like structure is known as a precursor of "hsa-miR-1273g-3p".

The term "hsa-miR-8059 gene" or "hsa-miR-8059" used herein includes the hsa-miR-8059 gene (miRBase Accession No. MIMAT0030986) described in SEQ ID NO: 86, a homolog or an ortholog of a different organism species, and the like. The hsa-miR-8059 gene can be obtained by a method described in Wang H J et al., 2013, Shock, Vol. 39, p. 480-487. Also, "hsa-mir-8059" (miRBase Accession No. MI0025895, SEQ ID NO: 261) having a hairpin-like structure is known as a precursor of "hsa-miR-8059".

The term "hsa-miR-4697-5p gene" or "hsa-miR-4697-5p" used herein includes the hsa-miR-4697-5p gene (miRBase Accession No. MIMAT0019791) described in SEQ ID NO: 87, a homolog or an ortholog of a different organism species, and the like. The hsa-miR-4697-5p gene can be obtained by a method described in Persson H et al., 2011, Cancer Res, Vol. 71, p. 78-86. Also, "hsa-mir-4697" (miRBase Accession No. MI0017330, SEQ ID NO: 262) having a hairpin-like structure is known as a precursor of "hsa-miR-4697-5p".

The term "hsa-miR-4674 gene" or "hsa-miR-4674" used herein includes the hsa-miR-4674 gene (miRBase Accession No. MIMAT0019756) described in SEQ ID NO: 88, a homolog or an ortholog of a different organism species, and the like. The hsa-miR-4674 gene can be obtained by a method described in Persson H et al., 2011, Cancer Res, Vol. 71, p. 78-86. Also, "hsa-mir-4674" (miRBase Accession No.

MI0017305, SEQ ID NO: 263) having a hairpin-like structure is known as a precursor of "hsa-miR-4674".

The term "hsa-miR-4433-3p gene" or "hsa-miR-4433-3p" used herein includes the hsa-miR-4433-3p gene (miRBase Accession No. MIMAT0018949) described in SEQ ID NO: 89, a homolog or an ortholog of a different organism species, and the like. The hsa-miR-4433-3p gene can be obtained by a method described in Jima D D et al., 2010, Blood, Vol. 116, e118-e127. Also, "hsa-mir-4433" (miRBase Accession No. MI0016773, SEQ ID NO: 264) having a hairpin-like structure is known as a precursor of "hsa-miR-4433-3p".

The term "hsa-miR-4257 gene" or "hsa-miR-4257" used herein includes the hsa-miR-4257 gene (miRBase Accession No. MIMAT0016878) described in SEQ ID NO: 90, a homolog or an ortholog of a different organism species, and the like. The hsa-miR-4257 gene can be obtained by a method described in Goff L A et al., 2009, PLoS One, Vol. 4, e7192. Also, "hsa-mir-4257" (miRBase Accession No. MI0015856, SEQ ID NO: 265) having a hairpin-like structure is known as a precursor of "hsa-miR-4257".

The term "hsa-miR-1915-5p gene" or "hsa-miR-1915-5p" used herein includes the hsa-miR-1915-5p gene (miRBase Accession No. MIMAT0007891) described in SEQ ID NO: 91, a homolog or an ortholog of a different organism species, and the like. The hsa-miR-1915-5p gene can be obtained by a method described in Bar M et al., 2008, Stem Cells, Vol. 26, p. 2496-2505. Also, "hsa-mir-1915" (miRBase Accession No. MI0008336, SEQ ID NO: 266) having a hairpin-like structure is known as a precursor of "hsa-miR-1915-5p".

The term "hsa-miR-4417 gene" or "hsa-miR-4417" used herein includes the hsa-miR-4417 gene (miRBase Accession No. MIMAT0018929) described in SEQ ID NO: 92, a homolog or an ortholog of a different organism species, and the like. The hsa-miR-4417 gene can be obtained by a method described in Jima D D et al., 2010, Blood, Vol. 116, e118-e127. Also, "hsa-mir-4417" (miRBase Accession No. MI0016753, SEQ ID NO: 267) having a hairpin-like structure is known as a precursor of "hsa-miR-4417".

The term "hsa-miR-1343-5p gene" or "hsa-miR-1343-5p" used herein includes the hsa-miR-1343-5p gene (miRBase Accession No. MIMAT0027038) described in SEQ ID NO: 93, a homolog or an ortholog of a different organism species, and the like. The hsa-miR-1343-5p gene can be obtained by a method described in Persson H et al., 2011, Cancer Res, Vol. 71, p. 78-86. Also, "hsa-mir-1343" (miRBase Accession No. MI0017320, SEQ ID NO: 182) having a hairpin-like structure is known as a precursor of "hsa-miR-1343-5p".

The term "hsa-miR-6781-5p gene" or "hsa-miR-6781-5p" used herein includes the hsa-miR-6781-5p gene (miRBase Accession No. MIMAT0027462) described in SEQ ID NO: 94, a homolog or an ortholog of a different organism species, and the like. The hsa-miR-6781-5p gene can be obtained by a method described in Ladewig E et al., 2012, Genome Res, Vol. 22, p. 1634-1645. Also, "hsa-mir-6781" (miRBase Accession No. MI0022626, SEQ ID NO: 268) having a hairpin-like structure is known as a precursor of "hsa-miR-6781-5p".

The term "hsa-miR-4695-5p gene" or "hsa-miR-4695-5p" used herein includes the hsa-miR-4695-5p gene (miRBase Accession No. MIMAT0019788) described in SEQ ID NO: 95, a homolog or an ortholog of a different organism species, and the like. The hsa-miR-4695-5p gene can be obtained by a method described in Persson H et al., 2011, Cancer Res, Vol. 71, p. 78-86. Also, "hsa-mir-4695" (miRBase Accession No. MI0017328, SEQ ID NO: 269) having a hairpin-like structure is known as a precursor of "hsa-miR-4695-5p".

The term "hsa-miR-1237-5p gene" or "hsa-miR-1237-5p" used herein includes the hsa-miR-1237-5p gene (miRBase Accession No. MIMAT0022946) described in SEQ ID NO: 96, a homolog or an ortholog of a different organism species, and the like. The hsa-miR-1237-5p gene can be obtained by a method described in Berezikov E et al., 2007, Mol Cell, Vol. 28, p. 328-336. Also, "hsa-mir-1237" (miRBase Accession No. MI0006327, SEQ ID NO: 270) having a hairpin-like structure is known as a precursor of "hsa-miR-1237-5p".

The term "hsa-miR-6775-5p gene" or "hsa-miR-6775-5p" used herein includes the hsa-miR-6775-5p gene (miRBase Accession No. MIMAT0027450) described in SEQ ID NO: 97, a homolog or an ortholog of a different organism species, and the like. The hsa-miR-6775-5p gene can be obtained by a method described in Ladewig E et al., 2012, Genome Res, Vol. 22, p. 1634-1645. Also, "hsa-mir-6775" (miRBase Accession No. MI0022620, SEQ ID NO: 271) having a hairpin-like structure is known as a precursor of "hsa-miR-6775-5p".

The term "hsa-miR-7845-5p gene" or "hsa-miR-7845-5p" used herein includes the hsa-miR-7845-5p gene (miRBase Accession No. MIMAT0030420) described in SEQ ID NO: 98, a homolog or an ortholog of a different organism species, and the like. The hsa-miR-7845-5p gene can be obtained by a method described in Ple H et al., 2012, PLoS One, Vol. 7, e50746. Also, "hsa-mir-7845" (miRBase Accession No. MI0025515, SEQ ID NO: 272) having a hairpin-like structure is known as a precursor of "hsa-miR-7845-5p".

The term "hsa-miR-4746-3p gene" or "hsa-miR-4746-3p" used herein includes the hsa-miR-4746-3p gene (miRBase Accession No. MIMAT0019881) described in SEQ ID NO: 99, a homolog or an ortholog of a different organism species, and the like. The hsa-miR-4746-3p gene can be obtained by a method described in Persson H et al., 2011, Cancer Res, Vol. 71, p. 78-86. Also, "hsa-mir-4746" (miRBase Accession No. MI0017385, SEQ ID NO: 273) having a hairpin-like structure is known as a precursor of "hsa-miR-4746-3p".

The term "hsa-miR-7641 gene" or "hsa-miR-7641" used herein includes the hsa-miR-7641 gene (miRBase Accession No. MIMAT0029782) described in SEQ ID NO: 100, a homolog or an ortholog of a different organism species, and the like. The hsa-miR-7641 gene can be obtained by a method described in Yoo J K et al., 2013, Arch Pharm Res, Vol. 36, p. 353-358. Also, "hsa-mir-7641-1 and hsa-mir-7641-2" (miRBase Accession Nos. MI0024975 and MI0024976, SEQ ID NOs: 274 and 275) having a hairpin-like structure are known as precursors of "hsa-miR-7641".

The term "hsa-miR-7847-3p gene" or "hsa-miR-7847-3p" used herein includes the hsa-miR-7847-3p gene (miRBase Accession No. MIMAT0030422) described in SEQ ID NO: 101, a homolog or an ortholog of a different organism species, and the like. The hsa-miR-7847-3p gene can be obtained by a method described in Ple H et al., 2012, PLoS One, Vol. 7, e50746. Also, "hsa-mir-7847" (miRBase Accession No. MI0025517, SEQ ID NO: 276) having a hairpin-like structure is known as a precursor of "hsa-miR-7847-3p".

The term "hsa-miR-6806-5p gene" or "hsa-miR-6806-5p" used herein includes the hsa-miR-6806-5p gene (miRBase Accession No. MIMAT0027512) described in SEQ ID NO: 102, a homolog or an ortholog of a different organism species, and the like. The hsa-miR-6806-5p gene can be obtained by a method described in Ladewig E et al., 2012, Genome Res, Vol. 22, p. 1634-1645. Also, "hsa-mir-6806"

(miRBase Accession No. MI0022651, SEQ ID NO: 277) having a hairpin-like structure is known as a precursor of "hsa-miR-6806-5p".

The term "hsa-miR-4467 gene" or "hsa-miR-4467" used herein includes the hsa-miR-4467 gene (miRBase Accession No. MIMAT0018994) described in SEQ ID NO: 103, a homolog or an ortholog of a different organism species, and the like. The hsa-miR-4467 gene can be obtained by a method described in Jima D D et al., 2010, Blood, Vol. 116, e118-e127. Also, "hsa-mir-4467" (miRBase Accession No. MI0016818, SEQ ID NO: 278) having a hairpin-like structure is known as a precursor of "hsa-miR-4467".

The term "hsa-miR-4726-5p gene" or "hsa-miR-4726-5p" used herein includes the hsa-miR-4726-5p gene (miRBase Accession No. MIMAT0019845) described in SEQ ID NO: 104, a homolog or an ortholog of a different organism species, and the like. The hsa-miR-4726-5p gene can be obtained by a method described in Persson H et al., 2011, Cancer Res, Vol. 71, p. 78-86. Also, "hsa-mir-4726" (miRBase Accession No. MI0017363, SEQ ID NO: 279) having a hairpin-like structure is known as a precursor of "hsa-miR-4726-5p".

The term "hsa-miR-4648 gene" or "hsa-miR-4648" used herein includes the hsa-miR-4648 gene (miRBase Accession No. MIMAT0019710) described in SEQ ID NO: 105, a homolog or an ortholog of a different organism species, and the like. The hsa-miR-4648 gene can be obtained by a method described in Persson H et al., 2011, Cancer Res, Vol. 71, p. 78-86. Also, "hsa-mir-4648" (miRBase Accession No. MI0017275, SEQ ID NO: 280) having a hairpin-like structure is known as a precursor of "hsa-miR-4648".

The term "hsa-miR-6089 gene" or "hsa-miR-6089" used herein includes the hsa-miR-6089 gene (miRBase Accession No. MIMAT0023714) described in SEQ ID NO: 106, a homolog or an ortholog of a different organism species, and the like. The hsa-miR-6089 gene can be obtained by a method described in Yoo J K et al., 2012, Stem Cells Dev, Vol. 21, p. 2049-2057. Also, "hsa-mir-6089-1 and hsa-mir-6089-2" (miRBase Accession Nos. MI0020366 and MI0023563, SEQ ID NOs: 281 and 282) having a hairpin-like structure are known as precursors of "hsa-miR-6089".

The term "hsa-miR-1260b gene" or "hsa-miR-1260b" used herein includes the hsa-miR-1260b gene (miRBase Accession No. MIMAT0015041) described in SEQ ID NO: 107, a homolog or an ortholog of a different organism species, and the like. The hsa-miR-1260b gene can be obtained by a method described in Stark M S et al., 2010, PLoS One, Vol. 5, e9685. Also, "hsa-mir-1260b" (miRBase Accession No. MI0014197, SEQ ID NO: 283) having a hairpin-like structure is known as a precursor of "hsa-miR-1260b".

The term "hsa-miR-4532 gene" or "hsa-miR-4532" used herein includes the hsa-miR-4532 gene (miRBase Accession No. MIMAT0019071) described in SEQ ID NO: 108, a homolog or an ortholog of a different organism species, and the like. The hsa-miR-4532 gene can be obtained by a method described in Jima D D et al., 2010, Blood, Vol. 116, e118-e127. Also, "hsa-mir-4532" (miRBase Accession No. MI0016899, SEQ ID NO: 284) having a hairpin-like structure is known as a precursor of "hsa-miR-4532".

The term "hsa-miR-5195-3p gene" or "hsa-miR-5195-3p" used herein includes the hsa-miR-5195-3p gene (miRBase Accession No. MIMAT0021127) described in SEQ ID NO: 109, a homolog or an ortholog of a different organism species, and the like. The hsa-miR-5195-3p gene can be obtained by a method described in Schotte D et al., 2011, Leukemia, Vol. 25, p. 1389-1399. Also, "hsa-mir-5195" (miRBase Accession No. MI0018174, SEQ ID NO: 285) having a hairpin-like structure is known as a precursor of "hsa-miR-5195-3p".

The term "hsa-miR-3188 gene" or "hsa-miR-3188" used herein includes the hsa-miR-3188 gene (miRBase Accession No. MIMAT0015070) described in SEQ ID NO: 110, a homolog or an ortholog of a different organism species, and the like. The hsa-miR-3188 gene can be obtained by a method described in Stark M S et al., 2010, PLoS One, Vol. 5, e9685. Also, "hsa-mir-3188" (miRBase Accession No. MI0014232, SEQ ID NO: 286) having a hairpin-like structure is known as a precursor of "hsa-miR-3188".

The term "hsa-miR-6848-5p gene" or "hsa-miR-6848-5p" used herein includes the hsa-miR-6848-5p gene (miRBase Accession No. MIMAT0027596) described in SEQ ID NO: 111, a homolog or an ortholog of a different organism species, and the like. The hsa-miR-6848-5p gene can be obtained by a method described in Ladewig E et al., 2012, Genome Res, Vol. 22, p. 1634-1645. Also, "hsa-mir-6848" (miRBase Accession No. MI0022694, SEQ ID NO: 287) having a hairpin-like structure is known as a precursor of "hsa-miR-6848-5p".

The term "hsa-miR-1233-5p gene" or "hsa-miR-1233-5p" used herein includes the hsa-miR-1233-5p gene (miRBase Accession No. MIMAT0022943) described in SEQ ID NO: 112, a homolog or an ortholog of a different organism species, and the like. The hsa-miR-1233-5p gene can be obtained by a method described in Berezikov E et al., 2007, Mol Cell, Vol. 28, p. 328-336. Also, "hsa-mir-1233-1 and hsa-mir-1233-2" (miRBase Accession Nos. MI0006323 and MI0015973, SEQ ID NOs: 288 and 289) having a hairpin-like structure are known as precursors of "hsa-miR-1233-5p".

The term "hsa-miR-6717-5p gene" or "hsa-miR-6717-5p" used herein includes the hsa-miR-6717-5p gene (miRBase Accession No. MIMAT0025846) described in SEQ ID NO: 113, a homolog or an ortholog of a different organism species, and the like. The hsa-miR-6717-5p gene can be obtained by a method described in Li Y et al., 2012, Gene, Vol. 497, p. 330-335. Also, "hsa-mir-6717" (miRBase Accession No. MI0022551, SEQ ID NO: 290) having a hairpin-like structure is known as a precursor of "hsa-miR-6717-5p".

The term "hsa-miR-3195 gene" or "hsa-miR-3195" used herein includes the hsa-miR-3195 gene (miRBase Accession No. MIMAT0015079) described in SEQ ID NO: 114, a homolog or an ortholog of a different organism species, and the like. The hsa-miR-3195 gene can be obtained by a method described in Stark M S et al., 2010, PLoS One, Vol. 5, e9685. Also, "hsa-mir-3195" (miRBase Accession No. MI0014240, SEQ ID NO: 291) having a hairpin-like structure is known as a precursor of "hsa-miR-3195".

The term "hsa-miR-6757-5p gene" or "hsa-miR-6757-5p" used herein includes the hsa-miR-6757-5p gene (miRBase Accession No. MIMAT0027414) described in SEQ ID NO: 115, a homolog or an ortholog of a different organism species, and the like. The hsa-miR-6757-5p gene can be obtained by a method described in Ladewig E et al., 2012, Genome Res, Vol. 22, p. 1634-1645. Also, "hsa-mir-6757" (miRBase Accession No. MI0022602, SEQ ID NO: 292) having a hairpin-like structure is known as a precursor of "hsa-miR-6757-5p".

The term "hsa-miR-8072 gene" or "hsa-miR-8072" used herein includes the hsa-miR-8072 gene (miRBase Accession No. MIMAT0030999) described in SEQ ID NO: 116, a homolog or an ortholog of a different organism species, and the like. The hsa-miR-8072 gene can be obtained by a method described in Wang H J et al., 2013, Shock, Vol. 39, p. 480-487. Also, "hsa-mir-8072" (miRBase Accession No. MI0025908, SEQ ID NO: 293) having a hairpin-like structure is known as a precursor of "hsa-miR-8072".

The term "hsa-miR-4745-5p gene" or "hsa-miR-4745-5p" used herein includes the hsa-miR-4745-5p gene (miRBase Accession No. MIMAT0019878) described in SEQ ID NO: 117, a homolog or an ortholog of a different organism species, and the like. The hsa-miR-4745-5p gene can be obtained by a method described in Persson H et al., 2011, Cancer Res, Vol. 71, p. 78-86. Also, "hsa-mir-4745" (miRBase Accession No. MI0017384, SEQ ID NO: 294) having a hairpin-like structure is known as a precursor of "hsa-miR-4745-5p".

The term "hsa-miR-6511a-5p gene" or "hsa-miR-6511a-5p" used herein includes the hsa-miR-6511a-5p gene (miRBase Accession No. MIMAT0025478) described in SEQ ID NO: 118, a homolog or an ortholog of a different organism species, and the like. The hsa-miR-6511a-5p gene can be obtained by a method described in Joyce C E et al., 2011, Hum Mol Genet, Vol. 20, p. 4025-4040. Also, "hsa-mir-6511a-1, hsa-mir-6511a-2, hsa-mir-6511a-3, and hsa-mir-6511a-4" (miRBase Accession Nos. MI0022223, MI0023564, MI0023565, and MI0023566, SEQ ID NOs: 295, 296, 297, and 298) having a hairpin-like structure are known as precursors of "hsa-miR-6511a-5p".

The term "hsa-miR-6776-5p gene" or "hsa-miR-6776-5p" used herein includes the hsa-miR-6776-5p gene (miRBase Accession No. MIMAT0027452) described in SEQ ID NO: 119, a homolog or an ortholog of a different organism species, and the like. The hsa-miR-6776-5p gene can be obtained by a method described in Ladewig E et al., 2012, Genome Res, Vol. 22, p. 1634-1645. Also, "hsa-mir-6776" (miRBase Accession No. MI0022621, SEQ ID NO: 299) having a hairpin-like structure is known as a precursor of "hsa-miR-6776-5p".

The term "hsa-miR-371a-5p gene" or "hsa-miR-371a-5p" used herein includes the hsa-miR-371a-5p gene (miRBase Accession No. MIMAT0004687) described in SEQ ID NO: 120, a homolog or an ortholog of a different organism species, and the like. The hsa-miR-371a-5p gene can be obtained by a method described in Suh M R et al., 2004, Dev Biol, Vol. 270, p. 488-498. Also, "hsa-mir-371a" (miRBase Accession No. MI0000779, SEQ ID NO: 300) having a hairpin-like structure is known as a precursor of "hsa-miR-371a-5p".

The term "hsa-miR-1227-5p gene" or "hsa-miR-1227-5p" used herein includes the hsa-miR-1227-5p gene (miRBase Accession No. MIMAT0022941) described in SEQ ID NO: 121, a homolog or an ortholog of a different organism species, and the like. The hsa-miR-1227-5p gene can be obtained by a method described in Berezikov E et al., 2007, Mol Cell, Vol. 28, p. 328-336. Also, "hsa-mir-1227" (miRBase Accession No. MI0006316, SEQ ID NO: 301) having a hairpin-like structure is known as a precursor of "hsa-miR-1227-5p".

The term "hsa-miR-7150 gene" or "hsa-miR-7150" used herein includes the hsa-miR-7150 gene (miRBase Accession No. MIMAT0028211) described in SEQ ID NO: 122, a homolog or an ortholog of a different organism species, and the like. The hsa-miR-7150 gene can be obtained by a method described in Oulas A et al., 2009, Nucleic Acids Res, Vol. 37, p. 3276-3287. Also, "hsa-mir-7150" (miRBase Accession No. MI0023610, SEQ ID NO: 302) having a hairpin-like structure is known as a precursor of "hsa-miR-7150".

The term "hsa-miR-1915-3p gene" or "hsa-miR-1915-3p" used herein includes the hsa-miR-1915-3p gene (miRBase Accession No. MIMAT0007892) described in SEQ ID NO: 123, a homolog or an ortholog of a different organism species, and the like. The hsa-miR-1915-3p gene can be obtained by a method described in Bar M et al., 2008, Stem Cells, Vol. 26, p. 2496-2505. Also, "hsa-mir-1915" (miRBase Accession No. MI0008336, SEQ ID NO: 266) having a hairpin-like structure is known as a precursor of "hsa-miR-1915-3p".

The term "hsa-miR-187-5p gene" or "hsa-miR-187-5p" used herein includes the hsa-miR-187-5p gene (miRBase Accession No. MIMAT0004561) described in SEQ ID NO: 124, a homolog or an ortholog of a different organism species, and the like. The hsa-miR-187-5p gene can be obtained by a method described in Lim L P et al., 2003, Science, Vol. 299, p. 1540. Also, "hsa-mir-187" (miRBase Accession No. MI0000274, SEQ ID NO: 303) having a hairpin-like structure is known as a precursor of "hsa-miR-187-5p".

The term "hsa-miR-614 gene" or "hsa-miR-614" used herein includes the hsa-miR-614 gene (miRBase Accession No. MIMAT0003282) described in SEQ ID NO: 125, a homolog or an ortholog of a different organism species, and the like. The hsa-miR-614 gene can be obtained by a method described in Cummins J M et al., 2006, Proc Natl Acad Sci USA, Vol. 103, p. 3687-3692. Also, "hsa-mir-614" (miRBase Accession No. MI0003627, SEQ ID NO: 304) having a hairpin-like structure is known as a precursor of "hsa-miR-614".

The term "hsa-miR-19b-3p gene" or "hsa-miR-19b-3p" used herein includes the hsa-miR-19b-3p gene (miRBase Accession No. MIMAT0000074) described in SEQ ID NO: 126, a homolog or an ortholog of a different organism species, and the like. The hsa-miR-19b-3p gene can be obtained by a method described in Lagos-Quintana M et al., 2001, Science, Vol. 294, p. 853-858. Also, "hsa-mir-19b-1 and hsa-mir-19b-2" (miRBase Accession Nos. MI0000074 and MI0000075, SEQ ID NOs: 305 and 306) having a hairpin-like structure are known as precursors of "hsa-miR-19b-3p".

The term "hsa-miR-1225-5p gene" or "hsa-miR-1225-5p" used herein includes the hsa-miR-1225-5p gene (miRBase Accession No. MIMAT0005572) described in SEQ ID NO: 127, a homolog or an ortholog of a different organism species, and the like. The hsa-miR-1225-5p gene can be obtained by a method described in Berezikov E et al., 2007, Mol Cell, Vol. 28, p. 328-336. Also, "hsa-mir-1225" (miRBase Accession No. MI0006311, SEQ ID NO: 307) having a hairpin-like structure is known as a precursor of "hsa-miR-1225-5p".

The term "hsa-miR-451a gene" or "hsa-miR-451a" used herein includes the hsa-miR-451a gene (miRBase Accession No. MIMAT0001631) described in SEQ ID NO: 128, a homolog or an ortholog of a different organism species, and the like. The hsa-miR-451a gene can be obtained by a method described in Altuvia Y et al., 2005, Nucleic Acids Res, Vol. 33, p. 2697-2706. Also, "hsa-mir-451a" (miRBase Accession No. MI0001729, SEQ ID NO: 308) having a hairpin-like structure is known as a precursor of "hsa-miR-451a".

The term "hsa-miR-939-5p gene" or "hsa-miR-939-5p" used herein includes the hsa-miR-939-5p gene (miRBase Accession No. MIMAT0004982) described in SEQ ID NO: 129, a homolog or an ortholog of a different organism species, and the like. The hsa-miR-939-5p gene can be obtained by a method described in Lui W O et al., 2007, Cancer Res, Vol. 67, p. 6031-6043. Also, "hsa-mir-939" (miRBase Accession No. MI0005761, SEQ ID NO: 309) having a hairpin-like structure is known as a precursor of "hsa-miR-939-5p".

The term "hsa-miR-223-3p gene" or "hsa-miR-223-3p" used herein includes the hsa-miR-223-3p gene (miRBase Accession No. MIMAT0000280) described in SEQ ID NO: 130, a homolog or an ortholog of a different organism species, and the like. The hsa-miR-223-3p gene can be obtained by a method described in Lim L P et al., 2003, Science, Vol. 299, p. 1540. Also, "hsa-mir-223" (miRBase Accession No. MI0000300, SEQ ID NO: 310) having a hairpin-like structure is known as a precursor of "hsa-miR-223-3p".

The term "hsa-miR-1228-5p gene" or "hsa-miR-1228-5p" used herein includes the hsa-miR-1228-5p gene (miRBase Accession No. MIMAT0005582) described in SEQ ID NO: 131, a homolog or an ortholog of a different organism species, and the like. The hsa-miR-1228-5p gene can be obtained by a method described in Berezikov E et al., 2007, Mol Cell, Vol. 28, p. 328-336. Also, "hsa-mir-1228" (miRBase Accession No. MI0006318, SEQ ID NO: 311) having a hairpin-like structure is known as a precursor of "hsa-miR-1228-5p".

The term "hsa-miR-125a-3p gene" or "hsa-miR-125a-3p" used herein includes the hsa-miR-125a-3p gene (miRBase Accession No. MIMAT0004602) described in SEQ ID NO: 132, a homolog or an ortholog of a different organism species, and the like. The hsa-miR-125a-3p gene can be obtained by a method described in Lagos-Quintana M et al., 2002, Curr Biol, Vol. 12, p. 735-739. Also, "hsa-mir-125a" (miRBase Accession No. MI0000469, SEQ ID NO: 312) having a hairpin-like structure is known as a precursor of "hsa-miR-125a-3p".

The term "hsa-miR-92b-5p gene" or "hsa-miR-92b-5p" used herein includes the hsa-miR-92b-5p gene (miRBase Accession No. MIMAT0004792) described in SEQ ID NO: 133, a homolog or an ortholog of a different organism species, and the like. The hsa-miR-92b-5p gene can be obtained by a method described in Cummins J M et al., 2006, Proc Natl Acad Sci USA, Vol. 103, p. 3687-3692. Also, "hsa-mir-92b" (miRBase Accession No. MI0003560, SEQ ID NO: 313) having a hairpin-like structure is known as a precursor of "hsa-miR-92b-5p".

The term "hsa-miR-22-3p gene" or "hsa-miR-22-3p" used herein includes the hsa-miR-22-3p gene (miRBase Accession No. MIMAT0000077) described in SEQ ID NO: 134, a homolog or an ortholog of a different organism species, and the like. The hsa-miR-22-3p gene can be obtained by a method described in Lagos-Quintana M et al., 2001, Science, Vol. 294, p. 853-858. Also, "hsa-mir-22" (miRBase Accession No. MI0000078, SEQ ID NO: 314) having a hairpin-like structure is known as a precursor of "hsa-miR-22-3p".

The term "hsa-miR-4271 gene" or "hsa-miR-4271" used herein includes the hsa-miR-4271 gene (miRBase Accession No. MIMAT0016901) described in SEQ ID NO: 135, a homolog or an ortholog of a different organism species, and the like. The hsa-miR-4271 gene can be obtained by a method described in Goff L A et al., 2009, PLoS One, Vol. 4, e7192. Also, "hsa-mir-4271" (miRBase Accession No. MI0015879, SEQ ID NO: 315) having a hairpin-like structure is known as a precursor of "hsa-miR-4271".

The term "hsa-miR-642b-3p gene" or "hsa-miR-642b-3p" used herein includes the hsa-miR-642b-3p gene (miRBase Accession No. MIMAT0018444) described in SEQ ID NO: 136, a homolog or an ortholog of a different organism species, and the like. The hsa-miR-642b-3p gene can be obtained by a method described in Witten D et al., 2010, BMC Biol, Vol. 8, p. 58. Also, "hsa-mir-642b" (miRBase Accession No. MI0016685, SEQ ID NO: 316) having a hairpin-like structure is known as a precursor of "hsa-miR-642b-3p".

The term "hsa-miR-6075 gene" or "hsa-miR-6075" used herein includes the hsa-miR-6075 gene (miRBase Accession No. MIMAT0023700) described in SEQ ID NO: 137, a homolog or an ortholog of a different organism species, and the like. The hsa-miR-6075 gene can be obtained by a method described in Voellenkle C et al., 2012, RNA, Vol. 18, p. 472-484. Also, "hsa-mir-6075" (miRBase Accession No. MI0020352, SEQ ID NO: 317) having a hairpin-like structure is known as a precursor of "hsa-miR-6075".

The term "hsa-miR-6125 gene" or "hsa-miR-6125" used herein includes the hsa-miR-6125 gene (miRBase Accession No. MIMAT0024598) described in SEQ ID NO: 138, a homolog or an ortholog of a different organism species, and the like. The hsa-miR-6125 gene can be obtained by a method described in Smith J L et al., 2012, J Virol, Vol. 86, p. 5278-5287. Also, "hsa-mir-6125" (miRBase Accession No. MI0021259, SEQ ID NO: 318) having a hairpin-like structure is known as a precursor of "hsa-miR-6125".

The term "hsa-miR-887-3p gene" or "hsa-miR-887-3p" used herein includes the hsa-miR-887-3p gene (miRBase Accession No. MIMAT0004951) described in SEQ ID NO: 139, a homolog or an ortholog of a different organism species, and the like. The hsa-miR-887-3p gene can be obtained by a method described in Berezikov E et al., 2006, Genome Res, Vol. 16, p. 1289-1298. Also, "hsa-mir-887" (miRBase Accession No. MI0005562, SEQ ID NO: 319) having a hairpin-like structure is known as a precursor of "hsa-miR-887-3p".

The term "hsa-miR-6851-5p gene" or "hsa-miR-6851-5p" used herein includes the hsa-miR-6851-5p gene (miRBase Accession No. MIMAT0027602) described in SEQ ID NO: 140, a homolog or an ortholog of a different organism species, and the like. The hsa-miR-6851-5p gene can be obtained by a method described in Ladewig E et al., 2012, Genome Res, Vol. 22, p. 1634-1645. Also, "hsa-mir-6851" (miRBase Accession No. MI0022697, SEQ ID NO: 320) having a hairpin-like structure is known as a precursor of "hsa-miR-6851-5p".

The term "hsa-miR-6763-5p gene" or "hsa-miR-6763-5p" used herein includes the hsa-miR-6763-5p gene (miRBase Accession No. MIMAT0027426) described in SEQ ID NO: 141, a homolog or an ortholog of a different organism species, and the like. The hsa-miR-6763-5p gene can be obtained by a method described in Ladewig E et al., 2012, Genome Res, Vol. 22, p. 1634-1645. Also, "hsa-mir-6763" (miRBase Accession No. MI0022608, SEQ ID NO: 321) having a hairpin-like structure is known as a precursor of "hsa-miR-6763-5p".

The term "hsa-miR-3928-3p gene" or "hsa-miR-3928-3p" used herein includes the hsa-miR-3928-3p gene (miRBase Accession No. MIMAT0018205) described in SEQ ID NO: 142, a homolog or an ortholog of a different organism species, and the like. The hsa-miR-3928-3p gene can be obtained by a method described in Creighton C J et al., 2010, PLoS One, Vol. 5, e9637. Also, "hsa-mir-3928" (miRBase Accession No. MI0016438, SEQ ID NO: 322) having a hairpin-like structure is known as a precursor of "hsa-miR-3928-3p".

The term "hsa-miR-4443 gene" or "hsa-miR-4443" used herein includes the hsa-miR-4443 gene (miRBase Accession No. MIMAT0018961) described in SEQ ID NO: 143, a homolog or an ortholog of a different organism species, and the like. The hsa-miR-4443 gene can be obtained by a method described in Jima D D et al., 2010, Blood, Vol. 116, e118-e127. Also, "hsa-mir-4443" (miRBase Accession No. MI0016786, SEQ ID NO: 323) having a hairpin-like structure is known as a precursor of "hsa-miR-4443".

The term "hsa-miR-3648 gene" or "hsa-miR-3648" used herein includes the hsa-miR-3648 gene (miRBase Accession No. MIMAT0018068) described in SEQ ID NO: 144, a homolog or an ortholog of a different organism species, and the like. The hsa-miR-3648 gene can be obtained by a method described in Meiri E et al., 2010, Nucleic Acids Res, Vol. 38, p. 6234-6246. Also, "hsa-mir-3648" (miRBase Accession No. MI0016048, SEQ ID NO: 324) having a hairpin-like structure is known as a precursor of "hsa-miR-3648".

The term "hsa-miR-149-3p gene" or "hsa-miR-149-3p" used herein includes the hsa-miR-149-3p gene (miRBase Accession No. MIMAT0004609) described in SEQ ID NO: 145, a homolog or an ortholog of a different organism species, and the like. The hsa-miR-149-3p gene can be obtained by a method described in Lagos-Quintana M et al., 2002, Curr Biol, Vol. 12, p. 735-739. Also, "hsa-mir-149" (miRBase Accession No. MI0000478, SEQ ID NO: 325) having a hairpin-like structure is known as a precursor of "hsa-miR-149-3p".

The term "hsa-miR-4689 gene" or "hsa-miR-4689" used herein includes the hsa-miR-4689 gene (miRBase Accession No. MIMAT0019778) described in SEQ ID NO: 146, a homolog or an ortholog of a different organism species, and the like. The hsa-miR-4689 gene can be obtained by a method described in Persson H et al., 2011, Cancer Res, Vol. 71, p. 78-86. Also, "hsa-mir-4689" (miRBase Accession No. MI0017322, SEQ ID NO: 326) having a hairpin-like structure is known as a precursor of "hsa-miR-4689".

The term "hsa-miR-4763-3p gene" or "hsa-miR-4763-3p" used herein includes the hsa-miR-4763-3p gene (miRBase Accession No. MIMAT0019913) described in SEQ ID NO: 147, a homolog or an ortholog of a different organism species, and the like. The hsa-miR-4763-3p gene can be obtained by a method described in Persson H et al., 2011, Cancer Res, Vol. 71, p. 78-86. Also, "hsa-mir-4763" (miRBase Accession No. MI0017404, SEQ ID NO: 327) having a hairpin-like structure is known as a precursor of "hsa-miR-4763-3p".

The term "hsa-miR-6729-5p gene" or "hsa-miR-6729-5p" used herein includes the hsa-miR-6729-5p gene (miRBase Accession No. MIMAT0027359) described in SEQ ID NO: 148, a homolog or an ortholog of a different organism species, and the like. The hsa-miR-6729-5p gene can be obtained by a method described in Ladewig E et al., 2012, Genome Res, Vol. 22, p. 1634-1645. Also, "hsa-mir-6729" (miRBase Accession No. MI0022574, SEQ ID NO: 328) having a hairpin-like structure is known as a precursor of "hsa-miR-6729-5p".

The term "hsa-miR-3196 gene" or "hsa-miR-3196" used herein includes the hsa-miR-3196 gene (miRBase Accession No. MIMAT0015080) described in SEQ ID NO: 149, a homolog or an ortholog of a different organism species, and the like. The hsa-miR-3196 gene can be obtained by a method described in Stark M S et al., 2010, PLoS One, Vol. 5, e9685. Also, "hsa-mir-3196" (miRBase Accession No. MI0014241, SEQ ID NO: 329) having a hairpin-like structure is known as a precursor of "hsa-miR-3196".

The term "hsa-miR-8069 gene" or "hsa-miR-8069" used herein includes the hsa-miR-8069 gene (miRBase Accession No. MIMAT0030996) described in SEQ ID NO: 150, a homolog or an ortholog of a different organism species, and the like. The hsa-miR-8069 gene can be obtained by a method described in Wang H J et al., 2013, Shock, Vol. 39, p. 480-487. Also, "hsa-mir-8069" (miRBase Accession No. MI0025905, SEQ ID NO: 330) having a hairpin-like structure is known as a precursor of "hsa-miR-8069".

The term "hsa-miR-1268a gene" or "hsa-miR-1268a" used herein includes the hsa-miR-1268a gene (miRBase Accession No. MIMAT0005922) described in SEQ ID NO: 151, a homolog or an ortholog of a different organism species, and the like. The hsa-miR-1268a gene can be obtained by a method described in Morin R D et al., 2008, Genome Res, Vol. 18, p. 610-621. Also, "hsa-mir-1268a" (miRBase Accession No. MI0006405, SEQ ID NO: 331) having a hairpin-like structure is known as a precursor of "hsa-miR-1268a".

The term "hsa-miR-4739 gene" or "hsa-miR-4739" used herein includes the hsa-miR-4739 gene (miRBase Accession No. MIMAT0019868) described in SEQ ID NO: 152, a homolog or an ortholog of a different organism species, and the like. The hsa-miR-4739 gene can be obtained by a method described in Persson H et al., 2011, Cancer Res, Vol. 71, p. 78-86. Also, "hsa-mir-4739" (miRBase Accession No. MI0017377, SEQ ID NO: 332) having a hairpin-like structure is known as a precursor of "hsa-miR-4739".

The term "hsa-miR-1268b gene" or "hsa-miR-1268b" used herein includes the hsa-miR-1268b gene (miRBase Accession No. MIMAT0018925) described in SEQ ID NO: 153, a homolog or an ortholog of a different organism species, and the like. The hsa-miR-1268b gene can be obtained by a method described in Jima D D et al., 2010, Blood, Vol. 116, e118-e127. Also, "hsa-mir-1268b" (miRBase Accession No. MI0016748, SEQ ID NO: 333) having a hairpin-like structure is known as a precursor of "hsa-miR-1268b".

The term "hsa-miR-5698 gene" or "hsa-miR-5698" used herein includes the hsa-miR-5698 gene (miRBase Accession No. MIMAT0022491) described in SEQ ID NO: 154, a homolog or an ortholog of a different organism species, and the like. The hsa-miR-5698 gene can be obtained by a method described in Watahiki A et al., 2011, PLoS One, Vol. 6, e24950. Also, "hsa-mir-5698" (miRBase Accession No. MI0019305, SEQ ID NO: 334) having a hairpin-like structure is known as a precursor of "hsa-miR-5698".

The term "hsa-miR-6752-5p gene" or "hsa-miR-6752-5p" used herein includes the hsa-miR-6752-5p gene (miRBase Accession No. MIMAT0027404) described in SEQ ID NO: 155, a homolog or an ortholog of a different organism species, and the like. The hsa-miR-6752-5p gene can be obtained by a method described in Ladewig E et al., 2012, Genome Res, Vol. 22, p. 1634-1645. Also, "hsa-mir-6752" (miRBase Accession No. MI0022597, SEQ ID NO: 335) having a hairpin-like structure is known as a precursor of "hsa-miR-6752-5p".

The term "hsa-miR-4507 gene" or "hsa-miR-4507" used herein includes the hsa-miR-4507 gene (miRBase Accession No. MIMAT0019044) described in SEQ ID NO: 156, a homolog or an ortholog of a different organism species, and the like. The hsa-miR-4507 gene can be obtained by a method described in Jima D D et al., 2010, Blood, Vol. 116, e118-e127. Also, "hsa-mir-4507" (miRBase Accession No. MI0016871, SEQ ID NO: 336) having a hairpin-like structure is known as a precursor of "hsa-miR-4507".

The term "hsa-miR-564 gene" or "hsa-miR-564" used herein includes the hsa-miR-564 gene (miRBase Accession No. MIMAT0003228) described in SEQ ID NO: 157, a homolog or an ortholog of a different organism species, and the like. The hsa-miR-564 gene can be obtained by a method described in Cummins J M et al., 2006, Proc Natl Acad Sci USA, Vol. 103, p. 3687-3692. Also, "hsa-mir-564" (miRBase Accession No. MI0003570, SEQ ID NO: 337) having a hairpin-like structure is known as a precursor of "hsa-miR-564".

The term "hsa-miR-4497 gene" or "hsa-miR-4497" used herein includes the hsa-miR-4497 gene (miRBase Accession No. MIMAT0019032) described in SEQ ID NO: 158, a homolog or an ortholog of a different organism species, and the like. The hsa-miR-4497 gene can be obtained by a method described in Jima D D et al., 2010, Blood, Vol. 116, e118-e127. Also, "hsa-mir-4497" (miRBase Accession No. MI0016859, SEQ ID NO: 338) having a hairpin-like structure is known as a precursor of "hsa-miR-4497".

The term "hsa-miR-6877-5p gene" or "hsa-miR-6877-5p" used herein includes the hsa-miR-6877-5p gene (miRBase Accession No. MIMAT0027654) described in SEQ ID NO: 159, a homolog or an ortholog of a different organism species, and the like. The hsa-miR-6877-5p gene can be obtained by a method described in Ladewig E et al., 2012, Genome Res, Vol. 22, p. 1634-1645. Also, "hsa-mir-6877" (miRBase Accession No. MI0022724, SEQ ID NO: 339) having a hairpin-like structure is known as a precursor of "hsa-miR-6877-5p".

The term "hsa-miR-6087 gene" or "hsa-miR-6087" used herein includes the hsa-miR-6087 gene (miRBase Accession No. MIMAT0023712) described in SEQ ID NO: 160, a homolog or an ortholog of a different organism species, and the like. The hsa-miR-6087 gene can be obtained by a method described in Yoo J K et al., 2012, Stem Cells Dev, Vol. 21, p. 2049-2057. Also, "hsa-mir-6087" (miRBase Accession No. MI0020364, SEQ ID NO: 340) having a hairpin-like structure is known as a precursor of "hsa-miR-6087".

The term "hsa-miR-4731-5p gene" or "hsa-miR-4731-5p" used herein includes the hsa-miR-4731-5p gene (miRBase Accession No. MIMAT0019853) described in SEQ ID NO: 161, a homolog or an ortholog of a different organism species, and the like. The hsa-miR-4731-5p gene can be obtained by a method described in Persson H et al., 2011, Cancer Res, Vol. 71, p. 78-86. Also, "hsa-mir-4731" (miRBase Accession No. MI0017368, SEQ ID NO: 341) having a hairpin-like structure is known as a precursor of "hsa-miR-4731-5p".

The term "hsa-miR-615-5p gene" or "hsa-miR-615-5p" used herein includes the hsa-miR-615-5p gene (miRBase Accession No. MIMAT0004804) described in SEQ ID NO: 162, a homolog or an ortholog of a different organism species, and the like. The hsa-miR-615-5p gene can be obtained by a method described in Cummins J M et al., 2006, Proc Natl Acad Sci USA, Vol. 103, p. 3687-3692. Also, "hsa-mir-615" (miRBase Accession No. MI0003628, SEQ ID NO: 342) having a hairpin-like structure is known as a precursor of "hsa-miR-615-5p".

The term "hsa-miR-760 gene" or "hsa-miR-760" used herein includes the hsa-miR-760 gene (miRBase Accession No. MIMAT0004957) described in SEQ ID NO: 163, a homolog or an ortholog of a different organism species, and the like. The hsa-miR-760 gene can be obtained by a method described in Berezikov E et al., 2006, Genome Res, Vol. 16, p. 1289-1298. Also, "hsa-mir-760" (miRBase Accession No. MI0005567, SEQ ID NO: 343) having a hairpin-like structure is known as a precursor of "hsa-miR-760".

The term "hsa-miR-6891-5p gene" or "hsa-miR-6891-5p" used herein includes the hsa-miR-6891-5p gene (miRBase Accession No. MIMAT0027682) described in SEQ ID NO: 164, a homolog or an ortholog of a different organism species, and the like. The hsa-miR-6891-5p gene can be obtained by a method described in Ladewig E et al., 2012, Genome Res, Vol. 22, p. 1634-1645. Also, "hsa-mir-6891" (miRBase Accession No. MI0022738, SEQ ID NO: 344) having a hairpin-like structure is known as a precursor of "hsa-miR-6891-5p".

The term "hsa-miR-6887-5p gene" or "hsa-miR-6887-5p" used herein includes the hsa-miR-6887-5p gene (miRBase Accession No. MIMAT0027674) described in SEQ ID NO: 165, a homolog or an ortholog of a different organism species, and the like. The hsa-miR-6887-5p gene can be obtained by a method described in Ladewig E et al., 2012, Genome Res, Vol. 22, p. 1634-1645. Also, "hsa-mir-6887" (miRBase Accession No. MI0022734, SEQ ID NO: 345) having a hairpin-like structure is known as a precursor of "hsa-miR-6887-5p".

The term "hsa-miR-4525 gene" or "hsa-miR-4525" used herein includes the hsa-miR-4525 gene (miRBase Accession No. MIMAT0019064) described in SEQ ID NO: 166, a homolog or an ortholog of a different organism species, and the like. The hsa-miR-4525 gene can be obtained by a method described in Jima D D et al., 2010, Blood, Vol. 116, e118-e127. Also, "hsa-mir-4525" (miRBase Accession No. MI0016892, SEQ ID NO: 346) having a hairpin-like structure is known as a precursor of "hsa-miR-4525".

The term "hsa-miR-1914-3p gene" or "hsa-miR-1914-3p" used herein includes the hsa-miR-1914-3p gene (miRBase Accession No. MIMAT0007890) described in SEQ ID NO: 167, a homolog or an ortholog of a different organism species, and the like. The hsa-miR-1914-3p gene can be obtained by a method described in Bar M et al., 2008, Stem Cells, Vol. 26, p. 2496-2505. Also, "hsa-mir-1914" (miRBase Accession No. MI0008335, SEQ ID NO: 347) having a hairpin-like structure is known as a precursor of "hsa-miR-1914-3p".

The term "hsa-miR-619-5p gene" or "hsa-miR-619-5p" used herein includes the hsa-miR-619-5p gene (miRBase Accession No. MIMAT0026622) described in SEQ ID NO: 168, a homolog or an ortholog of a different organism species, and the like. The hsa-miR-619-5p gene can be obtained by a method described in Cummins J M et al., 2006, Proc Natl Acad Sci USA, Vol. 103, p. 3687-3692. Also, "hsa-mir-619" (miRBase Accession No. MI0003633, SEQ ID NO: 348) having a hairpin-like structure is known as a precursor of "hsa-miR-619-5p".

The term "hsa-miR-5001-5p gene" or "hsa-miR-5001-5p" used herein includes the hsa-miR-5001-5p gene (miRBase Accession No. MIMAT0021021) described in SEQ ID NO: 169, a homolog or an ortholog of a different organism species, and the like. The hsa-miR-5001-5p gene can be obtained by a method described in Hansen T B et al., 2011, RNA Biol, Vol. 8, p. 378-383. Also, "hsa-mir-5001" (miRBase Accession No. MI0017867, SEQ ID NO: 349) having a hairpin-like structure is known as a precursor of "hsa-miR-5001-5p".

The term "hsa-miR-6722-3p gene" or "hsa-miR-6722-3p" used herein includes the hsa-miR-6722-3p gene (miRBase Accession No. MIMAT0025854) described in SEQ ID NO: 170, a homolog or an ortholog of a different organism species, and the like. The hsa-miR-6722-3p gene can be obtained by a method described in Li Y et al., 2012, Gene, Vol. 497, p. 330-335. Also, "hsa-mir-6722" (miRBase Accession No. MI0022557, SEQ ID NO: 350) having a hairpin-like structure is known as a precursor of "hsa-miR-6722-3p".

The term "hsa-miR-3621 gene" or "hsa-miR-3621" used herein includes the hsa-miR-3621 gene (miRBase Accession No. MIMAT0018002) described in SEQ ID NO: 171, a homolog or an ortholog of a different organism species, and the like. The hsa-miR-3621 gene can be obtained by a method described in Witten D et al., 2010, BMC Biol, Vol. 8, p. 58. Also, "hsa-mir-3621" (miRBase Accession No. MI0016012, SEQ ID NO: 351) having a hairpin-like structure is known as a precursor of "hsa-miR-3621".

The term "hsa-miR-4298 gene" or "hsa-miR-4298" used herein includes the hsa-miR-4298 gene (miRBase Accession No. MIMAT0016852) described in SEQ ID NO: 172, a homolog or an ortholog of a different organism species, and the like. The hsa-miR-4298 gene can be obtained by a method described in Goff L A et al., 2009, PLoS One, Vol. 4, e7192. Also, "hsa-mir-4298" (miRBase Accession No. MI0015830, SEQ ID NO: 352) having a hairpin-like structure is known as a precursor of "hsa-miR-4298".

The term "hsa-miR-675-5p gene" or "hsa-miR-675-5p" used herein includes the hsa-miR-675-5p gene (miRBase Accession No. MIMAT0004284) described in SEQ ID NO: 173, a homolog or an ortholog of a different organism species, and the like. The hsa-miR-675-5p gene can be obtained by a method described in Cai X et al., 2007, RNA, Vol. 13, p. 313-316. Also, "hsa-mir-675" (miRBase Accession No. MI0005416, SEQ ID NO: 353) having a hairpin-like structure is known as a precursor of "hsa-miR-675-5p".

The term "hsa-miR-4655-5p gene" or "hsa-miR-4655-5p" used herein includes the hsa-miR-4655-5p gene (miRBase Accession No. MIMAT0019721) described in SEQ ID NO: 174, a homolog or an ortholog of a different organism species, and the like. The hsa-miR-4655-5p gene can be obtained by a method described in Persson H et al., 2011, Cancer Res, Vol. 71, p. 78-86. Also, "hsa-mir-4655" (miRBase Accession No. MI0017283, SEQ ID NO: 354) having a hairpin-like structure is known as a precursor of "hsa-miR-4655-5p".

The term "hsa-miR-6073 gene" or "hsa-miR-6073" used herein includes the hsa-miR-6073 gene (miRBase Accession No. MIMAT0023698) described in SEQ ID NO: 561, a homolog or an ortholog of a different organism species, and the like. The hsa-miR-6073 gene can be obtained by a method described in Voellenkle C et al., 2012, RNA, Vol. 18, p. 472-484. Also, "hsa-mir-6073" (miRBase Accession No. MI0020350, SEQ ID NO: 580) having a hairpin-like structure is known as a precursor of "hsa-miR-6073".

The term "hsa-miR-6845-5p gene" or "hsa-miR-6845-5p" used herein includes the hsa-miR-6845-5p gene (miRBase Accession No. MIMAT0027590) described in SEQ ID NO: 562, a homolog or an ortholog of a different organism species, and the like. The hsa-miR-6845-5p gene can be obtained by a method described in Ladewig E et al., 2012, Genome Res, Vol. 22, p. 1634-1645. Also, "hsa-mir-6845" (miRBase Accession No. MI0022691, SEQ ID NO: 581) having a hairpin-like structure is known as a precursor of "hsa-miR-6845-5p".

The term "hsa-miR-6769b-5p gene" or "hsa-miR-6769b-5p" used herein includes the hsa-miR-6769b-5p gene (miRBase Accession No. MIMAT0027620) described in SEQ ID NO: 563, a homolog or an ortholog of a different organism species, and the like. The hsa-miR-6769b-5p gene can be obtained by a method described in Ladewig E et al., 2012, Genome Res, Vol. 22, p. 1634-1645. Also, "hsa-mir-6769b" (miRBase Accession No. MI0022706, SEQ ID NO: 582) having a hairpin-like structure is known as a precursor of "hsa-miR-6769b-5p".

The term "hsa-miR-4665-3p gene" or "hsa-miR-4665-3p" used herein includes the hsa-miR-4665-3p gene (miRBase Accession No. MIMAT0019740) described in SEQ ID NO: 564, a homolog or an ortholog of a different organism species, and the like. The hsa-miR-4665-3p gene can be obtained by a method described in Persson H et al., 2011, Cancer Res, Vol. 71, p. 78-86. Also, "hsa-mir-4665" (miRBase Accession No. MI0017295, SEQ ID NO: 583) having a hairpin-like structure is known as a precursor of "hsa-miR-4665-3p".

The term "hsa-miR-1913 gene" or "hsa-miR-1913" used herein includes the hsa-miR-1913 gene (miRBase Accession No. MIMAT0007888) described in SEQ ID NO: 565, a homolog or an ortholog of a different organism species, and the like. The hsa-miR-1913 gene can be obtained by a method described in Bar M et al., 2008, Stem Cells, Vol. 26, p. 2496-2505. Also, "hsa-mir-1913" (miRBase Accession No. MI0008334, SEQ ID NO: 584) having a hairpin-like structure is known as a precursor of "hsa-miR-1913".

The term "hsa-miR-1228-3p gene" or "hsa-miR-1228-3p" used herein includes the hsa-miR-1228-3p gene (miRBase Accession No. MIMAT0005583) described in SEQ ID NO: 566, a homolog or an ortholog of a different organism species, and the like. The hsa-miR-1228-3p gene can be obtained by a method described in Berezikov E et al., 2007, Mol Cell, Vol. 28, p. 328-336. Also, "hsa-mir-1228" (miRBase Accession No. MI0006318, SEQ ID NO: 311) having a hairpin-like structure is known as a precursor of "hsa-miR-1228-3p".

The term "hsa-miR-940 gene" or "hsa-miR-940" used herein includes the hsa-miR-940 gene (miRBase Accession No. MIMAT0004983) described in SEQ ID NO: 567, a homolog or an ortholog of a different organism species, and the like. The hsa-miR-940 gene can be obtained by a method described in Lui W O et al., 2007, Cancer Res, Vol. 67, p. 6031-6043. Also, "hsa-mir-940" (miRBase Accession No. MI0005762, SEQ ID NO: 585) having a hairpin-like structure is known as a precursor of "hsa-miR-940".

The term "hsa-miR-296-3p gene" or "hsa-miR-296-3p" used herein includes the hsa-miR-296-3p gene (miRBase Accession No. MIMAT0004679) described in SEQ ID NO: 568, a homolog or an ortholog of a different organism species, and the like. The hsa-miR-296-3p gene can be obtained by a method described in Houbaviy H B et al., 2003, Dev Cell, Vol. 5, p. 351-358. Also, "hsa-mir-296" (miRBase Accession No. MI0000747, SEQ ID NO: 586) having a hairpin-like structure is known as a precursor of "hsa-miR-296-3p".

The term "hsa-miR-4690-5p gene" or "hsa-miR-4690-5p" used herein includes the hsa-miR-4690-5p gene (miRBase Accession No. MIMAT0019779) described in SEQ ID NO: 569, a homolog or an ortholog of a different organism species, and the like. The hsa-miR-4690-5p gene can be obtained by a method described in Persson H et al., 2011, Cancer Res, Vol. 71, p. 78-86. Also, "hsa-mir-4690" (miRBase Accession No. MI0017323, SEQ ID NO: 587) having a hairpin-like structure is known as a precursor of "hsa-miR-4690-5p".

The term "hsa-miR-548q gene" or "hsa-miR-548q" used herein includes the hsa-miR-548q gene (miRBase Accession No. MIMAT0011163) described in SEQ ID NO: 570, a homolog or an ortholog of a different organism species, and the like. The hsa-miR-548q gene can be obtained by a method described in Wyman S K et al., 2009, PLoS One, Vol. 4, e5311. Also, "hsa-mir-548q" (miRBase Accession No. MI0010637, SEQ ID NO: 588) having a hairpin-like structure is known as a precursor of "hsa-miR-548q".

The term "hsa-miR-663a gene" or "hsa-miR-663a" used herein includes the hsa-miR-663a gene (miRBase Accession No. MIMAT0003326) described in SEQ ID NO: 571, a homolog or an ortholog of a different organism species, and the like. The hsa-miR-663a gene can be obtained by a method described in Cummins J M et al., 2006, Proc Natl Acad Sci USA, Vol. 103, p. 3687-3692. Also, "hsa-mir-663a" (miRBase Accession No. MI0003672, SEQ ID NO: 589) having a hairpin-like structure is known as a precursor of "hsa-miR-663a".

The term "hsa-miR-1249 gene" or "hsa-miR-1249" used herein includes the hsa-miR-1249 gene (miRBase Accession No. MIMAT0005901) described in SEQ ID NO: 572, a homolog or an ortholog of a different organism species, and the like. The hsa-miR-1249 gene can be obtained by a method described in Morin R D et al., 2008, Genome Res, Vol. 18, p. 610-621. Also, "hsa-mir-1249" (miRBase Accession No. MI0006384, SEQ ID NO: 590) having a hairpin-like structure is known as a precursor of "hsa-miR-1249".

The term "hsa-miR-1202 gene" or "hsa-miR-1202" used herein includes the hsa-miR-1202 gene (miRBase Accession No. MIMAT0005865) described in SEQ ID NO: 573, a homolog or an ortholog of a different organism species, and the like. The hsa-miR-1202 gene can be obtained by a method described in Marton S et al., 2008, Leukemia, Vol. 22, p. 330-338. Also, "hsa-mir-1202" (miRBase Accession No. MI0006334, SEQ ID NO: 591) having a hairpin-like structure is known as a precursor of "hsa-miR-1202".

The term "hsa-miR-7113-3p gene" or "hsa-miR-7113-3p" used herein includes the hsa-miR-7113-3p gene (miRBase Accession No. MIMAT0028124) described in SEQ ID NO: 574, a homolog or an ortholog of a different organism species, and the like. The hsa-miR-7113-3p gene can be obtained by a method described in Ladewig E et al., 2012, Genome Res, Vol. 22, p. 1634-1645. Also, "hsa-mir-7113" (miRBase Accession No. MI0022964, SEQ ID NO: 592) having a hairpin-like structure is known as a precursor of "hsa-miR-7113-3p".

The term "hsa-miR-1225-3p gene" or "hsa-miR-1225-3p" used herein includes the hsa-miR-1225-3p gene (miRBase Accession No. MIMAT0005573) described in SEQ ID NO: 575, a homolog or an ortholog of a different organism species, and the like. The hsa-miR-1225-3p gene can be obtained by a method described in Berezikov E et al., 2007, Mol Cell, Vol. 28, p. 328-336. Also, "hsa-mir-1225" (miRBase Accession No. M10006311, SEQ ID NO: 307) having a hairpin-like structure is known as a precursor of "hsa-miR-1225-3p".

The term "hsa-miR-4783-3p gene" or "hsa-miR-4783-3p" used herein includes the hsa-miR-4783-3p gene (miRBase Accession No. MIMAT0019947) described in SEQ ID NO: 576, a homolog or an ortholog of a different organism species, and the like. The hsa-miR-4783-3p gene can be obtained by a method described in Persson H et al., 2011, Cancer Res, Vol. 71, p. 78-86. Also, "hsa-mir-4783" (miRBase Accession No. MI0017428, SEQ ID NO: 593) having a hairpin-like structure is known as a precursor of "hsa-miR-4783-3p".

The term "hsa-miR-4448 gene" or "hsa-miR-4448" used herein includes the hsa-miR-4448 gene (miRBase Accession No. MIMAT0018967) described in SEQ ID NO: 577, a homolog or an ortholog of a different organism species, and the like. The hsa-miR-4448 gene can be obtained by a method described in Jima D D et al., 2010, Blood, Vol. 116, e118-e127. Also, "hsa-mir-4448" (miRBase Accession No. MI0016791, SEQ ID NO: 594) having a hairpin-like structure is known as a precursor of "hsa-miR-4448".

The term "hsa-miR-4534 gene" or "hsa-miR-4534" used herein includes the hsa-miR-4534 gene (miRBase Accession No. MIMAT0019073) described in SEQ ID NO: 578, a homolog or an ortholog of a different organism species, and the like. The hsa-miR-4534 gene can be obtained by a method described in Jima D D et al., 2010, Blood, Vol. 116, e118-e127. Also, "hsa-mir-4534" (miRBase Accession No. MI0016901, SEQ ID NO: 595) having a hairpin-like structure is known as a precursor of "hsa-miR-4534".

The term "hsa-miR-1307-3p gene" or "hsa-miR-1307-3p" used herein includes the hsa-miR-1307-3p gene (miRBase Accession No. MIMAT0005951) described in SEQ ID NO: 579, a homolog or an ortholog of a different organism species, and the like. The hsa-miR-1307-3p gene can be obtained by a method described in Morin R D et al., 2008, Genome Res, Vol. 18, p. 610-621. Also, "hsa-mir-1307" (miRBase Accession No. MI0006444, SEQ ID NO: 596) having a hairpin-like structure is known as a precursor of "hsa-miR-1307-3p".

A mature miRNA may become a variant due to the sequence cleaved shorter or longer by one to several upstream or downstream nucleotides or nucleotide substitution when cut out as the mature miRNA from its RNA precursor having a hairpin-like structure. This variant is called isomiR (Morin R D. et al., 2008, Genome Res., Vol. 18, p. 610-621). The miRBase Release 20 shows the nucleotide sequences represented by SEQ ID NOs: 1 to 174 and 561 to 579 as well as a large number of the nucleotide sequence variants and fragments represented by SEQ ID NOs: 355 to 560 and 597 to 618, called isomiRs. These variants can also be obtained as miRNAs having a nucleotide sequence represented by any of SEQ ID NOs: 1 to 174 and 561 to 579. Specifically, among the variants of polynucleotides consisting of the nucleotide sequence represented by any of SEQ ID NOs: 5, 8, 9, 11, 18, 20, 22, 23, 24, 28, 29, 30, 32, 34, 37, 40, 41, 47, 48, 49, 51, 52, 53, 56, 58, 59, 60, 61, 63, 64, 65, 66, 67, 69, 72, 73, 75, 78, 79, 80, 81, 82, 85, 88, 89, 91, 92, 95, 96, 103, 104, 105, 106, 107, 108, 109, 110, 112, 113, 114, 117, 118, 120, 123, 124, 125, 126, 128, 129, 130, 131, 132, 133, 134, 135, 136, 138, 139, 142, 143, 144, 145, 146, 147, 149, 151, 152, 153, 154, 156, 157, 158, 160, 161, 162, 163, 166, 167, 168, 169, 172, 173, 174, 565, 566, 567, 568, 569, 571, 572, 573, 576, 577, 579, or a nucleotide sequence derived from the nucleotide sequence by the replacement of u with t in the nucleotide sequence, examples of the longest variants registered in the miRBase Release 20 include polynucleotides represented by SEQ ID NOs: 355, 357, 359, 361, 363, 365, 367, 369, 371, 373, 375, 377, 379, 381, 383, 385, 387, 389, 391, 393, 395, 397, 399, 401, 403, 405, 407, 409, 411, 413, 415, 417, 419, 421, 423, 425, 427, 429, 431, 433, 435, 437, 439, 441, 443, 445, 447, 449, 451, 453, 455, 457, 459, 461, 463, 465, 467, 469, 471, 473, 475, 477, 479, 481, 483, 485, 487, 489, 491, 493, 495, 497, 499, 501, 503, 505, 507, 509, 511, 513, 515, 517, 519, 521, 523, 525, 527, 529, 531, 533, 535, 537, 539, 541, 543, 545, 547, 549, 551, 553, 555, 557, 559, 597, 599, 601, 603, 605, 607, 609, 611, 613, 615 and 617, respectively.

Also, among the variants of polynucleotides consisting of a nucleotide sequence represented by any of SEQ ID NOs: 5, 8, 9, 11, 18, 20, 22, 23, 24, 28, 29, 30, 32, 34, 37, 40, 41, 47, 48, 49, 51, 52, 53, 56, 58, 59, 60, 61, 63, 64, 65, 66, 67, 69, 72, 73, 75, 78, 79, 80, 81, 82, 85, 88, 89, 91, 92, 95, 96, 103, 104, 105, 106, 107, 108, 109, 110, 112, 113, 114, 117, 118, 120, 123, 124, 125, 126, 128, 129, 130, 131, 132, 133, 134, 135, 136, 138, 139, 142, 143, 144, 145, 146, 147, 149, 151, 152, 153, 154, 156, 157, 158, 160, 161, 162, 163, 166, 167, 168, 169, 172, 173, 174, 565, 566, 567, 568, 569, 571, 572, 573, 576, 577, 579 or a nucleotide sequence derived from the nucleotide sequence by the replacement of u with t in the nucleotide sequence, examples of the shortest variants registered in the miRBase Release 20 include polynucleotides having sequences represented by SEQ ID NOs: 356, 358, 360, 362, 364, 366, 368, 370, 372, 374, 376, 378, 380, 382, 384, 386, 388, 390, 392, 394, 396, 398, 400, 402, 404, 406, 408, 410, 412, 414, 416, 418, 420, 422, 424, 426, 428, 430, 432, 434, 436, 438, 440, 442, 444, 446, 448, 450, 452, 454, 456, 458, 460, 462, 464, 466, 468, 470, 472, 474, 476, 478, 480, 482, 484, 486, 488, 490, 492, 494, 496, 498, 500, 502, 504, 506, 508, 510, 512, 514, 516, 518, 520, 522, 524, 526, 528, 530, 532, 534, 536, 538, 540, 542, 544, 546, 548, 550, 552, 554, 556, 558, 560, 598, 600, 602, 604, 606, 608, 610, 612, 614, 616 and 618, respectively.

In addition to these variants and fragments, examples thereof include a large number of isomiR polynucleotides of SEQ ID NOs: 1 to 174 and 561 to 579 registered in miRBase.

Examples of the polynucleotide comprising a nucleotide sequence represented by any of SEQ ID NOs: 1 to 174 and 561 to 579 include a polynucleotide represented by any of SEQ ID NOs: 175 to 354 and 579 to 596, which are their respective precursors.

The names and miRBase Accession Nos. (registration numbers) of the genes represented by SEQ ID NOs: 1 to 618 are shown in Table 1.

As used herein, the term "capable of specifically binding" means that the nucleic acid probe or the primer used in the present invention binds to a particular target nucleic acid and cannot substantially bind to other nucleic acids.

TABLE 1

| SEQ ID NO: | Gene name | miRBase registration No. |
|---|---|---|
| 1 | hsa-miR-6768-5p | MIMAT0027436 |
| 2 | hsa-miR-6836-3p | MIMAT0027575 |
| 3 | hsa-miR-6782-5p | MIMAT0027464 |
| 4 | hsa-miR-3663-3p | MIMAT0018085 |
| 5 | hsa-miR-1908-3p | MIMAT0026916 |
| 6 | hsa-miR-6726-5p | MIMAT0027353 |
| 7 | hsa-miR-4258 | MIMAT0016879 |
| 8 | hsa-miR-1343-3p | MIMAT0019776 |
| 9 | hsa-miR-4516 | MIMAT0019053 |
| 10 | hsa-miR-6875-5p | MIMAT0027650 |
| 11 | hsa-miR-4651 | MIMAT0019715 |
| 12 | hsa-miR-6825-5p | MIMAT0027550 |
| 13 | hsa-miR-6840-3p | MIMAT0027583 |
| 14 | hsa-miR-6780b-5p | MIMAT0027572 |
| 15 | hsa-miR-6749-5p | MIMAT0027398 |
| 16 | hsa-miR-8063 | MIMAT0030990 |
| 17 | hsa-miR-6784-5p | MIMAT0027468 |
| 18 | hsa-miR-3679-5p | MIMAT0018104 |
| 19 | hsa-miR-3184-5p | MIMAT0015064 |
| 20 | hsa-miR-663b | MIMAT0005867 |
| 21 | hsa-miR-6880-5p | MIMAT0027660 |
| 22 | hsa-miR-1908-5p | MIMAT0007881 |
| 23 | hsa-miR-92a-2-5p | MIMAT0004508 |
| 24 | hsa-miR-7975 | MIMAT0031178 |
| 25 | hsa-miR-7110-5p | MIMAT0028117 |
| 26 | hsa-miR-6842-5p | MIMAT0027586 |
| 27 | hsa-miR-6857-5p | MIMAT0027614 |
| 28 | hsa-miR-5572 | MIMAT0022260 |
| 29 | hsa-miR-3197 | MIMAT0015082 |
| 30 | hsa-miR-6131 | MIMAT0024615 |
| 31 | hsa-miR-6889-5p | MIMAT0027678 |
| 32 | hsa-miR-4454 | MIMAT0018976 |
| 33 | hsa-miR-1199-5p | MIMAT0031119 |
| 34 | hsa-miR-1247-3p | MIMAT0022721 |
| 35 | hsa-miR-6800-5p | MIMAT0027500 |
| 36 | hsa-miR-6872-3p | MIMAT0027645 |
| 37 | hsa-miR-4649-5p | MIMAT0019711 |

TABLE 1-continued

| SEQ ID NO: | Gene name | miRBase registration No. |
|---|---|---|
| 38 | hsa-miR-6791-5p | MIMAT0027482 |
| 39 | hsa-miR-4433b-3p | MIMAT0030414 |
| 40 | hsa-miR-3135b | MIMAT0018985 |
| 41 | hsa-miR-128-2-5p | MIMAT0031095 |
| 42 | hsa-miR-4675 | MIMAT0019757 |
| 43 | hsa-miR-4472 | MIMAT0018999 |
| 44 | hsa-miR-6785-5p | MIMAT0027470 |
| 45 | hsa-miR-6741-5p | MIMAT0027383 |
| 46 | hsa-miR-7977 | MIMAT0031180 |
| 47 | hsa-miR-3665 | MIMAT0018087 |
| 48 | hsa-miR-128-1-5p | MIMAT0026477 |
| 49 | hsa-miR-4286 | MIMAT0016916 |
| 50 | hsa-miR-6765-3p | MIMAT0027431 |
| 51 | hsa-miR-4632-5p | MIMAT0022977 |
| 52 | hsa-miR-365a-5p | MIMAT0009199 |
| 53 | hsa-miR-6088 | MIMAT0023713 |
| 54 | hsa-miR-6816-5p | MIMAT0027532 |
| 55 | hsa-miR-6885-5p | MIMAT0027670 |
| 56 | hsa-miR-711 | MIMAT0012734 |
| 57 | hsa-miR-6765-5p | MIMAT0027430 |
| 58 | hsa-miR-3180 | MIMAT0018178 |
| 59 | hsa-miR-4442 | MIMAT0018960 |
| 60 | hsa-miR-4792 | MIMAT0019964 |
| 61 | hsa-miR-6721-5p | MIMAT0025852 |
| 62 | hsa-miR-6798-5p | MIMAT0027496 |
| 63 | hsa-miR-3162-5p | MIMAT0015036 |
| 64 | hsa-miR-6126 | MIMAT0024599 |
| 65 | hsa-miR-4758-5p | MIMAT0019903 |
| 66 | hsa-miR-2392 | MIMAT0019043 |
| 67 | hsa-miR-486-3p | MIMAT0004762 |
| 68 | hsa-miR-6727-5p | MIMAT0027355 |
| 69 | hsa-miR-4728-5p | MIMAT0019849 |
| 70 | hsa-miR-6746-5p | MIMAT0027392 |
| 71 | hsa-miR-4270 | MIMAT0016900 |
| 72 | hsa-miR-3940-5p | MIMAT0019229 |
| 73 | hsa-miR-4725-3p | MIMAT0019844 |
| 74 | hsa-miR-7108-5p | MIMAT0028113 |
| 75 | hsa-miR-3656 | MIMAT0018076 |
| 76 | hsa-miR-6879-5p | MIMAT0027658 |
| 77 | hsa-miR-6738-5p | MIMAT0027377 |
| 78 | hsa-miR-1260a | MIMAT0005911 |
| 79 | hsa-miR-4446-3p | MIMAT0018965 |
| 80 | hsa-miR-3131 | MIMAT0014996 |
| 81 | hsa-miR-4463 | MIMAT0018987 |
| 82 | hsa-miR-3185 | MIMAT0015065 |
| 83 | hsa-miR-6870-5p | MIMAT0027640 |
| 84 | hsa-miR-6779-5p | MIMAT0027458 |
| 85 | hsa-miR-1273g-3p | MIMAT0022742 |
| 86 | hsa-miR-8059 | MIMAT0030986 |
| 87 | hsa-miR-4697-5p | MIMAT0019791 |
| 88 | hsa-miR-4674 | MIMAT0019756 |
| 89 | hsa-miR-4433-3p | MIMAT0018949 |
| 90 | hsa-miR-4257 | MIMAT0016878 |
| 91 | hsa-miR-1915-5p | MIMAT0007891 |
| 92 | hsa-miR-4417 | MIMAT0018929 |
| 93 | hsa-miR-1343-5p | MIMAT0027038 |
| 94 | hsa-miR-6781-5p | MIMAT0027462 |
| 95 | hsa-miR-4695-5p | MIMAT0019788 |
| 96 | hsa-miR-1237-5p | MIMAT0022946 |
| 97 | hsa-miR-6775-5p | MIMAT0027450 |
| 98 | hsa-miR-7845-5p | MIMAT0030420 |
| 99 | hsa-miR-4746-3p | MIMAT0019881 |
| 100 | hsa-miR-7641 | MIMAT0029782 |
| 101 | hsa-miR-7847-3p | MIMAT0030422 |
| 102 | hsa-miR-6806-5p | MIMAT0027512 |
| 103 | hsa-miR-4467 | MIMAT0018994 |
| 104 | hsa-miR-4726-5p | MIMAT0019845 |
| 105 | hsa-miR-4648 | MIMAT0019710 |
| 106 | hsa-miR-6089 | MIMAT0023714 |
| 107 | hsa-miR-1260b | MIMAT0015041 |
| 108 | hsa-miR-4532 | MIMAT0019071 |
| 109 | hsa-miR-5195-3p | MIMAT0021127 |
| 110 | hsa-miR-3188 | MIMAT0015070 |
| 111 | hsa-miR-6848-5p | MIMAT0027596 |
| 112 | hsa-miR-1233-5p | MIMAT0022943 |
| 113 | hsa-miR-6717-5p | MIMAT0025846 |
| 114 | hsa-miR-3195 | MIMAT0015079 |

TABLE 1-continued

| SEQ ID NO: | Gene name | miRBase registration No. |
|---|---|---|
| 115 | hsa-miR-6757-5p | MIMAT0027414 |
| 116 | hsa-miR-8072 | MIMAT0030999 |
| 117 | hsa-miR-4745-5p | MIMAT0019878 |
| 118 | hsa-miR-6511a-5p | MIMAT0025478 |
| 119 | hsa-miR-6776-5p | MIMAT0027452 |
| 120 | hsa-miR-371a-5p | MIMAT0004687 |
| 121 | hsa-miR-1227-5p | MIMAT0022941 |
| 122 | hsa-miR-7150 | MIMAT0028211 |
| 123 | hsa-miR-1915-3p | MIMAT0007892 |
| 124 | hsa-miR-187-5p | MIMAT0004561 |
| 125 | hsa-miR-614 | MIMAT0003282 |
| 126 | hsa-miR-19b-3p | MIMAT0000074 |
| 127 | hsa-miR-1225-5p | MIMAT0005572 |
| 128 | hsa-miR-451a | MIMAT0001631 |
| 129 | hsa-miR-939-5p | MIMAT0004982 |
| 130 | hsa-miR-223-3p | MIMAT0000280 |
| 131 | hsa-miR-1228-5p | MIMAT0005582 |
| 132 | hsa-miR-125a-3p | MIMAT0004602 |
| 133 | hsa-miR-92b-5p | MIMAT0004792 |
| 134 | hsa-miR-22-3p | MIMAT0000077 |
| 135 | hsa-miR-4271 | MIMAT0016901 |
| 136 | hsa-miR-642b-3p | MIMAT0018444 |
| 137 | hsa-miR-6075 | MIMAT0023700 |
| 138 | hsa-miR-6125 | MIMAT0024598 |
| 139 | hsa-miR-887-3p | MIMAT0004951 |
| 140 | hsa-miR-6851-5p | MIMAT0027602 |
| 141 | hsa-miR-6763-5p | MIMAT0027426 |
| 142 | hsa-miR-3928-3p | MIMAT0018205 |
| 143 | hsa-miR-4443 | MIMAT0018961 |
| 144 | hsa-miR-3648 | MIMAT0018068 |
| 145 | hsa-miR-149-3p | MIMAT0004609 |
| 146 | hsa-miR-4689 | MIMAT0019778 |
| 147 | hsa-miR-4763-3p | MIMAT0019913 |
| 148 | hsa-miR-6729-5p | MIMAT0027359 |
| 149 | hsa-miR-3196 | MIMAT0015080 |
| 150 | hsa-miR-8069 | MIMAT0030996 |
| 151 | hsa-miR-1268a | MIMAT0005922 |
| 152 | hsa-miR-4739 | MIMAT0019868 |
| 153 | hsa-miR-1268b | MIMAT0018925 |
| 154 | hsa-miR-5698 | MIMAT0022491 |
| 155 | hsa-miR-6752-5p | MIMAT0027404 |
| 156 | hsa-miR-4507 | MIMAT0019044 |
| 157 | hsa-miR-564 | MIMAT0003228 |
| 158 | hsa-miR-4497 | MIMAT0019032 |
| 159 | hsa-miR-6877-5p | MIMAT0027654 |
| 160 | hsa-miR-6087 | MIMAT0023712 |
| 161 | hsa-miR-4731-5p | MIMAT0019853 |
| 162 | hsa-miR-615-5p | MIMAT0004804 |
| 163 | hsa-miR-760 | MIMAT0004957 |
| 164 | hsa-miR-6891-5p | MIMAT0027682 |
| 165 | hsa-miR-6887-5p | MIMAT0027674 |
| 166 | hsa-miR-4525 | MIMAT0019064 |
| 167 | hsa-miR-1914-3p | MIMAT0007890 |
| 168 | hsa-miR-619-5p | MIMAT0026622 |
| 169 | hsa-miR-5001-5p | MIMAT0021021 |
| 170 | hsa-miR-6722-3p | MIMAT0025854 |
| 171 | hsa-miR-3621 | MIMAT0018002 |
| 172 | hsa-miR-4298 | MIMAT0016852 |
| 173 | hsa-miR-675-5p | MIMAT0004284 |
| 174 | hsa-miR-4655-5p | MIMAT0019721 |
| 175 | hsa-mir-6768 | MI0022613 |
| 176 | hsa-mir-6836 | MI0022682 |
| 177 | hsa-mir-6782 | MI0022627 |
| 178 | hsa-mir-3663 | MI0016064 |
| 179 | hsa-mir-1908 | MI0008329 |
| 180 | hsa-mir-6726 | MI0022571 |
| 181 | hsa-mir-4258 | MI0015857 |
| 182 | hsa-mir-1343 | MI0017320 |
| 183 | hsa-mir-4516 | MI0016882 |
| 184 | hsa-mir-6875 | MI0022722 |
| 185 | hsa-mir-4651 | MI0017279 |
| 186 | hsa-mir-6825 | MI0022670 |
| 187 | hsa-mir-6840 | MI0022686 |
| 188 | hsa-mir-6780b | MI0022681 |
| 189 | hsa-mir-6749 | MI0022594 |
| 190 | hsa-mir-8063 | MI0025899 |
| 191 | hsa-mir-6784 | MI0022629 |
| 192 | hsa-mir-3679 | MI0016080 |
| 193 | hsa-mir-3184 | MI0014226 |
| 194 | hsa-mir-663b | MI0006336 |
| 195 | hsa-mir-6880 | MI0022727 |
| 196 | hsa-mir-92a-2 | MI0000094 |
| 197 | hsa-mir-7975 | MI0025751 |
| 198 | hsa-mir-7110 | MI0022961 |
| 199 | hsa-mir-6842 | MI0022688 |
| 200 | hsa-mir-6857 | MI0022703 |
| 201 | hsa-mir-5572 | MI0019117 |
| 202 | hsa-mir-3197 | MI0014245 |
| 203 | hsa-mir-6131 | MI0021276 |
| 204 | hsa-mir-6889 | MI0022736 |
| 205 | hsa-mir-4454 | MI0016800 |
| 206 | hsa-mir-1199 | MI0020340 |
| 207 | hsa-mir-1247 | MI0006382 |
| 208 | hsa-mir-6800 | MI0022645 |
| 209 | hsa-mir-6872 | MI0022719 |
| 210 | hsa-mir-4649 | MI0017276 |
| 211 | hsa-mir-6791 | MI0022636 |
| 212 | hsa-mir-4433b | MI0025511 |
| 213 | hsa-mir-3135b | MI0016809 |
| 214 | hsa-mir-128-2 | MI0000727 |
| 215 | hsa-mir-4675 | MI0017306 |
| 216 | hsa-mir-4472-1 | MI0016823 |
| 217 | hsa-mir-4472-2 | MI0016824 |
| 218 | hsa-mir-6785 | MI0022630 |
| 219 | hsa-mir-6741 | MI0022586 |
| 220 | hsa-mir-7977 | MI0025753 |
| 221 | hsa-mir-3665 | MI0016066 |
| 222 | hsa-mir-128-1 | MI0000447 |
| 223 | hsa-mir-4286 | MI0015894 |
| 224 | hsa-mir-6765 | MI0022610 |
| 225 | hsa-mir-4632 | MI0017259 |
| 226 | hsa-mir-365a | MI0000767 |
| 227 | hsa-mir-6088 | MI0020365 |
| 228 | hsa-mir-6816 | MI0022661 |
| 229 | hsa-mir-6885 | MI0022732 |
| 230 | hsa-mir-711 | MI0012488 |
| 231 | hsa-mir-3180-4 | MI0016408 |
| 232 | hsa-mir-3180-5 | MI0016409 |
| 233 | hsa-mir-4442 | MI0016785 |
| 234 | hsa-mir-4792 | MI0017439 |
| 235 | hsa-mir-6721 | MI0022556 |
| 236 | hsa-mir-6798 | MI0022643 |
| 237 | hsa-mir-3162 | MI0014192 |
| 238 | hsa-mir-6126 | MI0021260 |
| 239 | hsa-mir-4758 | MI0017399 |
| 240 | hsa-mir-2392 | MI0016870 |
| 241 | hsa-mir-486 | MI0002470 |
| 242 | hsa-mir-486-2 | MI0023622 |
| 243 | hsa-mir-6727 | MI0022572 |
| 244 | hsa-mir-4728 | MI0017365 |
| 245 | hsa-mir-6746 | MI0022591 |
| 246 | hsa-mir-4270 | MI0015878 |
| 247 | hsa-mir-3940 | MI0016597 |
| 248 | hsa-mir-4725 | MI0017362 |
| 249 | hsa-mir-7108 | MI0022959 |
| 250 | hsa-mir-3656 | MI0016056 |
| 251 | hsa-mir-6879 | MI0022726 |
| 252 | hsa-mir-6738 | MI0022583 |
| 253 | hsa-mir-1260a | MI0006394 |
| 254 | hsa-mir-4446 | MI0016789 |
| 255 | hsa-mir-3131 | MI0014151 |
| 256 | hsa-mir-4463 | MI0016811 |
| 257 | hsa-mir-3185 | MI0014227 |
| 258 | hsa-mir-6870 | MI0022717 |
| 259 | hsa-mir-6779 | MI0022624 |
| 260 | hsa-mir-1273g | MI0018003 |
| 261 | hsa-mir-8059 | MI0025895 |
| 262 | hsa-mir-4697 | MI0017330 |
| 263 | hsa-mir-4674 | MI0017305 |
| 264 | hsa-mir-4433 | MI0016773 |
| 265 | hsa-mir-4257 | MI0015856 |
| 266 | hsa-mir-1915 | MI0008336 |
| 267 | hsa-mir-4417 | MI0016753 |
| 268 | hsa-mir-6781 | MI0022626 |

TABLE 1-continued

| SEQ ID NO: | Gene name | miRBase registration No. |
|---|---|---|
| 269 | hsa-mir-4695 | MI0017328 |
| 270 | hsa-mir-1237 | MI0006327 |
| 271 | hsa-mir-6775 | MI0022620 |
| 272 | hsa-mir-7845 | MI0025515 |
| 273 | hsa-mir-4746 | MI0017385 |
| 274 | hsa-mir-7641-1 | MI0024975 |
| 275 | hsa-mir-7641-2 | MI0024976 |
| 276 | hsa-mir-7847 | MI0025517 |
| 277 | hsa-mir-6806 | MI0022651 |
| 278 | hsa-mir-4467 | MI0016818 |
| 279 | hsa-mir-4726 | MI0017363 |
| 280 | hsa-mir-4648 | MI0017275 |
| 281 | hsa-mir-6089-1 | MI0020366 |
| 282 | hsa-mir-6089-2 | MI0023563 |
| 283 | hsa-mir-1260b | MI0014197 |
| 284 | hsa-mir-4532 | MI0016899 |
| 285 | hsa-mir-5195 | MI0018174 |
| 286 | hsa-mir-3188 | MI0014232 |
| 287 | hsa-mir-6848 | MI0022694 |
| 288 | hsa-mir-1233-1 | MI0006323 |
| 289 | hsa-mir-1233-2 | MI0015973 |
| 290 | hsa-mir-6717 | MI0022551 |
| 291 | hsa-mir-3195 | MI0014240 |
| 292 | hsa-mir-6757 | MI0022602 |
| 293 | hsa-mir-8072 | MI0025908 |
| 294 | hsa-mir-4745 | MI0017384 |
| 295 | hsa-mir-6511a-1 | MI0022223 |
| 296 | hsa-mir-6511a-2 | MI0023564 |
| 297 | hsa-mir-6511a-3 | MI0023565 |
| 298 | hsa-mir-6511a-4 | MI0023566 |
| 299 | hsa-mir-6776 | MI0022621 |
| 300 | hsa-mir-371a | MI0000779 |
| 301 | hsa-mir-1227 | MI0006316 |
| 302 | hsa-mir-7150 | MI0023610 |
| 303 | hsa-mir-187 | MI0000274 |
| 304 | hsa-mir-614 | MI0003627 |
| 305 | hsa-mir-19b-1 | MI0000074 |
| 306 | hsa-mir-19b-2 | MI0000075 |
| 307 | hsa-mir-1225 | MI0006311 |
| 308 | hsa-mir-451a | MI0001729 |
| 309 | hsa-mir-939 | MI0005761 |
| 310 | hsa-mir-223 | MI0000300 |
| 311 | hsa-mir-1228 | MI0006318 |
| 312 | hsa-mir-125a | MI0000469 |
| 313 | hsa-mir-92b | MI0003 560 |
| 314 | hsa-mir-22 | MI0000078 |
| 315 | hsa-mir-4271 | MI0015879 |
| 316 | hsa-mir-642b | MI0016685 |
| 317 | hsa-mir-6075 | MI0020352 |
| 318 | hsa-mir-6125 | MI0021259 |
| 319 | hsa-mir-887 | MI0005562 |
| 320 | hsa-mir-6851 | MI0022697 |
| 321 | hsa-mir-6763 | MI0022608 |
| 322 | hsa-mir-3928 | MI0016438 |
| 323 | hsa-mir-4443 | MI0016786 |
| 324 | hsa-mir-3648 | MI0016048 |
| 325 | hsa-mir-149 | MI0000478 |
| 326 | hsa-mir-4689 | MI0017322 |
| 327 | hsa-mir-4763 | MI0017404 |
| 328 | hsa-mir-6729 | MI0022574 |
| 329 | hsa-mir-3196 | MI0014241 |
| 330 | hsa-mir-8069 | MI0025905 |
| 331 | hsa-mir-1268a | MI0006405 |
| 332 | hsa-mir-4739 | MI0017377 |
| 333 | hsa-mir-1268b | MI0016748 |
| 334 | hsa-mir-5698 | MI0019305 |
| 335 | hsa-mir-6752 | MI0022597 |
| 336 | hsa-mir-4507 | MI0016871 |
| 337 | hsa-mir-564 | MI0003570 |
| 338 | hsa-mir-4497 | MI0016859 |
| 339 | hsa-mir-6877 | MI0022724 |
| 340 | hsa-mir-6087 | MI0020364 |
| 341 | hsa-mir-4731 | MI0017368 |
| 342 | hsa-mir-615 | MI0003628 |
| 343 | hsa-mir-760 | MI0005567 |
| 344 | hsa-mir-6891 | MI0022738 |
| 345 | hsa-mir-6887 | MI0022734 |
| 346 | hsa-mir-4525 | MI0016892 |
| 347 | hsa-mir-1914 | MI0008335 |
| 348 | hsa-mir-619 | MI0003633 |
| 349 | hsa-mir-5001 | MI0017867 |
| 350 | hsa-mir-6722 | MI0022557 |
| 351 | hsa-mir-3621 | MI0016012 |
| 352 | hsa-mir-4298 | MI0015830 |
| 353 | hsa-mir-675 | MI0005416 |
| 354 | hsa-mir-4655 | MI0017283 |
| 355 | isomiR example 1 of SEQ ID NO: 5 | — |
| 356 | isomiR example 2 of SEQ ID NO: 5 | — |
| 357 | isomiR example 1 of SEQ ID NO: 8 | — |
| 358 | isomiR example 2 of SEQ ID NO: 8 | — |
| 359 | isomiR example 1 of SEQ ID NO: 9 | — |
| 360 | isomiR example 2 of SEQ ID NO: 9 | — |
| 361 | isomiR example 1 of SEQ ID NO: 11 | — |
| 362 | isomiR example 2 of SEQ ID NO: 11 | — |
| 363 | isomiR example 1 of SEQ ID NO: 18 | — |
| 364 | isomiR example 2 of SEQ ID NO: 18 | — |
| 365 | isomiR example 1 of SEQ ID NO: 20 | — |
| 366 | isomiR example 2 of SEQ ID NO: 20 | — |
| 367 | isomiR example 1 of SEQ ID NO: 22 | — |
| 368 | isomiR example 2 of SEQ ID NO: 22 | — |
| 369 | isomiR example 1 of SEQ ID NO: 23 | — |
| 370 | isomiR example 2 of SEQ ID NO: 23 | — |
| 371 | isomiR example 1 of SEQ ID NO: 24 | — |
| 372 | isomiR example 2 of SEQ ID NO: 24 | — |
| 373 | isomiR example 1 of SEQ ID NO: 28 | — |
| 374 | isomiR example 2 of SEQ ID NO: 28 | — |
| 375 | isomiR example 1 of SEQ ID NO: 29 | — |
| 376 | isomiR example 2 of SEQ ID NO: 29 | — |
| 377 | isomiR example 1 of SEQ ID NO: 30 | — |
| 378 | isomiR example 2 of SEQ ID NO: 30 | — |
| 379 | isomiR example 1 of SEQ ID NO: 32 | — |
| 380 | isomiR example 2 of SEQ ID NO: 32 | — |
| 381 | isomiR example 1 of SEQ ID NO: 34 | — |
| 382 | isomiR example 2 of SEQ ID NO: 34 | — |
| 383 | isomiR example 1 of SEQ ID NO: 37 | — |
| 384 | isomiR example 2 of SEQ ID NO: 37 | — |
| 385 | isomiR example 1 of SEQ ID NO: 40 | — |
| 386 | isomiR example 2 of SEQ ID NO: 40 | — |
| 387 | isomiR example 1 of SEQ ID NO: 41 | — |
| 388 | isomiR example 2 of SEQ ID NO: 41 | — |
| 389 | isomiR example 1 of SEQ ID NO: 47 | — |
| 390 | isomiR example 2 of SEQ ID NO: 47 | — |
| 391 | isomiR example 1 of SEQ ID NO: 48 | — |
| 392 | isomiR example 2 of SEQ ID NO: 48 | — |
| 393 | isomiR example 1 of SEQ ID NO: 49 | — |
| 394 | isomiR example 2 of SEQ ID NO: 49 | — |
| 395 | isomiR example 1 of SEQ ID NO: 51 | — |
| 396 | isomiR example 2 of SEQ ID NO: 51 | — |
| 397 | isomiR example 1 of SEQ ID NO: 52 | — |
| 398 | isomiR example 2 of SEQ ID NO: 52 | — |
| 399 | isomiR example 1 of SEQ ID NO: 53 | — |
| 400 | isomiR example 2 of SEQ ID NO: 53 | — |
| 401 | isomiR example 1 of SEQ ID NO: 56 | — |
| 402 | isomiR example 2 of SEQ ID NO: 56 | — |
| 403 | isomiR example 1 of SEQ ID NO: 58 | — |
| 404 | isomiR example 2 of SEQ ID NO: 58 | — |
| 405 | isomiR example 1 of SEQ ID NO: 59 | — |
| 406 | isomiR example 2 of SEQ ID NO: 59 | — |
| 407 | isomiR example 1 of SEQ ID NO: 60 | — |
| 408 | isomiR example 2 of SEQ ID NO: 60 | — |
| 409 | isomiR example 1 of SEQ ID NO: 61 | — |
| 410 | isomiR example 2 of SEQ ID NO: 61 | — |
| 411 | isomiR example 1 of SEQ ID NO: 63 | — |
| 412 | isomiR example 2 of SEQ ID NO: 63 | — |
| 413 | isomiR example 1 of SEQ ID NO: 64 | — |
| 414 | isomiR example 2 of SEQ ID NO: 64 | — |
| 415 | isomiR example 1 of SEQ ID NO: 65 | — |
| 416 | isomiR example 2 of SEQ ID NO: 65 | — |
| 417 | isomiR example 1 of SEQ ID NO: 66 | — |
| 418 | isomiR example 2 of SEQ ID NO: 66 | — |
| 419 | isomiR example 1 of SEQ ID NO: 67 | — |
| 420 | isomiR example 2 of SEQ ID NO: 67 | — |
| 421 | isomiR example 1 of SEQ ID NO: 69 | — |
| 422 | isomiR example 2 of SEQ ID NO: 69 | — |

TABLE 1-continued

| SEQ ID NO: | Gene name | miRBase registration No. |
|---|---|---|
| 423 | isomiR example 1 of SEQ ID NO: 72 | — |
| 424 | isomiR example 2 of SEQ ID NO: 72 | — |
| 425 | isomiR example 1 of SEQ ID NO: 73 | — |
| 426 | isomiR example 2 of SEQ ID NO: 73 | — |
| 427 | isomiR example 1 of SEQ ID NO: 75 | — |
| 428 | isomiR example 2 of SEQ ID NO: 75 | — |
| 429 | isomiR example 1 of SEQ ID NO: 78 | — |
| 430 | isomiR example 2 of SEQ ID NO: 78 | — |
| 431 | isomiR example 1 of SEQ ID NO: 79 | — |
| 432 | isomiR example 2 of SEQ ID NO: 79 | — |
| 433 | isomiR example 1 of SEQ ID NO: 80 | — |
| 434 | isomiR example 2 of SEQ ID NO: 80 | — |
| 435 | isomiR example 1 of SEQ ID NO: 81 | — |
| 436 | isomiR example 2 of SEQ ID NO: 81 | — |
| 437 | isomiR example 1 of SEQ ID NO: 82 | — |
| 438 | isomiR example 2 of SEQ ID NO: 82 | — |
| 439 | isomiR example 1 of SEQ ID NO: 85 | — |
| 440 | isomiR example 2 of SEQ ID NO: 85 | — |
| 441 | isomiR example 1 of SEQ ID NO: 88 | — |
| 442 | isomiR example 2 of SEQ ID NO: 88 | — |
| 443 | isomiR example 1 of SEQ ID NO: 89 | — |
| 444 | isomiR example 2 of SEQ ID NO: 89 | — |
| 445 | isomiR example 1 of SEQ ID NO: 91 | — |
| 446 | isomiR example 2 of SEQ ID NO: 91 | — |
| 447 | isomiR example 1 of SEQ ID NO: 92 | — |
| 448 | isomiR example 2 of SEQ ID NO: 92 | — |
| 449 | isomiR example 1 of SEQ ID NO: 95 | — |
| 450 | isomiR example 2 of SEQ ID NO: 95 | — |
| 451 | isomiR example 1 of SEQ ID NO: 96 | — |
| 452 | isomiR example 2 of SEQ ID NO: 96 | — |
| 453 | isomiR example 1 of SEQ ID NO: 103 | — |
| 454 | isomiR example 2 of SEQ ID NO: 103 | — |
| 455 | isomiR example 1 of SEQ ID NO: 104 | — |
| 456 | isomiR example 2 of SEQ ID NO: 104 | — |
| 457 | isomiR example 1 of SEQ ID NO: 105 | — |
| 458 | isomiR example 2 of SEQ ID NO: 105 | — |
| 459 | isomiR example 1 of SEQ ID NO: 106 | — |
| 460 | isomiR example 2 of SEQ ID NO: 106 | — |
| 461 | isomiR example 1 of SEQ ID NO: 107 | — |
| 462 | isomiR example 2 of SEQ ID NO: 107 | — |
| 463 | isomiR example 1 of SEQ ID NO: 108 | — |
| 464 | isomiR example 2 of SEQ ID NO: 108 | — |
| 465 | isomiR example 1 of SEQ ID NO: 109 | — |
| 466 | isomiR example 2 of SEQ ID NO: 109 | — |
| 467 | isomiR example 1 of SEQ ID NO: 110 | — |
| 468 | isomiR example 2 of SEQ ID NO: 110 | — |
| 469 | isomiR example 1 of SEQ ID NO: 112 | — |
| 470 | isomiR example 2 of SEQ ID NO: 112 | — |
| 471 | isomiR example 1 of SEQ ID NO: 113 | — |
| 472 | isomiR example 2 of SEQ ID NO: 113 | — |
| 473 | isomiR example 1 of SEQ ID NO: 114 | — |
| 474 | isomiR example 2 of SEQ ID NO: 114 | — |
| 475 | isomiR example 1 of SEQ ID NO: 117 | — |
| 476 | isomiR example 2 of SEQ ID NO: 117 | — |
| 477 | isomiR example 1 of SEQ ID NO: 118 | — |
| 478 | isomiR example 2 of SEQ ID NO: 118 | — |
| 479 | isomiR example 1 of SEQ ID NO: 120 | — |
| 480 | isomiR example 2 of SEQ ID NO: 120 | — |
| 481 | isomiR example 1 of SEQ ID NO: 123 | — |
| 482 | isomiR example 2 of SEQ ID NO: 123 | — |
| 483 | isomiR example 1 of SEQ ID NO: 124 | — |
| 484 | isomiR example 2 of SEQ ID NO: 124 | — |
| 485 | isomiR example 1 of SEQ ID NO: 125 | — |
| 486 | isomiR example 2 of SEQ ID NO: 125 | — |
| 487 | isomiR example 1 of SEQ ID NO: 126 | — |
| 488 | isomiR example 2 of SEQ ID NO: 126 | — |
| 489 | isomiR example 1 of SEQ ID NO: 128 | — |
| 490 | isomiR example 2 of SEQ ID NO: 128 | — |
| 491 | isomiR example 1 of SEQ ID NO: 129 | — |
| 492 | isomiR example 2 of SEQ ID NO: 129 | — |
| 493 | isomiR example 1 of SEQ ID NO: 130 | — |
| 494 | isomiR example 2 of SEQ ID NO: 130 | — |
| 495 | isomiR example 1 of SEQ ID NO: 131 | — |
| 496 | isomiR example 2 of SEQ ID NO: 131 | — |
| 497 | isomiR example 1 of SEQ ID NO: 132 | — |
| 498 | isomiR example 2 of SEQ ID NO: 132 | — |
| 499 | isomiR example 1 of SEQ ID NO: 133 | — |
| 500 | isomiR example 2 of SEQ ID NO: 133 | — |
| 501 | isomiR example 1 of SEQ ID NO: 134 | — |
| 502 | isomiR example 2 of SEQ ID NO: 134 | — |
| 503 | isomiR example 1 of SEQ ID NO: 135 | — |
| 504 | isomiR example 2 of SEQ ID NO: 135 | — |
| 505 | isomiR example 1 of SEQ ID NO: 136 | — |
| 506 | isomiR example 2 of SEQ ID NO: 136 | — |
| 507 | isomiR example 1 of SEQ ID NO: 138 | — |
| 508 | isomiR example 2 of SEQ ID NO: 138 | — |
| 509 | isomiR example 1 of SEQ ID NO: 139 | — |
| 510 | isomiR example 2 of SEQ ID NO: 139 | — |
| 511 | isomiR example 1 of SEQ ID NO: 142 | — |
| 512 | isomiR example 2 of SEQ ID NO: 142 | — |
| 513 | isomiR example 1 of SEQ ID NO: 143 | — |
| 514 | isomiR example 2 of SEQ ID NO: 143 | — |
| 515 | isomiR example 1 of SEQ ID NO: 144 | — |
| 516 | isomiR example 2 of SEQ ID NO: 144 | — |
| 517 | isomiR example 1 of SEQ ID NO: 145 | — |
| 518 | isomiR example 2 of SEQ ID NO: 145 | — |
| 519 | isomiR example 1 of SEQ ID NO: 146 | — |
| 520 | isomiR example 2 of SEQ ID NO: 146 | — |
| 521 | isomiR example 1 of SEQ ID NO: 147 | — |
| 522 | isomiR example 2 of SEQ ID NO: 147 | — |
| 523 | isomiR example 1 of SEQ ID NO: 149 | — |
| 524 | isomiR example 2 of SEQ ID NO: 149 | — |
| 525 | isomiR example 1 of SEQ ID NO: 151 | — |
| 526 | isomiR example 2 of SEQ ID NO: 151 | — |
| 527 | isomiR example 1 of SEQ ID NO: 152 | — |
| 528 | isomiR example 2 of SEQ ID NO: 152 | — |
| 529 | isomiR example 1 of SEQ ID NO: 153 | — |
| 530 | isomiR example 2 of SEQ ID NO: 153 | — |
| 531 | isomiR example 1 of SEQ ID NO: 154 | — |
| 532 | isomiR example 2 of SEQ ID NO: 154 | — |
| 533 | isomiR example 1 of SEQ ID NO: 156 | — |
| 534 | isomiR example 2 of SEQ ID NO: 156 | — |
| 535 | isomiR example 1 of SEQ ID NO: 157 | — |
| 536 | isomiR example 2 of SEQ ID NO: 157 | — |
| 537 | isomiR example 1 of SEQ ID NO: 158 | — |
| 538 | isomiR example 2 of SEQ ID NO: 158 | — |
| 539 | isomiR example 1 of SEQ ID NO: 160 | — |
| 540 | isomiR example 2 of SEQ ID NO: 160 | — |
| 541 | isomiR example 1 of SEQ ID NO: 161 | — |
| 542 | isomiR example 2 of SEQ ID NO: 161 | — |
| 543 | isomiR example 1 of SEQ ID NO: 162 | — |
| 544 | isomiR example 2 of SEQ ID NO: 162 | — |
| 545 | isomiR example 1 of SEQ ID NO: 163 | — |
| 546 | isomiR example 2 of SEQ ID NO: 163 | — |
| 547 | isomiR example 1 of SEQ ID NO: 166 | — |
| 548 | isomiR example 2 of SEQ ID NO: 166 | — |
| 549 | isomiR example 1 of SEQ ID NO: 167 | — |
| 550 | isomiR example 2 of SEQ ID NO: 167 | — |
| 551 | isomiR example 1 of SEQ ID NO: 168 | — |
| 552 | isomiR example 2 of SEQ ID NO: 168 | — |
| 553 | isomiR example 1 of SEQ ID NO: 169 | — |
| 554 | isomiR example 2 of SEQ ID NO: 169 | — |
| 555 | isomiR example 1 of SEQ ID NO: 172 | — |
| 556 | isomiR example 2 of SEQ ID NO: 172 | — |
| 557 | isomiR example 1 of SEQ ID NO: 173 | — |
| 558 | isomiR example 2 of SEQ ID NO: 173 | — |
| 559 | isomiR example 1 of SEQ ID NO: 174 | — |
| 560 | isomiR example 2 of SEQ ID NO: 174 | — |
| 561 | hsa-miR-6073 | MIMAT0023698 |
| 562 | hsa-miR-6845-5p | MIMAT0027590 |
| 563 | hsa-miR-6769b-5p | MIMAT0027620 |
| 564 | hsa-miR-4665-3p | MIMAT0019740 |
| 565 | hsa-miR-1913 | MIMAT0007888 |
| 566 | hsa-miR-1228-3p | MIMAT0005583 |
| 567 | hsa-miR-940 | MIMAT0004983 |
| 568 | hsa-miR-296-3p | MIMAT0004679 |
| 569 | hsa-miR-4690-5p | MIMAT0019779 |
| 570 | hsa-miR-548q | MIMAT0011163 |
| 571 | hsa-miR-663a | MIMAT0003326 |
| 572 | hsa-miR-1249 | MIMAT0005901 |
| 573 | hsa-miR-1202 | MIMAT0005865 |
| 574 | hsa-miR-7113-3p | MIMAT0028124 |
| 575 | hsa-miR-1225-3p | MIMAT0005573 |
| 576 | hsa-miR-4783-3p | MIMAT0019947 |

TABLE 1-continued

| SEQ ID NO: | Gene name | miRBase registration No. |
|---|---|---|
| 577 | hsa-miR-4448 | MIMAT0018967 |
| 578 | hsa-miR-4534 | MIMAT0019073 |
| 579 | hsa-miR-1307-3p | MIMAT0005951 |
| 580 | hsa-mir-6073 | MI0020350 |
| 581 | hsa-mir-6845 | MI0022691 |
| 582 | hsa-mir-6769b | MI0022706 |
| 583 | hsa-mir-4665 | MI0017295 |
| 584 | hsa-mir-1913 | MI0008334 |
| 585 | hsa-mir-940 | MI0005762 |
| 586 | hsa-mir-296 | MI0000747 |
| 587 | hsa-mir-4690 | MI0017323 |
| 588 | hsa-mir-548q | MI0010637 |
| 589 | hsa-mir-663a | MI0003672 |
| 590 | hsa-mir-1249 | MI0006384 |
| 591 | hsa-mir-1202 | MI0006334 |
| 592 | hsa-mir-7113 | MI0022964 |
| 593 | hsa-mir-4783 | MI0017428 |
| 594 | hsa-mir-4448 | MI0016791 |
| 595 | hsa-mir-4534 | MI0016901 |
| 596 | hsa-mir-1307 | MI0006444 |
| 597 | isomiR example 1 of SEQ ID NO: 565 | — |
| 598 | isomiR example 2 of SEQ ID NO: 565 | — |
| 599 | isomiR example 1 of SEQ ID NO: 566 | — |
| 600 | isomiR example 2 of SEQ ID NO: 566 | — |
| 601 | isomiR example 1 of SEQ ID NO: 567 | — |
| 602 | isomiR example 2 of SEQ ID NO: 567 | — |
| 603 | isomiR example 1 of SEQ ID NO: 568 | — |
| 604 | isomiR example 2 of SEQ ID NO: 568 | — |
| 605 | isomiR example 1 of SEQ ID NO: 569 | — |
| 606 | isomiR example 2 of SEQ ID NO: 569 | — |
| 607 | isomiR example 1 of SEQ ID NO: 571 | — |
| 608 | isomiR example 2 of SEQ ID NO: 571 | — |
| 609 | isomiR example 1 of SEQ ID NO: 572 | — |
| 610 | isomiR example 2 of SEQ ID NO: 572 | — |
| 611 | isomiR example 1 of SEQ ID NO: 573 | — |
| 612 | isomiR example 2 of SEQ ID NO: 573 | — |
| 613 | isomiR example 1 of SEQ ID NO: 576 | — |
| 614 | isomiR example 2 of SEQ ID NO: 576 | — |
| 615 | isomiR example 1 of SEQ ID NO: 577 | — |
| 616 | isomiR example 2 of SEQ ID NO: 577 | — |
| 617 | isomiR example 1 of SEQ ID NO: 579 | — |
| 618 | isomiR example 2 of SEQ ID NO: 579 | — |

The present specification encompasses the contents described in the specification and/or drawings of Japanese Patent Application No. 2014-125561 on which the priority of the present application is based.

Advantageous Effects of Invention

According to the present invention, lung cancer can be detected easily and in high accuracy.

For example, the presence or absence of lung cancer in a patient can be easily detected by using, as an index, the expression level measurement values of several miRNAs in blood, serum, and/or plasma of the patient, which can be collected with limited invasiveness.

BRIEF DESCRIPTION OF DRAWINGS

FIGS. 2A and 2B FIG. 2A: the expression level measurement values of hsa-miR-6768-5p (SEQ ID NO: 1) in healthy subjects (100 persons) and lung cancer patients (17 persons) selected as a training cohort were each plotted on the ordinate. The horizontal line in the diagram depicts a threshold (10.08) that was optimized by Fisher's discriminant analysis and discriminated between the two groups. FIG. 2B: the expression level measurement values of hsa-miR-6768-5p (SEQ ID NO: 1) in healthy subjects (50 persons) and lung cancer patients (8 persons) selected as a validation cohort were each plotted on the ordinate. The horizontal line in the diagram depicts the threshold (10.08) that was set in the training cohort and discriminated between the two groups.

FIGS. 3A and 3B FIG. 3A: the expression level measurement values of hsa-miR-6768-5p (SEQ ID NO: 1) in healthy subjects (100 persons, circles) and lung cancer patients (17 persons, triangles) selected as a training cohort were each plotted on the abscissa against their expression level measurement values of hsa-miR-6836-3p (SEQ ID NO: 2) on the ordinate. The line in the diagram depicts a discriminant function (0=−1.42x+y+4.7) that was optimized by Fisher's discriminant analysis and discriminated between the two groups. FIG. 3B: the expression level measurement values of hsa-miR-6768-5p (SEQ ID NO: 1) in healthy subjects (50 persons, circles) and lung cancer patients (8 persons, triangles) selected as a validation cohort were each plotted on the abscissa against their expression level measurement values of hsa-miR-6836-3p (SEQ ID NO: 2) on the ordinate. The line in the diagram depicts the threshold (0=−1.42x+y+4.7) that was set in the training cohort and discriminated between the two groups.

FIG. 4B: discriminant scores obtained from the discriminant prepared in the training cohort as to the expression level measurement values of hsa-miR-6768-5p (SEQ ID NO: 1), hsa-miR-6717-5p (SEQ ID NO: 113), hsa-miR-19b-3p (SEQ ID NO: 126), and hsa-miR-6073 (SEQ ID NO: 561) in 8 lung cancer patients, 51 healthy subjects, 23 pancreatic cancer patients, 38 biliary tract cancer patients, 18 colorectal cancer patients, 15 stomach cancer patients, 18 esophageal cancer patients, 19 liver cancer patients, and 8 benign pancreaticobiliary disease patients selected as a validation cohort were plotted on the ordinate against the sample groups on the abscissa. The dotted line in the diagram depicts the discriminant boundary that offered a discriminant score of 0 and discriminated between the two groups.

DESCRIPTION OF EMBODIMENTS

Figure 1:
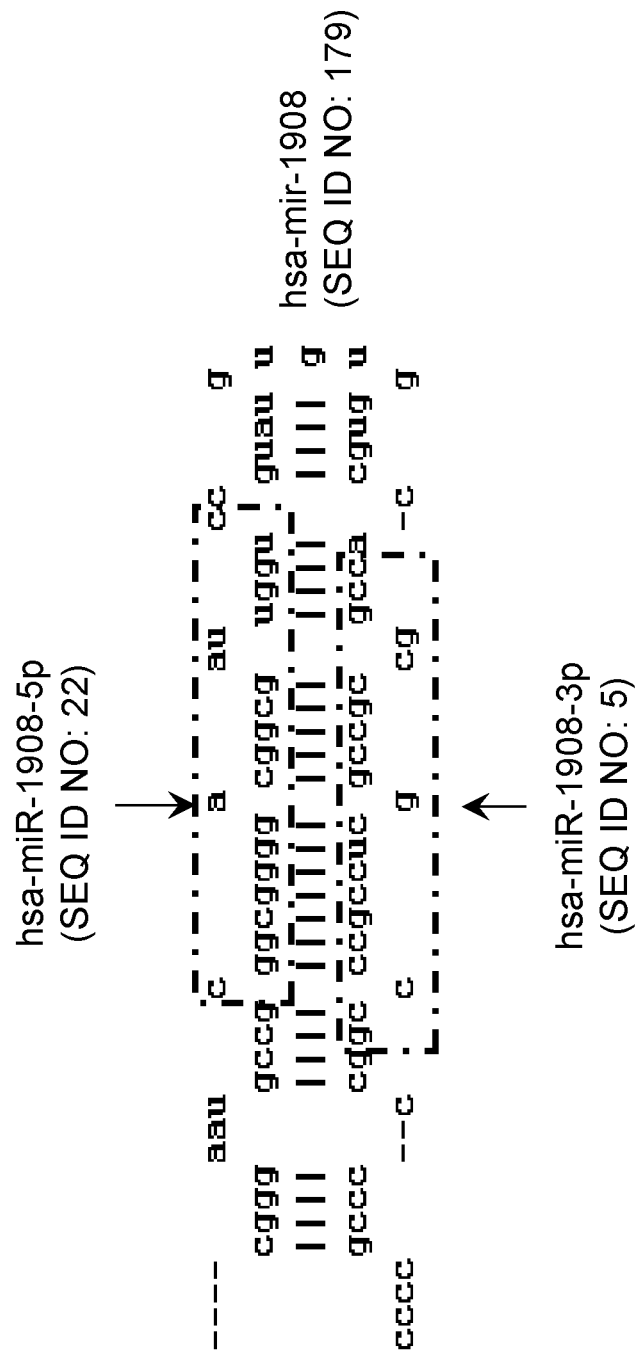
FIG. 1 This figure shows the relationship between the nucleotide sequences of hsa-miR-1908-5p represented by SEQ ID NO: 22 and hsa-miR-1908-3p represented by SEQ ID NO: 5, which are produced from a precursor hsa-mir-1908 represented by SEQ ID NO: 179.

Hereinafter, the present invention will be described further specifically.

1. Target Nucleic Acid for Lung Cancer

A primary target nucleic acid used as a lung cancer marker for detecting the presence and/or absence of lung cancer or lung cancer cells using the nucleic acid probe or the primer for the detection of lung cancer defined above according to the present invention can be at least one or more miRNA(s) selected from the group consisting of hsa-miR-6768-5p, hsa-miR-6836-3p, hsa-miR-6782-5p, hsa-miR-3663-3p, hsa-miR-1908-3p, hsa-miR-6726-5p, hsa-miR-4258, hsa-miR-1343-3p, hsa-miR-4516, hsa-miR-6875-5p, hsa-miR-4651, hsa-miR-6825-5p, hsa-miR-6840-3p, hsa-miR-6780b-5p, hsa-miR-6749-5p, hsa-miR-8063, hsa-miR-6784-5p, hsa-miR-3679-5p, hsa-miR-3184-5p, hsa-miR-663b, hsa-miR-6880-5p, hsa-miR-1908-5p, hsa-miR-92a-2-5p, hsa-miR-7975, hsa-miR-7110-5p, hsa-miR-6842-5p, hsa-miR-6857-5p, hsa-miR-5572, hsa-miR-3197, hsa-miR-6131, hsa-miR-6889-5p, hsa-miR-4454, hsa-miR-1199-5p, hsa-miR-1247-3p, hsa-miR-6800-5p, hsa-miR-6872-3p, hsa-miR-4649-5p, hsa-miR-6791-5p, hsa-miR-4433b-3p, hsa-miR-3135b, hsa-miR-128-2-5p, hsa-miR-4675, hsa-miR-4472, hsa-miR-6785-5p, hsa-miR-6741-5p, hsa-miR-7977, hsa-miR-3665, hsa-miR-128-1-5p, hsa-miR-4286, hsa-miR-6765-3p, hsa-miR-4632-5p, hsa-miR-365a-5p, hsa-miR-6088, hsa-miR-6816-5p, hsa-miR-6885-5p, hsa-miR-711, hsa-miR-6765-5p, hsa-miR-3180, hsa-miR-4442, hsa-miR-4792, hsa-miR-6721-5p, hsa-miR-6798-5p, hsa-miR-3162-5p, hsa-miR-6126, hsa-miR-4758-5p, hsa-miR-2392, hsa-miR-486-3p, hsa-miR-6727-5p, hsa-miR-4728-5p, hsa-miR-6746-5p, hsa-miR-4270, hsa-miR-3940-5p, hsa-miR-4725-3p, hsa-miR-7108-5p, hsa-miR-3656, hsa-miR-6879-5p, hsa-miR-6738-5p, hsa-miR-1260a, hsa-miR-4446-3p, hsa-miR-3131, hsa-miR-4463, hsa-miR-3185, hsa-miR-6870-5p, hsa-miR-6779-5p, hsa-miR-1273g-3p, hsa-miR-8059, hsa-miR-4697-5p, hsa-miR-4674, hsa-miR-4433-3p, hsa-miR-4257, hsa-miR-1915-5p, hsa-miR-4417, hsa-miR-1343-5p, hsa-miR-6781-5p, hsa-miR-4695-5p, hsa-miR-1237-5p, hsa-miR-6775-5p, hsa-miR-7845-5p, hsa-miR-4746-3p, hsa-miR-7641, hsa-miR-7847-3p, hsa-miR-6806-5p, hsa-miR-4467, hsa-miR-4726-5p, hsa-miR-4648, hsa-miR-6089, hsa-miR-1260b, hsa-miR-4532, hsa-miR-5195-3p, hsa-miR-3188, hsa-miR-6848-5p, hsa-miR-1233-5p, hsa-miR-6717-5p, hsa-miR-3195, hsa-miR-6757-5p, hsa-miR-8072, hsa-miR-4745-5p, hsa-miR-6511a-5p, hsa-miR-6776-5p, hsa-miR-371a-5p, hsa-miR-1227-5p, hsa-miR-7150, hsa-miR-1915-3p, hsa-miR-187-5p, hsa-miR-614, hsa-miR-1225-5p, hsa-miR-451a, hsa-miR-939-5p, hsa-miR-223-3p, hsa-miR-125a-3p, hsa-miR-92b-5p, hsa-miR-22-3p, hsa-miR-6073, hsa-miR-6845-5p, hsa-miR-6769b-5p, hsa-miR-4665-3p, hsa-miR-1913, hsa-miR-1228-3p, hsa-miR-940, hsa-miR-296-3p, hsa-miR-4690-5p, hsa-miR-548q, hsa-miR-663a, hsa-miR-1249, hsa-miR-1202, hsa-miR-7113-3p, hsa-miR-1225-3p, hsa-miR-4783-3p, hsa-miR-4448 and hsa-miR-4534. Furthermore, at least one or more miRNA(s) selected from the group consisting of other lung cancer markers that can be combined with these miRNAs, i.e., hsa-miR-19b-3p, hsa-miR-1228-5p, and hsa-miR-1307-3p, can also be preferably used as a target nucleic acid. Moreover, at least one or more miRNA(s) selected from the group consisting of other lung cancer markers that can be combined with these miRNAs, i.e., hsa-miR-4271, hsa-miR-642b-3p, hsa-miR-6075, hsa-miR-6125, hsa-miR-887-3p, hsa-miR-6851-5p, hsa-miR-6763-5p, hsa-miR-3928-3p, hsa-miR-4443, hsa-miR-3648, hsa-miR-149-3p, hsa-miR-4689, hsa-miR-4763-3p, hsa-miR-6729-5p, hsa-miR-3196, hsa-miR-8069, hsa-miR-1268a, hsa-miR-4739, hsa-miR-1268b, hsa-miR-5698, hsa-miR-6752-5p, hsa-miR-4507, hsa-miR-564, hsa-miR-4497, hsa-miR-6877-5p, hsa-miR-6087, hsa-miR-4731-5p, hsa-miR-615-5p, hsa-miR-760, hsa-miR-6891-5p, hsa-miR-6887-5p, hsa-miR-4525, hsa-miR-1914-3p, hsa-miR-619-5p, hsa-miR-5001-5p, hsa-miR-6722-3p, hsa-miR-3621, hsa-miR-4298, hsa-miR-675-5p and hsa-miR-4655-5p can also be preferably used as a target nucleic acid.

These miRNAs include, for example, a human gene comprising a nucleotide sequence represented by any of SEQ ID NOs: 1 to 174 and 561 to 579 (i.e., hsa-miR-6768-5p, hsa-miR-6836-3p, hsa-miR-6782-5p, hsa-miR-3663-3p, hsa-miR-1908-3p, hsa-miR-6726-5p, hsa-miR-4258, hsa-miR-1343-3p, hsa-miR-4516, hsa-miR-6875-5p, hsa-miR-4651, hsa-miR-6825-5p, hsa-miR-6840-3p, hsa-miR-6780b-5p, hsa-miR-6749-5p, hsa-miR-8063, hsa-miR-6784-5p, hsa-miR-3679-5p, hsa-miR-3184-5p, hsa-miR-663b, hsa-miR-6880-5p, hsa-miR-1908-5p, hsa-miR-92a-2-5p, hsa-miR-7975, hsa-miR-7110-5p, hsa-miR-6842-5p, hsa-miR-6857-5p, hsa-miR-5572, hsa-miR-3197, hsa-miR-6131, hsa-miR-6889-5p, hsa-miR-4454, hsa-miR-1199-5p, hsa-miR-1247-3p, hsa-miR-6800-5p, hsa-miR-6872-3p, hsa-miR-4649-5p, hsa-miR-6791-5p, hsa-miR-4433b-3p, hsa-miR-3135b, hsa-miR-128-2-5p, hsa-miR-4675, hsa-miR-4472, hsa-miR-6785-5p, hsa-miR-6741-5p, hsa-miR-7977, hsa-miR-3665, hsa-miR-128-1-5p, hsa-miR-4286, hsa-miR-6765-3p, hsa-miR-4632-5p, hsa-miR-365a-5p, hsa-miR-6088, hsa-miR-6816-5p, hsa-miR-6885-5p, hsa-miR-711, hsa-miR-6765-5p, hsa-miR-3180, hsa-miR-4442, hsa-miR-4792, hsa-miR-6721-5p, hsa-miR-6798-5p, hsa-miR-3162-5p, hsa-miR-6126, hsa-miR-4758-5p, hsa-miR-2392, hsa-miR-486-3p, hsa-miR-6727-5p, hsa-miR-4728-5p, hsa-miR-6746-5p, hsa-miR-4270, hsa-miR-3940-5p, hsa-miR-4725-3p, hsa-miR-7108-5p, hsa-miR-3656, hsa-miR-6879-5p, hsa-miR-6738-5p, hsa-miR-1260a, hsa-miR-4446-3p, hsa-miR-3131, hsa-miR-4463, hsa-miR-3185, hsa-miR-6870-5p, hsa-miR-6779-5p, hsa-miR-1273g-3p, hsa-miR-8059, hsa-miR-4697-5p, hsa-miR-4674, hsa-miR-4433-3p, hsa-miR-4257, hsa-miR-1915-5p, hsa-miR-4417, hsa-miR-1343-5p, hsa-miR-6781-5p, hsa-miR-4695-5p, hsa-miR-1237-5p, hsa-miR-6775-5p, hsa-miR-7845-5p, hsa-miR-4746-3p, hsa-miR-7641, hsa-miR-7847-3p, hsa-miR-6806-5p, hsa-miR-4467, hsa-miR-4726-5p, hsa-miR-4648, hsa-miR-6089, hsa-miR-1260b, hsa-miR-4532, hsa-miR-5195-3p, hsa-miR-3188, hsa-miR-6848-5p, hsa-miR-1233-5p, hsa-miR-6717-5p, hsa-miR-3195, hsa-miR-6757-5p, hsa-miR-8072, hsa-miR-4745-5p, hsa-miR-6511a-5p, hsa-miR-6776-5p, hsa-miR-371a-5p, hsa-miR-1227-5p, hsa-miR-7150, hsa-miR-1915-3p, hsa-miR-187-5p, hsa-miR-614, hsa-miR-19b-3p, hsa-miR-1225-5p, hsa-miR-451a, hsa-miR-939-5p, hsa-miR-223-3p, hsa-miR-1228-5p, hsa-miR-125a-3p, hsa-miR-92b-5p, hsa-miR-22-3p, hsa-miR-6073, hsa-miR-6845-5p, hsa-miR-6769b-5p, hsa-miR-4665-3p, hsa-miR-1913, hsa-miR-1228-3p, hsa-miR-940, hsa-miR-296-3p, hsa-miR-4690-5p, hsa-miR-548q, hsa-miR-663a, hsa-miR-1249, hsa-miR-1202, hsa-miR-7113-3p, hsa-miR-1225-3p, hsa-miR-4783-3p, hsa-miR-4448 and hsa-miR-4534, hsa-miR-1307-3p, hsa-miR-4271, hsa-miR-642b-3p, hsa-miR-6075, hsa-miR-6125, hsa-miR-887-3p, hsa-miR-6851-5p, hsa-miR-6763-5p, hsa-miR-3928-3p, hsa-miR-4443, hsa-miR-3648, hsa-miR-149-3p, hsa-miR-4689, hsa-miR-4763-3p, hsa-miR-6729-5p, hsa-miR-3196, hsa-miR-8069, hsa-miR-1268a, hsa-miR-4739, hsa-miR-1268b, hsa-miR-5698, hsa-miR-6752-5p, hsa-miR-4507, hsa-miR-564, hsa-miR-4497, hsa-miR-6877-5p, hsa-miR-6087, hsa-miR-4731-5p, hsa-miR-615-5p, hsa-miR-760, hsa-miR-6891-5p, hsa-miR-6887-5p, hsa-miR-4525, hsa-miR-1914-3p, hsa-miR-619-5p, hsa-miR-5001-5p, hsa-miR-6722-3p, hsa-miR-3621, hsa-miR-4298, hsa-miR-675-5p and hsa-miR-4655-5p, respectively), a congener thereof, a transcript thereof, and a variant or a derivative thereof. In this context, the gene, the congener, the transcript, the variant, and the derivative are as defined above.

The target nucleic acid is preferably a human gene comprising a nucleotide sequence represented by any of SEQ ID NOs: 1 to 618 or a transcript thereof, more preferably the transcript, i.e., a miRNA or its precursor RNA (pri-miRNA or pre-miRNA).

The first target gene is the hsa-miR-6768-5p gene, a congener thereof, a transcript thereof, or a variant or a derivative thereof. None of the previously known reports show that change in the expression of the gene or the transcript thereof can serve as a marker for lung cancer.

The second target gene is the hsa-miR-6836-3p gene, a congener thereof, a transcript thereof, or a variant or a derivative thereof. None of the previously known reports show that change in the expression of the gene or the transcript thereof can serve as a marker for lung cancer.

The third target gene is the hsa-miR-6782-5p gene, a congener thereof, a transcript thereof, or a variant or a derivative thereof. None of the previously known reports show that change in the expression of the gene or the transcript thereof can serve as a marker for lung cancer.

The fourth target gene is the hsa-miR-3663-3p gene, a congener thereof, a transcript thereof, or a variant or a derivative thereof. None of the previously known reports show that change in the expression of the gene or the transcript thereof can serve as a marker for lung cancer.

The fifth target gene is the hsa-miR-1908-3p gene, a congener thereof, a transcript thereof, or a variant or a derivative thereof. None of the previously known reports show that change in the expression of the gene or the transcript thereof can serve as a marker for lung cancer.

The sixth target gene is the hsa-miR-6726-5p gene, a congener thereof, a transcript thereof, or a variant or a derivative thereof. None of the previously known reports show that change in the expression of the gene or the transcript thereof can serve as a marker for lung cancer.

The seventh target gene is the hsa-miR-4258 gene, a congener thereof, a transcript thereof, or a variant or a derivative thereof. None of the previously known reports show that change in the expression of the gene or the transcript thereof can serve as a marker for lung cancer.

The eighth target gene is the hsa-miR-1343-3p gene, a congener thereof, a transcript thereof, or a variant or a derivative thereof. None of the previously known reports show that change in the expression of the gene or the transcript thereof can serve as a marker for lung cancer.

The ninth target gene is the hsa-miR-4516 gene, a congener thereof, a transcript thereof, or a variant or a derivative thereof. None of the previously known reports show that change in the expression of the gene or the transcript thereof can serve as a marker for lung cancer.

The 10th target gene is the hsa-miR-6875-5p gene, a congener thereof, a transcript thereof, or a variant or a derivative thereof. None of the previously known reports show that change in the expression of the gene or the transcript thereof can serve as a marker for lung cancer.

The 11th target gene is the hsa-miR-4651 gene, a congener thereof, a transcript thereof, or a variant or a derivative thereof. None of the previously known reports show that change in the expression of the gene or the transcript thereof can serve as a marker for lung cancer.

The 12th target gene is the hsa-miR-6825-5p gene, a congener thereof, a transcript thereof, or a variant or a derivative thereof. None of the previously known reports show that change in the expression of the gene or the transcript thereof can serve as a marker for lung cancer.

The 13th target gene is the hsa-miR-6840-3p gene, a congener thereof, a transcript thereof, or a variant or a derivative thereof. None of the previously known reports show that change in the expression of the gene or the transcript thereof can serve as a marker for lung cancer.

The 14th target gene is the hsa-miR-6780b-5p gene, a congener thereof, a transcript thereof, or a variant or a derivative thereof. None of the previously known reports show that change in the expression of the gene or the transcript thereof can serve as a marker for lung cancer.

The 15th target gene is the hsa-miR-6749-5p gene, a congener thereof, a transcript thereof, or a variant or a derivative thereof. None of the previously known reports show that change in the expression of the gene or the transcript thereof can serve as a marker for lung cancer.

The 16th target gene is the hsa-miR-8063 gene, a congener thereof, a transcript thereof, or a variant or a derivative thereof. None of the previously known reports show that change in the expression of the gene or the transcript thereof can serve as a marker for lung cancer.

The 17th target gene is the hsa-miR-6784-5p gene, a congener thereof, a transcript thereof, or a variant or a derivative thereof. None of the previously known reports show that change in the expression of the gene or the transcript thereof can serve as a marker for lung cancer.

The 18th target gene is the hsa-miR-3679-5p gene, a congener thereof, a transcript thereof, or a variant or a derivative thereof. None of the previously known reports show that change in the expression of the gene or the transcript thereof can serve as a marker for lung cancer.

The 19th target gene is the hsa-miR-3184-5p gene, a congener thereof, a transcript thereof, or a variant or a derivative thereof. None of the previously known reports show that change in the expression of the gene or the transcript thereof can serve as a marker for lung cancer.

The 20th target gene is the hsa-miR-663b gene, a congener thereof, a transcript thereof, or a variant or a derivative thereof. None of the previously known reports show that change in the expression of the gene or the transcript thereof can serve as a marker for lung cancer.

The 21st target gene is the hsa-miR-6880-5p gene, a congener thereof, a transcript thereof, or a variant or a derivative thereof. None of the previously known reports show that change in the expression of the gene or the transcript thereof can serve as a marker for lung cancer.

The 22nd target gene is the hsa-miR-1908-5p gene, a congener thereof, a transcript thereof, or a variant or a derivative thereof. None of the previously known reports show that change in the expression of the gene or the transcript thereof can serve as a marker for lung cancer.

The 23rd target gene is the hsa-miR-92a-2-5p gene, a congener thereof, a transcript thereof, or a variant or a derivative thereof. None of the previously known reports show that change in the expression of the gene or the transcript thereof can serve as a marker for lung cancer.

The 24th target gene is the hsa-miR-7975 gene, a congener thereof, a transcript thereof, or a variant or a derivative thereof. None of the previously known reports show that change in the expression of the gene or the transcript thereof can serve as a marker for lung cancer.

The 25th target gene is the hsa-miR-7110-5p gene, a congener thereof, a transcript thereof, or a variant or a derivative thereof. None of the previously known reports show that change in the expression of the gene or the transcript thereof can serve as a marker for lung cancer.

The 26th target gene is the hsa-miR-6842-5p gene, a congener thereof, a transcript thereof, or a variant or a The 27th target gene is the hsa-miR-6857-5p gene, a congener thereof, a transcript thereof, or a variant or a derivative thereof. None of the previously known reports show that change in the expression of the gene or the transcript thereof can serve as a marker for lung cancer.

The 28th target gene is the hsa-miR-5572 gene, a congener thereof, a transcript thereof, or a variant or a derivative thereof. None of the previously known reports show that change in the expression of the gene or the transcript thereof can serve as a marker for lung cancer.

The 29th target gene is the hsa-miR-3197 gene, a congener thereof, a transcript thereof, or a variant or a derivative thereof. None of the previously known reports show that change in the expression of the gene or the transcript thereof can serve as a marker for lung cancer.

The 30th target gene is the hsa-miR-6131 gene, a congener thereof, a transcript thereof, or a variant or a derivative thereof. None of the previously known reports show that change in the expression of the gene or the transcript thereof can serve as a marker for lung cancer.

The 31st target gene is the hsa-miR-6889-5p gene, a congener thereof, a transcript thereof, or a variant or a derivative thereof. None of the previously known reports show that change in the expression of the gene or the transcript thereof can serve as a marker for lung cancer.

The 32nd target gene is the hsa-miR-4454 gene, a congener thereof, a transcript thereof, or a variant or a derivative thereof. None of the previously known reports show that change in the expression of the gene or the transcript thereof can serve as a marker for lung cancer.

The 33rd target gene is the hsa-miR-1199-5p gene, a congener thereof, a transcript thereof, or a variant or a derivative thereof. None of the previously known reports show that change in the expression of the gene or the transcript thereof can serve as a marker for lung cancer.

The 34th target gene is the hsa-miR-1247-3p gene, a congener thereof, a transcript thereof, or a variant or a derivative thereof. None of the previously known reports show that change in the expression of the gene or the transcript thereof can serve as a marker for lung cancer.

The 35th target gene is the hsa-miR-6800-5p gene, a congener thereof, a transcript thereof, or a variant or a derivative thereof. None of the previously known reports show that change in the expression of the gene or the transcript thereof can serve as a marker for lung cancer.

The 36th target gene is the hsa-miR-6872-3p gene, a congener thereof, a transcript thereof, or a variant or a derivative thereof. None of the previously known reports show that change in the expression of the gene or the transcript thereof can serve as a marker for lung cancer.

The 37th target gene is the hsa-miR-4649-5p gene, a congener thereof, a transcript thereof, or a variant or a derivative thereof. None of the previously known reports show that change in the expression of the gene or the transcript thereof can serve as a marker for lung cancer.

The 38th target gene is the hsa-miR-6791-5p gene, a congener thereof, a transcript thereof, or a variant or a derivative thereof. None of the previously known reports show that change in the expression of the gene or the transcript thereof can serve as a marker for lung cancer.

The 39th target gene is the hsa-miR-4433b-3p gene, a congener thereof, a transcript thereof, or a variant or a derivative thereof. None of the previously known reports show that change in the expression of the gene or the transcript thereof can serve as a marker for lung cancer.

The 40th target gene is the hsa-miR-3135b gene, a congener thereof, a transcript thereof, or a variant or a derivative thereof. None of the previously known reports show that change in the expression of the gene or the transcript thereof can serve as a marker for lung cancer.

The 41st target gene is the hsa-miR-128-2-5p gene, a congener thereof, a transcript thereof, or a variant or a derivative thereof. None of the previously known reports show that change in the expression of the gene or the transcript thereof can serve as a marker for lung cancer.

The 42nd target gene is the hsa-miR-4675 gene, a congener thereof, a transcript thereof, or a variant or a derivative thereof. None of the previously known reports show that change in the expression of the gene or the transcript thereof can serve as a marker for lung cancer.

The 43rd target gene is the hsa-miR-4472 gene, a congener thereof, a transcript thereof, or a variant or a derivative thereof. None of the previously known reports show that change in the expression of the gene or the transcript thereof can serve as a marker for lung cancer.

The 44th target gene is the hsa-miR-6785-5p gene, a congener thereof, a transcript thereof, or a variant or a derivative thereof. None of the previously known reports show that change in the expression of the gene or the transcript thereof can serve as a marker for lung cancer.

The 45th target gene is the hsa-miR-6741-5p gene, a congener thereof, a transcript thereof, or a variant or a derivative thereof. None of the previously known reports show that change in the expression of the gene or the transcript thereof can serve as a marker for lung cancer.

The 46th target gene is the hsa-miR-7977 gene, a congener thereof, a transcript thereof, or a variant or a derivative thereof. None of the previously known reports show that change in the expression of the gene or the transcript thereof can serve as a marker for lung cancer.

The 47th target gene is the hsa-miR-3665 gene, a congener thereof, a transcript thereof, or a variant or a derivative thereof. None of the previously known reports show that change in the expression of the gene or the transcript thereof can serve as a marker for lung cancer.

The 48th target gene is the hsa-miR-128-1-5p gene, a congener thereof, a transcript thereof, or a variant or a derivative thereof. None of the previously known reports show that change in the expression of the gene or the transcript thereof can serve as a marker for lung cancer.

The 49th target gene is the hsa-miR-4286 gene, a congener thereof, a transcript thereof, or a variant or a derivative thereof. None of the previously known reports show that change in the expression of the gene or the transcript thereof can serve as a marker for lung cancer.

The 50th target gene is the hsa-miR-6765-3p gene, a congener thereof, a transcript thereof, or a variant or a derivative thereof. None of the previously known reports show that change in the expression of the gene or the transcript thereof can serve as a marker for lung cancer.

The 51st target gene is the hsa-miR-4632-5p gene, a congener thereof, a transcript thereof, or a variant or a derivative thereof. None of the previously known reports show that change in the expression of the gene or the transcript thereof can serve as a marker for lung cancer.

The 52nd target gene is the hsa-miR-365a-5p gene, a congener thereof, a transcript thereof, or a variant or a derivative thereof. None of the previously known reports show that change in the expression of the gene or the transcript thereof can serve as a marker for lung cancer.

The 53rd target gene is the hsa-miR-6088 gene, a congener thereof, a transcript thereof, or a variant or a derivative thereof. None of the previously known reports show that change in the expression of the gene or the transcript thereof can serve as a marker for lung cancer.

The 54th target gene is the hsa-miR-6816-5p gene, a congener thereof, a transcript thereof, or a variant or a derivative thereof. None of the previously known reports show that change in the expression of the gene or the transcript thereof can serve as a marker for lung cancer.

The 55th target gene is the hsa-miR-6885-5p gene, a congener thereof, a transcript thereof, or a variant or a derivative thereof. None of the previously known reports show that change in the expression of the gene or the transcript thereof can serve as a marker for lung cancer.

The 56th target gene is the hsa-miR-711 gene, a congener thereof, a transcript thereof, or a variant or a derivative thereof. None of the previously known reports show that change in the expression of the gene or the transcript thereof can serve as a marker for lung cancer.

The 57th target gene is the hsa-miR-6765-5p gene, a congener thereof, a transcript thereof, or a variant or a derivative thereof. None of the previously known reports show that change in the expression of the gene or the transcript thereof can serve as a marker for lung cancer.

The 58th target gene is the hsa-miR-3180 gene, a congener thereof, a transcript thereof, or a variant or a derivative thereof. None of the previously known reports show that change in the expression of the gene or the transcript thereof can serve as a marker for lung cancer.

The 59th target gene is the hsa-miR-4442 gene, a congener thereof, a transcript thereof, or a variant or a derivative thereof. None of the previously known reports show that change in the expression of the gene or the transcript thereof can serve as a marker for lung cancer.

The 60th target gene is the hsa-miR-4792 gene, a congener thereof, a transcript thereof, or a variant or a derivative thereof. None of the previously known reports show that change in the expression of the gene or the transcript thereof can serve as a marker for lung cancer.

The 61st target gene is the hsa-miR-6721-5p gene, a congener thereof, a transcript thereof, or a variant or a derivative thereof. None of the previously known reports show that change in the expression of the gene or the transcript thereof can serve as a marker for lung cancer.

The 62nd target gene is the hsa-miR-6798-5p gene, a congener thereof, a transcript thereof, or a variant or a derivative thereof. None of the previously known reports show that change in the expression of the gene or the transcript thereof can serve as a marker for lung cancer.

The 63rd target gene is the hsa-miR-3162-5p gene, a congener thereof, a transcript thereof, or a variant or a derivative thereof. None of the previously known reports show that change in the expression of the gene or the transcript thereof can serve as a marker for lung cancer.

The 64th target gene is the hsa-miR-6126 gene, a congener thereof, a transcript thereof, or a variant or a derivative thereof. None of the previously known reports show that change in the expression of the gene or the transcript thereof can serve as a marker for lung cancer.

The 65th target gene is the hsa-miR-4758-5p gene, a congener thereof, a transcript thereof, or a variant or a derivative thereof. None of the previously known reports show that change in the expression of the gene or the transcript thereof can serve as a marker for lung cancer.

The 66th target gene is the hsa-miR-2392 gene, a congener thereof, a transcript thereof, or a variant or a derivative thereof. None of the previously known reports show that change in the expression of the gene or the transcript thereof can serve as a marker for lung cancer.

The 67th target gene is the hsa-miR-486-3p gene, a congener thereof, a transcript thereof, or a variant or a derivative thereof. None of the previously known reports show that change in the expression of the gene or the transcript thereof can serve as a marker for lung cancer.

The 68th target gene is the hsa-miR-6727-5p gene, a congener thereof, a transcript thereof, or a variant or a derivative thereof. None of the previously known reports show that change in the expression of the gene or the transcript thereof can serve as a marker for lung cancer.

The 69th target gene is the hsa-miR-4728-5p gene, a congener thereof, a transcript thereof, or a variant or a derivative thereof. None of the previously known reports show that change in the expression of the gene or the transcript thereof can serve as a marker for lung cancer.

The 70th target gene is the hsa-miR-6746-5p gene, a congener thereof, a transcript thereof, or a variant or a derivative thereof. None of the previously known reports show that change in the expression of the gene or the transcript thereof can serve as a marker for lung cancer.

The 71st target gene is the hsa-miR-4270 gene, a congener thereof, a transcript thereof, or a variant or a derivative thereof. None of the previously known reports show that change in the expression of the gene or the transcript thereof can serve as a marker for lung cancer.

The 72nd target gene is the hsa-miR-3940-5p gene, a congener thereof, a transcript thereof, or a variant or a derivative thereof. None of the previously known reports show that change in the expression of the gene or the transcript thereof can serve as a marker for lung cancer.

The 73rd target gene is the hsa-miR-4725-3p gene, a congener thereof, a transcript thereof, or a variant or a derivative thereof. None of the previously known reports show that change in the expression of the gene or the transcript thereof can serve as a marker for lung cancer.

The 74th target gene is the hsa-miR-7108-5p gene, a congener thereof, a transcript thereof, or a variant or a derivative thereof. None of the previously known reports show that change in the expression of the gene or the transcript thereof can serve as a marker for lung cancer.

The 75th target gene is the hsa-miR-3656 gene, a congener thereof, a transcript thereof, or a variant or a derivative thereof. None of the previously known reports show that change in the expression of the gene or the transcript thereof can serve as a marker for lung cancer.

The 76th target gene is the hsa-miR-6879-5p gene, a congener thereof, a transcript thereof, or a variant or a derivative thereof. None of the previously known reports show that change in the expression of the gene or the transcript thereof can serve as a marker for lung cancer.

The 77th target gene is the hsa-miR-6738-5p gene, a congener thereof, a transcript thereof, or a variant or a derivative thereof. None of the previously known reports show that change in the expression of the gene or the transcript thereof can serve as a marker for lung cancer.

The 78th target gene is the hsa-miR-1260a gene, a congener thereof, a transcript thereof, or a variant or a derivative thereof. None of the previously known reports show that change in the expression of the gene or the transcript thereof can serve as a marker for lung cancer.

The 79th target gene is the hsa-miR-4446-3p gene, a congener thereof, a transcript thereof, or a variant or a derivative thereof. None of the previously known reports show that change in the expression of the gene or the transcript thereof can serve as a marker for lung cancer.

The 80th target gene is the hsa-miR-3131 gene, a congener thereof, a transcript thereof, or a variant or a derivative thereof. None of the previously known reports show that change in the expression of the gene or the transcript thereof can serve as a marker for lung cancer.

The 81st target gene is the hsa-miR-4463 gene, a congener thereof, a transcript thereof, or a variant or a derivative thereof. None of the previously known reports show that change in the expression of the gene or the transcript thereof can serve as a marker for lung cancer.

The 82nd target gene is the hsa-miR-3185 gene, a congener thereof, a transcript thereof, or a variant or a derivative thereof. None of the previously known reports show that change in the expression of the gene or the transcript thereof can serve as a marker for lung cancer.

The 83rd target gene is the hsa-miR-6870-5p gene, a congener thereof, a transcript thereof, or a variant or a derivative thereof. None of the previously known reports show that change in the expression of the gene or the transcript thereof can serve as a marker for lung cancer.

The 84th target gene is the hsa-miR-6779-5p gene, a congener thereof, a transcript thereof, or a variant or a derivative thereof. None of the previously known reports show that change in the expression of the gene or the transcript thereof can serve as a marker for lung cancer.

The 85th target gene is the hsa-miR-1273g-3p gene, a congener thereof, a transcript thereof, or a variant or a derivative thereof. None of the previously known reports show that change in the expression of the gene or the transcript thereof can serve as a marker for lung cancer.

The 86th target gene is the hsa-miR-8059 gene, a congener thereof, a transcript thereof, or a variant or a derivative thereof. None of the previously known reports show that change in the expression of the gene or the transcript thereof can serve as a marker for lung cancer.

The 87th target gene is the hsa-miR-4697-5p gene, a congener thereof, a transcript thereof, or a variant or a derivative thereof. None of the previously known reports show that change in the expression of the gene or the transcript thereof can serve as a marker for lung cancer.

The 88th target gene is the hsa-miR-4674 gene, a congener thereof, a transcript thereof, or a variant or a derivative thereof. None of the previously known reports show that change in the expression of the gene or the transcript thereof can serve as a marker for lung cancer.

The 89th target gene is the hsa-miR-4433-3p gene, a congener thereof, a transcript thereof, or a variant or a derivative thereof. None of the previously known reports show that change in the expression of the gene or the transcript thereof can serve as a marker for lung cancer.

The 90th target gene is the hsa-miR-4257 gene, a congener thereof, a transcript thereof, or a variant or a derivative thereof. None of the previously known reports show that change in the expression of the gene or the transcript thereof can serve as a marker for lung cancer.

The 91st target gene is the hsa-miR-1915-5p gene, a congener thereof, a transcript thereof, or a variant or a derivative thereof. None of the previously known reports show that change in the expression of the gene or the transcript thereof can serve as a marker for lung cancer.

The 92nd target gene is the hsa-miR-4417 gene, a congener thereof, a transcript thereof, or a variant or a derivative thereof. None of the previously known reports show that change in the expression of the gene or the transcript thereof can serve as a marker for lung cancer.

The 93rd target gene is the hsa-miR-1343-5p gene, a congener thereof, a transcript thereof, or a variant or a derivative thereof. None of the previously known reports show that change in the expression of the gene or the transcript thereof can serve as a marker for lung cancer.

The 94th target gene is the hsa-miR-6781-5p gene, a congener thereof, a transcript thereof, or a variant or a derivative thereof. None of the previously known reports show that change in the expression of the gene or the transcript thereof can serve as a marker for lung cancer.

The 95th target gene is the hsa-miR-4695-5p gene, a congener thereof, a transcript thereof, or a variant or a derivative thereof. None of the previously known reports show that change in the expression of the gene or the transcript thereof can serve as a marker for lung cancer.

The 96th target gene is the hsa-miR-1237-5p gene, a congener thereof, a transcript thereof, or a variant or a derivative thereof. None of the previously known reports show that change in the expression of the gene or the transcript thereof can serve as a marker for lung cancer.

The 97th target gene is the hsa-miR-6775-5p gene, a congener thereof, a transcript thereof, or a variant or a derivative thereof. None of the previously known reports show that change in the expression of the gene or the transcript thereof can serve as a marker for lung cancer.

The 98th target gene is the hsa-miR-7845-5p gene, a congener thereof, a transcript thereof, or a variant or a derivative thereof. None of the previously known reports show that change in the expression of the gene or the transcript thereof can serve as a marker for lung cancer.

The 99th target gene is the hsa-miR-4746-3p gene, a congener thereof, a transcript thereof, or a variant or a derivative thereof. None of the previously known reports show that change in the expression of the gene or the transcript thereof can serve as a marker for lung cancer.

The 100th target gene is the hsa-miR-7641 gene, a congener thereof, a transcript thereof, or a variant or a derivative thereof. None of the previously known reports show that change in the expression of the gene or the transcript thereof can serve as a marker for lung cancer.

The 101st target gene is the hsa-miR-7847-3p gene, a congener thereof, a transcript thereof, or a variant or a derivative thereof. None of the previously known reports show that change in the expression of the gene or the transcript thereof can serve as a marker for lung cancer.

The 102nd target gene is the hsa-miR-6806-5p gene, a congener thereof, a transcript thereof, or a variant or a derivative thereof. None of the previously known reports show that change in the expression of the gene or the transcript thereof can serve as a marker for lung cancer.

The 103rd target gene is the hsa-miR-4467 gene, a congener thereof, a transcript thereof, or a variant or a derivative thereof. None of the previously known reports show that change in the expression of the gene or the transcript thereof can serve as a marker for lung cancer.

The 104th target gene is the hsa-miR-4726-5p gene, a congener thereof, a transcript thereof, or a variant or a derivative thereof. None of the previously known reports show that change in the expression of the gene or the transcript thereof can serve as a marker for lung cancer.

The 105th target gene is the hsa-miR-4648 gene, a congener thereof, a transcript thereof, or a variant or a derivative thereof. None of the previously known reports show that change in the expression of the gene or the transcript thereof can serve as a marker for lung cancer.

The 106th target gene is the hsa-miR-6089 gene, a congener thereof, a transcript thereof, or a variant or a derivative thereof. None of the previously known reports show that change in the expression of the gene or the transcript thereof can serve as a marker for lung cancer.

The 107th target gene is the hsa-miR-1260b gene, a congener thereof, a transcript thereof, or a variant or a derivative thereof. None of the previously known reports show that change in the expression of the gene or the transcript thereof can serve as a marker for lung cancer.

The 108th target gene is the hsa-miR-4532 gene, a congener thereof, a transcript thereof, or a variant or a derivative thereof. None of the previously known reports show that change in the expression of the gene or the transcript thereof can serve as a marker for lung cancer.

The 109th target gene is the hsa-miR-5195-3p gene, a congener thereof, a transcript thereof, or a variant or a derivative thereof. None of the previously known reports show that change in the expression of the gene or the transcript thereof can serve as a marker for lung cancer.

The 110th target gene is the hsa-miR-3188 gene, a congener thereof, a transcript thereof, or a variant or a derivative thereof. None of the previously known reports show that change in the expression of the gene or the transcript thereof can serve as a marker for lung cancer.

The 111st target gene is the hsa-miR-6848-5p gene, a congener thereof, a transcript thereof, or a variant or a derivative thereof. None of the previously known reports show that change in the expression of the gene or the transcript thereof can serve as a marker for lung cancer.

The 112nd target gene is the hsa-miR-1233-5p gene, a congener thereof, a transcript thereof, or a variant or a derivative thereof. None of the previously known reports show that change in the expression of the gene or the transcript thereof can serve as a marker for lung cancer.

The 113rd target gene is the hsa-miR-6717-5p gene, a congener thereof, a transcript thereof, or a variant or a derivative thereof. None of the previously known reports show that change in the expression of the gene or the transcript thereof can serve as a marker for lung cancer.

The 114th target gene is the hsa-miR-3195 gene, a congener thereof, a transcript thereof, or a variant or a derivative thereof. None of the previously known reports show that change in the expression of the gene or the transcript thereof can serve as a marker for lung cancer.

The 115th target gene is the hsa-miR-6757-5p gene, a congener thereof, a transcript thereof, or a variant or a derivative thereof. None of the previously known reports show that change in the expression of the gene or the transcript thereof can serve as a marker for lung cancer.

The 116th target gene is the hsa-miR-8072 gene, a congener thereof, a transcript thereof, or a variant or a derivative thereof. None of the previously known reports show that change in the expression of the gene or the transcript thereof can serve as a marker for lung cancer.

The 117th target gene is the hsa-miR-4745-5p gene, a congener thereof, a transcript thereof, or a variant or a derivative thereof. None of the previously known reports show that change in the expression of the gene or the transcript thereof can serve as a marker for lung cancer.

The 118th target gene is the hsa-miR-6511a-5p gene, a congener thereof, a transcript thereof, or a variant or a derivative thereof. None of the previously known reports show that change in the expression of the gene or the transcript thereof can serve as a marker for lung cancer.

The 119th target gene is the hsa-miR-6776-5p gene, a congener thereof, a transcript thereof, or a variant or a derivative thereof. None of the previously known reports show that change in the expression of the gene or the transcript thereof can serve as a marker for lung cancer.

The 120th target gene is the hsa-miR-371a-5p gene, a congener thereof, a transcript thereof, or a variant or a derivative thereof. None of the previously known reports show that change in the expression of the gene or the transcript thereof can serve as a marker for lung cancer.

The 121st target gene is the hsa-miR-1227-5p gene, a congener thereof, a transcript thereof, or a variant or a derivative thereof. None of the previously known reports show that change in the expression of the gene or the transcript thereof can serve as a marker for lung cancer.

The 122nd target gene is the hsa-miR-7150 gene, a congener thereof, a transcript thereof, or a variant or a derivative thereof. None of the previously known reports show that change in the expression of the gene or the transcript thereof can serve as a marker for lung cancer.

The 123rd target gene is the hsa-miR-1915-3p gene, a congener thereof, a transcript thereof, or a variant or a derivative thereof. None of the previously known reports show that change in the expression of the gene or the transcript thereof can serve as a marker for lung cancer.

The 124th target gene is the hsa-miR-187-5p gene, a congener thereof, a transcript thereof, or a variant or a derivative thereof. None of the previously known reports show that change in the expression of the gene or the transcript thereof can serve as a marker for lung cancer.

The 125th target gene is the hsa-miR-614 gene, a congener thereof, a transcript thereof, or a variant or a derivative thereof. None of the previously known reports show that change in the expression of the gene or the transcript thereof can serve as a marker for lung cancer.

The 126th target gene is the hsa-miR-19b-3p gene, a congener thereof, a transcript thereof, or a variant or a derivative thereof. The previously known report shows that change in the expression of the gene or the transcript thereof can serve as a marker for lung cancer (Patent Literature 1).

The 127th target gene is the hsa-miR-1225-5p gene, a congener thereof, a transcript thereof, or a variant or a derivative thereof. None of the previously known reports show that change in the expression of the gene or the transcript thereof can serve as a marker for lung cancer.

The 128th target gene is the hsa-miR-451a gene, a congener thereof, a transcript thereof, or a variant or a derivative thereof. None of the previously known reports show that change in the expression of the gene or the transcript thereof can serve as a marker for lung cancer.

The 129th target gene is the hsa-miR-939-5p gene, a congener thereof, a transcript thereof, or a variant or a derivative thereof. None of the previously known reports show that change in the expression of the gene or the transcript thereof can serve as a marker for lung cancer.

The 130th target gene is the hsa-miR-223-3p gene, a congener thereof, a transcript thereof, or a variant or a derivative thereof. None of the previously known reports show that change in the expression of the gene or the transcript thereof can serve as a marker for lung cancer.

The 131st target gene is the hsa-miR-1228-5p gene, a congener thereof, a transcript thereof, or a variant or a derivative thereof. The previously known report shows that change in the expression of the gene or the transcript thereof can serve as a marker for lung cancer (Patent Literature 2).

The 132nd target gene is the hsa-miR-125a-3p gene, a congener thereof, a transcript thereof, or a variant or a derivative thereof. None of the previously known reports show that change in the expression of the gene or the transcript thereof can serve as a marker for lung cancer.

The 133rd target gene is the hsa-miR-92b-5p gene, a congener thereof, a transcript thereof, or a variant or a derivative thereof. None of the previously known reports show that change in the expression of the gene or the transcript thereof can serve as a marker for lung cancer.

The 134th target gene is the hsa-miR-22-3p gene, a congener thereof, a transcript thereof, or a variant or a derivative thereof. None of the previously known reports show that change in the expression of the gene or the transcript thereof can serve as a marker for lung cancer.

The 135th target gene is the hsa-miR-4271 gene, a congener thereof, a transcript thereof, or a variant or a derivative thereof. None of the previously known reports show that change in the expression of the gene or the transcript thereof can serve as a marker for lung cancer.

The 136th target gene is the hsa-miR-642b-3p gene, a congener thereof, a transcript thereof, or a variant or a derivative thereof. None of the previously known reports show that change in the expression of the gene or the transcript thereof can serve as a marker for lung cancer.

The 137th target gene is the hsa-miR-6075 gene, a congener thereof, a transcript thereof, or a variant or a derivative thereof. None of the previously known reports show that change in the expression of the gene or the transcript thereof can serve as a marker for lung cancer.

The 138th target gene is the hsa-miR-6125 gene, a congener thereof, a transcript thereof, or a variant or a derivative thereof. None of the previously known reports show that change in the expression of the gene or the transcript thereof can serve as a marker for lung cancer.

The 139th target gene is the hsa-miR-887-3p gene, a congener thereof, a transcript thereof, or a variant or a derivative thereof. None of the previously known reports show that change in the expression of the gene or the transcript thereof can serve as a marker for lung cancer.

The 140th target gene is the hsa-miR-6851-5p gene, a congener thereof, a transcript thereof, or a variant or a derivative thereof. None of the previously known reports show that change in the expression of the gene or the transcript thereof can serve as a marker for lung cancer.

The 141st target gene is the hsa-miR-6763-5p gene, a congener thereof, a transcript thereof, or a variant or a derivative thereof. None of the previously known reports show that change in the expression of the gene or the transcript thereof can serve as a marker for lung cancer.

The 142nd target gene is the hsa-miR-3928-3p gene, a congener thereof, a transcript thereof, or a variant or a derivative thereof. None of the previously known reports show that change in the expression of the gene or the transcript thereof can serve as a marker for lung cancer.

The 143rd target gene is the hsa-miR-4443 gene, a congener thereof, a transcript thereof, or a variant or a derivative thereof. None of the previously known reports show that change in the expression of the gene or the transcript thereof can serve as a marker for lung cancer.

The 144th target gene is the hsa-miR-3648 gene, a congener thereof, a transcript thereof, or a variant or a derivative thereof. None of the previously known reports show that change in the expression of the gene or the transcript thereof can serve as a marker for lung cancer.

The 145th target gene is the hsa-miR-149-3p gene, a congener thereof, a transcript thereof, or a variant or a derivative thereof. None of the previously known reports show that change in the expression of the gene or the transcript thereof can serve as a marker for lung cancer.

The 146th target gene is the hsa-miR-4689 gene, a congener thereof, a transcript thereof, or a variant or a derivative thereof. None of the previously known reports show that change in the expression of the gene or the transcript thereof can serve as a marker for lung cancer.

The 147th target gene is the hsa-miR-4763-3p gene, a congener thereof, a transcript thereof, or a variant or a derivative thereof. None of the previously known reports show that change in the expression of the gene or the transcript thereof can serve as a marker for lung cancer.

The 148th target gene is the hsa-miR-6729-5p gene, a congener thereof, a transcript thereof, or a variant or a derivative thereof. None of the previously known reports show that change in the expression of the gene or the transcript thereof can serve as a marker for lung cancer.

The 149th target gene is the hsa-miR-3196 gene, a congener thereof, a transcript thereof, or a variant or a derivative thereof. None of the previously known reports show that change in the expression of the gene or the transcript thereof can serve as a marker for lung cancer.

The 150th target gene is the hsa-miR-8069 gene, a congener thereof, a transcript thereof, or a variant or a derivative thereof. None of the previously known reports show that change in the expression of the gene or the transcript thereof can serve as a marker for lung cancer.

The 151st target gene is the hsa-miR-1268a gene, a congener thereof, a transcript thereof, or a variant or a derivative thereof. None of the previously known reports show that change in the expression of the gene or the transcript thereof can serve as a marker for lung cancer (Patent Literature 2).

The 152nd target gene is the hsa-miR-4739 gene, a congener thereof, a transcript thereof, or a variant or a derivative thereof. None of the previously known reports show that change in the expression of the gene or the transcript thereof can serve as a marker for lung cancer.

The 153rd target gene is the hsa-miR-1268b gene, a congener thereof, a transcript thereof, or a variant or a derivative thereof. None of the previously known reports show that change in the expression of the gene or the transcript thereof can serve as a marker for lung cancer.

The 154th target gene is the hsa-miR-5698 gene, a congener thereof, a transcript thereof, or a variant or a derivative thereof. None of the previously known reports show that change in the expression of the gene or the transcript thereof can serve as a marker for lung cancer.

The 155th target gene is the hsa-miR-6752-5p gene, a congener thereof, a transcript thereof, or a variant or a derivative thereof. None of the previously known reports show that change in the expression of the gene or the transcript thereof can serve as a marker for lung cancer.

The 156th target gene is the hsa-miR-4507 gene, a congener thereof, a transcript thereof, or a variant or a derivative thereof. None of the previously known reports show that change in the expression of the gene or the transcript thereof can serve as a marker for lung cancer.

The 157th target gene is the hsa-miR-564 gene, a congener thereof, a transcript thereof, or a variant or a derivative thereof. None of the previously known reports show that change in the expression of the gene or the transcript thereof can serve as a marker for lung cancer.

The 158th target gene is the hsa-miR-4497 gene, a congener thereof, a transcript thereof, or a variant or a derivative thereof. None of the previously known reports show that change in the expression of the gene or the transcript thereof can serve as a marker for lung cancer.

The 159th target gene is the hsa-miR-6877-5p gene, a congener thereof, a transcript thereof, or a variant or a derivative thereof. None of the previously known reports show that change in the expression of the gene or the transcript thereof can serve as a marker for lung cancer.

The 160th target gene is the hsa-miR-6087 gene, a congener thereof, a transcript thereof, or a variant or a derivative thereof. None of the previously known reports show that change in the expression of the gene or the transcript thereof can serve as a marker for lung cancer.

The 161st target gene is the hsa-miR-4731-5p gene, a congener thereof, a transcript thereof, or a variant or a derivative thereof. None of the previously known reports show that change in the expression of the gene or the transcript thereof can serve as a marker for lung cancer.

The 162nd target gene is the hsa-miR-615-5p gene, a congener thereof, a transcript thereof, or a variant or a derivative thereof. None of the previously known reports show that change in the expression of the gene or the transcript thereof can serve as a marker for lung cancer.

The 163rd target gene is the hsa-miR-760 gene, a congener thereof, a transcript thereof, or a variant or a derivative thereof. None of the previously known reports show that change in the expression of the gene or the transcript thereof can serve as a marker for lung cancer.

The 164th target gene is the hsa-miR-6891-5p gene, a congener thereof, a transcript thereof, or a variant or a derivative thereof. None of the previously known reports show that change in the expression of the gene or the transcript thereof can serve as a marker for lung cancer.

The 165th target gene is the hsa-miR-6887-5p gene, a congener thereof, a transcript thereof, or a variant or a derivative thereof. None of the previously known reports show that change in the expression of the gene or the transcript thereof can serve as a marker for lung cancer.

The 166th target gene is the hsa-miR-4525 gene, a congener thereof, a transcript thereof, or a variant or a derivative thereof. None of the previously known reports show that change in the expression of the gene or the transcript thereof can serve as a marker for lung cancer.

The 167th target gene is the hsa-miR-1914-3p gene, a congener thereof, a transcript thereof, or a variant or a derivative thereof. None of the previously known reports show that change in the expression of the gene or the transcript thereof can serve as a marker for lung cancer.

The 168th target gene is the hsa-miR-619-5p gene, a congener thereof, a transcript thereof, or a variant or a derivative thereof. None of the previously known reports show that change in the expression of the gene or the transcript thereof can serve as a marker for lung cancer.

The 169th target gene is the hsa-miR-5001-5p gene, a congener thereof, a transcript thereof, or a variant or a derivative thereof. None of the previously known reports show that change in the expression of the gene or the transcript thereof can serve as a marker for lung cancer.

The 170th target gene is the hsa-miR-6722-3p gene, a congener thereof, a transcript thereof, or a variant or a derivative thereof. None of the previously known reports show that change in the expression of the gene or the transcript thereof can serve as a marker for lung cancer.

The 171st target gene is the hsa-miR-3621 gene, a congener thereof, a transcript thereof, or a variant or a derivative thereof. None of the previously known reports show that change in the expression of the gene or the transcript thereof can serve as a marker for lung cancer.

The 172nd target gene is the hsa-miR-4298 gene, a congener thereof, a transcript thereof, or a variant or a derivative thereof. None of the previously known reports show that change in the expression of the gene or the transcript thereof can serve as a marker for lung cancer.

The 173rd target gene is the hsa-miR-675-5p gene, a congener thereof, a transcript thereof, or a variant or a derivative thereof. None of the previously known reports show that change in the expression of the gene or the transcript thereof can serve as a marker for lung cancer.

The 174th target gene is the hsa-miR-4655-5p gene, a congener thereof, a transcript thereof, or a variant or a derivative thereof. None of the previously known reports show that change in the expression of the gene or the transcript thereof can serve as a marker for lung cancer.

The 175th target gene is the hsa-miR-6073 gene, a congener thereof, a transcript thereof, or a variant or a derivative thereof. None of the previously known reports show that change in the expression of the gene or the transcript thereof can serve as a marker for lung cancer.

The 176th target gene is the hsa-miR-6845-5p gene, a congener thereof, a transcript thereof, or a variant or a derivative thereof. None of the previously known reports show that change in the expression of the gene or the transcript thereof can serve as a marker for lung cancer.

The 177th target gene is the hsa-miR-6769b-5p gene, a congener thereof, a transcript thereof, or a variant or a derivative thereof. None of the previously known reports show that change in the expression of the gene or the transcript thereof can serve as a marker for lung cancer.

The 178th target gene is the hsa-miR-4665-3p gene, a congener thereof, a transcript thereof, or a variant or a derivative thereof. None of the previously known reports show that change in the expression of the gene or the transcript thereof can serve as a marker for lung cancer.

The 179th target gene is the hsa-miR-1913 gene, a congener thereof, a transcript thereof, or a variant or a derivative thereof. None of the previously known reports show that change in the expression of the gene or the transcript thereof can serve as a marker for lung cancer.

The 180th target gene is the hsa-miR-1228-3p gene, a congener thereof, a transcript thereof, or a variant or a derivative thereof. None of the previously known reports show that change in the expression of the gene or the transcript thereof can serve as a marker for lung cancer.

The 181st target gene is the hsa-miR-940 gene, a congener thereof, a transcript thereof, or a variant or a derivative thereof. None of the previously known reports show that change in the expression of the gene or the transcript thereof can serve as a marker for lung cancer.

The 182nd target gene is the hsa-miR-296-3p gene, a congener thereof, a transcript thereof, or a variant or a derivative thereof. None of the previously known reports show that change in the expression of the gene or the transcript thereof can serve as a marker for lung cancer.

The 183rd target gene is the hsa-miR-4690-5p gene, a congener thereof, a transcript thereof, or a variant or a derivative thereof. None of the previously known reports show that change in the expression of the gene or the transcript thereof can serve as a marker for lung cancer.

The 184th target gene is the hsa-miR-548q gene, a congener thereof, a transcript thereof, or a variant or a derivative thereof. None of the previously known reports show that change in the expression of the gene or the transcript thereof can serve as a marker for lung cancer.

The 185th target gene is the hsa-miR-663a gene, a congener thereof, a transcript thereof, or a variant or a derivative thereof. None of the previously known reports show that change in the expression of the gene or the transcript thereof can serve as a marker for lung cancer.

The 186th target gene is the hsa-miR-1249 gene, a congener thereof, a transcript thereof, or a variant or a derivative thereof. None of the previously known reports show that change in the expression of the gene or the transcript thereof can serve as a marker for lung cancer.

The 187th target gene is the hsa-miR-1202 gene, a congener thereof, a transcript thereof, or a variant or a derivative thereof. None of the previously known reports show that change in the expression of the gene or the transcript thereof can serve as a marker for lung cancer.

The 188th target gene is the hsa-miR-7113-3p gene, a congener thereof, a transcript thereof, or a variant or a derivative thereof. None of the previously known reports show that change in the expression of the gene or the transcript thereof can serve as a marker for lung cancer.

The 189th target gene is the hsa-miR-1225-3p gene, a congener thereof, a transcript thereof, or a variant or a derivative thereof. None of the previously known reports show that change in the expression of the gene or the transcript thereof can serve as a marker for lung cancer.

The 190th target gene is the hsa-miR-4783-3p gene, a congener thereof, a transcript thereof, or a variant or a derivative thereof. None of the previously known reports show that change in the expression of the gene or the transcript thereof can serve as a marker for lung cancer.

The 191st target gene is the hsa-miR-4448 gene, a congener thereof, a transcript thereof, or a variant or a derivative thereof. None of the previously known reports show that change in the expression of the gene or the transcript thereof can serve as a marker for lung cancer.

The 192nd target gene is the hsa-miR-4534 gene, a congener thereof, a transcript thereof, or a variant or a derivative thereof. None of the previously known reports show that change in the expression of the gene or the transcript thereof can serve as a marker for lung cancer.

The 193rd target gene is the hsa-miR-1307-3p gene, a congener thereof, a transcript thereof, or a variant or a derivative thereof. The previously known report shows that change in the expression of the gene or the transcript thereof can serve as a marker for lung cancer (Patent Literature 3).

2. Nucleic Acid Probe or Primer for Detection of Lung Cancer

In the present invention, a nucleic acid capable of specifically binding to any of the target nucleic acids as the lung cancer markers described above can be used as a nucleic acid, for example, a nucleic acid probe or a primer, for the detection or diagnosis of lung cancer.

In the present invention, the nucleic acid probe or the primer that can be used for detecting lung cancer or for diagnosing lung cancer permits qualitative and/or quantitative measurement of the presence, expression level, or abundance of any of the target nucleic acids as the lung cancer markers described above, for example, human-derived hsa-miR-6768-5p, hsa-miR-6836-3p, hsa-miR-6782-5p, hsa-miR-3663-3p, hsa-miR-1908-3p, hsa-miR-6726-5p, hsa-miR-4258, hsa-miR-1343-3p, hsa-miR-4516, hsa-miR-6875-5p, hsa-miR-4651, hsa-miR-6825-5p, hsa-miR-6840-3p, hsa-miR-6780b-5p, hsa-miR-6749-5p, hsa-miR-8063, hsa-miR-6784-5p, hsa-miR-3679-5p, hsa-miR-3184-5p, hsa-miR-663b, hsa-miR-6880-5p, hsa-miR-1908-5p, hsa-miR-92a-2-5p, hsa-miR-7975, hsa-miR-7110-5p, hsa-miR-6842-5p, hsa-miR-6857-5p, hsa-miR-5572, hsa-miR-3197, hsa-miR-6131, hsa-miR-6889-5p, hsa-miR-4454, hsa-miR-1199-5p, hsa-miR-1247-3p, hsa-miR-6800-5p, hsa-miR-6872-3p, hsa-miR-4649-5p, hsa-miR-6791-5p, hsa-miR-4433b-3p, hsa-miR-3135b, hsa-miR-128-2-5p, hsa-miR-4675, hsa-miR-4472, hsa-miR-6785-5p, hsa-miR-6741-5p, hsa-miR-7977, hsa-miR-3665, hsa-miR-128-1-5p, hsa-miR-4286, hsa-miR-6765-3p, hsa-miR-4632-5p, hsa-miR-365a-5p, hsa-miR-6088, hsa-miR-6816-5p, hsa-miR-6885-5p, hsa-miR-711, hsa-miR-6765-5p, hsa-miR-3180, hsa-miR-4442, hsa-miR-4792, hsa-miR-6721-5p, hsa-miR-6798-5p, hsa-miR-3162-5p, hsa-miR-6126, hsa-miR-4758-5p, hsa-miR-2392, hsa-miR-486-3p, hsa-miR-6727-5p, hsa-miR-4728-5p, hsa-miR-6746-5p, hsa-miR-4270, hsa-miR-3940-5p, hsa-miR-4725-3p, hsa-miR-7108-5p, hsa-miR-3656, hsa-miR-6879-5p, hsa-miR-6738-5p, hsa-miR-1260a, hsa-miR-4446-3p, hsa-miR-3131, hsa-miR-4463, hsa-miR-3185, hsa-miR-6870-5p, hsa-miR-6779-5p, hsa-miR-1273g-3p, hsa-miR-8059, hsa-miR-4697-5p, hsa-miR-4674, hsa-miR-4433-3p, hsa-miR-4257, hsa-miR-1915-5p, hsa-miR-4417, hsa-miR-1343-5p, hsa-miR-6781-5p, hsa-miR-4695-5p, hsa-miR-1237-5p, hsa-miR-6775-5p, hsa-miR-7845-5p, hsa-miR-4746-3p, hsa-miR-7641, hsa-miR-7847-3p, hsa-miR-6806-5p, hsa-miR-4467, hsa-miR-4726-5p, hsa-miR-4648, hsa-miR-6089, hsa-miR-1260b, hsa-miR-4532, hsa-miR-5195-3p, hsa-miR-3188, hsa-miR-6848-5p, hsa-miR-1233-5p, hsa-miR-6717-5p, hsa-miR-3195, hsa-miR-6757-5p, hsa-miR-8072, hsa-miR-4745-5p, hsa-miR-6511a-5p, hsa-miR-6776-5p, hsa-miR-371a-5p, hsa-miR-1227-5p, hsa-miR-7150, hsa-miR-1915-3p, hsa-miR-187-5p, hsa-miR-614, hsa-miR-1225-5p, hsa-miR-451a, hsa-miR-939-5p, hsa-miR-223-3p, hsa-miR-125a-3p, hsa-miR-92b-5p, hsa-miR-22-3p, hsa-miR-6073, hsa-miR-6845-5p, hsa-miR-6769b-5p, hsa-miR-4665-3p, hsa-miR-1913, hsa-miR-1228-3p, hsa-miR-940, hsa-miR-296-3p, hsa-miR-4690-5p, hsa-miR-548q, hsa-miR-663a, hsa-miR-1249, hsa-miR-1202, hsa-miR-7113-3p, hsa-miR-1225-3p, hsa-miR-4783-3p, hsa-miR-4448, and hsa-miR-4534 or a combination thereof, congeners thereof, transcripts thereof, or variants or derivatives thereof, optionally in combination therewith, hsa-miR-19b-3p, hsa-miR-1228-5p, and hsa-miR-1307-3p or a combination thereof, congeners thereof, transcripts thereof, or variants or derivatives thereof, and, optionally in combination therewith, hsa-miR-4271, hsa-miR-642b-3p, hsa-miR-6075, hsa-miR-6125, hsa-miR-887-3p, hsa-miR-6851-5p, hsa-miR-6763-5p, hsa-miR-3928-3p, hsa-miR-4443, hsa-miR-3648, hsa-miR-149-3p, hsa-miR-4689, hsa-miR-4763-3p, hsa-miR-6729-5p, hsa-miR-3196, hsa-miR-8069, hsa-miR-1268a, hsa-miR-4739, hsa-miR-1268b, hsa-miR-5698, hsa-miR-6752-5p, hsa-miR-4507, hsa-miR-564, hsa-miR-4497, hsa-miR-6877-5p, hsa-miR-6087, hsa-miR-4731-5p, hsa-miR-615-5p, hsa-miR-760, hsa-miR-6891-5p, hsa-miR-6887-5p, hsa-miR-4525, hsa-miR-1914-3p, hsa-miR-619-5p, hsa-miR-5001-5p, hsa-miR-6722-3p, hsa-miR-3621, hsa-miR-4298, hsa-miR-675-5p and hsa-miR-4655-5p or a combination thereof, congeners thereof, transcripts thereof, or variants or derivatives thereof.

The expression level of each target nucleic acid described above is increased or decreased (hereinafter, referred to as "increased/decreased") according to the type of the target nucleic acid in a subject who has lung cancer as compared with a healthy subject. Hence, the nucleic acid of the present invention can be effectively used for measuring the expression level of the target nucleic acid in a body fluid derived from a subject (e.g., a human) who is suspected of having lung cancer and a body fluid derived from a healthy subject, and detecting lung cancer by the comparison thereof.

The nucleic acid probe or the primer that can be used in the present invention is a nucleic acid probe capable of specifically binding to a polynucleotide consisting of a nucleotide sequence represented by at least one of SEQ ID NOs: 1 to 125, 127 to 130, 132 to 134, and 561 to 578, or a primer for amplifying a polynucleotide consisting of a nucleotide sequence represented by at least one of SEQ ID NOs: 1 to 125, 127 to 130, 132 to 134, and 561 to 578.

The nucleic acid probe or the primer that can be further used in the present invention can comprise a nucleic acid probe capable of specifically binding to a polynucleotide consisting of a nucleotide sequence represented by at least one of SEQ ID NOs: 126, 131, and 579, or a primer for amplifying a polynucleotide consisting of a nucleotide sequence represented by at least one of SEQ ID NOs: 126, 131, and 579.

The nucleic acid probe or the primer that can be further used in the present invention can comprise a nucleic acid probe capable of specifically binding to a polynucleotide consisting of a nucleotide sequence represented by at least one of SEQ ID NOs: 135 to 174, or a primer for amplifying a polynucleotide consisting of a nucleotide sequence represented by at least one of SEQ ID NOs: 135 to 174.

Specifically, these nucleic acid probes or primers comprise a combination of one or more polynucleotides selected from a polynucleotide group comprising nucleotide sequences represented by any of SEQ ID NOs: 1 to 618, or nucleotide sequences derived from the nucleotide sequences by the replacement of u with t, and a complementary polynucleotide group thereof, a polynucleotide group respectively hybridizing under stringent conditions (mentioned later) to DNAs consisting of nucleotide sequences complementary to these nucleotide sequences, and a complementary polynucleotide group thereof, and a polynucleotide group comprising 15 or more, preferably 17 or more consecutive nucleotides in the nucleotide sequences of these polynucleotide groups. These polynucleotides can be used as nucleic acid probes and primers for detecting the lung cancer markers as target nucleic acids.

More specifically, examples of the nucleic acid probe or the primer that can be used in the present invention include one or more polynucleotide(s) selected from the group consisting of the following polynucleotides (a) to (e):
  (a) a polynucleotide consisting of a nucleotide sequence represented by any of SEQ ID NOs: 1 to 125, 127 to 130, 132 to 134, and 561 to 578 or a nucleotide sequence derived from the nucleotide sequence by the replacement of u with t, a variant thereof, a derivative thereof, or a fragment thereof comprising 15 or more consecutive nucleotides,
  (b) a polynucleotide comprising a nucleotide sequence represented by any of SEQ ID NOs: 1 to 125, 127 to 130, 132 to 134, and 561 to 578,
  (c) a polynucleotide consisting of a nucleotide sequence complementary to a nucleotide sequence represented by any of SEQ ID NOs: 1 to 125, 127 to 130, 132 to 134, and 561 to 578 or a nucleotide sequence derived from the nucleotide sequence by the replacement of u with t, a variant thereof, a derivative thereof, or a fragment thereof comprising 15 or more consecutive nucleotides,
  (d) a polynucleotide comprising a nucleotide sequence complementary to a nucleotide sequence represented by any of SEQ ID NOs: 1 to 125, 127 to 130, 132 to 134, and 561 to 578 or a nucleotide sequence derived from the nucleotide sequence by the replacement of u with t, and (e) a polynucleotide hybridizing under stringent conditions to any of the polynucleotides (a) to (d).

In addition to at least one or more polynucleotide(s) selected from the polynucleotides (a) to (e), the nucleic acid probe or the primer that can be further used in the present invention can comprise the polynucleotides selected from the group consisting of the following polynucleotides (f) to (j):
  (f) a polynucleotide consisting of a nucleotide sequence represented by any of SEQ ID NOs: 126, 131, and 579 or a nucleotide sequence derived from the nucleotide sequence by the replacement of u with t, a variant thereof, a derivative thereof, or a fragment thereof comprising 15 or more consecutive nucleotides,
  (g) a polynucleotide comprising a nucleotide sequence represented by any of SEQ ID NOs: 126, 131, and 579,
  (h) a polynucleotide consisting of a nucleotide sequence complementary to a nucleotide sequence represented by any of SEQ ID NOs: 126, 131, and 579 or a nucleotide sequence derived from the nucleotide sequence by the replacement of u with t, a variant thereof, a derivative thereof, or a fragment thereof comprising 15 or more consecutive nucleotides,
  (i) a polynucleotide comprising a nucleotide sequence complementary to a nucleotide sequence represented by any of SEQ ID NOs: 126, 131, and 579 or a nucleotide sequence derived from the nucleotide sequence by the replacement of u with t, and
  (j) a polynucleotide hybridizing under stringent conditions to any of the polynucleotides (f) to (i).

In addition to at least one or more polynucleotide(s) selected from the polynucleotides (a) to (j), the nucleic acid probe or the primer that can be further used in the present invention can comprise the polynucleotides selected from the group consisting of the following polynucleotides (k) to (o):
  (k) a polynucleotide consisting of a nucleotide sequence represented by any of SEQ ID NOs: 135 to 174 or a nucleotide sequence derived from the nucleotide sequence by the replacement of u with t, a variant thereof, a derivative thereof, or a fragment thereof comprising 15 or more consecutive nucleotides,
  (l) a polynucleotide comprising a nucleotide sequence represented by any of SEQ ID NOs: 135 to 174,
  (m) a polynucleotide consisting of a nucleotide sequence complementary to a nucleotide sequence represented by any of SEQ ID NOs: 135 to 174 or a nucleotide sequence derived from the nucleotide sequence by the replacement of u with t, a variant thereof, a derivative thereof, or a fragment thereof comprising 15 or more consecutive nucleotides,
  (n) a polynucleotide comprising a nucleotide sequence complementary to a nucleotide sequence represented by any of SEQ ID NOs: 135 to 174 or a nucleotide sequence derived from the nucleotide sequence by the replacement of u with t, and
  (o) a polynucleotide hybridizing under stringent conditions to any of the polynucleotides (k) to (n).

For these polynucleotides, the "fragment thereof comprising 15 or more consecutive nucleotides" can contain the number of nucleotides in the range from, for example, 15 consecutive nucleotides to less than the total number of nucleotides of the sequence, from 17 consecutive nucleotides to less than the total number of nucleotides of the sequence, or from 19 consecutive nucleotides to less than the total number of nucleotides of the sequence, in the nucleotide sequence of each polynucleotide, though the fragment is not limited thereto.

These polynucleotides or the fragments thereof used in the present invention may each be DNA or may each be RNA.

The polynucleotides that can be used in the present invention can each be prepared by use of a general technique such as a DNA recombination technique, PCR, or a method using an automatic DNA/RNA synthesizer.

The DNA recombination technique and the PCR can employ a technique described in, for example, Ausubel et al., Current Protocols in Molecular Biology, John Willey & Sons, US (1993); and Sambrook et al., Molecular Cloning—A Laboratory Manual, Cold Spring Harbor Laboratory Press, US (1989).

The human-derived hsa-miR-6768-5p, hsa-miR-6836-3p, hsa-miR-6782-5p, hsa-miR-3663-3p, hsa-miR-1908-3p, hsa-miR-6726-5p, hsa-miR-4258, hsa-miR-1343-3p, hsa-miR-4516, hsa-miR-6875-5p, hsa-miR-4651, hsa-miR-6825-5p, hsa-miR-6840-3p, hsa-miR-6780b-5p, hsa-miR-6749-5p, hsa-miR-8063, hsa-miR-6784-5p, hsa-miR-3679-5p, hsa-miR-3184-5p, hsa-miR-663b, hsa-miR-6880-5p, hsa-miR-1908-5p, hsa-miR-92a-2-5p, hsa-miR-7975, hsa-miR-7110-5p, hsa-miR-6842-5p, hsa-miR-6857-5p, hsa-miR-5572, hsa-miR-3197, hsa-miR-6131, hsa-miR-6889-5p, hsa-miR-4454, hsa-miR-1199-5p, hsa-miR-1247-3p, hsa-miR-6800-5p, hsa-miR-6872-3p, hsa-miR-4649-5p, hsa-miR-6791-5p, hsa-miR-4433b-3p, hsa-miR-3135b, hsa-miR-128-2-5p, hsa-miR-4675, hsa-miR-4472, hsa-miR-6785-5p, hsa-miR-6741-5p, hsa-miR-7977, hsa-miR-3665, hsa-miR-128-1-5p, hsa-miR-4286, hsa-miR-6765-3p, hsa-miR-4632-5p, hsa-miR-365a-5p, hsa-miR-6088, hsa-miR-6816-5p, hsa-miR-6885-5p, hsa-miR-711, hsa-miR-6765-5p, hsa-miR-3180, hsa-miR-4442, hsa-miR-4792, hsa-miR-6721-5p, hsa-miR-6798-5p, hsa-miR-3162-5p, hsa-miR-6126, hsa-miR-4758-5p, hsa-miR-2392, hsa-miR-486-3p, hsa-miR-6727-5p, hsa-miR-4728-5p, hsa-miR-6746-5p, hsa-miR-4270, hsa-miR-3940-5p, hsa-miR-4725-3p, hsa-miR-7108-5p, hsa-miR-3656, hsa-miR-6879-5p, hsa-miR-6738-5p, hsa-miR-1260a, hsa-miR-4446-3p, hsa-miR-3131, hsa-miR-4463, hsa-miR-3185, hsa-miR-6870-5p, hsa-miR-6779-5p, hsa-miR-1273g-3p, hsa-miR-8059, hsa-miR-4697-5p, hsa-miR-4674, hsa-miR-4433-3p, hsa-miR-4257, hsa-miR-1915-5p, hsa-miR-4417, hsa-miR-1343-5p, hsa-miR-6781-5p, hsa-miR-4695-5p, hsa-miR-1237-5p, hsa-miR-6775-5p, hsa-miR-7845-5p, hsa-miR-4746-3p, hsa-miR-7641, hsa-miR-7847-3p, hsa-miR-6806-5p, hsa-miR-4467, hsa-miR-4726-5p, hsa-miR-4648, hsa-miR-6089, hsa-miR-1260b, hsa-miR-4532, hsa-miR-5195-3p, hsa-miR-3188, hsa-miR-6848-5p, hsa-miR-1233-5p, hsa-miR-6717-5p, hsa-miR-3195, hsa-miR-6757-5p, hsa-miR-8072, hsa-miR-4745-5p, hsa-miR-6511a-5p, hsa-miR-6776-5p, hsa-miR-371a-5p, hsa-miR-1227-5p, hsa-miR-7150, hsa-miR-1915-3p, hsa-miR-187-5p, hsa-miR-614, hsa-miR-19b-3p, hsa-miR-1225-5p, hsa-miR-451a, hsa-miR-939-5p, hsa-miR-223-3p, hsa-miR-1228-5p, hsa-miR-125a-3p, hsa-miR-92b-5p, hsa-miR-22-3p, hsa-miR-6073, hsa-miR-6845-5p, hsa-miR-6769b-5p, hsa-miR-4665-3p, hsa-miR-1913, hsa-miR-1228-3p, hsa-miR-940, hsa-miR-296-3p, hsa-miR-4690-5p, hsa-miR-548q, hsa-miR-663a, hsa-miR-1249, hsa-miR-1202, hsa-miR-7113-3p, hsa-miR-1225-3p, hsa-miR-4783-3p, hsa-miR-4448 and hsa-miR-4534, hsa-miR-1307-3p, hsa-miR-4271, hsa-miR-642b-3p, hsa-miR-6075, hsa-miR-6125, hsa-miR-887-3p, hsa-miR-6851-5p, hsa-miR-6763-5p, hsa-miR-3928-3p, hsa-miR-4443, hsa-miR-3648, hsa-miR-149-3p, hsa-miR-4689, hsa-miR-4763-3p, hsa-miR-6729-5p, hsa-miR-3196, hsa-miR-8069, hsa-miR-1268a, hsa-miR-4739, hsa-miR-1268b, hsa-miR-5698, hsa-miR-6752-5p, hsa-miR-4507, hsa-miR-564, hsa-miR-4497, hsa-miR-6877-5p, hsa-miR-6087, hsa-miR-4731-5p, hsa-miR-615-5p, hsa-miR-760, hsa-miR-6891-5p, hsa-miR-6887-5p, hsa-miR-4525, hsa-miR-1914-3p, hsa-miR-619-5p, hsa-miR-5001-5p, hsa-miR-6722-3p, hsa-miR-3621, hsa-miR-4298, hsa-miR-675-5p and hsa-miR-4655-5p represented by SEQ ID NOs: 1 to 174, and 561 to 579 are known in the art, and their acquisition methods are also known as mentioned above. Therefore, each polynucleotide that can be used as a nucleic acid probe or a primer in the present invention can be prepared by cloning the gene.

Such a nucleic acid probe or a primer can be chemically synthesized using an automatic DNA synthesis apparatus. In general, a phosphoramidite method is used in this synthesis, and single-stranded DNA up to approximately 100 nucleotides can be automatically synthesized by this method. The automatic DNA synthesis apparatus is commercially available from, for example, Polygen GmbH, ABI, or Applied Biosystems, Inc.

Alternatively, the polynucleotide of the present invention can also be prepared by a cDNA cloning method. The cDNA cloning technique can employ, for example, microRNA Cloning Kit Wako.

In this context, the sequences of the nucleic acid probe and the primer for detecting the polynucleotide consisting of a nucleotide sequence represented by any of SEQ ID NOs: 1 to 174, and 561 to 579 do not exist as miRNAs or precursors thereof in vivo. For example, the nucleotide sequences represented by SEQ ID NO: 5 and SEQ ID NO: 22 are produced from the precursor represented by SEQ ID NO: 179. This precursor has a hairpin-like structure as shown in FIG. 1, and the nucleotide sequences represented by SEQ ID NO: 5 and SEQ ID NO: 22 have mismatch sequences with each other. Likewise, a nucleotide sequence completely complementary to the nucleotide sequence represented by SEQ ID NO: 5 or SEQ ID NO: 22 is not naturally produced in vivo. Therefore, the nucleic acid probe and the primer for detecting the nucleotide sequence represented by any of SEQ ID NOs: 1 to 174, and 561 to 579 each have an artificial nucleotide sequence that does not exist in vivo.

3. Kit or Device for Detection of Lung Cancer

The present invention also provides a kit or a device for the detection of lung cancer, comprising one or more polynucleotide(s) (which can include a variant, a fragment, and a derivative; hereinafter, also referred to as a polynucleotide for detection) that can be used as a nucleic acid probe or a primer in the present invention for measuring a target nucleic acid as a lung cancer marker.

The target nucleic acid as a lung cancer marker according to the present invention is preferably selected from the following group 1: hsa-miR-6768-5p, hsa-miR-6836-3p, hsa-miR-6782-5p, hsa-miR-3663-3p, hsa-miR-1908-3p, hsa-miR-6726-5p, hsa-miR-4258, hsa-miR-1343-3p, hsa-miR-4516, hsa-miR-6875-5p, hsa-miR-4651, hsa-miR-6825-5p, hsa-miR-6840-3p, hsa-miR-6780b-5p, hsa-miR-6749-5p, hsa-miR-8063, hsa-miR-6784-5p, hsa-miR-3679-5p, hsa-miR-3184-5p, hsa-miR-663b, hsa-miR-6880-5p, hsa-miR-1908-5p, hsa-miR-92a-2-5p, hsa-miR-7975, hsa-miR-7110-5p, hsa-miR-6842-5p, hsa-miR-6857-5p, hsa-miR-5572, hsa-miR-3197, hsa-miR-6131, hsa-miR-6889-5p, hsa-miR-4454, hsa-miR-1199-5p, hsa-miR-1247-3p, hsa-miR-6800-5p, hsa-miR-6872-3p, hsa-miR-4649-5p, hsa-miR-6791-5p, hsa-miR-4433b-3p, hsa-miR-3135b, hsa-miR-128-2-5p, hsa-miR-4675, hsa-miR-4472, hsa-miR-6785-5p, hsa-miR-6741-5p, hsa-miR-7977, hsa-miR-3665, hsa-miR-128-1-5p, hsa-miR-4286, hsa-miR-6765-3p, hsa-miR-4632-5p, hsa-miR-365a-5p, hsa-miR-6088, hsa-miR-6816-5p, hsa-miR-6885-5p, hsa-miR-711, hsa-miR-6765-5p, hsa-miR-3180, hsa-miR-4442, hsa-miR-4792, hsa-miR-6721-5p, hsa-miR-6798-5p, hsa-miR-3162-5p, hsa-miR- 6126, hsa-miR-4758-5p, hsa-miR-2392, hsa-miR-486-3p, hsa-miR-6727-5p, hsa-miR-4728-5p, hsa-miR-6746-5p, hsa-miR-4270, hsa-miR-3940-5p, hsa-miR-4725-3p, hsa-miR-7108-5p, hsa-miR-3656, hsa-miR-6879-5p, hsa-miR-6738-5p, hsa-miR-1260a, hsa-miR-4446-3p, hsa-miR-3131, hsa-miR-4463, hsa-miR-3185, hsa-miR-6870-5p, hsa-miR-6779-5p, hsa-miR-1273g-3p, hsa-miR-8059, hsa-miR-4697-5p, hsa-miR-4674, hsa-miR-4433-3p, hsa-miR-4257, hsa-miR-1915-5p, hsa-miR-4417, hsa-miR-1343-5p, hsa-miR-6781-5p, hsa-miR-4695-5p, hsa-miR-1237-5p, hsa-miR-6775-5p, hsa-miR-7845-5p, hsa-miR-4746-3p, hsa-miR-7641, hsa-miR-7847-3p, hsa-miR-6806-5p, hsa-miR-4467, hsa-miR-4726-5p, hsa-miR-4648, hsa-miR-6089, hsa-miR-1260b, hsa-miR-4532, hsa-miR-5195-3p, hsa-miR-3188, hsa-miR-6848-5p, hsa-miR-1233-5p, hsa-miR-6717-5p, hsa-miR-3195, hsa-miR-6757-5p, hsa-miR-8072, hsa-miR-4745-5p, hsa-miR-6511a-5p, hsa-miR-6776-5p, hsa-miR-371a-5p, hsa-miR-1227-5p, hsa-miR-7150, hsa-miR-1915-3p, hsa-miR-187-5p, hsa-miR-614, hsa-miR-1225-5p, hsa-miR-451a, hsa-miR-939-5p, hsa-miR-223-3p, hsa-miR-125a-3p, hsa-miR-92b-5p, hsa-miR-22-3p, hsa-miR-6073, hsa-miR-6845-5p, hsa-miR-6769b-5p, hsa-miR-4665-3p, hsa-miR-1913, hsa-miR-1228-3p, hsa-miR-940, hsa-miR-296-3p, hsa-miR-4690-5p, hsa-miR-548q, hsa-miR-663a, hsa-miR-1249, hsa-miR-1202, hsa-miR-7113-3p, hsa-miR-1225-3p, hsa-miR-4783-3p, hsa-miR-4448 and hsa-miR-4534.

An additional target nucleic acid that can be optionally used in the measurement is selected from the following group 2: hsa-miR-19b-3p, hsa-miR-1228-5p and hsa-miR-1307-3p.

An additional target nucleic acid that can be optionally further used in the measurement is selected from the following group 3: hsa-miR-4271, hsa-miR-642b-3p, hsa-miR-6075, hsa-miR-6125, hsa-miR-887-3p, hsa-miR-6851-5p, hsa-miR-6763-5p, hsa-miR-3928-3p, hsa-miR-4443, hsa-miR-3648, hsa-miR-149-3p, hsa-miR-4689, hsa-miR-4763-3p, hsa-miR-6729-5p, hsa-miR-3196, hsa-miR-8069, hsa-miR-1268a, hsa-miR-4739, hsa-miR-1268b, hsa-miR-5698, hsa-miR-6752-5p, hsa-miR-4507, hsa-miR-564, hsa-miR-4497, hsa-miR-6877-5p, hsa-miR-6087, hsa-miR-4731-5p, hsa-miR-615-5p, hsa-miR-760, hsa-miR-6891-5p, hsa-miR-6887-5p, hsa-miR-4525, hsa-miR-1914-3p, hsa-miR-619-5p, hsa-miR-5001-5p, hsa-miR-6722-3p, hsa-miR-3621, hsa-miR-4298, hsa-miR-675-5p and hsa-miR-4655-5p.

The kit or the device of the present invention comprises a nucleic acid capable of specifically binding to any of the target nucleic acids as the lung cancer markers described above, preferably one or more polynucleotide(s) selected from the nucleic acid probes or the primers described in the preceding Section 2, specifically, the polynucleotides described in the preceding paragraph 2, or variant(s) thereof.

Specifically, the kit or the device of the present invention can comprise at least one or more polynucleotide(s) comprising (or consisting of) a nucleotide sequence represented by any of SEQ ID NOs: 1 to 125, 127 to 130, 132 to 134, and 561 to 578 or a nucleotide sequence derived from the nucleotide sequence by the replacement of u with t, polynucleotide(s) comprising (or consisting of) a complementary sequence thereof, polynucleotide(s) hybridizing under stringent conditions to any of these polynucleotides, or variant(s) or fragment(s) comprising 15 or more consecutive nucleotides of any of these polynucleotide sequences.

The kit or the device of the present invention can further comprise one or more polynucleotide(s) comprising (or consisting of) a nucleotide sequence represented by any of SEQ ID NOs: 126 and 131 or a nucleotide sequence derived from the nucleotide sequence by the replacement of u with t, polynucleotide(s) comprising (or consisting of) a complementary sequence thereof, polynucleotide(s) hybridizing under stringent conditions to any of these polynucleotides, variant(s) or fragment(s) comprising 15 or more consecutive nucleotides of any of these polynucleotide sequences.

The kit or the device of the present invention can further comprise one or more polynucleotide(s) comprising (or consisting of) a nucleotide sequence represented by any of SEQ ID NOs: 135 to 174 or a nucleotide sequence derived from the nucleotide sequence by the replacement of u with t, polynucleotide(s) comprising (or consisting of) a complementary sequence thereof, polynucleotide(s) hybridizing under stringent conditions to any of these polynucleotides, variant(s) or fragment(s) comprising 15 or more consecutive nucleotides of any of these polynucleotide sequences.

The fragment that can be contained in the kit or the device of the present invention is, for example, one or more, preferably two or more polynucleotides selected from the group consisting of the following polynucleotides (1) to (3):

(1) a polynucleotide comprising 15 or more consecutive nucleotides in a nucleotide sequence derived from a nucleotide sequence represented by any of SEQ ID NOs: 1 to 125, 127 to 130, 132 to 134, and 561 to 578 by the replacement of u with t, or a complementary sequence thereof;

(2) a polynucleotide comprising 15 or more consecutive nucleotides in a nucleotide sequence derived from a nucleotide sequence represented by any of SEQ ID NOs: 126, 131 and 579 by the replacement of u with t, or a complementary sequence thereof; and (3) a polynucleotide comprising 15 or more consecutive nucleotides in a nucleotide sequence derived from a nucleotide sequence represented by any of SEQ ID NOs: 135 to 174 by the replacement of u with t, or a complementary sequence thereof.

In a preferred embodiment, the polynucleotide is a polynucleotide consisting of a nucleotide sequence represented by any of SEQ ID NOs: 1 to 125, 127 to 130, 132 to 134, and 561 to 578, or a nucleotide sequence derived from the nucleotide sequence by the replacement of u with t, a polynucleotide consisting of a complementary sequence thereof, a polynucleotide hybridizing under stringent conditions to any of these polynucleotides, or a variant thereof comprising 15 or more, preferably 17 or more, more preferably 19 or more consecutive nucleotides.

In a preferred embodiment, the polynucleotide is a polynucleotide consisting of a nucleotide sequence represented by any of SEQ ID NOs: 126, 134 and 579 or a nucleotide sequence derived from the nucleotide sequence by the replacement of u with t, a polynucleotide consisting of a complementary sequence thereof, a polynucleotide hybridizing under stringent conditions to any of these polynucleotides, or a variant thereof comprising 15 or more, preferably 17 or more, more preferably 19 or more consecutive nucleotides.

In a preferred embodiment, the polynucleotide is a polynucleotide consisting of a nucleotide sequence represented by any of SEQ ID NOs: 135 to 174 or a nucleotide sequence derived from the nucleotide sequence by the replacement of u with t, a polynucleotide consisting of a complementary sequence thereof, a polynucleotide hybridizing under stringent conditions to any of these polynucleotides, or a variant thereof comprising 15 or more, preferably 17 or more, more preferably 19 or more consecutive nucleotides.

In a preferred embodiment, the fragment can be a polynucleotide comprising 15 or more, preferably 17 or more, more preferably 19 or more consecutive nucleotides.

In the present invention, the size of the polynucleotide fragment is the number of bases in the range from, for example, 15 consecutive nucleotides to less than the total number of bases of the sequence, from 17 consecutive nucleotides to less than the total number of bases of the sequence, or from 19 consecutive nucleotides to less than the total number of nucleotides of the sequence, in the nucleotide sequence of each polynucleotide.

Specific examples of the aforementioned combination of the polynucleotides constituting the kit or the device of the present invention can include the polynucleotides as to combinations of SEQ ID NOs shown in Table 1 (SEQ ID NOs: 1 to 174, and 561 to 579 corresponding to the miRNA markers in Table 1). However, these are given merely for illustrative purposes, and various other possible combinations are included in the present invention.

The aforementioned combination constituting the kit or the device for discriminating a lung cancer patient from a healthy subject according to the present invention is desirably, for example, a combination of two or more of the aforementioned polynucleotides consisting of nucleotide sequences represented by SEQ ID NOs shown in Table 1. Usually, a combination of two of these polynucleotides can produce adequate performance.

The combination of two polynucleotides consisting of the nucleotide sequences or the complementary sequences thereof for specifically discriminating a lung cancer patient from a healthy subject is preferably a combination comprising at least one or more of newly found polynucleotides consisting of the nucleotide sequences represented by SEQ ID NOs: 1 to 125, 127 to 130, 132 to 174, and 561 to 578, among the combinations constituted by two of the polynucleotides consisting of the nucleotide sequences represented by SEQ ID NOs: 1 to 174, and 561 to 579.

The combination of polynucleotides with cancer type specificity capable of discriminating a lung cancer patient not only from a healthy subject but also from other cancer patients is preferably, for example, a combination of multiple polynucleotides comprising at least one polynucleotide selected from the group consisting of polynucleotides of SEQ ID NOs: 1, 2, 3, 4, 5, 7, 9, 10, 11, 19, 21, 26, 29, 31, 52, 53, 63, 65, 69, 72, 87, 90, 113, 124, 125, 126, 128, 130, 143, 148, 160, 162, 561, 562, 563, 564, 565, 566, 567, 568, 569, 570, 571, 572, 573, 574, 575, 576, 577, 578 and 579 (hereinafter, this group is referred to as "cancer type-specific polynucleotide group 1"), with any of the polynucleotides of the other SEQ ID NOs.

The combination of polynucleotides with cancer type specificity capable of discriminating a lung cancer patient not only from a healthy subject but also from other cancer patients is more preferably a combination of multiple polynucleotides selected from the cancer type-specific polynucleotide group 1.

The combination of polynucleotides with cancer type specificity capable of discriminating a lung cancer patient not only from a healthy subject but also from other cancer patients is more preferably a combination comprising at least one or more polynucleotide(s) selected from the group consisting of polynucleotides of SEQ ID NOs: 1, 2, 3, 10, 63, 113, 124, 125, 126, 128, 130, 143, 160, 561, 568, 573 and 578 (hereinafter, this group is referred to as "cancer type-specific polynucleotide group 2") included in the cancer type-specific polynucleotide group 1, among the combinations of multiple polynucleotides selected from the cancer type-specific polynucleotide group 1.

The number of the polynucleotides with cancer type specificity in the aforementioned combination can be 1, 2, 3, 4, 5, 6, 7, 8, 9, 10 or more for the combination and is more preferably 4 or more for the combination. Usually, the combination of 4 of these polynucleotides can produce adequate performance.

Non-limiting examples of the combination of the polynucleotide consisting of the nucleotide sequence represented by SEQ ID NO: 1 or a complementary sequence thereof with polynucleotides consisting of nucleotide sequences represented by SEQ ID NOs of five polynucleotides selected from the cancer type-specific polynucleotide group 1 or complementary sequences thereof will be listed below.

(1) a combination of SEQ ID NOs: 1, 53, 113, and 125 (markers: hsa-miR-6768-5p, hsa-miR-6088, hsa-miR-6717-5p, and hsa-miR-614);

(2) a combination of SEQ ID NOs: 1, 10, 63, and 113 (markers: hsa-miR-6768-5p, hsa-miR-6875-5p, hsa-miR-3162-5p, and hsa-miR-6717-5p);

(3) a combination of SEQ ID NOs: 1, 19, 113, and 143 (markers: hsa-miR-6768-5p, hsa-miR-3184-5p, hsa-miR-6717-5p, and hsa-miR-4443);

(4) a combination of SEQ ID NOs: 1, 10, 113, and 126 (markers: hsa-miR-6768-5p, hsa-miR-6875-5p, hsa-miR-6717-5p, and hsa-miR-19b-3p); and (5) a combination of SEQ ID NOs: 1, 2, 10, and 113 (markers: hsa-miR-6768-5p, hsa-miR-6836-3p, hsa-miR-6875-5p, and hsa-miR-6717-5p).

Non-limiting examples of the combination of the polynucleotide consisting of the nucleotide sequence represented by SEQ ID NO: 2 or a complementary sequence thereof with polynucleotides consisting of nucleotide sequences represented by SEQ ID NOs of five polynucleotides selected from the cancer type-specific polynucleotide group 1 or complementary sequences thereof will be further listed below.

(1) a combination of SEQ ID NOs: 2, 19, 53, and 113 (markers: hsa-miR-6836-3p, hsa-miR-3184-5p, hsa-miR-6088, and hsa-miR-6717-5p);

(2) a combination of SEQ ID NOs: 2, 72, 113, and 125 (markers: hsa-miR-6836-3p, hsa-miR-3940-5p, hsa-miR-6717-5p, and hsa-miR-614);

(3) a combination of SEQ ID NOs: 2, 19, 72, and 113 (markers: hsa-miR-6836-3p, hsa-miR-3184-5p, hsa-miR-3940-5p, and hsa-miR-6717-5p);

(4) a combination of SEQ ID NOs: 2, 19, 113, and 579 (markers: hsa-miR-6836-3p, hsa-miR-3184-5p, hsa-miR-6717-5p, and hsa-miR-1307-3p); and (5) a combination of SEQ ID NOs: 1, 2, 19, and 113 (markers: hsa-miR-6768-5p, hsa-miR-6836-3p, hsa-miR-3184-5p, and hsa-miR-6717-5p).

Non-limiting examples of the combination of the polynucleotide consisting of the nucleotide sequence represented by SEQ ID NO: 3 or a complementary sequence thereof with polynucleotides consisting of nucleotide sequences represented by SEQ ID NOs of five polynucleotides selected from the cancer type-specific polynucleotide group 1 or complementary sequences thereof will be further listed below.

(1) a combination of SEQ ID NOs: 3, 125, 128, and 568 (markers: hsa-miR-6782-5p, hsa-miR-614, hsa-miR-451a, and hsa-miR-296-3p);

(2) a combination of SEQ ID NOs: 1, 3, 10, and 113 (markers: hsa-miR-6768-5p, hsa-miR-6782-5p, hsa-miR-6875-5p, and hsa-miR-6717-5p);

(3) a combination of SEQ ID NOs: 3, 113, 125, and 126 (markers: hsa-miR-6782-5p, hsa-miR-6717-5p, hsa-miR-614, and hsa-miR-19b-3p);
(4) a combination of SEQ ID NOs: 1, 3, 126, and 573 (markers: hsa-miR-6768-5p, hsa-miR-6782-5p, hsa-miR-19b-3p, and hsa-miR-1202); and
(5) a combination of SEQ ID NOs: 3, 126, 130, and 561 (markers: hsa-miR-6782-5p, hsa-miR-19b-3p, hsa-miR-223-3p, and hsa-miR-6073).

Non-limiting examples of the combination of the polynucleotide consisting of the nucleotide sequence represented by SEQ ID NO: 10 or a complementary sequence thereof with polynucleotides consisting of nucleotide sequences represented by SEQ ID NOs of five polynucleotides selected from the cancer type-specific polynucleotide group 1 or complementary sequences thereof will be further listed below.

(1) a combination of SEQ ID NOs: 1, 10, 113, and 143 (markers: hsa-miR-6768-5p, hsa-miR-6875-5p, hsa-miR-6717-5p, and hsa-miR-4443);
(2) a combination of SEQ ID NOs: 1, 10, 113, and 569 (markers: hsa-miR-6768-5p, hsa-miR-6875-5p, hsa-miR-6717-5p, and hsa-miR-4690-5p);
(3) a combination of SEQ ID NOs: 1, 10, 113, and 562 (markers: hsa-miR-6768-5p, hsa-miR-6875-5p, hsa-miR-6717-5p, and hsa-miR-6845-5p);
(4) a combination of SEQ ID NOs: 1, 10, 113, and 578 (markers: hsa-miR-6768-5p, hsa-miR-6875-5p, hsa-miR-6717-5p, hsa-miR-4534); and
(5) a combination of SEQ ID NOs: 1, 7, 10, and 113 (markers: hsa-miR-6768-5p, hsa-miR-4258, hsa-miR-6875-5p, and hsa-miR-6717-5p).

Non-limiting examples of the combination of the polynucleotide consisting of the nucleotide sequence represented by SEQ ID NO: 63 or a complementary sequence thereof with polynucleotides consisting of nucleotide sequences represented by SEQ ID NOs of five polynucleotides selected from the cancer type-specific polynucleotide group 1 or complementary sequences thereof will be further listed below.

(1) a combination of SEQ ID NOs: 1, 63, 567, and 578 (markers: hsa-miR-6768-5p, hsa-miR-3162-5p, hsa-miR-940, and hsa-miR-4534);
(2) a combination of SEQ ID NOs: 1, 53, 63, and 578 (markers: hsa-miR-6768-5p, hsa-miR-6088, hsa-miR-3162-5p, and hsa-miR-4534);
(3) a combination of SEQ ID NOs: 1, 63, 162, and 573 (markers: hsa-miR-6768-5p, hsa-miR-3162-5p, hsa-miR-615-5p, and hsa-miR-1202);
(4) a combination of SEQ ID NOs: 1, 63, 162, and 578 (markers: hsa-miR-6768-5p, hsa-miR-3162-5p, hsa-miR-615-5p, and hsa-miR-4534); and
(5) a combination of SEQ ID NOs: 1, 63, 576, and 578 (markers: hsa-miR-6768-5p, hsa-miR-3162-5p, hsa-miR-4783-3p, and hsa-miR-4534).

Non-limiting examples of the combination of the polynucleotide consisting of the nucleotide sequence represented by SEQ ID NO: 113 or a complementary sequence thereof with polynucleotides consisting of nucleotide sequences represented by SEQ ID NOs of five polynucleotides selected from the cancer type-specific polynucleotide group 1 or complementary sequences thereof will be further listed below.

(1) a combination of SEQ ID NOs: 1, 10, 113, and 567 (markers: hsa-miR-6768-5p, hsa-miR-6875-5p, hsa-miR-6717-5p, and hsa-miR-940);
(2) a combination of SEQ ID NOs: 1, 53, 63, and 113 (markers: hsa-miR-6768-5p, hsa-miR-6088, hsa-miR-3162-5p, and hsa-miR-6717-5p);
(3) a combination of SEQ ID NOs: 1, 53, 113, and 143 (markers: hsa-miR-6768-5p, hsa-miR-6088, hsa-miR-6717-5p, and hsa-miR-4443);
(4) a combination of SEQ ID NOs: 2, 19, 113, and 125 (markers: hsa-miR-6836-3p, hsa-miR-3184-5p, hsa-miR-6717-5p, and hsa-miR-614); and
(5) a combination of SEQ ID NOs: 2, 10, 113, and 130 (markers: hsa-miR-6836-3p, hsa-miR-6875-5p, hsa-miR-6717-5p, and hsa-miR-223-3p).

Non-limiting examples of the combination of the polynucleotide consisting of the nucleotide sequence represented by SEQ ID NO: 124 or a complementary sequence thereof with polynucleotides consisting of nucleotide sequences represented by SEQ ID NOs of five polynucleotides selected from the cancer type-specific polynucleotide group 1 or complementary sequences thereof will be further listed below.

(1) a combination of SEQ ID NOs: 113, 124, 125, and 126 (markers: hsa-miR-6717-5p, hsa-miR-187-5p, hsa-miR-614, and hsa-miR-19b-3p);
(2) a combination of SEQ ID NOs: 124, 125, 128, and 568 (markers: hsa-miR-187-5p, hsa-miR-614, hsa-miR-451a, and hsa-miR-296-3p);
(3) a combination of SEQ ID NOs: 113, 124, 125, and 162 (markers: hsa-miR-6717-5p, hsa-miR-187-5p, hsa-miR-614, and hsa-miR-615-5p);
(4) a combination of SEQ ID NOs: 52, 124, 126, and 561 (markers: hsa-miR-365a-5p, hsa-miR-187-5p, hsa-miR-19b-3p, and hsa-miR-6073); and
(5) a combination of SEQ ID NOs: 19, 113, 124, and 126 (markers: hsa-miR-3184-5p, hsa-miR-6717-5p, hsa-miR-187-5p, and hsa-miR-19b-3p).

Non-limiting examples of the combination of the polynucleotide consisting of the nucleotide sequence represented by SEQ ID NO: 125 or a complementary sequence thereof with polynucleotides consisting of nucleotide sequences represented by SEQ ID NOs of five polynucleotides selected from the cancer type-specific polynucleotide group 1 or complementary sequences thereof will be further listed below.

(1) a combination of SEQ ID NOs: 1, 113, 125, and 160 (markers: hsa-miR-6768-5p, hsa-miR-6717-5p, hsa-miR-614, and hsa-miR-6087);
(2) a combination of SEQ ID NOs: 31, 113, 125, and 568 (markers: hsa-miR-6889-5p, hsa-miR-6717-5p, hsa-miR-614, and hsa-miR-296-3p);
(3) a combination of SEQ ID NOs: 2, 53, 113, and 125 (markers: hsa-miR-6836-3p, hsa-miR-6088, hsa-miR-6717-5p, and hsa-miR-614);
(4) a combination of SEQ ID NOs: 1, 10, 113, and 125 (markers: hsa-miR-6768-5p, hsa-miR-6875-5p, hsa-miR-6717-5p, and hsa-miR-614); and
(5) a combination of SEQ ID NOs: 1, 113, 125, and 143 (markers: hsa-miR-6768-5p, hsa-miR-6717-5p, hsa-miR-614, and hsa-miR-4443).

Non-limiting examples of the combination of the polynucleotide consisting of the nucleotide sequence represented by SEQ ID NO: 126 or a complementary sequence thereof with polynucleotides consisting of nucleotide sequences represented by SEQ ID NOs of five polynucleotides selected from the cancer type-specific polynucleotide group 1 or complementary sequences thereof will be further listed below.

(1) a combination of SEQ ID NOs: 1, 126, 561, and 573 (markers: hsa-miR-6768-5p, hsa-miR-19b-3p, hsa-miR-6073, and hsa-miR-1202);

(2) a combination of SEQ ID NOs: 113, 125, 126, and 568 (markers: hsa-miR-6717-5p, hsa-miR-614, hsa-miR-19b-3p, and hsa-miR-296-3p);

(3) a combination of SEQ ID NOs: 113, 125, 126, and 561 (markers: hsa-miR-6717-5p, hsa-miR-614, hsa-miR-19b-3p, and hsa-miR-6073);

(4) a combination of SEQ ID NOs: 1, 113, 125, and 126 (markers: hsa-miR-6768-5p, hsa-miR-6717-5p, hsa-miR-614, and hsa-miR-19b-3p); and (5) a combination of SEQ ID NOs: 1, 52, 126, and 561 (markers: hsa-miR-6768-5p, hsa-miR-365a-5p, hsa-miR-19b-3p, and hsa-miR-6073).

Non-limiting examples of the combination of the polynucleotide consisting of the nucleotide sequence represented by SEQ ID NO: 128 or a complementary sequence thereof with polynucleotides consisting of nucleotide sequences represented by SEQ ID NOs of five polynucleotides selected from the cancer type-specific polynucleotide group 1 or complementary sequences thereof will be further listed below.

(1) a combination of SEQ ID NOs: 26, 113, 125, and 128 (markers: hsa-miR-6842-5p, hsa-miR-6717-5p, hsa-miR-614, and hsa-miR-451a);

(2) a combination of SEQ ID NOs: 1, 113, 125, and 128 (markers: hsa-miR-6768-5p, hsa-miR-6717-5p, hsa-miR-614, and hsa-miR-451a);

(3) a combination of SEQ ID NOs: 1, 10, 113, and 128 (markers: hsa-miR-6768-5p, hsa-miR-6875-5p, hsa-miR-6717-5p, and hsa-miR-451a);

(4) a combination of SEQ ID NOs: 31, 113, 125, and 128 (markers: hsa-miR-6889-5p, hsa-miR-6717-5p, hsa-miR-614, and hsa-miR-451a); and (5) a combination of SEQ ID NOs: 2, 19, 113, and 128 (markers: hsa-miR-6836-3p, hsa-miR-3184-5p, hsa-miR-6717-5p, and hsa-miR-451a).

Non-limiting examples of the combination of the polynucleotide consisting of the nucleotide sequence represented by SEQ ID NO: 130 or a complementary sequence thereof with polynucleotides consisting of nucleotide sequences represented by SEQ ID NOs of five polynucleotides selected from the cancer type-specific polynucleotide group 1 or complementary sequences thereof will be further listed below.

(1) a combination of SEQ ID NOs: 1, 3, 130, and 143 (markers: hsa-miR-6768-5p, hsa-miR-6782-5p, hsa-miR-223-3p, and hsa-miR-4443);

(2) a combination of SEQ ID NOs: 1, 10, 113, and 130 (markers: hsa-miR-6768-5p, hsa-miR-6875-5p, hsa-miR-6717-5p, and hsa-miR-223-3p);

(3) a combination of SEQ ID NOs: 1, 63, 130, and 578 (markers: hsa-miR-6768-5p, hsa-miR-3162-5p, hsa-miR-223-3p, and hsa-miR-4534);

(4) a combination of SEQ ID NOs: 124, 125, 130, and 568 (markers: hsa-miR-187-5p, hsa-miR-614, hsa-miR-223-3p, and hsa-miR-296-3p); and (5) a combination of SEQ ID NOs: 2, 19, 113, and 130 (markers: hsa-miR-6836-3p, hsa-miR-3184-5p, hsa-miR-6717-5p, and hsa-miR-223-3p).

Non-limiting examples of the combination of the polynucleotide consisting of the nucleotide sequence represented by SEQ ID NO: 143 or a complementary sequence thereof with polynucleotides consisting of nucleotide sequences represented by SEQ ID NOs of five polynucleotides selected from the cancer type-specific polynucleotide group 1 or complementary sequences thereof will be further listed below.

(1) a combination of SEQ ID NOs: 1, 3, 126, and 143 (markers: hsa-miR-6768-5p, hsa-miR-6782-5p, hsa-miR-19b-3p, and hsa-miR-4443);

(2) a combination of SEQ ID NOs: 1, 63, 130, and 143 (markers: hsa-miR-6768-5p, hsa-miR-3162-5p, hsa-miR-223-3p, and hsa-miR-4443);

(3) a combination of SEQ ID NOs: 1, 10, 52, and 143 (markers: hsa-miR-6768-5p, hsa-miR-6875-5p, hsa-miR-365a-5p, and hsa-miR-4443);

(4) a combination of SEQ ID NOs: 2, 19, 113, and 143 (markers: hsa-miR-6836-3p, hsa-miR-3184-5p, hsa-miR-6717-5p, and hsa-miR-4443); and (5) a combination of SEQ ID NOs: 63, 124, 130, and 143 (markers: hsa-miR-3162-5p, hsa-miR-187-5p, hsa-miR-223-3p, and hsa-miR-4443).

Non-limiting examples of the combination of the polynucleotide consisting of the nucleotide sequence represented by SEQ ID NO: 160 or a complementary sequence thereof with polynucleotides consisting of nucleotide sequences represented by SEQ ID NOs of five polynucleotides selected from the cancer type-specific polynucleotide group 1 or complementary sequences thereof will be further listed below.

(1) a combination of SEQ ID NOs: 1, 10, 113, and 160 (markers: hsa-miR-6768-5p, hsa-miR-6875-5p, hsa-miR-6717-5p, and hsa-miR-6087);

(2) a combination of SEQ ID NOs: 7, 113, 125, and 160 (markers: hsa-miR-4258, hsa-miR-6717-5p, hsa-miR-614, and hsa-miR-6087);

(3) a combination of SEQ ID NOs: 1, 113, 160, and 567 (markers: hsa-miR-6768-5p, hsa-miR-6717-5p, hsa-miR-6087, and hsa-miR-940);

(4) a combination of SEQ ID NOs: 1, 113, 160, and 578 (markers: hsa-miR-6768-5p, hsa-miR-6717-5p, hsa-miR-6087, and hsa-miR-4534); and (5) a combination of SEQ ID NOs: 2, 19, 113, and 160 (markers: hsa-miR-6836-3p, hsa-miR-3184-5p, hsa-miR-6717-5p, and hsa-miR-6087).

Non-limiting examples of the combination of the polynucleotide consisting of the nucleotide sequence represented by SEQ ID NO: 561 or a complementary sequence thereof with polynucleotides consisting of nucleotide sequences represented by SEQ ID NOs of five polynucleotides selected from the cancer type-specific polynucleotide group 1 or complementary sequences thereof will be further listed below.

(1) a combination of SEQ ID NOs: 113, 125, 130, and 561 (markers: hsa-miR-6717-5p, hsa-miR-614, hsa-miR-223-3p, and hsa-miR-6073);

(2) a combination of SEQ ID NOs: 7, 126, 143, and 561 (markers: hsa-miR-4258, hsa-miR-19b-3p, hsa-miR-4443, and hsa-miR-6073);

(3) a combination of SEQ ID NOs: 1, 113, and 126, 561 (markers: hsa-miR-6768-5p, hsa-miR-6717-5p, hsa-miR-19b-3p, and hsa-miR-6073);

(4) a combination of SEQ ID NOs: 1, 126, 561, and 568 (markers: hsa-miR-6768-5p, hsa-miR-19b-3p, hsa-miR-6073, and hsa-miR-296-3p); and (5) a combination of SEQ ID NOs: 7, 113, 126, and 561 (markers: hsa-miR-4258, hsa-miR-6717-5p, hsa-miR-19b-3p, and hsa-miR-6073).

Non-limiting examples of the combination of the polynucleotide consisting of the nucleotide sequence represented by SEQ ID NO: 568 or a complementary sequence thereof with polynucleotides consisting of nucleotide sequences represented by SEQ ID NOs of five polynucleotides selected from the cancer type-specific polynucleotide group 1 or complementary sequences thereof will be further listed below.

(1) a combination of SEQ ID NOs: 7, 125, 126, and 568 (markers: hsa-miR-4258, hsa-miR-614, hsa-miR-19b-3p, and hsa-miR-296-3p);
(2) a combination of SEQ ID NOs: 124, 125, 126, and 568 (markers: hsa-miR-187-5p, hsa-miR-614, hsa-miR-19b-3p, and hsa-miR-296-3p);
(3) a combination of SEQ ID NOs: 7, 113, 125, and 568 (markers: hsa-miR-4258, hsa-miR-6717-5p, hsa-miR-614, and hsa-miR-296-3p);
(4) a combination of SEQ ID NOs: 1, 113, 125, and 568 (markers: hsa-miR-6768-5p, hsa-miR-6717-5p, hsa-miR-614, and hsa-miR-296-3p); and
(5) a combination of SEQ ID NOs: 113, 125, 128, and 568 (markers: hsa-miR-6717-5p, hsa-miR-614, hsa-miR-451a, and hsa-miR-296-3p).

Non-limiting examples of the combination of the polynucleotide consisting of the nucleotide sequence represented by SEQ ID NO: 573 or a complementary sequence thereof with polynucleotides consisting of nucleotide sequences represented by SEQ ID NOs of five polynucleotides selected from the cancer type-specific polynucleotide group 1 or complementary sequences thereof will be further listed below.

(1) a combination of SEQ ID NOs: 113, 125, 126, and 573 (markers: hsa-miR-6717-5p, hsa-miR-614, hsa-miR-19b-3p, and hsa-miR-1202);
(2) a combination of SEQ ID NOs: 1, 113, 125, and 573 (markers: hsa-miR-6768-5p, hsa-miR-6717-5p, hsa-miR-614, and hsa-miR-1202);
(3) a combination of SEQ ID NOs: 1, 53, 113, and 573 (markers: hsa-miR-6768-5p, hsa-miR-6088, hsa-miR-6717-5p, and hsa-miR-1202);
(4) a combination of SEQ ID NOs: 1, 124, 126, and 573 (markers: hsa-miR-6768-5p, hsa-miR-187-5p, hsa-miR-19b-3p, and hsa-miR-1202); and
(5) a combination of SEQ ID NOs: 1, 63, 130, and 573 (markers: hsa-miR-6768-5p, hsa-miR-3162-5p, hsa-miR-223-3p, and hsa-miR-1202).

Non-limiting examples of the combination of the polynucleotide consisting of the nucleotide sequence represented by SEQ ID NO: 578 or a complementary sequence thereof with polynucleotides consisting of nucleotide sequences represented by SEQ ID NOs of five polynucleotides selected from the cancer type-specific polynucleotide group 1 or complementary sequences thereof will be further listed below.

(1) a combination of SEQ ID NOs: 1, 126, 567, and 578 (markers: hsa-miR-6768-5p, hsa-miR-19b-3p, hsa-miR-940, and hsa-miR-4534);
(2) a combination of SEQ ID NOs: 1, 19, 113, and 578 (markers: hsa-miR-6768-5p, hsa-miR-3184-5p, hsa-miR-6717-5p, and hsa-miR-4534);
(3) a combination of SEQ ID NOs: 31, 126, 561, and 578 (markers: hsa-miR-6889-5p, hsa-miR-19b-3p, hsa-miR-6073, and hsa-miR-4534);
(4) a combination of SEQ ID NOs: 1, 126, 160, and 578 (markers: hsa-miR-6768-5p, hsa-miR-19b-3p, hsa-miR-6087, and hsa-miR-4534); and
(5) a combination of SEQ ID NOs: 1, 113, 125, 578 (markers: hsa-miR-6768-5p, hsa-miR-6717-5p, hsa-miR-614, and hsa-miR-4534).

The kit or the device of the present invention can also contain a polynucleotide that is already known or that will be found in the future, to enable detection of lung cancer, in addition to the polynucleotide(s) (which can include the variant(s), the fragment(s), and the derivative(s)) according to the present invention described above.

The kit of the present invention can also contain an antibody for measuring a marker for lung cancer examination known in the art, such as CEA, or CYFRA21-1, in addition to the polynucleotide(s) according to the present invention described above.

These polynucleotides contained in the kit of the present invention can be packaged in different containers either individually or in any combination.

The kit of the present invention can contain a kit for extracting a nucleic acid (e.g., total RNA) from body fluids, cells, or tissues, a fluorescent material for labeling, an enzyme and a medium for nucleic acid amplification, an instruction manual, etc.

The device of the present invention is a device for cancer marker measurement in which nucleic acids such as the polynucleotides according to the present invention described above are bonded or attached to, for example, a solid phase. Examples of the material for the solid phase include plastics, paper, glass, and silicon. The material for the solid phase is preferably a plastic from the viewpoint of easy processability. The solid phase has any shape and is, for example, square, round, reed-shaped, or film-shaped. The device of the present invention includes, for example, a device for measurement by a hybridization technique. Specific examples thereof include blotting devices and nucleic acid arrays (e.g., microarrays, DNA chips, and RNA chips).

The nucleic acid array technique is a technique which involves bonding or attaching the nucleic acids one by one by use of a method [e.g., a method of spotting the nucleic acids using a high-density dispenser called spotter or arrayer onto the surface of the solid phase surface-treated, if necessary, by coating with L-lysine or the introduction of a functional group such as an amino group or a carboxyl group, a method of spraying the nucleic acids onto the solid phase using an inkjet which injects very small liquid droplets by a piezoelectric element or the like from a nozzle, or a method of sequentially synthesizing nucleotides on the solid phase] to prepare an array such as a chip and measuring a target nucleic acid through the use of hybridization using this array.

The kit or the device of the present invention comprises nucleic acids capable of specifically binding to the polynucleotides of at least one or more, preferably at least two or more, more preferably at least three or more, most preferably at least five or more to all of the lung cancer marker miRNAs, respectively, of the group 1 described above. The kit or the device of the present invention can optionally further comprise nucleic acids capable of specifically binding to the polynucleotides of at least one or more, preferably at least two or more, more preferably at least three or more, most preferably at least five or more to all of the lung cancer marker miRNAs, respectively, of the group 2 described above. The kit or the device of the present invention can optionally further comprise nucleic acids capable of specifically binding to the polynucleotides of at least one or more, preferably at least two or more, more preferably at least three or more, most preferably at least five or more to all of the lung cancer marker miRNAs, respectively, of the group 3 described above.

The kit or the device of the present invention can be used for detecting lung cancer as described in Section 4 below.

4. Method for Detecting Lung Cancer

The present invention further provides a method for detecting lung cancer, comprising using the kit or the device of the present invention (including the aforementioned nucleic acid(s) that can be used in the present invention) described in Section 3 above to measure an expression level(s) of one or more lung cancer-derived gene(s) represented by an expression level(s) of lung cancer-derived gene(s) selected from the following group A: hsa-miR-6768-5p, hsa-miR-6836-3p, hsa-miR-6782-5p, hsa-miR-3663-3p, hsa-miR-1908-3p, hsa-miR-6726-5p, hsa-miR-4258, hsa-miR-1343-3p, hsa-miR-4516, hsa-miR-6875-5p, hsa-miR-4651, hsa-miR-6825-5p, hsa-miR-6840-3p, hsa-miR-6780b-5p, hsa-miR-6749-5p, hsa-miR-8063, hsa-miR-6784-5p, hsa-miR-3679-5p, hsa-miR-3184-5p, hsa-miR-663b, hsa-miR-6880-5p, hsa-miR-1908-5p, hsa-miR-92a-2-5p, hsa-miR-7975, hsa-miR-7110-5p, hsa-miR-6842-5p, hsa-miR-6857-5p, hsa-miR-5572, hsa-miR-3197, hsa-miR-6131, hsa-miR-6889-5p, hsa-miR-4454, hsa-miR-1199-5p, hsa-miR-1247-3p, hsa-miR-6800-5p, hsa-miR-6872-3p, hsa-miR-4649-5p, hsa-miR-6791-5p, hsa-miR-4433b-3p, hsa-miR-3135b, hsa-miR-128-2-5p, hsa-miR-4675, hsa-miR-4472, hsa-miR-6785-5p, hsa-miR-6741-5p, hsa-miR-7977, hsa-miR-3665, hsa-miR-128-1-5p, hsa-miR-4286, hsa-miR-6765-3p, hsa-miR-4632-5p, hsa-miR-365a-5p, hsa-miR-6088, hsa-miR-6816-5p, hsa-miR-6885-5p, hsa-miR-711, hsa-miR-6765-5p, hsa-miR-3180, hsa-miR-4442, hsa-miR-4792, hsa-miR-6721-5p, hsa-miR-6798-5p, hsa-miR-3162-5p, hsa-miR-6126, hsa-miR-4758-5p, hsa-miR-2392, hsa-miR-486-3p, hsa-miR-6727-5p, hsa-miR-4728-5p, hsa-miR-6746-5p, hsa-miR-4270, hsa-miR-3940-5p, hsa-miR-4725-3p, hsa-miR-7108-5p, hsa-miR-3656, hsa-miR-6879-5p, hsa-miR-6738-5p, hsa-miR-1260a, hsa-miR-4446-3p, hsa-miR-3131, hsa-miR-4463, hsa-miR-3185, hsa-miR-6870-5p, hsa-miR-6779-5p, hsa-miR-1273g-3p, hsa-miR-8059, hsa-miR-4697-5p, hsa-miR-4674, hsa-miR-4433-3p, hsa-miR-4257, hsa-miR-1915-5p, hsa-miR-4417, hsa-miR-1343-5p, hsa-miR-6781-5p, hsa-miR-4695-5p, hsa-miR-1237-5p, hsa-miR-6775-5p, hsa-miR-7845-5p, hsa-miR-4746-3p, hsa-miR-7641, hsa-miR-7847-3p, hsa-miR-6806-5p, hsa-miR-4467, hsa-miR-4726-5p, hsa-miR-4648, hsa-miR-6089, hsa-miR-1260b, hsa-miR-4532, hsa-miR-5195-3p, hsa-miR-3188, hsa-miR-6848-5p, hsa-miR-1233-5p, hsa-miR-6717-5p, hsa-miR-3195, hsa-miR-6757-5p, hsa-miR-8072, hsa-miR-4745-5p, hsa-miR-6511a-5p, hsa-miR-6776-5p, hsa-miR-371a-5p, hsa-miR-1227-5p, hsa-miR-7150, hsa-miR-1915-3p, hsa-miR-187-5p, hsa-miR-614, hsa-miR-1225-5p, hsa-miR-451a, hsa-miR-939-5p, hsa-miR-223-3p, hsa-miR-125a-3p, hsa-miR-92b-5p, hsa-miR-22-3p, hsa-miR-6073, hsa-miR-6845-5p, hsa-miR-6769b-5p, hsa-miR-4665-3p, hsa-miR-1913, hsa-miR-1228-3p, hsa-miR-940, hsa-miR-296-3p, hsa-miR-4690-5p, hsa-miR-548q, hsa-miR-663a, hsa-miR-1249, hsa-miR-1202, hsa-miR-7113-3p, hsa-miR-1225-3p, hsa-miR-4783-3p, hsa-miR-4448 and hsa-miR-4534, optionally an expression level of lung cancer-derived gene(s) selected from the following group B: hsa-miR-19b-3p, hsa-miR-1228-5p, and hsa-miR-1307-3p, and optionally an expression level of lung cancer-derived gene(s) selected from the following group C: hsa-miR-4271, hsa-miR-642b-3p, hsa-miR-6075, hsa-miR-6125, hsa-miR-887-3p, hsa-miR-6851-5p, hsa-miR-6763-5p, hsa-miR-3928-3p, hsa-miR-4443, hsa-miR-3648, hsa-miR-149-3p, hsa-miR-4689, hsa-miR-4763-3p, hsa-miR-6729-5p, hsa-miR-3196, hsa-miR-8069, hsa-miR-1268a, hsa-miR-4739, hsa-miR-1268b, hsa-miR-5698, hsa-miR-6752-5p, hsa-miR-4507, hsa-miR-564, hsa-miR-4497, hsa-miR-6877-5p, hsa-miR-6087, hsa-miR-4731-5p, hsa-miR-615-5p, hsa-miR-760, hsa-miR-6891-5p, hsa-miR-6887-5p, hsa-miR-4525, hsa-miR-1914-3p, hsa-miR-619-5p, hsa-miR-5001-5p, hsa-miR-6722-3p, hsa-miR-3621, hsa-miR-4298, hsa-miR-675-5p and hsa-miR-4655-5p in a sample in vitro, further comparing, for example, the expression level(s) of the aforementioned gene(s) in the sample (e.g., blood, serum, or plasma) collected from a subject who is suspected of having lung cancer with a control expression level in the sample collected from a healthy subject (including a non-lung cancer patient), and evaluating the subject as having lung cancer when the expression level(s) of the target nucleic acid(s) is statistically significantly different between the samples.

This method of the present invention permits limitedly-invasive early diagnosis of cancer with high sensitivity and specificity, and thereby brings about early treatment and improved prognosis. In addition, exacerbation of the disease or the effectiveness of surgical, radiotherapeutic, and chemotherapeutic treatments can be monitored.

The method for extracting the lung cancer-derived gene from the sample such as blood, serum, or plasma according to the present invention is particularly preferably prepared by the addition of a reagent for RNA extraction in 3D-Gene™ RNA extraction reagent from liquid sample kit (Toray Industries, Inc.). A general acidic phenol method (acid guanidinium-phenol-chloroform (AGPC)) may be used, or Trizol™ (Life Technologies Corp.) may be used. The lung cancer-derived gene may be prepared by the addition of a reagent for RNA extraction containing acidic phenol, such as Trizol (Life Technologies Corp.) or Isogen (Nippon Gene Co., Ltd.). Alternatively, a kit such as miRNeasy™ Mini Kit (Qiagen N.V.) can be used, though the method is not limited thereto.

The present invention also provides use of the kit or the device of the present invention for detecting in vitro an expression product of a lung cancer-derived miRNA gene in a sample derived from a subject.

In the method of the present invention, a kit or a device comprising, each alone or in every possible composition, the polynucleotides that can be used in the present invention as described above is used as the kit or the device.

In the detection or (genetic) diagnosis of lung cancer according to the present invention, each polynucleotide contained in the kit or the device of the present invention can be used as a probe or a primer. In the case of using the polynucleotide as a primer, TaqMan™ MicroRNA Assays from Life Technologies Corp., miScript PCR System from Qiagen N.V., or the like can be used, though the method is not limited thereto.

The polynucleotide contained in the kit or the device of the present invention can be used as a primer or a probe according to a routine method in a method known in the art for specifically detecting the particular gene, for example, a hybridization technique such as Northern blot, Southern blot, in situ hybridization, Northern hybridization, or Southern hybridization, or a quantitative amplification technique such as quantitative RT-PCR. A body fluid such as blood, serum, plasma, or urine from a subject is collected as a sample to be assayed according to the type of the detection method used. Alternatively, total RNA prepared from such a body fluid by the method described above may be used, and various polynucleotides including cDNA prepared on the basis of the RNA may be used.

The kit or the device of the present invention is useful for the diagnosis of lung cancer or the detection of the presence or absence of lung cancer. Specifically, the detection of lung cancer using the kit or the device can be performed by detecting in vitro an expression level of a gene using the nucleic acid probe or the primer contained in the kit or the device in a sample such as blood, serum, plasma, or urine from a subject suspected of having lung cancer. The subject suspected of having lung cancer can be evaluated as having lung cancer when the expression level of a target miRNA marker measured using polynucleotide(s) (including a variant(s), a fragment(s), and a derivative(s) thereof) consisting of a nucleotide sequence represented by at least one or more of SEQ ID NOs: 1 to 125, 127 to 130, 132 to 134 and 561 to 578 or a complementary sequence thereof, optionally a nucleotide sequence represented by one or more of SEQ ID NOs: 126 and 131 or a complementary sequence thereof, and optionally a nucleotide sequence represented by one or more of SEQ ID NOs: 135 to 174 or a complementary sequence thereof in the sample such as blood, serum, plasma, or urine of the subject is statistically significantly different from the expression level thereof in the sample such as blood, serum, or plasma, or urine of a healthy subject.

The method of the present invention can be combined with chest X-ray examination as well as a diagnostic imaging method such as CT, MRI, or PET. The method of the present invention is capable of specifically detecting lung cancer and can substantially discriminate lung cancer from the other cancers.

The method for detecting the absence of an expression product of a lung cancer-derived gene or the presence of the expression product of a lung cancer-derived gene in a sample using the kit or the device of the present invention comprises collecting a body fluid such as blood, serum, plasma, or urine from a subject, and measuring the expression level of the target gene contained therein using one or more polynucleotide(s) (including a variant(s), a fragment(s), and a derivative(s)) selected from the polynucleotide group of the present invention, to evaluate the presence or absence of lung cancer or to detect lung cancer. Using the method for detecting lung cancer according to the present invention, for example, the presence or absence of amelioration of the disease or the degree of amelioration thereof in a lung cancer patient given a therapeutic drug for the amelioration of the disease can be also evaluated or diagnosed.

The method of the present invention can comprise, for example, the following steps (a), (b), and (c):
(a) a step of contacting a sample derived from a subject with a polynucleotide in the kit or the device of the present invention in vitro;
(b) a step of measuring an expression level of the target nucleic acid in the sample using the polynucleotide as a nucleic acid probe or a primer; and
(c) a step of evaluating the presence or absence of lung cancer (cells) in the subject on the basis of the step (b).

Specifically, the present invention provides a method for detecting lung cancer, comprising measuring an expression level of a target nucleic acid in a sample of a subject using a nucleic acid capable of specifically binding to at least one or more (preferably at least two or more) polynucleotide(s) selected from the group consisting of miR-6768-5p, miR-6836-3p, miR-6782-5p, miR-3663-3p, miR-1908-3p, miR-6726-5p, miR-4258, miR-1343-3p, miR-4516, miR-6875-5p, miR-4651, miR-6825-5p, miR-6840-3p, miR-6780b-5p, miR-6749-5p, miR-8063, miR-6784-5p, miR-3679-5p, miR-3184-5p, miR-663b, miR-6880-5p, miR-1908-5p, miR-92a-2-5p, miR-7975, miR-7110-5p, miR-6842-5p, miR-6857-5p, miR-5572, miR-3197, miR-6131, miR-6889-5p, miR-4454, miR-1199-5p, miR-1247-3p, miR-6800-5p, miR-6872-3p, miR-4649-5p, miR-6791-5p, miR-4433b-3p, miR-3135b, miR-128-2-5p, miR-4675, miR-4472, miR-6785-5p, miR-6741-5p, miR-7977, miR-3665, miR-128-1-5p, miR-4286, miR-6765-3p, miR-4632-5p, miR-365a-5p, miR-6088, miR-6816-5p, miR-6885-5p, miR-711, miR-6765-5p, miR-3180, miR-4442, miR-4792, miR-6721-5p, miR-6798-5p, miR-3162-5p, miR-6126, miR-4758-5p, miR-2392, miR-486-3p, miR-6727-5p, miR-4728-5p, miR-6746-5p, miR-4270, miR-3940-5p, miR-4725-3p, miR-7108-5p, miR-3656, miR-6879-5p, miR-6738-5p, miR-1260a, miR-4446-3p, miR-3131, miR-4463, miR-3185, miR-6870-5p, miR-6779-5p, miR-1273g-3p, miR-8059, miR-4697-5p, miR-4674, miR-4433-3p, miR-4257, miR-1915-5p, miR-4417, miR-1343-5p, miR-6781-5p, miR-4695-5p, miR-1237-5p, miR-6775-5p, miR-7845-5p, miR-4746-3p, miR-7641, miR-7847-3p, miR-6806-5p, miR-4467, miR-4726-5p, miR-4648, miR-6089, miR-1260b, miR-4532, miR-5195-3p, miR-3188, miR-6848-5p, miR-1233-5p, miR-6717-5p, miR-3195, miR-6757-5p, miR-8072, miR-4745-5p, miR-6511a-5p, miR-6776-5p, miR-371a-5p, miR-1227-5p, miR-7150, miR-1915-3p, miR-187-5p, miR-614, miR-1225-5p, miR-451a, miR-939-5p, miR-223-3p, miR-125a-3p, miR-92b-5p, miR-22-3p, miR-6073, miR-6845-5p, miR-6769b-5p, miR-4665-3p, miR-1913, miR-1228-3p, miR-940, miR-296-3p, miR-4690-5p, miR-548q, miR-663a, miR-1249, miR-1202, miR-7113-3p, miR-1225-3p, miR-4783-3p, miR-4448 and miR-4534, and evaluating in vitro whether or not the subject has lung cancer using the measured expression level and a control expression level of a healthy subject measured in the same way as above.

As used herein, the term "evaluation" is evaluation support based on results of in vitro examination, not physician's judgment.

As described above, as for the target nucleic acids in a preferred embodiment of the method of the present invention, specifically, miR-6768-5p is hsa-miR-6768-5p, miR-6836-3p is hsa-miR-6836-3p, miR-6782-5p is hsa-miR-6782-5p, miR-3663-3p is hsa-miR-3663-3p, miR-1908-3p is hsa-miR-1908-3p, miR-6726-5p is hsa-miR-6726-5p, miR-4258 is hsa-miR-4258, miR-1343-3p is hsa-miR-1343-3p, miR-4516 is hsa-miR-4516, miR-6875-5p is hsa-miR-6875-5p, miR-4651 is hsa-miR-4651, miR-6825-5p is hsa-miR-6825-5p, miR-6840-3p is hsa-miR-6840-3p, miR-6780b-5p is hsa-miR-6780b-5p, miR-6749-5p is hsa-miR-6749-5p, miR-8063 is hsa-miR-8063, miR-6784-5p is hsa-miR-6784-5p, miR-3679-5p is hsa-miR-3679-5p, miR-3184-5p is hsa-miR-3184-5p, miR-663b is hsa-miR-663b, miR-6880-5p is hsa-miR-6880-5p, miR-1908-5p is hsa-miR-1908-5p, miR-92a-2-5p is hsa-miR-92a-2-5p, miR-7975 is hsa-miR-7975, miR-7110-5p is hsa-miR-7110-5p, miR-6842-5p is hsa-miR-6842-5p, miR-6857-5p is hsa-miR-6857-5p, miR-5572 is hsa-miR-5572, miR-3197 is hsa-miR-3197, miR-6131 is hsa-miR-6131, miR-6889-5p is hsa-miR-6889-5p, miR-4454 is hsa-miR-4454, miR-1199-5p is hsa-miR-1199-5p, miR-1247-3p is hsa-miR-1247-3p, miR-6800-5p is hsa-miR-6800-5p, miR-6872-3p is hsa-miR-6872-3p, miR-4649-5p is hsa-miR-4649-5p, miR-6791-5p is hsa-miR-6791-5p, miR-4433b-3p is hsa-miR-4433b-3p, miR-3135b is hsa-miR-3135b, miR-128-2-5p is hsa-miR-128-2-5p, miR-4675 is hsa-miR-4675, miR-4472 is hsa-miR-4472, miR-6785-5p is hsa-miR-6785-5p, miR-6741-5p is hsa-miR-6741-5p, miR-7977 is hsa-miR-7977, miR-3665 is hsa-miR-3665, miR-128-1-5p is hsa-miR-128-1-5p, miR-4286 is hsa-miR-4286, miR-6765-3p is hsa-miR-6765-3p, miR-4632-5p is hsa-miR-4632-5p, miR-365a-5p is hsa-miR-365a-5p, miR-6088 is hsa-miR-6088, miR-6816-5p is hsa-miR-6816-5p, miR-6885-5p is hsa-miR-6885-5p, miR-711 is hsa-miR-711, miR-6765-5p is hsa-miR-6765-5p, miR-3180 is hsa-miR-3180, miR-4442 is hsa-miR-4442, miR-4792 is hsa-miR-4792, miR-6721-5p is hsa-miR-6721-5p, miR-6798-5p is hsa-miR-6798-5p, miR-3162-5p is hsa-miR-3162-5p, miR-6126 is hsa-miR-6126, miR-4758-5p is hsa-miR-4758-5p, miR-2392 is hsa-miR-2392, miR-486-3p is hsa-miR-486-3p, miR-6727-5p is hsa-miR-6727-5p, miR-4728-5p is hsa-miR-4728-5p, miR-6746-5p is hsa-miR-6746-5p, miR-4270 is hsa-miR-4270, miR-3940-5p is hsa-miR-3940-5p, miR-4725-3p is hsa-miR-4725-3p, miR-7108-5p is hsa-miR-7108-5p, miR-3656 is hsa-miR-3656, miR-6879-5p is hsa-miR-6879-5p, miR-6738-5p is hsa-miR-6738-5p, miR-1260a is hsa-miR-1260a, miR-4446-3p is hsa-miR-4446-3p, miR-3131 is hsa-miR-3131, miR-4463 is hsa-miR-4463, miR-3185 is hsa-miR-3185, miR-6870-5p is hsa-miR-6870-5p, miR-6779-5p is hsa-miR-6779-5p, miR-1273g-3p is hsa-miR-1273g-3p, miR-8059 is hsa-miR-8059, miR-4697-5p is hsa-miR-4697-5p, miR-4674 is hsa-miR-4674, miR-4433-3p is hsa-miR-4433-3p, miR-4257 is hsa-miR-4257, miR-1915-5p is hsa-miR-1915-5p, miR-4417 is hsa-miR-4417, miR-1343-5p is hsa-miR-1343-5p, miR-6781-5p is hsa-miR-6781-5p, miR-4695-5p is hsa-miR-4695-5p, miR-1237-5p is hsa-miR-1237-5p, miR-6775-5p is hsa-miR-6775-5p, miR-7845-5p is hsa-miR-7845-5p, miR-4746-3p is hsa-miR-4746-3p, miR-7641 is hsa-miR-7641, miR-7847-3p is hsa-miR-7847-3p, miR-6806-5p is hsa-miR-6806-5p, miR-4467 is hsa-miR-4467, miR-4726-5p is hsa-miR-4726-5p, miR-4648 is hsa-miR-4648, miR-6089 is hsa-miR-6089, miR-1260b is hsa-miR-1260b, miR-4532 is hsa-miR-4532, miR-5195-3p is hsa-miR-5195-3p, miR-3188 is hsa-miR-3188, miR-6848-5p is hsa-miR-6848-5p, miR-1233-5p is hsa-miR-1233-5p, miR-6717-5p is hsa-miR-6717-5p, miR-3195 is hsa-miR-3195, miR-6757-5p is hsa-miR-6757-5p, miR-8072 is hsa-miR-8072, miR-4745-5p is hsa-miR-4745-5p, miR-6511a-5p is hsa-miR-6511a-5p, miR-6776-5p is hsa-miR-6776-5p, miR-371a-5p is hsa-miR-371a-5p, miR-1227-5p is hsa-miR-1227-5p, miR-7150 is hsa-miR-7150, miR-1915-3p is hsa-miR-1915-3p, miR-187-5p is hsa-miR-187-5p, miR-614 is hsa-miR-614, miR-1225-5p is hsa-miR-1225-5p, miR-451a is hsa-miR-451a, miR-939-5p is hsa-miR-939-5p, miR-223-3p is hsa-miR-223-3p, miR-125a-3p is hsa-miR-125a-3p, miR-92b-5p is hsa-miR-92b-5p, miR-22-3p is hsa-miR-22-3p, miR-6073 is hsa-miR-6073, miR-6845-5p is hsa-miR-6845-5p, miR-6769b-5p is hsa-miR-6769b-5p, miR-4665-3p is hsa-miR-4665-3p, miR-1913 is hsa-miR-1913, miR-1228-3p is hsa-miR-1228-3p, miR-940 is hsa-miR-940, miR-296-3p is hsa-miR-296-3p, miR-4690-5p is hsa-miR-4690-5p, miR-548q is hsa-miR-548q, miR-663a is hsa-miR-663a, miR-1249 is hsa-miR-1249, miR-1202 is hsa-miR-1202, miR-7113-3p is hsa-miR-7113-3p, miR-1225-3p is hsa-miR-1225-3p, miR-4783-3p is hsa-miR-4783-3p, miR-4448 is hsa-miR-4448, and miR-4534 is hsa-miR-4534.

In a preferred embodiment of the method of the present invention, specifically, the nucleic acid (specifically, probe or primer) is selected from the group consisting of the following polynucleotides (a) to (e):

(a) a polynucleotide consisting of a nucleotide sequence represented by any of SEQ ID NOs: 1 to 125, 127 to 130, 132 to 134, and 561 to 578 or a nucleotide sequence derived from the nucleotide sequence by the replacement of u with t, a variant thereof, a derivative thereof, or a fragment thereof comprising 15 or more consecutive nucleotides, (b) a polynucleotide comprising a nucleotide sequence represented by any of SEQ ID NOs: 1 to 125, 127 to 130, 132 to 134, and 561 to 578, (c) a polynucleotide consisting of a nucleotide sequence complementary to a nucleotide sequence represented by any of SEQ ID NOs: 1 to 125, 127 to 130, 132 to 134, and 561 to 578 or a nucleotide sequence derived from the nucleotide sequence by the replacement of u with t, a variant thereof, a derivative thereof, or a fragment thereof comprising 15 or more consecutive nucleotides, (d) a polynucleotide comprising a nucleotide sequence complementary to a nucleotide sequence represented by any of SEQ ID NOs: 1 to 125, 127 to 130, 132 to 134, and 561 to 578 or a nucleotide sequence derived from the nucleotide sequence by the replacement of u with t, and (e) a polynucleotide hybridizing under stringent conditions to any of the polynucleotides (a) to (d).

The method of the present invention can further employ a nucleic acid capable of specifically binding to at least one or more polynucleotide(s) selected from the group consisting of miR-19b-3p, miR-1228-5p, and miR-1307-3p.

As for such a nucleic acid, specifically, miR-19b-3p is hsa-miR-19b-3p, miR-1228-5p is hsa-miR-1228-5p, and miR-1307-3p is hsa-miR-1307-3p.

In a preferred embodiment, such a nucleic acid is specifically selected from the group consisting of the following polynucleotides (f) to (j):

(f) a polynucleotide consisting of a nucleotide sequence represented by any of SEQ ID NOs: 126, 131, and 579 or a nucleotide sequence derived from the nucleotide sequence by the replacement of u with t, a variant thereof, a derivative thereof, or a fragment thereof comprising 15 or more consecutive nucleotides, (g) a polynucleotide comprising a nucleotide sequence represented by any of SEQ ID NOs: 126, 131, and 579, (h) a polynucleotide consisting of a nucleotide sequence complementary to a nucleotide sequence represented by any of SEQ ID NOs: 126, 131, and 579 or a nucleotide sequence derived from the nucleotide sequence by the replacement of u with t, a variant thereof, a derivative thereof, or a fragment thereof comprising 15 or more consecutive nucleotides, (i) a polynucleotide comprising a nucleotide sequence complementary to a nucleotide sequence represented by any of SEQ ID NOs: 126, 131, and 579 or a nucleotide sequence derived from the nucleotide sequence by the replacement of u with t, and (j) a polynucleotide hybridizing under stringent conditions to any of the polynucleotides (f) to (i).

The nucleic acid further used in the method of the present invention can comprise a nucleic acid capable of specifically binding to at least one or more polynucleotide(s) selected from the group consisting of miR-4271, miR-642b-3p, miR-6075, miR-6125, miR-887-3p, miR-6851-5p, miR-6763-5p, miR-3928-3p, miR-4443, miR-3648, miR-149-3p, miR-4689, miR-4763-3p, miR-6729-5p, miR-3196, miR-8069, miR-1268a, miR-4739, miR-1268b, miR-5698, miR-6752-5p, miR-4507, miR-564, miR-4497, miR-6877-5p, miR-6087, miR-4731-5p, miR-615-5p, miR-760, miR-6891-5p, miR-6887-5p, miR-4525, miR-1914-3p, miR-619-5p, miR-5001-5p, miR-6722-3p, miR-3621, miR-4298, miR-675-5p and miR-4655-5p.

As for such a nucleic acid, specifically, miR-4271 is hsa-miR-4271, miR-642b-3p is hsa-miR-642b-3p, miR-6075 is hsa-miR-6075, miR-6125 is hsa-miR-6125, miR- 887-3p is hsa-miR-887-3p, miR-6851-5p is hsa-miR-6851-5p, miR-6763-5p is hsa-miR-6763-5p, miR-3928-3p is hsa-miR-3928-3p, miR-4443 is hsa-miR-4443, miR-3648 is hsa-miR-3648, miR-149-3p is hsa-miR-149-3p, miR-4689 is hsa-miR-4689, miR-4763-3p is hsa-miR-4763-3p, miR-6729-5p is hsa-miR-6729-5p, miR-3196 is hsa-miR-3196, miR-8069 is hsa-miR-8069, miR-1268a is hsa-miR-1268a, miR-4739 is hsa-miR-4739, miR-1268b is hsa-miR-1268b, miR-5698 is hsa-miR-5698, miR-6752-5p is hsa-miR-6752-5p, miR-4507 is hsa-miR-4507, miR-564 is hsa-miR-564, miR-4497 is hsa-miR-4497, miR-6877-5p is hsa-miR-6877-5p, miR-6087 is hsa-miR-6087, miR-4731-5p is hsa-miR-4731-5p, miR-615-5p is hsa-miR-615-5p, miR-760 is hsa-miR-760, miR-6891-5p is hsa-miR-6891-5p, miR-6887-5p is hsa-miR-6887-5p, miR-4525 is hsa-miR-4525, miR-1914-3p is hsa-miR-1914-3p, miR-619-5p is hsa-miR-619-5p, miR-5001-5p is hsa-miR-5001-5p, miR-6722-3p is hsa-miR-6722-3p, miR-3621 is hsa-miR-3621, miR-4298 is hsa-miR-4298, miR-675-5p is hsa-miR-675-5p, and miR-4655-5p is hsa-miR-4655-5p.

In a preferred embodiment, such a nucleic acid is specifically a polynucleotide selected from the group consisting of the following polynucleotides (k) to (o):

(k) a polynucleotide consisting of a nucleotide sequence represented by any of SEQ ID NOs: 135 to 174 or a nucleotide sequence derived from the nucleotide sequence by the replacement of u with t, a variant thereof, a derivative thereof, or a fragment thereof comprising 15 or more consecutive nucleotides, (l) a polynucleotide comprising a nucleotide sequence represented by any of SEQ ID NOs: 135 to 174, (m) a polynucleotide consisting of a nucleotide sequence complementary to a nucleotide sequence represented by any of SEQ ID NOs: 135 to 174 or a nucleotide sequence derived from the nucleotide sequence by the replacement of u with t, a variant thereof, a derivative thereof, or a fragment thereof comprising 15 or more consecutive nucleotides, (n) a polynucleotide comprising a nucleotide sequence complementary to a nucleotide sequence represented by any of SEQ ID NOs: 135 to 174 or a nucleotide sequence derived from the nucleotide sequence by the replacement of u with t, and (o) a polynucleotide hybridizing under stringent conditions to any of the polynucleotides (k) to (n).

Examples of the sample used in the method of the present invention can include samples prepared from a living tissue (preferably a lung tissue) or a body fluid such as blood, serum, plasma, or urine from the subject. Specifically, for example, an RNA-containing sample prepared from the tissue, a polynucleotide-containing sample further prepared therefrom, a body fluid such as blood, serum, plasma, or urine, a portion or the whole of a living tissue collected from the subject by biopsy or the like, or a living tissue excised by surgery can be used, and the sample for measurement can be prepared therefrom.

As used herein, the subject refers to a mammal, for example, a human, a monkey, a mouse and a rat, without any limitation, and is preferably a human.

The steps of the method of the present invention can be changed according to the type of the sample to be assayed.

In the case of using RNA as an analyte, the detection of lung cancer (cells) can comprise, for example, the following steps (a), (b), and (c):

(a) a step of binding RNA prepared from the sample of the subject or a complementary polynucleotide (cDNA) transcribed therefrom to a polynucleotide in the kit or the device of the present invention;

(b) a step of measuring the sample-derived RNA or the cDNA synthesized from the RNA, bound with the polynucleotide by hybridization using the polynucleotide as a nucleic acid probe or by quantitative RT-PCR using the polynucleotide as a primer; and (c) a step of evaluating the presence or absence of lung cancer (or lung cancer-derived gene expression) on the basis of the measurement results of the step (b).

For example, various hybridization methods can be used for detecting, examining, evaluating, or diagnosing lung cancer (or lung cancer-derived gene expression) in vitro according to the present invention. For example, Northern blot, Southern blot, RT-PCR, DNA chip analysis, in situ hybridization, Northern hybridization, or Southern hybridization can be used as such a hybridization method.

In the case of using the Northern blot, the presence or absence of expression of each gene or the expression level thereof in the RNA can be detected or measured by use of the nucleic acid probe that can be used in the present invention. Specific examples thereof can include a method which involves labeling the nucleic acid probe (or its complementary strand) with a radioisotope ($^{32}$P, $^{33}$P, $^{35}$S, etc.), a fluorescent material, or the like, hybridizing the labeled product with the living tissue-derived RNA from a subject transferred to a nylon membrane or the like according to a routine method, and then detecting and measuring a signal derived from the label (radioisotope or fluorescent material) on the formed DNA/RNA duplex using a radiation detector (examples thereof can include BAS-1800 II (Fujifilm Corp.)) or a fluorescence detector (examples thereof can include STORM 865 (GE Healthcare Japan Corp.)).

In the case of using the quantitative RT-PCR, the presence or absence of expression of each gene or the expression level thereof in the RNA can be detected or measured by use of the primer that can be used in the present invention. Specific examples thereof can include a method which involves preparing cDNA from the living tissue-derived RNA of a subject according to a routine method, hybridizing a pair of primers (consisting of a plus strand and a reverse strand binding to the cDNA) of the present invention with the cDNA such that the region of each target gene can be amplified with the cDNA as a template, and performing PCR according to a routine method to detect the obtained double-stranded DNA. The method for detecting the double-stranded DNA can include a method of performing the PCR using the primers labeled in advance with a radioisotope or a fluorescent material, a method of electrophoresing the PCR product on an agarose gel and staining the double-stranded DNA with ethidium bromide or the like for detection, and a method of transferring the produced double-stranded DNA to a nylon membrane or the like according to a routine method and hybridizing the double-stranded DNA to a labeled nucleic acid probe for detection.

In the case of using the nucleic acid array analysis, an RNA chip or a DNA chip in which the nucleic acid probes (single-stranded or double-stranded) of the present invention is attached to a substrate (solid phase) is used. Regions having the attached nucleic acid probes are referred to as probe spots, and regions having no attached nucleic acid probe are referred to as blank spots. A gene group immobilized on a solid-phase substrate is generally called a nucleic acid chip, a nucleic acid array, a microarray, or the like. The DNA or RNA array includes a DNA or RNA macroarray and a DNA or RNA microarray. The term "chip" used herein includes all of them. 3D-Gene™ Human miRNA Oligo chip (Toray Industries, Inc.) can be used as the DNA chip, though the DNA chip is not limited thereto.

Examples of the measurement using the DNA chip can include, but are not limited to, a method of detecting and measuring a signal derived from the label on the nucleic acid probes using an image detector (examples thereof can include Typhoon 9410 (GE Healthcare Japan Corp.) and 3D-Gene™ scanner (Toray Industries, Inc.)).

The "stringent conditions" used herein are, as mentioned above, conditions under which a nucleic acid probe hybridizes to its target sequence to a larger extent (e.g., a measurement value equal to or larger than a mean of background measurement values+a standard deviation of the background measurement values×2) than that for other sequences.

The stringent conditions are defined by hybridization and subsequent washing conditions. The hybridization conditions are not limited and are conditions involving, for example, 30° C. to 60° C. for 1 to 24 hours in a solution containing SSC, a surfactant, formamide, dextran sulfate, a blocking agent, etc. In this context, 1×SSC is an aqueous solution (pH 7.0) containing 150 mM sodium chloride and 15 mM sodium citrate. The surfactant includes, for example, SDS (sodium dodecyl sulfate), Triton, or Tween. The hybridization conditions more preferably involve 3 to 10×SSC and 0.1 to 1% SDS. Examples of the conditions of the washing, following the hybridization, which is another condition to define the stringent conditions, can include conditions involving continuous washing at 30° C. in a solution containing 0.5×SSC and 0.1% SDS, at 30° C. in a solution containing 0.2×SSC and 0.1% SDS, and at 30° C. in a 0.05×SSC solution. It is desirable that the complementary strand should maintain its hybridized state with a target plus strand even by washing under such conditions. Specifically, examples of such a complementary strand can include a strand consisting of a nucleotide sequence in a completely complementary relationship with the nucleotide sequence of the target plus strand, and a strand consisting of a nucleotide sequence having at least 80%, preferably at least 85%, more preferably at least 90% or at least 95%, for example, at least 98% or at least 99% identity to the strand.

Other examples of the "stringent conditions" for the hybridization are described in, for example, Sambrook, J. & Russel, D., Molecular Cloning, A LABORATORY MANUAL, Cold Spring Harbor Laboratory Press, published on Jan. 15, 2001, Vol. 1, 7.42 to 7.45 and Vol. 2, 8.9 to 8.17, and can be used in the present invention.

Examples of the conditions for carrying out PCR using a polynucleotide fragment in the kit of the present invention as a primer include treatment for approximately 15 seconds to 1 minute at 5 to 10° C. plus a Tm value calculated from the sequence of the primer, using a PCR buffer with composition such as 10 mM Tris-HCL (pH 8.3), 50 mM KCL, and 1 to 2 mM $MgCl_2$. Examples of the method for calculating such a Tm value include Tm value=2×(the number of adenine residues+the number of thymine residues)+4× (the number of guanine residues+the number of cytosine residues).

In the case of using the quantitative RT-PCR, a commercially available kit for measurement specially designed for quantitatively measuring miRNA, such as TaqMan™ MicroRNA Assays (Life Technologies Corp.), LNA™-based MicroRNA PCR (Exiqon), or Ncode™ miRNA qRT-PCT kit (Invitrogen Corp.) may be used.

For the calculation of gene expression levels, statistical treatment described in, for example, Statistical analysis of gene expression microarray data (Speed T., Chapman and Hall/CRC), and A beginner's guide Microarray gene expression data analysis (Causton H. C. et al., Blackwell publishing) can be used in the present invention, though the calculation method is not limited thereto. For example, twice, preferably 3 times, more preferably 6 times the standard deviation of the measurement values of the blank spots are added to the average measurement value of the blank spots on the DNA chip, and probe spots having a signal value equal to or larger than the resulting value can be regarded as detection spots. Alternatively, the average measurement value of the blank spots is regarded as a background and can be subtracted from the measurement values of the probe spots to determine gene expression levels. A missing value for a gene expression level can be excluded from the analyte, preferably replaced with the smallest value of the gene expression level in each DNA chip, or more preferably replaced with a value obtained by subtracting 0.1 from a logarithmic value of the smallest value of the gene expression level. In order to eliminate low-signal genes, only a gene having a gene expression level of $2^6$, preferably $2^8$, more preferably $2^{11}$ or larger, in 20% or more, preferably 50% or more, more preferably 80% or more of the number of measurement samples can be selected as the analyte. Examples of the normalization of the gene expression level include, but are not limited to, global normalization and quantile normalization (Bolstad, B. M. et al., 2003, Bioinformatics, Vol. 19, p. 185-193).

The present invention also provides a method comprising measuring a target gene or gene expression level in a sample derived from a subject using the polynucleotide, the kit, or the device (e.g., chip) for detection of the present invention, or a combination thereof, preparing a discriminant (discriminant function) with gene expression levels in a sample derived from a lung cancer patient and a sample derived from a healthy subject as supervising samples, and determining or evaluating the presence and/or absence of the lung cancer-derived gene in the sample.

Specifically, the present invention further provides the method comprising: a first step of measuring in vitro an expression level of a target gene in multiple samples that were known to be able to determine or evaluate the presence and/or absence of the lung cancer-derived gene in the samples, using the polynucleotide, the kit, or the device (e.g., chip) for detection of the present invention, or a combination thereof; a second step of constructing a discriminant with the measurement values of the expression level of the target gene (target nucleic acids) that was obtained in the first step as supervising samples; a third step of measuring in vitro an expression level of the target gene in a sample derived from a subject in the same way as in the first step; and a fourth step of assigning the measurement value of the expression level of the target gene obtained in the third step into the discriminant obtained in the second step, and determining or evaluating the presence and/or absence of the lung cancer-derived gene in the sample on the basis of the results obtained from the discriminant, wherein the target gene can be detected using a polynucleotide for the detection, that was contained in the polynucleotide, the kit or the device (e.g., chip). In this context, the discriminant can be prepared by use of Fisher's discriminant analysis, non-linear discriminant analysis based on Mahalanobis' distance, neural network, Support Vector Machine (SVM), or the like, though the method is not limited thereto.

When a clustering boundary is a straight line or a hyperplane, the linear discriminant analysis is a method for determining the association of a cluster using Formula 1 as a discriminant. In Formula 1, x represents an explanatory variable, w represents a coefficient of the explanatory variable, and w0 represents a constant term.

$$f(x) = w_0 + \sum_{i=1}^{n} w_i x_i \qquad \text{Formula 1}$$

Values obtained from the discriminant are referred to as discriminant scores. The measurement values of a newly offered data set can be assigned as explanatory variables to the discriminant to determine clusters by the signs of the discriminant scores.

The Fisher's discriminant analysis, one type of linear discriminant analysis, is a dimensionality reduction method for selecting a dimension suitable for discriminating classes, and constructs a highly discriminating synthetic variable by focusing on the variance of synthetic variables and minimizing the variance of data having the same label (Venables, W. N. et al., Modern Applied Statistics with S. Fourth edition. Springer, 2002). In the Fisher's linear discriminant analysis, direction w of projection is determined so as to maximize Formula 2. In this Formula, represents an average input, ng represents the number of data associate with class g, and g represents an average input of the data associated with class g. The numerator and the denominator are the inter-classe variance and the intra-classe variance, respectively, when each data is projected in the direction of the vector w. Discriminant coefficient wi is determined by maximizing this ratio (Takafumi Kanamori et al., "Pattern Recognition", Kyoritsu Shuppan Co., Ltd. (2009); and Richard O. et al., Pattern Classification Second Edition, Wiley-Interscience, 2000).

$$J(w) = \frac{\sum_{g=1}^{G} n_g (w^T \mu_g - w^T \mu)(w^T \mu_g - w^T \mu)^T}{\sum_{g=1}^{G} \sum_{i:y_i=g} (w^T x_i - w^T \mu_g)(w^T x_i - w^T \mu_g)} \qquad \text{Formula 2}$$

$$\text{subject to } \mu = \sum_{i=1}^{n} \frac{x_i}{n}, \mu_g = \sum_{i:u_i=g}^{n} \frac{x_i}{n_g}$$

The Mahalanobis' distance is calculated according to Formula 3 in consideration of data correlation and can be used as nonlinear discriminant analysis for determining an associated cluster that shows a closer Mahalanobis' distance from each cluster. In this Formula 3, represents a central vector of each cluster, and S-1 represents an inverse matrix of the variance-covariance matrix of the cluster. The central vector is calculated from explanatory variable x, and an average vector, a median value vector, or the like can be used.

$$D(x, \mu) = \{(x-\mu)^t S^{-1}(x-\mu)\}^{\frac{1}{2}} \qquad \text{Formula 3}$$

SVM is a discriminant analysis method devised by V. Vapnik (The Nature of Statistical Leaning Theory, Springer, 1995). Particular data points of a data set having known classes are defined as explanatory variables, and classes are defined as objective variables. A boundary plane called hyperplane for correctly classifying the data set into the known classes is determined, and a discriminant for data classification is determined using the boundary plane. Then, the measurement values of a newly offered data set can be assigned as explanatory variables to the discriminant to determine classes. In this respect, the results of the discriminant analysis may be classes, may be a probability of data to be classified into correct classes, or may be the distance from the hyperplane. In SVM, a method of nonlinearly converting a feature vector to a high dimension and performing linear discriminant in the space is known as a method for tackling nonlinear problems. An expression in which an inner product of two factors in a nonlinearly mapped space is expressed only by inputs in their original spaces is called kernel. Examples of the kernel can include a linear kernel, a RBF (Radial Basis Function) kernel, and a Gaussian kernel. While highly dimensional mapping is performed according to the kernel, the optimum discriminant, i.e., a discriminant, can be actually constructed by mere calculation according to the kernel, which avoids calculating features in the mapped space (e.g., Hideki Aso et al., Frontier of Statistical Science 6 "Statistics of pattern recognition and learning—New concepts and approaches", Iwanami Shoten, Publishers (2004); Nello Cristianini et al., Introduction to SVM, Kyoritsu Shuppan Co., Ltd. (2008)).

C-support vector classification (C-SVC), one type of SVM, involves preparing a hyperplane by supervising with the explanatory variables of two groups and classifying an unknown data set into either of the groups (C. Cortes et al., 1995, Machine Learning, Vol. 20, p. 273-297).

Exemplary calculation of the C-SVC discriminant that can be used in the method of the present invention will be given below. First, all subjects are divided into two groups, i.e., a lung cancer patient group and a healthy subject group. For example, lung tissue examination can be used for a reference under which each subject is confirmed either as a lung cancer patient or as a healthy subject.

Next, a data set consisting of comprehensive gene expression levels of serum-derived samples of the two divided groups (hereinafter, this data set is referred to as a training cohort) is prepared, and a C-SVC discriminant is determined by using genes that were found to differ clearly in their gene expression levels between the two groups as explanatory variables, and using this grouping as objective variables (e.g., −1 and +1). An optimizing objective function is represented by Formula 4 wherein e represents all input vectors, y represents an objective variable, a represents a Lagrange's undetermined multiplier vector, Q represents a positive definite matrix, and C represents a parameter for adjusting constrained conditions.

$$\min_{a} \frac{1}{2} a^T Q a - e^T a \qquad \text{Formula 4}$$

$$\text{subject to } y^T a = 0, 0 \leq a_i \leq C, i = 1, \ldots, l,$$

Formula 5 is a finally obtained discriminant, and an associated group can be determined on the basis of the sign of a value obtained according to the discriminant. In this Formula, x represents a support vector, y represents a label indicating the association of a group, a represents the corresponding coefficient, b represents a constant term, and K represents a kernel function.

$$f(x) = \text{sgn}\left(\sum_{i=1}^{l} y_i a_i K(x_i, x) + b\right) \qquad \text{Formula 5}$$

For example, a RBF kernel defined by Formula 6 can be used as the kernel function. In this Formula, x represents a support vector, and y represents a kernel parameter for adjusting the complexity of the hyperplane.

$$K(x_i, x_j) = \exp(-r\|x_i - x_j\|^2), r < 0 \qquad \text{Formula 6}$$

In addition, an approach such as neural network, k-nearest neighbor algorithms, decision trees, or logistic regression analysis can be selected as a method for determining or evaluating the presence and/or absence of expression of a lung cancer-derived target gene in a sample derived from a subject, or for evaluating the expression level thereof by comparison with a control derived from a healthy subject.

The method of the present invention can comprise, for example, the following steps (a), (b), and (c):

(a) a step of measuring an expression level of a target gene in tissues containing lung cancer-derived genes derived from lung cancer patients and/or samples that are already known to contain no lung cancer-derived gene derived from healthy subjects, using the polynucleotide, the kit, or the device (e.g., DNA chip) for detection according to the present invention;

(b) a step of preparing the discriminants of Formulas 1 to 3, 5, and 6 described above from the measurement values of the expression level measured in the step (a); and (c) a step of measuring an expression level of the target gene in a sample derived from a subject using the polynucleotide, the kit, or the device (e.g., DNA chip) for detection according to the present invention, assigning the obtained measurement value to the discriminants prepared in the step (b), and determining or evaluating the presence and/or absence of expression of the lung cancer-derived target gene in the sample, or evaluating the expression level thereof by comparison with a healthy subject-derived control, on the basis of the obtained results. In this context, in the discriminants of Formulas 1 to 3, 5, and 6, x represents an explanatory variable and includes a value obtained by measuring a polynucleotide selected from the polynucleotides described in Section 2 above, or a fragment thereof, etc. Specifically, the explanatory variable for discriminating a lung cancer patient from a healthy subject according to the present invention is a gene expression level selected from, for example, the following expression levels (1) to (3):

(1) a gene expression level in the serum of a lung cancer patient or a healthy subject measured by any DNA comprising 15 or more consecutive nucleotides in a nucleotide sequence represented by any of SEQ ID NOs: 1 to 125, 127 to 130, 132 to 134 and 561 to 578 or a complementary sequence thereof, (2) a gene expression level in the serum of a lung cancer patient or a healthy subject measured by any DNA comprising 15 or more consecutive nucleotides in a nucleotide sequence represented by any of SEQ ID NOs: 126, 131 and 579 or a complementary sequence thereof, and (3) a gene expression level in the serum of a lung cancer patient or a healthy subject measured by any DNA comprising 15 or more consecutive nucleotides in a nucleotide sequence represented by any of SEQ ID NOs: 135 to 174 or a complementary sequence thereof.

As described above, for the method for determining or evaluating the presence and/or absence of a lung cancer-derived gene in a sample derived from a subject, the preparation of a discriminant requires a discriminant prepared in a training cohort. For enhancing the discriminant accuracy of the discriminant, it is necessary for the discriminant to use genes that show clear difference between two groups in the training cohort.

Each gene that is used for an explanatory variable in a discriminant is preferably determined as follows. First, comprehensive gene expression levels of a lung cancer patient group and comprehensive gene expression levels of a healthy subject group in a training cohort are used as a data set, the degree of difference in the expression level of each gene between the two groups is determined through the use of, for example, the P value of t test, which is parametric analysis, or the P value of Mann-Whitney's U test or Wilcoxon test, which is nonparametric analysis.

The gene can be regarded as being statistically significant when the critical rate (significance level) of the P value obtained by the test is smaller than, for example, 5%, 1%, or 0.01%.

In order to correct an increased probability of type I error attributed to the repetition of a test, a method known in the art, for example, Bonferroni or Holm method, can be used for the correction (e.g., Yasushi Nagata et al., "Basics of statistical multiple comparison methods", Scientist Press Co., Ltd. (2007)). As an example of the Bonferroni correction, for example, the P value obtained by a test is multiplied by the number of repetitions of the test, i.e., the number of genes used in the analysis, and the obtained value can be compared with a desired significance level to suppress a probability of causing type I error in the whole test.

Instead of the statistical test, the absolute value (fold change) of an expression ratio of a median value of each gene expression level between gene expression levels of a lung cancer patient group and gene expression levels of a healthy subject group may be calculated to select a gene that is used for an explanatory variable in a discriminant. Alternatively, ROC curves may be prepared using gene expression levels of a lung cancer patient group and a healthy subject group, and a gene that is used for an explanatory variable in a discriminant can be selected on the basis of an AUROC value.

Next, a discriminant that can be calculated by various methods described above is prepared using any number of genes having large difference in their gene expression levels determined here. Examples of the method for constructing a discriminant that produces the largest discriminant accuracy include a method of constructing a discriminant in every combination of genes that satisfy the significance level of P value, and a method of repetitively evaluating a discriminant while increasing the number of genes for use one by one in a descending order of difference in gene expression level (Furey T S. et al., 2000, Bioinformatics, Vol. 16, p. 906-14). A gene expression level of another independent lung cancer patient or healthy subject is assigned as an explanatory variable to this discriminant to calculate discriminant results of the group to which this independent lung cancer patient or healthy subject associates. Specifically, the found gene set for diagnosis and the discriminant constructed using the gene set for diagnosis can be evaluated in an independent sample group to find a more universal gene set for diagnosis capable of detecting lung cancer and a more universal method for discriminating lung cancer.

Split-sample method is preferably used for evaluating the discriminant performance (generality) of the discriminant. Specifically, a data set is divided into a training cohort and a validation cohort, and gene selection by a statistical test and discriminant preparation are performed in the training cohort. Accuracy, sensitivity, and specificity are calculated using results of discriminating a validation cohort according to the discriminant and a true group to which the validation cohort associates, to evaluate the discriminant performance. On the other hand, instead of dividing a data set, gene selection by a statistical test and discriminant preparation may be performed using all of samples, and accuracy, sensitivity, and specificity can be calculated by the discriminant of newly prepared samples according to the discriminant to evaluate the discriminant performance.

The present invention provides a polynucleotide for detection and for disease diagnosis useful in the diagnosis and treatment of lung cancer, a method for detecting lung cancer using the polynucleotide, and a kit and a device for the detection of lung cancer, comprising the polynucleotide. Particularly, in order to select a gene for diagnosis and prepare a discriminant so as to exhibit accuracy beyond a lung cancer diagnosis method using existing tumor markers CEA, a gene set for diagnosis and a discriminant for the method of the present invention, that exhibit accuracy beyond CEA, can be constructed, for example, by comparing genes expressed in serum derived from a patient confirmed to be negative using CEA but finally found to have lung cancer by detailed examination such as computed tomography using a contrast medium, with genes expressed in serum derived from a patient having no lung cancer.

For example, the gene set for diagnosis is set to any combination selected from one or two or more of the polynucleotides based on a nucleotide sequence represented by any of SEQ ID NOs: 1 to 125, 127 to 130, 132 to 134, and 561 to 578, or a complementary sequence thereof as described above, optionally one or two or more of the polynucleotides based on a nucleotide sequence represented by any of SEQ ID NOs: 126, 131 and 579, or a complementary sequence thereof, and optionally one or two or more of the polynucleotides based on a nucleotide sequence represented by any of SEQ ID NOs: 135 to 174, or a complementary sequence thereof. Further, a discriminant is constructed using expression levels of the gene set for diagnosis in samples derived from class I lung cancer patients and samples derived from class II healthy subjects as a result of tissue diagnosis. As a result, the presence or absence of lung cancer-derived genes in an unknown sample can be determined with 100% accuracy at the maximum by measuring expression levels of the gene set for diagnosis in the unknown sample.

EXAMPLES

Hereinafter, the present invention will be described further specifically with reference to Examples below. However, the scope of the present invention is not intended to be limited by these Examples.

Reference Example 1

<Collection of Samples from Lung Cancer Patients and Healthy Subjects>

Serum was collected using VENOJECT II vacuum blood collecting tube VP-AS109K60 (Terumo Corp.) from each of 100 healthy subjects and 17 lung cancer patients (8 lung adenocarcinoma cases involving 6 cases with T2N0M0, 1 case with T2N1M0, and 1 case with T2N2M0; and 8 squamous cell cancer cases involving 5 cases with T2N0M0, 1 case with T4N0M0, 1 case with T2N1M0, and 1 case with T4N2M0) confirmed to have no primary cancer other than lung cancer after acquisition of informed consent, and used as a training cohort. Likewise, serum was collected using VENOJECT II vacuum blood collecting tube VP-AS109K60 (Terumo Corp.) from each of 50 healthy subjects and 8 lung cancer patients (5 adenocarcinoma cases involving 3 cases with T2N0M0, 1 case with T3N0M0, and 1 case with T4N2M0; and 3 squamous cell cancer cases involving 1 case with T2N0M0, 1 case with T4N0M0, and 1 case with T2N1M0) confirmed to have no primary cancer other than lung cancer after acquisition of informed consent, and used as a validation cohort. The histological types and stages of these lung cancer samples are summarized in Tables 2-1 and 2-2.

<Extraction of Total RNA>

Total RNA was obtained from 300 µL of the serum sample obtained from each of 175 persons in total of 150 healthy subjects and 25 lung cancer patients included in the training cohort and the validation cohort, using a reagent for RNA extraction in 3D-Gene™ RNA extraction reagent from liquid sample kit (Toray Industries, Inc.) according to the protocol provided by the manufacturer.

<Measurement of Gene Expression Level> miRNAs in the total RNA obtained from the serum sample of each of 175 persons in total of 150 healthy subjects and 25 lung cancer patients included in the training cohort and the validation cohort were fluorescently labeled using 3D-Gene™ miRNA Labeling kit (Toray Industries, Inc.) according to the protocol (ver 2.20) provided by the manufacturer. The oligo DNA chip used was 3D-Gene™ Human miRNA Oligo chip (Toray Industries, Inc.) with attached probes having sequences complementary to 2,555 miRNAs among the miRNAs registered in miRBase Release 20. Hybridization between the miRNAs in the total RNA and the probes on the DNA chip under stringent conditions and washing following the hybridization were performed according to the protocol provided by the manufacturer. The DNA chip was scanned using 3D-Gene™ scanner (Toray Industries, Inc.) to obtain images. Fluorescence intensity was digitized using 3D-Gene™ Extraction (Toray Industries, Inc.). The digitized fluorescence intensity was converted to a logarithmic value having a base of 2 and used as a gene expression level, from which a blank value was subtracted. A missing value was replaced with a value obtained by subtracting 0.1 from a logarithmic value of the smallest value of the gene expression level in each DNA chip. As a result, the comprehensive gene expression levels of the miRNAs in the serum were obtained for the 25 lung cancer patients and the 150 healthy subjects. Calculation and statistical analysis using the digitized gene expression levels of the miRNAs were carried out using R language 3.0.2 (R Development Core Team (2013). R: A language and environment for statistical computing. R Foundation for Statistical Computing, URL http://www.R-project.org/) and MASS package 7.3-30 (Venables, W. N. & Ripley, B. D. (2002) Modern Applied Statistics with S. Fourth Edition. Springer, New York. ISBN 0-387-95457-0).

Reference Example 2

<Collection of Samples from Patients with Cancers Other than Lung Cancer>

Serum was collected using VENOJECT II vacuum blood collecting tube VP-AS109K60 (Terumo Corp.) from each of 75 pancreatic cancer patients, 62 biliary tract cancer patients, 32 colorectal cancer patients, 35 stomach cancer patients, 32 esophageal cancer patients, 33 liver cancer patients, and 13 benign pancreaticobiliary disease patients confirmed to have no cancer in other organs after acquisition of informed consent, and used as a training cohort together with the samples of 17 lung cancer patients and 99 healthy subjects of Reference Example 1. Likewise, serum was collected using VENOJECT II vacuum blood collecting tube VP-AS109K60 (Terumo Corp.) from each of 28 pancreatic cancer patients, 38 biliary tract cancer patients, 18 colorectal cancer patients, 15 stomach cancer patients, 18 esophageal cancer patients, 19 liver cancer patients, and 8 benign pancreaticobiliary disease patients confirmed to have no cancer in other organs after acquisition of informed consent, and used as a validation cohort together with the samples of 8 lung cancer patients confirmed to have no cancer in organs except for lung cancer and 51 healthy subjects of Reference Example 1. Subsequent operations were conducted in the same way as in Reference Example 1.

TABLE 2-1

Training cohort

| | Sample name | Cancer stage |
|---|---|---|
| Lung adenocarcinoma | LC01 | T2N0M0 |
| | LC02 | T2N0M0 |
| | LC03 | T2N0M0 |
| | LC05 | T2N0M0 |
| | LC07 | T2N0M0 |
| | LC08 | T2N2M0 |
| | LC11 | T2N0M0 |
| | LC12 | T2N1M0 |
| | LC14 | T2N0M0 |
| Squamous cell cancer | LC15 | T2N0M0 |
| | LC18 | T2N0M0 |
| | LC20 | T2N0M0 |
| | LC21 | T2N0M0 |
| | LC22 | T4N2M0 |
| | LC23 | T2N1M0 |
| | LC24 | T2N0M0 |
| | LC25 | T4N0M0 |

TABLE 2-2

Validation cohort

| | Sample name | Cancer stage |
|---|---|---|
| Lung adenocarcinoma | LC04 | T2N0M0 |
| | LC06 | T2N0M0 |
| | LC09 | T3N0M0 |
| | LC10 | T4N2M0 |
| | LC13 | T2N0M0 |
| Squamous cell cancer | LC16 | T2N1M0 |
| | LC17 | T2N0M0 |
| | LC19 | T4N0M0 |

Example 1

<Selection of Gene Marker Using Samples in the Training Cohort, and Method for Evaluating Lung Cancer Discriminant Performance of Single Gene Marker Using Samples in the Validation Cohort>

In this Example, a gene marker for discriminating a lung cancer patient from a healthy subject was selected from the training cohort and studied in samples of the validation cohort independent of the training cohort, for a method for evaluating the lung cancer discriminant performance of each selected gene marker alone.

Specifically, first, the miRNA expression levels in the training cohort and the validation cohort obtained in the preceding Reference Examples were combined and normalized by quantile normalization.

Next, genes for diagnosis were selected in the training cohort. Here, in order to acquire diagnostic markers with higher reliability, only genes having a gene expression level of $2^6$ or higher in 50% or more of the samples in either of the lung cancer patient group in the training cohort or the healthy subject group in the training cohort were selected. In order to further acquire statistically significant genes for discriminating a lung cancer patient group from a healthy subject group, the P value obtained by two-sample t-test assuming equal variance as to each gene expression level was corrected by the Bonferroni method, and genes that satisfied p<0.01 were acquired as gene markers for use in explanatory variables of a discriminant. The result is described in Table 3.

In this way, hsa-miR-6768-5p, hsa-miR-6836-3p, hsa-miR-6782-5p, hsa-miR-3663-3p, hsa-miR-1908-3p, hsa-miR-6726-5p, hsa-miR-4258, hsa-miR-1343-3p, hsa-miR-4516, hsa-miR-6875-5p, hsa-miR-4651, hsa-miR-6825-5p, hsa-miR-6840-3p, hsa-miR-6780b-5p, hsa-miR-6749-5p, hsa-miR-8063, hsa-miR-6784-5p, hsa-miR-3679-5p, hsa-miR-3184-5p, hsa-miR-663b, hsa-miR-6880-5p, hsa-miR-1908-5p, hsa-miR-92a-2-5p, hsa-miR-7975, hsa-miR-7110-5p, hsa-miR-6842-5p, hsa-miR-6857-5p, hsa-miR-5572, hsa-miR-3197, hsa-miR-6131, hsa-miR-6889-5p, hsa-miR-4454, hsa-miR-1199-5p, hsa-miR-1247-3p, hsa-miR-6800-5p, hsa-miR-6872-3p, hsa-miR-4649-5p, hsa-miR-6791-5p, hsa-miR-4433b-3p, hsa-miR-3135b, hsa-miR-128-2-5p, hsa-miR-4675, hsa-miR-4472, hsa-miR-6785-5p, hsa-miR-6741-5p, hsa-miR-7977, hsa-miR-3665, hsa-miR-128-1-5p, hsa-miR-4286, hsa-miR-6765-3p, hsa-miR-4632-5p, hsa-miR-365a-5p, hsa-miR-6088, hsa-miR-6816-5p, hsa-miR-6885-5p, hsa-miR-711, hsa-miR-6765-5p, hsa-miR-3180, hsa-miR-4442, hsa-miR-4792, hsa-miR-6721-5p, hsa-miR-6798-5p, hsa-miR-3162-5p, hsa-miR-6126, hsa-miR-4758-5p, hsa-miR-2392, hsa-miR-486-3p, hsa-miR-6727-5p, hsa-miR-4728-5p, hsa-miR-6746-5p, hsa-miR-4270, hsa-miR-3940-5p, hsa-miR-4725-3p, hsa-miR-7108-5p, hsa-miR-3656, hsa-miR-6879-5p, hsa-miR-6738-5p, hsa-miR-1260a, hsa-miR-4446-3p, hsa-miR-3131, hsa-miR-4463, hsa-miR-3185, hsa-miR-6870-5p, hsa-miR-6779-5p, hsa-miR-1273g-3p, hsa-miR-8059, hsa-miR-4697-5p, hsa-miR-4674, hsa-miR-4433-3p, hsa-miR-4257, hsa-miR-1915-5p, hsa-miR-4417, hsa-miR-1343-5p, hsa-miR-6781-5p, hsa-miR-4695-5p, hsa-miR-1237-5p, hsa-miR-6775-5p, hsa-miR-7845-5p, hsa-miR-4746-3p, hsa-miR-7641, hsa-miR-7847-3p, hsa-miR-6806-5p, hsa-miR-4467, hsa-miR-4726-5p, hsa-miR-4648, hsa-miR-6089, hsa-miR-1260b, hsa-miR-4532, hsa-miR-5195-3p, hsa-miR-3188, hsa-miR-6848-5p, hsa-miR-1233-5p, hsa-miR-6717-5p, hsa-miR-3195, hsa-miR-6757-5p, hsa-miR-8072, hsa-miR-4745-5p, hsa-miR-6511a-5p, hsa-miR-6776-5p, hsa-miR-371a-5p, hsa-miR-1227-5p, hsa-miR-7150, hsa-miR-1915-3p, hsa-miR-187-5p, hsa-miR-614, hsa-miR-19b-3p, hsa-miR-1225-5p, hsa-miR-451a, hsa-miR-939-5p, hsa-miR-223-3p, hsa-miR-1228-5p, hsa-miR-125a-3p, hsa-miR-92b-5p, and hsa-miR-22-3p genes, and polynucleotides consisting of the nucleotide sequences of SEQ ID NOs: 1 to 134 related thereto were found.

Among them, genes newly found as markers for examining the presence or absence of lung cancer are polynucleotides consisting of the nucleotide sequences represented by SEQ ID NOs: 1 to 125, 127 to 130, and 132 to 134.

A discriminant for determining the presence or absence of lung cancer was further prepared by Fisher's discriminant analysis with the expression levels of these genes as an index. Specifically, any newly found polynucleotide consisting of a nucleotide sequence represented by any of SEQ ID NOs: 1 to 134 in the training cohort was apply for Formula 2 above to construct a discriminant. Calculated accuracy, sensitivity, and specificity are shown in Table 4. In this respect, a discriminant coefficient and a constant term are shown in Table 5.

Accuracy, sensitivity, and specificity in the validation cohort were calculated using the discriminant thus prepared, and the discriminant performance of the selected polynucleotides was validated using independent samples (Table 4). For example, the expression level measurement value of the nucleotide sequence represented by SEQ ID NO: 1 was compared between the healthy subjects (100 persons) and the lung cancer patients (17 persons) in the training cohort. As a result, the gene expression level measurement values were found to be significantly lower in the lung cancer patient group than in the healthy subject group (see FIG. 2A). These results were also reproducible for the healthy subjects (50 persons) and the lung cancer patients (8 persons) in the validation cohort (see FIG. 2B). Likewise, the results obtained about the other polynucleotides shown in SEQ ID NOs: 2 to 134 showed that the gene expression level measurement values were significantly lower (−) or higher (+) in the lung cancer patient group than in the healthy subject group (Table 3). These results were able to be validated in the validation cohort. For example, as for this nucleotide sequence represented by SEQ ID NO: 1, the number of samples that were correctly identified in the detection of lung cancer was calculated using the threshold (10.08) that was set in the training cohort and discriminated between the two groups. As a result, 7 true positives, 50 true negatives, 0 false positives, and 1 false negative were obtained. From these values, 98.3% accuracy, 87.5% sensitivity, and 100% specificity were obtained as detection performance. In this way, the detection performance was calculated as to all of the polynucleotides shown in SEQ ID NOs: 1 to 134, and described in Table 4.

For example, 33 polynucleotides consisting of the nucleotide sequences represented by SEQ ID NOs: 1, 2, 3, 5, 7, 8, 9, 10, 11, 12, 13, 14, 15, 16, 17, 18, 19, 20, 22, 26, 27, 28, 29, 33, 34, 38, 41, 42, 44, 65, 124, 125, and 133 exhibited sensitivity of 87.5%, 100%, 100%, 75%, 75%, 75%, 87.5%, 87.5%, 87.5%, 87.5%, 87.5%, 87.5%, 87.5%, 87.5%, 87.5%, 100%, 75%, 87.5%, 87.5%, 87.5%, 87.5%, 87.5%, 87.5%, 87.5%, 75%, 87.5%, 75%, 75%, 75%, 75%, 75%, 75% and 75% respectively, in the validation cohort (Table 4). In this context, the tumor markers CEA and CYFRA21-1 in blood for lung cancer reportedly have general lung cancer detection sensitivity of 69% and 43%, respectively (Non Patent Literature 3). These results demonstrated that the 33 polynucleotides consisting of the nucleotide sequences represented by SEQ ID NOs: 1, 2, 3, 5, 7, 8, 9, 10, 11, 12, 13, 14, 15, 16, 17, 18, 19, 20, 22, 26, 27, 28, 29, 33, 34, 38, 41, 42, 44, 65, 124, 125, and 133 can discriminate, each alone, lung cancer in the validation cohort with sensitivity beyond the existing markers CEA and CYFRA21-1.

For example, 10 polynucleotides consisting of the nucleotide sequences represented by SEQ ID NOs: 2, 3, 11, 13, 20, 21, 22, 30, 31, and 37 were able to correctly determine lung cancer as to all of 4 samples from lung adenocarcinoma or squamous cell cancer having a tumor size of less than 7 cm and having no lymph node metastasis, contained in the validation cohort. Thus, these polynucleotides can detect even relatively early lung cancer and contributes to the early diagnosis of lung cancer.

TABLE 3

| SEQ ID NO: | Gene name | P value after Bonferroni correction | Expression level in lung cancer patient with respect to healthy subject |
|---|---|---|---|
| 1 | hsa-miR-6768-5p | 6.71E−24 | + |
| 2 | hsa-miR-6836-3p | 1.44E−20 | − |
| 3 | hsa-miR-6782-5p | 2.89E−20 | + |
| 4 | hsa-miR-3663-3p | 2.77E−18 | − |
| 5 | hsa-miR-1908-3p | 3.58E−18 | − |
| 6 | hsa-miR-6726-5p | 1.02E−17 | − |
| 7 | hsa-miR-4258 | 3.38E−17 | − |
| 8 | hsa-miR-1343-3p | 7.45E−17 | − |
| 9 | hsa-miR-4516 | 7.91E−17 | − |
| 10 | hsa-miR-6875-5p | 3.69E−16 | + |
| 11 | hsa-miR-4651 | 5.14E−16 | − |
| 12 | hsa-miR-6825-5p | 1.28E−14 | + |
| 13 | hsa-miR-6840-3p | 2.69E−14 | − |
| 14 | hsa-miR-6780b-5p | 3.47E−14 | + |
| 15 | hsa-miR-6749-5p | 3.82E−14 | − |
| 16 | hsa-miR-8063 | 3.58E−13 | − |
| 17 | hsa-miR-6784-5p | 7.06E−13 | + |
| 18 | hsa-miR-3679-5p | 7.64E−13 | + |
| 19 | hsa-miR-3184-5p | 1.78E−12 | + |
| 20 | hsa-miR-663b | 5.72E−12 | − |
| 21 | hsa-miR-6880-5p | 9.41E−12 | + |
| 22 | hsa-miR-1908-5p | 1.84E−11 | + |
| 23 | hsa-miR-92a-2-5p | 1.85E−11 | + |
| 24 | hsa-miR-7975 | 2.06E−11 | − |
| 25 | hsa-miR-7110-5p | 2.64E−11 | + |
| 26 | hsa-miR-6842-5p | 2.66E−11 | + |
| 27 | hsa-miR-6857-5p | 5.09E−11 | + |
| 28 | hsa-miR-5572 | 7.39E−11 | + |
| 29 | hsa-miR-3197 | 8.45E−11 | + |
| 30 | hsa-miR-6131 | 1.51E−10 | − |
| 31 | hsa-miR-6889-5p | 2.73E−10 | + |
| 32 | hsa-miR-4454 | 2.92E−10 | − |
| 33 | hsa-miR-1199-5p | 6.01E−10 | − |
| 34 | hsa-miR-1247-3p | 7.10E−10 | + |
| 35 | hsa-miR-6800-5p | 8.76E−10 | + |
| 36 | hsa-miR-6872-3p | 1.18E−09 | − |
| 37 | hsa-miR-4649-5p | 1.37E−09 | − |
| 38 | hsa-miR-6791-5p | 1.51E−09 | + |
| 39 | hsa-miR-4433b-3p | 1.57E−09 | + |
| 40 | hsa-miR-3135b | 1.78E−09 | − |
| 41 | hsa-miR-128-2-5p | 2.59E−09 | + |
| 42 | hsa-miR-4675 | 2.65E−09 | − |
| 43 | hsa-miR-4472 | 3.21E−09 | + |
| 44 | hsa-miR-6785-5p | 3.84E−09 | − |
| 45 | hsa-miR-6741-5p | 6.85E−09 | − |
| 46 | hsa-miR-7977 | 8.90E−09 | − |
| 47 | hsa-miR-3665 | 2.49E−08 | − |
| 48 | hsa-miR-128-1-5p | 3.03E−08 | + |
| 49 | hsa-miR-4286 | 3.07E−08 | − |
| 50 | hsa-miR-6765-3p | 3.14E−08 | − |
| 51 | hsa-miR-4632-5p | 4.02E−08 | + |
| 52 | hsa-miR-365a-5p | 4.58E−08 | + |
| 53 | hsa-miR-6088 | 7.80E−08 | − |
| 54 | hsa-miR-6816-5p | 1.19E−07 | + |
| 55 | hsa-miR-6885-5p | 1.59E−07 | + |
| 56 | hsa-miR-711 | 1.93E−07 | + |
| 57 | hsa-miR-6765-5p | 2.99E−07 | + |
| 58 | hsa-miR-3180 | 3.65E−07 | + |
| 59 | hsa-miR-4442 | 3.89E−07 | + |
| 60 | hsa-miR-4792 | 3.97E−07 | + |
| 61 | hsa-miR-6721-5p | 6.66E−07 | + |
| 62 | hsa-miR-6798-5p | 8.81E−07 | + |
| 63 | hsa-miR-3162-5p | 1.07E−06 | + |
| 64 | hsa-miR-6126 | 1.26E−06 | + |
| 65 | hsa-miR-4758-5p | 1.35E−06 | − |
| 66 | hsa-miR-2392 | 1.58E−06 | + |
| 67 | hsa-miR-486-3p | 3.01E−06 | − |
| 68 | hsa-miR-6727-5p | 3.06E−06 | − |
| 69 | hsa-miR-4728-5p | 3.61E−06 | − |
| 70 | hsa-miR-6746-5p | 5.00E−06 | − |
| 71 | hsa-miR-4270 | 5.64E−06 | − |
| 72 | hsa-miR-3940-5p | 6.33E−06 | + |
| 73 | hsa-miR-4725-3p | 6.79E−06 | + |
| 74 | hsa-miR-7108-5p | 7.35E−06 | + |
| 75 | hsa-miR-3656 | 1.20E−05 | + |

TABLE 3-continued

| SEQ ID NO: | Gene name | P value after Bonferroni correction | Expression level in lung cancer patient with respect to healthy subject |
|---|---|---|---|
| 76 | hsa-miR-6879-5p | 1.22E−05 | + |
| 77 | hsa-miR-6738-5p | 1.25E−05 | − |
| 78 | hsa-miR-1260a | 1.51E−05 | − |
| 79 | hsa-miR-4446-3p | 1.67E−05 | − |
| 80 | hsa-miR-3131 | 1.91E−05 | − |
| 81 | hsa-miR-4463 | 2.63E−05 | + |
| 82 | hsa-miR-3185 | 3.31E−05 | + |
| 83 | hsa-miR-6870-5p | 3.95E−05 | + |
| 84 | hsa-miR-6779-5p | 4.61E−05 | − |
| 85 | hsa-miR-1273g-3p | 4.73E−05 | − |
| 86 | hsa-miR-8059 | 5.08E−05 | − |
| 87 | hsa-miR-4697-5p | 5.16E−05 | − |
| 88 | hsa-miR-4674 | 7.31E−05 | − |
| 89 | hsa-miR-4433-3p | 8.12E−05 | + |
| 90 | hsa-miR-4257 | 9.79E−05 | − |
| 91 | hsa-miR-1915-5p | 1.18E−04 | − |
| 92 | hsa-miR-4417 | 1.36E−04 | + |
| 93 | hsa-miR-1343-5p | 1.45E−04 | + |
| 94 | hsa-miR-6781-5p | 1.54E−04 | + |
| 95 | hsa-miR-4695-5p | 1.57E−04 | + |
| 96 | hsa-miR-1237-5p | 1.80E−04 | + |
| 97 | hsa-miR-6775-5p | 2.34E−04 | − |
| 98 | hsa-miR-7845-5p | 2.40E−04 | + |
| 99 | hsa-miR-4746-3p | 2.62E−04 | + |
| 100 | hsa-miR-7641 | 4.57E−04 | − |
| 101 | hsa-miR-7847-3p | 5.01E−04 | − |
| 102 | hsa-miR-6806-5p | 5.86E−04 | − |
| 103 | hsa-miR-4467 | 6.28E−04 | + |
| 104 | hsa-miR-4726-5p | 6.35E−04 | − |
| 105 | hsa-miR-4648 | 6.87E−04 | + |
| 106 | hsa-miR-6089 | 8.08E−04 | + |
| 107 | hsa-miR-1260b | 8.29E−04 | − |
| 108 | hsa-miR-4532 | 8.69E−04 | − |
| 109 | hsa-miR-5195-3p | 1.02E−03 | − |
| 110 | hsa-miR-3188 | 1.12E−03 | + |
| 111 | hsa-miR-6848-5p | 1.36E−03 | + |
| 112 | hsa-miR-1233-5p | 1.41E−03 | − |
| 113 | hsa-miR-6717-5p | 1.63E−03 | + |
| 114 | hsa-miR-3195 | 1.95E−03 | + |
| 115 | hsa-miR-6757-5p | 2.65E−03 | − |
| 116 | hsa-miR-8072 | 3.49E−03 | + |
| 117 | hsa-miR-4745-5p | 4.17E−03 | − |
| 118 | hsa-miR-6511a-5p | 4.77E−03 | − |
| 119 | hsa-miR-6776-5p | 5.08E−03 | + |
| 120 | hsa-miR-371a-5p | 6.92E−03 | − |
| 121 | hsa-miR-1227-5p | 7.47E−03 | + |
| 122 | hsa-miR-7150 | 8.50E−03 | + |
| 123 | hsa-miR-1915-3p | 9.50E−03 | + |
| 124 | hsa-miR-187-5p | 1.56E−18 | − |
| 125 | hsa-miR-614 | 2.22E−14 | − |
| 126 | hsa-miR-19b-3p | 1.77E−13 | + |
| 127 | hsa-miR-1225-5p | 2.30E−08 | + |
| 128 | hsa-miR-451a | 5.96E−08 | + |
| 129 | hsa-miR-939-5p | 1.29E−07 | + |
| 130 | hsa-miR-223-3p | 4.79E−06 | + |
| 131 | hsa-miR-1228-5p | 5.66E−06 | + |
| 132 | hsa-miR-125a-3p | 1.47E−04 | − |
| 133 | hsa-miR-92b-5p | 2.51E−04 | + |
| 134 | hsa-miR-22-3p | 6.49E−04 | + |

Example 2

<Method for Evaluating Lung Cancer Discriminant Performance by Combination of Multiple Gene Markers Using Samples in the Validation Cohort>

In this Example, a method for evaluating lung cancer discriminant performance by a combination of the gene markers selected in Example 1 was studied. Specifically, Fisher's discriminant analysis was conducted as to 8,910 combinations of two polynucleotides comprising at least one or more of the expression level measurement values of any of the newly found polynucleotides consisting of the nucleotide sequences represented by SEQ ID NOs: 1 to 125, 127 to 130, and 132 to 134 among the polynucleotides consisting of the nucleotide sequences represented by SEQ ID NOs: 1 to 134 selected in Example 1, to construct a discriminant for determining the presence or absence of lung cancer. Next, accuracy, sensitivity, and specificity in the validation cohort were calculated using the discriminant thus prepared, and the discriminant performance of the selected polynucleotides was validated using the independent samples.

For example, the expression level measurement values of the nucleotide sequences represented by SEQ ID NO: 1 and SEQ ID NO: 2 were compared between the healthy subjects (100 persons) and the lung cancer patients (17 persons) in the training cohort. As a result, a scatter diagram that significantly separated the gene expression level measurement values of the lung cancer patient group from those of the healthy subject group was obtained (see FIG. 3A). These results were also reproducible for the healthy subjects (50 persons) and the lung cancer patients (8 persons) in the validation cohort (see FIG. 3B). Likewise, a scatter diagram that significantly separated the gene expression level measurement values of the lung cancer patient group from those of the healthy subject group was also obtained as to the other combinations of two expression level measurement values comprising at least one or more of the expression level measurement values of any of the newly found polynucleotides consisting of the nucleotide sequences represented by SEQ ID NOs: 1 to 125, 127 to 130, and 132 to 134 among the polynucleotides consisting of the nucleotide sequences represented by SEQ ID NOs: 1 to 134. These results were able to be validated in the validation cohort. For example, as for these nucleotide sequences represented by SEQ ID NO: 1 and SEQ ID NO: 2, the number of samples that correctly identified in the detection of lung cancer was calculated using the function (0=−1.42x+y+4.7) that was set in the training cohort and discriminated between the two groups. As a result, 7 true positives, 50 true negatives, 0 false positives, and 1 false negative were obtained. From these values, 98.3% accuracy, 87.5% sensitivity, and 100% specificity were obtained as detection performance. In this way, the detection performance was calculated as to all of the combinations of two expression level measurement values comprising at least one or more of the expression level measurement values of any of the newly found polynucleotides consisting of the nucleotide sequences represented by SEQ ID NOs: 1 to 125, 127 to 130, and 132 to 134 among the polynucleotides consisting of the nucleotide sequences represented by SEQ ID NOs: 1 to 134. Among them, 133 combinations comprising the expression level measurement value of the polynucleotide consisting of the nucleotide sequence represented by SEQ ID NO: 1 and the detection performance thereof were described in Table 6 as an example. For example, all of 9 combinations of the expression level measurement values of the polynucleotides consisting of the nucleotide sequences represented by SEQ ID NOs: 1 and 6, SEQ ID NOs: 1 and 11, SEQ ID NOs: 1 and 19, SEQ ID NOs: 1 and 34, SEQ ID NOs: 1 and 38, SEQ ID NOs: 1 and 52, SEQ ID NOs: 1 and 53, SEQ ID NOs: 1 and 56, and SEQ ID NOs: 1 and 113 exhibited sensitivity of 100% in the validation cohort. Likewise, all of the 133 combinations of two polynucleotides consisting of the nucleotide sequence represented by SEQ ID NO: 1 and a nucleotide sequence represented by any of SEQ ID NOs: 2 to 134 exhibited sensitivity of 75% or higher. These values of sensitivity were higher than the sensitivity of the existing tumor markers CEA (69%) and CYFRA21-1 (43%) in blood (Non Patent Literature 3). Likewise, 5,742 combinations of the measurement values of the polynucleotides having sensitivity beyond the existing markers CEA and CYFRA21-1 were obtained in the validation cohort. All of the nucleotide sequences 1 to 134 described in Table 3 obtained in Example 1 were employed at least once in these combinations. Thus, the combinations of two of the polynucleotides that consist of the nucleotide sequences represented by SEQ ID NOs: 1 to 134 also produced excellent lung cancer detection sensitivity.

Markers for the detection of lung cancer with better sensitivity are obtained by further combining 3, 4, 5, 6, 7, 8, 9, 10 or more of the expression level measurement values of the polynucleotides consisting of the nucleotide sequences represented by SEQ ID NOs: 1 to 134. For example, the polynucleotides consisting of the nucleotide sequences represented by SEQ ID NOs: 1 to 134 selected in Example 1 were measured to obtain their expression levels between the healthy subject group and the lung cancer group in the validation cohort. All of the polynucleotides were ranked in the descending order of their P values based on the Student's t-test which indicates statistical significance of difference between groups (i.e., one having the lowest P value was ranked in the first place), and lung cancer detection sensitivity was evaluated using combinations of one or more polynucleotides to which the polynucleotides were added one by one from the top to the bottom according to the rank. In short, the order in which the polynucleotides were combined in this evaluation is in reverse in terms of SEQ ID NOs from SEQ ID NO: 134 to SEQ ID NOs: 133, 132, . . . shown in Table 3. As a result, the sensitivity in the validation cohort was 62.5% for 1 polynucleotide (SEQ ID NO: 134), 75% for 3 polynucleotides (SEQ ID NOs: 132 to 134), 87.5% for 5 polynucleotides (SEQ ID NOs: 130 to 134), 100% for 6 polynucleotides (SEQ ID NOs: 129 to 134), 100% for 10 polynucleotides (SEQ ID NOs: 125 to 134), 100% for 20 polynucleotides (SEQ ID NOs: 115 to 134), 100% for 30 polynucleotides (SEQ ID NOs: 105 to 134), 100% for 50 polynucleotides (SEQ ID NOs: 85 to 134), 100% for 80 polynucleotides (SEQ ID NOs: 55 to 134), 100% for 120 polynucleotides (SEQ ID NOs: 15 to 134), and 100% for 134 polynucleotides (SEQ ID NOs: 1 to 134).

These results demonstrated that a combination of multiple polynucleotides can produce higher lung cancer discriminant performance than that of each polynucleotide alone or a combination of a fewer number of polynucleotides. In this context, the combinations of multiple polynucleotides are not limited to the combinations of the polynucleotides added in the order of statistically significant difference as described above, and any combination of multiple polynucleotides can be used in the detection of lung cancer.

From these results, it can be concluded that all of the polynucleotides consisting of the nucleotide sequences represented by SEQ ID NOs: 1 to 134 serve as excellent markers for the detection of lung cancer.

TABLE 4

| SEQ ID NO: | Training cohort | | | Validation cohort | | |
|---|---|---|---|---|---|---|
| | Accuracy (%) | Sensitivity (%) | Specificity (%) | Accuracy (%) | Sensitivity (%) | Specificity (%) |
| 1 | 97.4 | 94.1 | 98 | 98.3 | 87.5 | 100 |
| 2 | 94.9 | 82.4 | 97 | 100 | 100 | 100 |
| 3 | 97.4 | 82.4 | 100 | 96.6 | 100 | 96 |
| 4 | 94 | 70.6 | 98 | 93.1 | 62.5 | 98 |
| 5 | 95.7 | 76.5 | 99 | 96.6 | 75 | 100 |
| 6 | 92.3 | 64.7 | 97 | 93.1 | 62.5 | 98 |
| 7 | 94.9 | 76.5 | 98 | 94.8 | 75 | 98 |
| 8 | 94.9 | 94.1 | 95 | 94.8 | 75 | 98 |
| 9 | 97.4 | 82.4 | 100 | 98.3 | 87.5 | 100 |
| 10 | 96.6 | 82.4 | 99 | 91.4 | 87.5 | 92 |
| 11 | 94.9 | 76.5 | 98 | 96.6 | 87.5 | 98 |
| 12 | 96.6 | 88.2 | 98 | 93.1 | 87.5 | 94 |
| 13 | 92.3 | 64.7 | 97 | 94.8 | 87.5 | 96 |
| 14 | 92.3 | 70.6 | 96 | 98.3 | 87.5 | 100 |
| 15 | 95.7 | 82.4 | 98 | 98.3 | 87.5 | 100 |
| 16 | 91.5 | 76.5 | 94 | 94.8 | 87.5 | 96 |
| 17 | 94 | 82.4 | 96 | 93.1 | 87.5 | 94 |
| 18 | 94.9 | 70.6 | 99 | 100 | 100 | 100 |
| 19 | 89.7 | 64.7 | 94 | 93.1 | 75 | 96 |
| 20 | 93.2 | 58.8 | 99 | 98.3 | 87.5 | 100 |
| 21 | 93.2 | 64.7 | 98 | 93.1 | 62.5 | 98 |
| 22 | 91.5 | 64.7 | 96 | 94.8 | 87.5 | 96 |
| 23 | 94 | 70.6 | 98 | 87.9 | 37.5 | 96 |
| 24 | 93.2 | 58.8 | 99 | 91.4 | 50 | 98 |
| 25 | 89.7 | 64.7 | 94 | 91.4 | 62.5 | 96 |
| 26 | 93.2 | 64.7 | 98 | 94.8 | 87.5 | 96 |
| 27 | 93.2 | 76.5 | 96 | 94.8 | 87.5 | 96 |
| 28 | 92.3 | 82.4 | 94 | 93.1 | 87.5 | 94 |
| 29 | 89.7 | 52.9 | 96 | 96.6 | 87.5 | 98 |
| 30 | 89.7 | 35.3 | 99 | 93.1 | 62.5 | 98 |
| 31 | 90.6 | 47.1 | 98 | 94.8 | 62.5 | 100 |
| 32 | 93.2 | 58.8 | 99 | 91.4 | 50 | 98 |
| 33 | 92.3 | 64.7 | 97 | 96.6 | 87.5 | 98 |
| 34 | 89.7 | 41.2 | 98 | 93.1 | 75 | 96 |
| 35 | 89.7 | 52.9 | 96 | 93.1 | 50 | 100 |
| 36 | 92.3 | 64.7 | 97 | 89.7 | 50 | 96 |
| 37 | 88.9 | 41.2 | 97 | 93.1 | 50 | 100 |
| 38 | 87.2 | 47.1 | 94 | 96.6 | 87.5 | 98 |
| 39 | 90.6 | 58.8 | 96 | 84.5 | 50 | 90 |
| 40 | 91.5 | 47.1 | 99 | 91.4 | 37.5 | 100 |
| 41 | 91.5 | 52.9 | 98 | 96.6 | 75 | 100 |
| 42 | 90.6 | 47.1 | 98 | 96.6 | 75 | 100 |
| 43 | 94 | 64.7 | 99 | 91.4 | 50 | 98 |
| 44 | 88 | 47.1 | 95 | 93.1 | 75 | 96 |
| 45 | 91.5 | 47.1 | 99 | 87.9 | 37.5 | 96 |
| 46 | 89.7 | 47.1 | 97 | 87.9 | 50 | 94 |
| 47 | 92.3 | 52.9 | 99 | 93.1 | 50 | 100 |
| 48 | 88 | 41.2 | 96 | 87.9 | 62.5 | 92 |
| 49 | 87.2 | 41.2 | 95 | 89.7 | 62.5 | 94 |
| 50 | 88.9 | 47.1 | 96 | 87.9 | 37.5 | 96 |
| 51 | 92.3 | 47.1 | 100 | 94.8 | 62.5 | 100 |
| 52 | 91.5 | 47.1 | 99 | 94.8 | 62.5 | 100 |
| 53 | 91.5 | 47.1 | 99 | 91.4 | 62.5 | 96 |
| 54 | 86.3 | 41.2 | 94 | 94.8 | 62.5 | 100 |
| 55 | 90.6 | 41.2 | 99 | 94.8 | 62.5 | 100 |
| 56 | 90.6 | 58.8 | 96 | 94.8 | 62.5 | 100 |
| 57 | 91.5 | 52.9 | 98 | 93.1 | 62.5 | 98 |
| 58 | 88.9 | 35.3 | 98 | 93.1 | 62.5 | 98 |
| 59 | 86.3 | 41.2 | 94 | 87.9 | 50 | 94 |
| 60 | 89.7 | 47.1 | 97 | 89.7 | 37.5 | 98 |
| 61 | 90.6 | 52.9 | 97 | 86.2 | 37.5 | 94 |
| 62 | 87.2 | 29.4 | 97 | 87.9 | 62.5 | 92 |
| 63 | 88.9 | 41.2 | 97 | 82.8 | 0 | 96 |
| 64 | 89.7 | 35.3 | 99 | 93.1 | 50 | 100 |
| 65 | 89.7 | 41.2 | 98 | 94.8 | 75 | 98 |
| 66 | 89.7 | 29.4 | 100 | 91.4 | 37.5 | 100 |
| 67 | 90.6 | 41.2 | 99 | 94.8 | 62.5 | 100 |
| 68 | 88 | 47.1 | 95 | 87.9 | 25 | 98 |
| 69 | 88 | 35.3 | 97 | 91.4 | 50 | 98 |
| 70 | 87.2 | 41.2 | 95 | 86.2 | 25 | 96 |
| 71 | 88 | 35.3 | 97 | 84.5 | 25 | 94 |
| 72 | 88 | 23.5 | 99 | 89.7 | 37.5 | 98 |
| 73 | 88 | 35.3 | 97 | 86.2 | 12.5 | 98 |
| 74 | 89.7 | 35.3 | 99 | 87.9 | 37.5 | 96 |
| 75 | 88 | 41.2 | 96 | 93.1 | 62.5 | 98 |
| 76 | 89.7 | 35.3 | 99 | 94.8 | 62.5 | 100 |
| 77 | 88.9 | 35.3 | 98 | 87.9 | 37.5 | 96 |
| 78 | 88 | 35.3 | 97 | 87.9 | 50 | 94 |
| 79 | 88.9 | 29.4 | 99 | 93.1 | 50 | 100 |

TABLE 4-continued

| SEQ ID NO: | Training cohort | | | Validation cohort | | |
|---|---|---|---|---|---|---|
| | Accuracy (%) | Sensitivity (%) | Specificity (%) | Accuracy (%) | Sensitivity (%) | Specificity (%) |
| 80 | 88.9 | 29.4 | 99 | 87.9 | 25 | 98 |
| 81 | 88 | 23.5 | 99 | 87.9 | 12.5 | 100 |
| 82 | 83.8 | 11.8 | 96 | 87.9 | 37.5 | 96 |
| 83 | 88.9 | 23.5 | 100 | 87.9 | 12.5 | 100 |
| 84 | 87.2 | 23.5 | 98 | 87.9 | 12.5 | 100 |
| 85 | 89.7 | 47.1 | 97 | 94.8 | 62.5 | 100 |
| 86 | 87.2 | 29.4 | 97 | 86.2 | 12.5 | 98 |
| 87 | 88 | 23.5 | 99 | 86.2 | 37.5 | 94 |
| 88 | 85.5 | 29.4 | 95 | 91.4 | 37.5 | 100 |
| 89 | 87.2 | 29.4 | 97 | 86.2 | 25 | 96 |
| 90 | 88.9 | 35.3 | 98 | 87.9 | 50 | 94 |
| 91 | 89.7 | 41.2 | 98 | 91.4 | 62.5 | 96 |
| 92 | 86.3 | 23.5 | 97 | 84.5 | 12.5 | 96 |
| 93 | 89.7 | 41.2 | 98 | 94.8 | 62.5 | 100 |
| 94 | 87.2 | 17.6 | 99 | 81 | 0 | 94 |
| 95 | 89.7 | 41.2 | 98 | 94.8 | 62.5 | 100 |
| 96 | 87.2 | 29.4 | 97 | 89.7 | 37.5 | 98 |
| 97 | 86.3 | 17.6 | 98 | 81 | 0 | 94 |
| 98 | 89.7 | 35.3 | 99 | 87.9 | 37.5 | 96 |
| 99 | 87.2 | 17.6 | 99 | 94.8 | 62.5 | 100 |
| 100 | 84.5 | 18.8 | 95 | 86.2 | 25 | 96 |
| 101 | 83.8 | 11.8 | 96 | 84.5 | 0 | 98 |
| 102 | 86.3 | 5.9 | 100 | 91.4 | 37.5 | 100 |
| 103 | 83.8 | 11.8 | 96 | 86.2 | 12.5 | 98 |
| 104 | 84.6 | 17.6 | 96 | 86.2 | 25 | 96 |
| 105 | 85.5 | 11.8 | 98 | 89.7 | 25 | 100 |
| 106 | 89.7 | 41.2 | 98 | 89.7 | 37.5 | 98 |
| 107 | 87.2 | 23.5 | 98 | 91.4 | 50 | 98 |
| 108 | 88 | 23.5 | 99 | 91.4 | 37.5 | 100 |
| 109 | 87.2 | 17.6 | 99 | 87.9 | 25 | 98 |
| 110 | 86.3 | 23.5 | 97 | 89.7 | 25 | 100 |
| 111 | 85.5 | 11.8 | 98 | 86.2 | 25 | 96 |
| 112 | 86.3 | 17.6 | 98 | 86.2 | 0 | 100 |
| 113 | 84.6 | 23.5 | 95 | 89.7 | 25 | 100 |
| 114 | 86.3 | 23.5 | 97 | 84.5 | 25 | 94 |
| 115 | 82.9 | 0 | 97 | 89.7 | 25 | 100 |
| 116 | 88 | 23.5 | 99 | 89.7 | 25 | 100 |
| 117 | 88 | 17.6 | 100 | 89.7 | 25 | 100 |
| 118 | 84.6 | 11.8 | 97 | 86.2 | 0 | 100 |
| 119 | 85.5 | 5.9 | 99 | 89.7 | 25 | 100 |
| 120 | 84.6 | 0 | 99 | 84.5 | 0 | 98 |
| 121 | 88.9 | 23.5 | 100 | 87.9 | 12.5 | 100 |
| 122 | 88 | 17.6 | 100 | 89.7 | 25 | 100 |
| 123 | 84.6 | 5.9 | 98 | 94.8 | 62.5 | 100 |
| 124 | 99.1 | 94.1 | 100 | 96.6 | 75 | 100 |
| 125 | 94 | 76.5 | 97 | 93.1 | 75 | 96 |
| 126 | 95.7 | 82.4 | 98 | 93.1 | 62.5 | 98 |
| 127 | 89.7 | 52.9 | 96 | 93.1 | 50 | 100 |
| 128 | 93.2 | 58.8 | 99 | 89.7 | 37.5 | 98 |
| 129 | 91.5 | 58.8 | 97 | 86.2 | 50 | 92 |
| 130 | 94 | 58.8 | 100 | 94.8 | 62.5 | 100 |
| 131 | 84.6 | 17.6 | 96 | 87.9 | 25 | 98 |
| 132 | 89.7 | 35.3 | 99 | 89.7 | 25 | 100 |
| 133 | 89.7 | 35.3 | 99 | 96.6 | 75 | 100 |
| 134 | 87.2 | 23.5 | 98 | 86.2 | 12.5 | 98 |

TABLE 5

| SEQ ID NO: | Discriminant coefficient | Constant term |
|---|---|---|
| 1 | 3.665 | 36.958 |
| 2 | 3.482 | 28.279 |
| 3 | 3.305 | 21.564 |
| 4 | 3.967 | 46.907 |
| 5 | 2.921 | 18.418 |
| 6 | 3.258 | 31.351 |
| 7 | 2.321 | 19.901 |
| 8 | 2.482 | 17.979 |
| 9 | 5.340 | 69.250 |
| 10 | 3.780 | 34.781 |
| 11 | 6.053 | 65.389 |
| 12 | 2.169 | 14.787 |
| 13 | 3.363 | 28.960 |
| 14 | 3.278 | 29.867 |
| 15 | 4.768 | 47.106 |
| 16 | 2.668 | 21.511 |
| 17 | 3.933 | 49.822 |
| 18 | 2.781 | 19.688 |
| 19 | 2.340 | 19.400 |
| 20 | 3.173 | 27.138 |
| 21 | 2.395 | 19.027 |
| 22 | 4.481 | 51.987 |
| 23 | 1.923 | 18.732 |
| 24 | 2.221 | 21.483 |
| 25 | 1.879 | 15.097 |
| 26 | 3.449 | 21.201 |
| 27 | 1.940 | 10.546 |
| 28 | 2.467 | 16.896 |
| 29 | 3.381 | 32.369 |
| 30 | 1.883 | 19.278 |
| 31 | 2.995 | 22.556 |
| 32 | 2.257 | 25.609 |
| 33 | 2.593 | 16.685 |
| 34 | 4.054 | 25.898 |
| 35 | 4.316 | 37.567 |
| 36 | 2.347 | 13.660 |
| 37 | 2.787 | 28.233 |
| 38 | 4.929 | 45.747 |
| 39 | 3.956 | 32.281 |
| 40 | 2.822 | 21.631 |
| 41 | 2.892 | 30.757 |
| 42 | 3.016 | 22.359 |
| 43 | 2.179 | 11.954 |
| 44 | 2.956 | 26.296 |
| 45 | 4.228 | 28.830 |
| 46 | 2.347 | 22.562 |
| 47 | 7.619 | 102.957 |
| 48 | 2.849 | 21.598 |
| 49 | 2.506 | 18.167 |
| 50 | 1.885 | 16.130 |
| 51 | 4.534 | 36.471 |
| 52 | 3.307 | 19.440 |
| 53 | 3.370 | 33.776 |
| 54 | 4.473 | 45.416 |
| 55 | 3.058 | 33.429 |
| 56 | 4.044 | 33.691 |
| 57 | 4.924 | 52.340 |
| 58 | 4.740 | 41.821 |
| 59 | 3.556 | 33.458 |
| 60 | 2.051 | 13.913 |
| 61 | 4.118 | 31.479 |
| 62 | 2.848 | 30.006 |
| 63 | 2.967 | 23.118 |
| 64 | 3.094 | 33.898 |
| 65 | 6.747 | 57.639 |
| 66 | 3.115 | 18.546 |
| 67 | 2.952 | 23.150 |
| 68 | 6.267 | 79.386 |
| 69 | 5.244 | 36.656 |
| 70 | 3.634 | 23.502 |
| 71 | 5.682 | 45.289 |
| 72 | 4.756 | 58.458 |
| 73 | 3.941 | 38.866 |
| 74 | 4.639 | 42.673 |
| 75 | 4.686 | 54.180 |
| 76 | 3.379 | 28.223 |
| 77 | 3.897 | 27.668 |
| 78 | 2.497 | 17.033 |
| 79 | 2.622 | 18.728 |
| 80 | 2.639 | 18.344 |
| 81 | 4.764 | 52.837 |
| 82 | 2.582 | 18.301 |
| 83 | 3.517 | 26.318 |
| 84 | 6.525 | 46.333 |
| 85 | 2.880 | 21.133 |
| 86 | 3.254 | 24.541 |
| 87 | 4.996 | 39.036 |

TABLE 5-continued

| SEQ ID NO: | Discriminant coefficient | Constant term |
|---|---|---|
| 88 | 3.508 | 36.118 |
| 89 | 3.944 | 29.161 |
| 90 | 3.193 | 21.619 |
| 91 | 1.406 | 8.631 |
| 92 | 5.754 | 47.280 |
| 93 | 3.850 | 40.213 |
| 94 | 5.850 | 61.192 |
| 95 | 4.464 | 33.686 |
| 96 | 4.601 | 58.630 |
| 97 | 6.817 | 56.624 |
| 98 | 3.273 | 21.990 |
| 99 | 2.934 | 19.283 |
| 100 | 1.405 | 10.220 |
| 101 | 3.974 | 25.352 |
| 102 | 3.294 | 21.365 |
| 103 | 2.273 | 22.405 |
| 104 | 4.014 | 26.327 |
| 105 | 1.371 | 8.370 |
| 106 | 5.947 | 79.958 |
| 107 | 2.441 | 20.646 |
| 108 | 3.287 | 38.733 |
| 109 | 3.026 | 20.705 |
| 110 | 3.417 | 20.796 |
| 111 | 5.205 | 38.779 |
| 112 | 2.897 | 32.216 |
| 113 | 2.584 | 17.226 |
| 114 | 3.934 | 32.685 |
| 115 | 3.076 | 22.309 |
| 116 | 5.228 | 64.304 |
| 117 | 2.180 | 25.963 |
| 118 | 2.566 | 14.847 |
| 119 | 3.282 | 19.125 |
| 120 | 3.663 | 26.980 |
| 121 | 6.563 | 62.775 |
| 122 | 4.018 | 31.312 |
| 123 | 4.220 | 46.687 |
| 124 | 2.174 | 20.711 |
| 125 | 1.889 | 11.995 |
| 126 | 1.102 | 5.734 |
| 127 | 3.626 | 27.002 |
| 128 | 0.979 | 9.798 |
| 129 | 2.534 | 19.444 |
| 130 | 1.051 | 6.668 |
| 131 | 3.974 | 47.286 |
| 132 | 1.456 | 9.155 |
| 133 | 3.272 | 26.342 |
| 134 | 1.514 | 8.925 |

TABLE 6

| SEQ ID NO: | Training set | | | Validation set | | |
|---|---|---|---|---|---|---|
| | Accuracy (%) | Sensitivity (%) | Specificity (%) | Accuracy (%) | Sensitivity (%) | Specificity (%) |
| 1_2 | 98.3 | 94.1 | 99 | 98.3 | 87.5 | 100 |
| 1_3 | 100 | 100 | 100 | 98.3 | 87.5 | 100 |
| 1_4 | 97.4 | 88.2 | 99 | 98.3 | 87.5 | 100 |
| 1_5 | 99.1 | 100 | 99 | 98.3 | 87.5 | 100 |
| 1_6 | 99.1 | 100 | 99 | 100 | 100 | 100 |
| 1_7 | 99.1 | 100 | 99 | 98.3 | 87.5 | 100 |
| 1_8 | 98.3 | 94.1 | 99 | 98.3 | 87.5 | 100 |
| 1_9 | 99.1 | 100 | 99 | 98.3 | 87.5 | 100 |
| 1_10 | 100 | 100 | 100 | 98.3 | 87.5 | 100 |
| 1_11 | 98.3 | 100 | 98 | 100 | 100 | 100 |
| 1_12 | 98.3 | 100 | 98 | 98.3 | 87.5 | 100 |
| 1_13 | 98.3 | 100 | 98 | 98.3 | 87.5 | 100 |
| 1_14 | 100 | 100 | 100 | 98.3 | 87.5 | 100 |
| 1_15 | 98.3 | 100 | 98 | 98.3 | 87.5 | 100 |
| 1_16 | 99.1 | 100 | 99 | 98.3 | 87.5 | 100 |
| 1_17 | 98.3 | 100 | 98 | 98.3 | 87.5 | 100 |
| 1_18 | 99.1 | 100 | 99 | 98.3 | 87.5 | 100 |
| 1_19 | 99.1 | 100 | 99 | 100 | 100 | 100 |
| 1_20 | 98.3 | 94.1 | 99 | 98.3 | 87.5 | 100 |
| 1_21 | 98.3 | 94.1 | 99 | 96.6 | 87.5 | 98 |
| 1_22 | 98.3 | 100 | 98 | 98.3 | 87.5 | 100 |
| 1_23 | 97.4 | 94.1 | 98 | 98.3 | 87.5 | 100 |
| 1_24 | 97.4 | 94.1 | 98 | 98.3 | 87.5 | 100 |
| 1_25 | 98.3 | 100 | 98 | 98.3 | 87.5 | 100 |
| 1_26 | 99.1 | 100 | 99 | 96.6 | 87.5 | 98 |
| 1_27 | 98.3 | 100 | 98 | 98.3 | 87.5 | 100 |
| 1_28 | 98.3 | 100 | 98 | 98.3 | 87.5 | 100 |
| 1_29 | 98.3 | 94.1 | 99 | 98.3 | 87.5 | 100 |
| 1_30 | 97.4 | 94.1 | 98 | 98.3 | 87.5 | 100 |
| 1_31 | 98.3 | 100 | 98 | 98.3 | 87.5 | 100 |
| 1_32 | 97.4 | 94.1 | 98 | 96.6 | 75 | 100 |
| 1_33 | 98.3 | 94.1 | 99 | 98.3 | 87.5 | 100 |
| 1_34 | 99.1 | 100 | 99 | 100 | 100 | 100 |
| 1_35 | 98.3 | 100 | 98 | 98.3 | 87.5 | 100 |
| 1_36 | 97.4 | 94.1 | 98 | 96.6 | 75 | 100 |
| 1_37 | 98.3 | 100 | 98 | 98.3 | 87.5 | 100 |
| 1_38 | 98.3 | 100 | 98 | 100 | 100 | 100 |
| 1_39 | 97.4 | 94.1 | 98 | 98.3 | 87.5 | 100 |
| 1_40 | 98.3 | 100 | 98 | 96.6 | 75 | 100 |
| 1_41 | 98.3 | 100 | 98 | 98.3 | 87.5 | 100 |
| 1_42 | 98.3 | 100 | 98 | 98.3 | 87.5 | 100 |
| 1_43 | 97.4 | 94.1 | 98 | 98.3 | 87.5 | 100 |
| 1_44 | 97.4 | 94.1 | 98 | 98.3 | 87.5 | 100 |
| 1_45 | 97.4 | 94.1 | 98 | 98.3 | 87.5 | 100 |
| 1_46 | 96.6 | 88.2 | 98 | 96.6 | 75 | 100 |
| 1_47 | 98.3 | 100 | 98 | 98.3 | 87.5 | 100 |
| 1_48 | 99.1 | 100 | 99 | 98.3 | 87.5 | 100 |
| 1_49 | 97.4 | 94.1 | 98 | 96.6 | 75 | 100 |
| 1_50 | 97.4 | 94.1 | 98 | 96.6 | 75 | 100 |
| 1_51 | 99.1 | 100 | 99 | 98.3 | 87.5 | 100 |
| 1_52 | 99.1 | 100 | 99 | 100 | 100 | 100 |
| 1_53 | 99.1 | 100 | 99 | 100 | 100 | 100 |
| 1_54 | 98.3 | 100 | 98 | 98.3 | 87.5 | 100 |
| 1_55 | 98.3 | 100 | 98 | 98.3 | 87.5 | 100 |
| 1_56 | 100 | 100 | 100 | 100 | 100 | 100 |
| 1_57 | 98.3 | 100 | 98 | 98.3 | 87.5 | 100 |
| 1_58 | 98.3 | 100 | 98 | 98.3 | 87.5 | 100 |
| 1_59 | 98.3 | 100 | 98 | 98.3 | 87.5 | 100 |
| 1_60 | 97.4 | 94.1 | 98 | 98.3 | 87.5 | 100 |
| 1_61 | 98.3 | 100 | 98 | 98.3 | 87.5 | 100 |
| 1_62 | 97.4 | 94.1 | 98 | 98.3 | 87.5 | 100 |
| 1_63 | 98.3 | 100 | 98 | 98.3 | 87.5 | 100 |
| 1_64 | 98.3 | 100 | 98 | 98.3 | 87.5 | 100 |
| 1_65 | 97.4 | 94.1 | 98 | 98.3 | 87.5 | 100 |
| 1_66 | 98.3 | 100 | 98 | 98.3 | 87.5 | 100 |
| 1_67 | 98.3 | 100 | 98 | 98.3 | 87.5 | 100 |
| 1_68 | 98.3 | 100 | 98 | 98.3 | 87.5 | 100 |
| 1_69 | 97.4 | 94.1 | 98 | 98.3 | 87.5 | 100 |
| 1_70 | 97.4 | 94.1 | 98 | 98.3 | 87.5 | 100 |
| 1_71 | 97.4 | 94.1 | 98 | 98.3 | 87.5 | 100 |
| 1_72 | 97.4 | 94.1 | 98 | 98.3 | 87.5 | 100 |
| 1_73 | 98.3 | 94.1 | 99 | 98.3 | 87.5 | 100 |
| 1_74 | 98.3 | 100 | 98 | 98.3 | 87.5 | 100 |
| 1_75 | 97.4 | 100 | 97 | 98.3 | 87.5 | 100 |
| 1_76 | 99.1 | 94.1 | 100 | 98.3 | 87.5 | 100 |
| 1_77 | 97.4 | 94.1 | 98 | 98.3 | 87.5 | 100 |
| 1_78 | 97.4 | 94.1 | 98 | 98.3 | 87.5 | 100 |
| 1_79 | 97.4 | 94.1 | 98 | 98.3 | 87.5 | 100 |
| 1_80 | 98.3 | 94.1 | 99 | 98.3 | 87.5 | 100 |
| 1_81 | 97.4 | 94.1 | 98 | 98.3 | 87.5 | 100 |
| 1_82 | 99.1 | 100 | 99 | 98.3 | 87.5 | 100 |
| 1_83 | 98.3 | 100 | 98 | 98.3 | 87.5 | 100 |
| 1_84 | 98.3 | 100 | 98 | 98.3 | 87.5 | 100 |
| 1_85 | 97.4 | 88.2 | 99 | 98.3 | 87.5 | 100 |
| 1_86 | 97.4 | 94.1 | 98 | 98.3 | 87.5 | 100 |
| 1_87 | 98.3 | 100 | 98 | 98.3 | 87.5 | 100 |
| 1_88 | 98.3 | 100 | 98 | 98.3 | 87.5 | 100 |
| 1_89 | 97.4 | 94.1 | 98 | 98.3 | 87.5 | 100 |
| 1_90 | 97.4 | 94.1 | 98 | 98.3 | 87.5 | 100 |
| 1_91 | 98.3 | 94.1 | 99 | 98.3 | 87.5 | 100 |
| 1_92 | 97.4 | 94.1 | 98 | 98.3 | 87.5 | 100 |
| 1_93 | 98.3 | 100 | 98 | 98.3 | 87.5 | 100 |

TABLE 6-continued

| SEQ ID NO: | Training set | | | Validation set | | |
|---|---|---|---|---|---|---|
| | Accuracy (%) | Sensitivity (%) | Specificity (%) | Accuracy (%) | Sensitivity (%) | Specificity (%) |
| 1_94 | 98.3 | 100 | 98 | 98.3 | 87.5 | 100 |
| 1_95 | 98.3 | 94.1 | 99 | 98.3 | 87.5 | 100 |
| 1_96 | 98.3 | 100 | 98 | 98.3 | 87.5 | 100 |
| 1_97 | 97.4 | 94.1 | 98 | 98.3 | 87.5 | 100 |
| 1_98 | 98.3 | 94.1 | 99 | 98.3 | 87.5 | 100 |
| 1_99 | 98.3 | 100 | 98 | 98.3 | 87.5 | 100 |
| 1_100 | 99.1 | 100 | 99 | 98.3 | 87.5 | 100 |
| 1_101 | 97.4 | 94.1 | 98 | 98.3 | 87.5 | 100 |
| 1_102 | 97.4 | 94.1 | 98 | 98.3 | 87.5 | 100 |
| 1_103 | 99.1 | 100 | 99 | 98.3 | 87.5 | 100 |
| 1_104 | 97.4 | 94.1 | 98 | 98.3 | 87.5 | 100 |
| 1_105 | 97.4 | 94.1 | 98 | 98.3 | 87.5 | 100 |
| 1_106 | 98.3 | 94.1 | 99 | 98.3 | 87.5 | 100 |
| 1_107 | 96.6 | 88.2 | 98 | 96.6 | 75 | 100 |
| 1_108 | 98.3 | 100 | 98 | 98.3 | 87.5 | 100 |
| 1_109 | 99.1 | 100 | 99 | 98.3 | 87.5 | 100 |
| 1_110 | 97.4 | 94.1 | 98 | 98.3 | 87.5 | 100 |
| 1_111 | 97.4 | 94.1 | 98 | 98.3 | 87.5 | 100 |
| 1_112 | 97.4 | 94.1 | 98 | 98.3 | 87.5 | 100 |
| 1_113 | 99.1 | 100 | 99 | 100 | 100 | 100 |
| 1_114 | 98.3 | 100 | 98 | 98.3 | 87.5 | 100 |
| 1_115 | 97.4 | 94.1 | 98 | 98.3 | 87.5 | 100 |
| 1_116 | 98.3 | 100 | 98 | 98.3 | 87.5 | 100 |
| 1_117 | 97.4 | 94.1 | 98 | 98.3 | 87.5 | 100 |
| 1_118 | 97.4 | 94.1 | 98 | 98.3 | 87.5 | 100 |
| 1_119 | 97.4 | 94.1 | 98 | 98.3 | 87.5 | 100 |
| 1_120 | 98.3 | 100 | 98 | 98.3 | 87.5 | 100 |
| 1_121 | 98.3 | 94.1 | 99 | 98.3 | 87.5 | 100 |
| 1_122 | 98.3 | 100 | 98 | 98.3 | 87.5 | 100 |
| 1_123 | 98.3 | 100 | 98 | 98.3 | 87.5 | 100 |
| 1_124 | 98.3 | 100 | 98 | 98.3 | 87.5 | 100 |
| 1_125 | 97.4 | 94.1 | 98 | 98.3 | 87.5 | 100 |
| 1_126 | 99.1 | 100 | 99 | 98.3 | 87.5 | 100 |
| 1_127 | 98.3 | 100 | 98 | 98.3 | 87.5 | 100 |
| 1_128 | 98.3 | 100 | 98 | 98.3 | 87.5 | 100 |
| 1_129 | 98.3 | 100 | 98 | 98.3 | 87.5 | 100 |
| 1_130 | 98.3 | 100 | 98 | 98.3 | 87.5 | 100 |
| 1_131 | 97.4 | 94.1 | 98 | 98.3 | 87.5 | 100 |
| 1_132 | 98.3 | 88.2 | 100 | 98.3 | 87.5 | 100 |
| 1_133 | 97.4 | 94.1 | 98 | 98.3 | 87.5 | 100 |
| 1_134 | 98.3 | 100 | 98 | 98.3 | 87.5 | 100 |

Example 3

<Selection of Gene Marker Using all Samples and Method for Evaluating Lung Cancer Discriminant Performance of Acquired Gene Marker>

In this Example, the samples in the training cohort and the validation cohort used in Examples 1 and 2 were integrated, and selection of a gene marker and evaluation of its lung cancer discriminant performance were conducted using all of the samples.

Specifically, the miRNA expression levels in the serum of the 25 lung cancer patients and the 150 healthy subjects obtained in the preceding Reference Examples were normalized by quantile normalization. In order to acquire diagnostic markers with higher reliability, only genes having a gene expression level of $2^6$ or higher in 50% or more of the samples in either of the lung cancer patient group or the healthy subject group were selected in the gene marker selection. In order to further acquire statistical significance for discriminating a lung cancer patient group from a healthy subject group, the P value obtained by two-sample t-test assuming equal variance as to each gene expression level was corrected by the Bonferroni method, and genes that satisfied p<0.01 were selected as gene markers for use in explanatory variables of a discriminant. The acquired genes are described in Table 7. In this way, hsa-miR-4271, hsa-miR-642b-3p, hsa-miR-6075, hsa-miR-6125, hsa-miR-887-3p, hsa-miR-6851-5p, hsa-miR-6763-5p, hsa-miR-3928-3p, hsa-miR-4443, hsa-miR-3648, hsa-miR-149-3p, hsa-miR-4689, hsa-miR-4763-3p, hsa-miR-6729-5p, hsa-miR-3196, hsa-miR-8069, hsa-miR-1268a, hsa-miR-4739, hsa-miR-1268b, hsa-miR-5698, hsa-miR-6752-5p, hsa-miR-4507, hsa-miR-564, hsa-miR-4497, hsa-miR-6877-5p, hsa-miR-6087, hsa-miR-4731-5p, hsa-miR-615-5p, hsa-miR-760, hsa-miR-6891-5p, hsa-miR-6887-5p, hsa-miR-4525, hsa-miR-1914-3p, hsa-miR-619-5p, hsa-miR-5001-5p, hsa-miR-6722-3p, hsa-miR-3621, hsa-miR-4298, hsa-miR-675-5p, and hsa-miR-4655-5p genes, and the nucleotide sequences of SEQ ID NOs: 135 to 174 related thereto were found in addition to the genes described in Table 3. As with the nucleotide sequences of SEQ ID NOs: 1 to 134, the results obtained about the polynucleotides shown in SEQ ID NOs: 135 to 174 also showed that the measurement values were significantly lower (−) or higher (+) in the lung cancer patient group than in the healthy subject group (Table 7). These results were able to be validated in the validation cohort. Thus, the presence or absence of lung cancer in the newly obtained samples can be determined by the methods described in Examples 1 and 2 by using the gene expression level measurement values described in Table 7 either alone or in combination with the gene expression level measurement values described in Table 3.

TABLE 7

| SEQ ID NO: | Gene name | P value after Bonferroni correction | Expression level in lung cancer patient with respect to healthy subject |
|---|---|---|---|
| 1 | hsa-miR-6768-5p | 6.12E−37 | + |
| 2 | hsa-miR-6836-3p | 4.68E−36 | − |
| 3 | hsa-miR-6782-5p | 7.67E−29 | − |
| 4 | hsa-miR-3663-3p | 4.91E−29 | − |
| 5 | hsa-miR-1908-3p | 2.76E−30 | − |
| 6 | hsa-miR-6726-5p | 1.23E−26 | + |
| 7 | hsa-miR-4258 | 6.12E−28 | − |
| 8 | hsa-miR-1343-3p | 7.70E−26 | − |
| 9 | hsa-miR-4516 | 1.71E−29 | − |
| 10 | hsa-miR-6875-5p | 1.59E−18 | − |
| 11 | hsa-miR-4651 | 6.58E−26 | + |
| 12 | hsa-miR-6825-5p | 230E−22 | − |
| 13 | hsa-miR-6840-3p | 4.47E−24 | + |
| 14 | hsa-miR-6780b-5p | 7.12E−26 | − |
| 15 | hsa-miR-6749-5p | 3.83E−25 | − |
| 16 | hsa-miR-8063 | 7.83E−21 | − |
| 17 | hsa-miR-6784-5p | 1.37E−17 | + |
| 18 | hsa-miR-3679-5p | 2.70E−25 | − |
| 19 | hsa-miR-3184-5p | 5.58E−19 | + |
| 20 | hsa-miR-663b | 2.07E−22 | − |
| 21 | hsa-miR-6880-5p | 4.49E−19 | + |
| 22 | hsa-miR-1908-5p | 7.91E−21 | + |
| 23 | hsa-miR-92a-2-5p | 6.69E−15 | + |
| 24 | hsa-miR-7975 | 3.32E−17 | + |
| 25 | hsa-miR-7110-5p | 2.07E−16 | + |
| 26 | hsa-miR-6842-5p | 3.25E−19 | − |
| 27 | hsa-miR-6857-5p | 7.70E−16 | − |
| 28 | hsa-miR-5572 | 1.14E−17 | + |
| 29 | hsa-miR-3197 | 7.43E−21 | + |
| 30 | hsa-miR-6131 | 8.81E−19 | + |
| 31 | hsa-miR-6889-5p | 7.76E−18 | + |
| 32 | hsa-miR-4454 | 6.20E−15 | − |
| 33 | hsa-miR-1199-5p | 1.10E−16 | − |
| 34 | hsa-miR-1247-3p | 2.61E−15 | − |
| 35 | hsa-miR-6800-5p | 1.65E−14 | − |
| 36 | hsa-miR-6872-3p | 3.40E−13 | + |
| 37 | hsa-miR-4649-5p | 2.50E−16 | − |
| 38 | hsa-miR-6791-5p | 2.29E−18 | − |
| 39 | hsa-miR-4433b-3p | 1.12E−12 | + |
| 40 | hsa-miR-3135b | 7.14E−09 | + |

TABLE 7-continued

| SEQ ID NO: | Gene name | P value after Bonferroni correction | Expression level in lung cancer patient with respect to healthy subject |
|---|---|---|---|
| 41 | hsa-miR-128-2-5p | 3.95E−17 | + |
| 42 | hsa-miR-4675 | 3.41E−17 | − |
| 43 | hsa-miR-4472 | 1.34E−15 | − |
| 44 | hsa-miR-6785-5p | 7.27E−16 | + |
| 45 | hsa-miR-6741-5p | 1.57E−11 | + |
| 46 | hsa-miR-7977 | 4.98E−13 | + |
| 47 | hsa-miR-3665 | 1.23E−11 | + |
| 48 | hsa-miR-128-1-5p | 6.12E−11 | + |
| 49 | hsa-miR-4286 | 8.20E−12 | + |
| 50 | hsa-miR-6765-3p | 3.54E−12 | + |
| 51 | hsa-miR-4632-5p | 1.23E−14 | − |
| 52 | hsa-miR-365a-5p | 3.37E−12 | − |
| 53 | hsa-miR-6088 | 2.65E−13 | − |
| 54 | hsa-miR-6816-5p | 3.35E−14 | + |
| 55 | hsa-miR-6885-5p | 1.83E−13 | − |
| 56 | hsa-miR-711 | 2.81E−14 | + |
| 57 | hsa-miR-6765-5p | 1.37E−11 | + |
| 58 | hsa-miR-3180 | 1.69E−14 | + |
| 59 | hsa-miR-4442 | 2.64E−12 | − |
| 60 | hsa-miR-4792 | 2.35E−11 | + |
| 61 | hsa-miR-6721-5p | 1.63E−09 | + |
| 62 | hsa-miR-6798-5p | 9.64E−11 | − |
| 63 | hsa-miR-3162-5p | 1.05E−08 | − |
| 64 | hsa-miR-6126 | 3.64E−14 | + |
| 65 | hsa-miR-4758-5p | 3.51E−15 | − |
| 66 | hsa-miR-2392 | 2.75E−12 | + |
| 67 | hsa-miR-486-3p | 2.02E−11 | − |
| 68 | hsa-miR-6727-5p | 3.30E−09 | + |
| 69 | hsa-miR-4728-5p | 9.06E−11 | − |
| 70 | hsa-miR-6746-5p | 1.45E−08 | + |
| 71 | hsa-miR-4270 | 1.52E−08 | + |
| 72 | hsa-miR-3940-5p | 3.98E−09 | + |
| 73 | hsa-miR-4725-3p | 2.40E−08 | − |
| 74 | hsa-miR-7108-5p | 5.64E−10 | + |
| 75 | hsa-miR-3656 | 6.69E−13 | + |
| 76 | hsa-miR-6879-5p | 3.97E−13 | + |
| 77 | hsa-miR-6738-5p | 1.60E−09 | + |
| 78 | hsa-miR-1260a | 1.22E−08 | + |
| 79 | hsa-miR-4446-3p | 3.23E−10 | − |
| 80 | hsa-miR-3131 | 2.40E−09 | + |
| 81 | hsa-miR-4463 | 1.54E−08 | − |
| 82 | hsa-miR-3185 | 5.62E−10 | − |
| 83 | hsa-miR-6870-5p | 3.81E−08 | + |
| 84 | hsa-miR-6779-5p | 3.02E−07 | + |
| 85 | hsa-miR-1273g-3p | 2.06E−09 | + |
| 86 | hsa-miR-8059 | 2.01E−06 | − |
| 87 | hsa-miR-4697-5p | 1.86E−08 | + |
| 88 | hsa-miR-4674 | 4.38E−10 | − |
| 89 | hsa-miR-4433-3p | 2.20E−07 | − |
| 90 | hsa-miR-4257 | 1.87E−08 | + |
| 91 | hsa-miR-1915-5p | 4.76E−10 | − |
| 92 | hsa-miR-4417 | 2.14E−07 | − |
| 93 | hsa-miR-1343-5p | 1.06E−10 | + |
| 94 | hsa-miR-6781-5p | 4.10E−05 | − |
| 95 | hsa-miR-4695-5p | 3.31E−11 | − |
| 96 | hsa-miR-1237-5p | 3.95E−10 | + |
| 97 | hsa-miR-6775-5p | 4.09E−05 | + |
| 98 | hsa-miR-7845-5p | 2.84E−07 | − |
| 99 | hsa-miR-4746-3p | 9.11E−11 | − |
| 100 | hsa-miR-7641 | 1.14E−06 | − |
| 101 | hsa-miR-7847-3p | 5.71E−05 | + |
| 102 | hsa-miR-6806-5p | 1.87E−09 | − |
| 103 | hsa-miR-4467 | 2.48E−08 | − |
| 104 | hsa-miR-4726-5p | 8.08E−07 | + |
| 105 | hsa-miR-4648 | 1.15E−08 | + |
| 106 | hsa-miR-6089 | 1.19E−07 | + |
| 107 | hsa-miR-1260b | 1.62E−05 | + |
| 108 | hsa-miR-4532 | 8.30E−09 | + |
| 109 | hsa-miR-5195-3p | 2.03E−07 | + |
| 110 | hsa-miR-3188 | 4.84E−08 | − |
| 111 | hsa-miR-6848-5p | 6.01E−07 | − |
| 112 | hsa-miR-1233-5p | 3.76E−06 | + |
| 113 | hsa-miR-6717-5p | 2.38E−05 | + |
| 114 | hsa-miR-3195 | 7.67E−06 | − |
| 115 | hsa-miR-6757-5p | 1.58E−06 | − |
| 116 | hsa-miR-8072 | 1.17E−05 | − |
| 117 | hsa-miR-4745-5p | 5.89E−07 | + |
| 119 | hsa-miR-6776-5p | 1.26E−07 | − |
| 120 | hsa-miR-371a-5p | 9.22E−05 | + |
| 121 | hsa-miR-1227-5p | 9.64E−05 | − |
| 122 | hsa-miR-7150 | 0.000252 | − |
| 123 | hsa-miR-1915-3p | 2.18E−09 | − |
| 124 | hsa-miR-187-5p | 2.81E−27 | − |
| 125 | hsa-miR-614 | 1.65E−21 | − |
| 126 | hsa-miR-19b-3p | 1.33E−19 | + |
| 127 | hsa-miR-1225-5p | 6.67E−13 | − |
| 128 | hsa-miR-451a | 2.23E−10 | − |
| 129 | hsa-miR-939-5p | 1.89E−11 | + |
| 130 | hsa-miR-223-3p | 9.32E−11 | − |
| 131 | hsa-miR-1228-5p | 1.49E−09 | + |
| 132 | hsa-miR-125a-3p | 1.07E−05 | + |
| 133 | hsa-miR-92b-5p | 1.09E−11 | + |
| 134 | hsa-miR-22-3p | 9.71E−07 | + |
| 135 | hsa-miR-4271 | 5.64E−07 | + |
| 136 | hsa-miR-642b-3p | 6.99E−06 | − |
| 137 | hsa-miR-6075 | 1.17E−05 | + |
| 138 | hsa-miR-6125 | 1.63E−05 | + |
| 139 | hsa-miR-887-3p | 1.68E−05 | + |
| 140 | hsa-miR-6851-5p | 1.97E−05 | − |
| 141 | hsa-miR-6763-5p | 3.54E−05 | − |
| 142 | hsa-miR-3928-3p | 4.67E−05 | − |
| 143 | hsa-miR-4443 | 5.36E−05 | + |
| 144 | hsa-miR-3648 | 6.01E−05 | + |
| 145 | hsa-miR-149-3p | 9.80E−05 | − |
| 146 | hsa-miR-4689 | 1.01E−04 | + |
| 147 | hsa-miR-4763-3p | 1.20E−04 | + |
| 148 | hsa-miR-6729-5p | 1.28E−04 | + |
| 149 | hsa-miR-3196 | 1.31E−04 | + |
| 150 | hsa-miR-8069 | 1.84E−04 | + |
| 151 | hsa-miR-1268a | 2.58E−04 | + |
| 152 | hsa-miR-4739 | 2.68E−04 | + |
| 153 | hsa-miR-1268b | 3.37E−04 | + |
| 154 | hsa-miR-5698 | 4.34E−04 | − |
| 155 | hsa-miR-6752-5p | 5.63E−04 | + |
| 156 | hsa-miR-4507 | 6.34E−04 | + |
| 157 | hsa-miR-564 | 6.68E−04 | − |
| 158 | hsa-miR-4497 | 8.11E−04 | − |
| 159 | hsa-miR-6877-5p | 8.21E−04 | − |
| 160 | hsa-miR-6087 | 8.91E−04 | − |
| 161 | hsa-miR-4731-5p | 1.15E−03 | − |
| 162 | hsa-miR-615-5p | 1.25E−03 | − |
| 163 | hsa-miR-760 | 1.42E−03 | − |
| 164 | hsa-miR-6891-5p | 1.71E−03 | + |
| 165 | hsa-miR-6887-5p | 1.82E−03 | − |
| 166 | hsa-miR-4525 | 2.09E−03 | − |
| 167 | hsa-miR-1914-3p | 2.11E−03 | − |
| 168 | hsa-miR-619-5p | 2.61E−03 | − |
| 169 | hsa-miR-5001-5p | 3.01E−03 | − |
| 170 | hsa-miR-6722-3p | 3.88E−03 | + |
| 171 | hsa-miR-3621 | 4.02E−03 | − |
| 172 | hsa-miR-4298 | 7.88E−03 | − |
| 173 | hsa-miR-675-5p | 8.33E−03 | − |
| 174 | hsa-miR-4655-5p | 9.06E−03 | + |

Example 4

<Method for Evaluating Lung Cancer-Specific Discriminant Performance by Combination of Multiple Gene Markers Using Samples in the Validation Cohort>

In this Example, gene markers for diagnosis were selected by comparing gene expression levels of miRNAs in serum of lung cancer patients with that of a control group consisting of healthy subjects, pancreatic cancer patients, biliary tract cancer patients, colorectal cancer patients, stomach cancer patients, liver cancer patients, and benign pancreaticobiliary disease patients, in the same way as the method described in Example 1, using the gene markers selected in Example 1, and targeting the training cohort as the sample group described in Reference Example 2. The polynucleotides consisting of the nucleotide sequences represented by SEQ ID NOs: 561 to 579 thus selected were further combined therewith to study a method for evaluating lung cancer-specific discriminant performance.

Specifically, first, the miRNA expression levels in the training cohort and the validation cohort obtained in Reference Example 2 mentioned above were combined and normalized by quantile normalization. Next, Fisher's discriminant analysis was conducted as to combinations of 1 to 4 expression level measurement values comprising at least one or more of the expression level measurement values of the polynucleotides consisting of the nucleotide sequences represented by SEQ ID NOs: 1 to 174, and 561 to 579, to construct a discriminant for determining the presence or absence of lung cancer. Next, accuracy, sensitivity, and specificity in the validation cohort were calculated using the discriminant thus prepared, with the lung cancer patient group as a positive sample group and, on the other hand, the healthy subject group, the pancreatic cancer patient group, the biliary tract cancer patient group, the colorectal cancer patient group, the stomach cancer patient group, the liver cancer patient group, and the benign pancreaticobiliary disease patient group as a negative sample group. The discriminant performance of the selected polynucleotides was validated using the independent samples.

Most of polynucleotides consisting of the nucleotide sequences represented by these SEQ ID NOs (SEQ ID NOs: 1 to 174, and 561 to 579 corresponding to the miRNA markers of Table 1) or complementary sequences thereof mentioned above were able to provide relatively high accuracy, sensitivity, and specificity in the determination of the presence or absence of lung cancer, and furthermore, were able to specifically discriminate lung cancer from the other cancers. For example, among the combinations of multiple polynucleotides selected from the group consisting of polynucleotides consisting of the nucleotide sequences represented by SEQ ID NOs: 1, 2, 3, 4, 5, 7, 9, 10, 11, 19, 21, 26, 29, 31, 52, 53, 63, 65, 69, 72, 87, 90, 113, 124, 125, 126, 128, 130, 143, 148, 160, 162, 561, 562, 563, 564, 565, 566, 567, 568, 569, 570, 571, 572, 573, 574, 575, 576, 577, 578 and 579 or complementary sequences thereof (the cancer type-specific polynucleotide group 1) as polynucleotides capable of specifically binding to target markers, combinations comprising at least one or more polynucleotide(s) selected from the group consisting of polynucleotides consisting of the nucleotide sequences represented by SEQ ID NOs: 1, 2, 3, 10, 63, 113, 124, 125, 126, 128, 130, 143, 160, 561, 568, 573 and 578 or complementary sequences thereof (the cancer type-specific polynucleotide group 2) included in the cancer type-specific polynucleotide group 1 were able to specifically discriminate lung cancer from the other cancers with high accuracy.

The number of the polynucleotides with cancer type specificity in the combination can be 1, 2, 3, 4, 5, 6, 7, 8, 9, 10 or more for the combination. The combinations of 4 or more of these polynucleotides were able to exhibit discriminant accuracy of 90% or higher.

Specifically, the discriminant accuracy of the measurement using the polynucleotide consisting of the nucleotide sequence represented by SEQ ID NO: 1 or a complementary sequence thereof is shown in Table 8-1. For example, the measurement using the combination of one polynucleotide comprising at least one polynucleotide consisting of the nucleotide sequence represented by SEQ ID NO: 1 or a complementary sequence thereof exhibited accuracy of 94.2% in the training cohort and accuracy of 91.4% in the validation cohort. Also, for example, the measurement using the combinations of two polynucleotides comprising at least one polynucleotide consisting of the nucleotide sequence represented by SEQ ID NO: 1 or a complementary sequence thereof exhibited accuracy of 98.7% in the training cohort and accuracy of 97.5% in the validation cohort. Furthermore, for example, the measurement using the combinations of three polynucleotides comprising at least one polynucleotide consisting of the nucleotide sequence represented by SEQ ID NO: 1 or a complementary sequence thereof exhibited accuracy of 99.2% in the training cohort and accuracy of 98.5% in the validation cohort. Furthermore, for example, the measurement using the combinations of four polynucleotides comprising at least one polynucleotide consisting of the nucleotide sequence represented by SEQ ID NO: 1 or a complementary sequence thereof exhibited accuracy of 99.7% in the training cohort and accuracy of 99.0% in the validation cohort.

Specifically, the discriminant accuracy of the measurement using the polynucleotide consisting of the nucleotide sequence represented by SEQ ID NO: 2 or a complementary sequence thereof is shown in Table 8-2. For example, the measurement using the combination of one polynucleotide comprising at least one polynucleotide consisting of the nucleotide sequence represented by SEQ ID NO: 2 or a complementary sequence thereof exhibited accuracy of 94.0% in the training cohort and accuracy of 92.4% in the validation cohort. Also, for example, the measurement using the combinations of two polynucleotides comprising at least one polynucleotide consisting of the nucleotide sequence represented by SEQ ID NO: 2 or a complementary sequence thereof exhibited accuracy of 97.2% in the training cohort and accuracy of 96.0% in the validation cohort. Furthermore, for example, the measurement using the combinations of three polynucleotides comprising at least one polynucleotide consisting of the nucleotide sequence represented by SEQ ID NO: 2 or a complementary sequence thereof exhibited accuracy of 99.5% in the training cohort and accuracy of 98.0% in the validation cohort. Furthermore, for example, the measurement using the combinations of four polynucleotides comprising at least one polynucleotide consisting of the nucleotide sequence represented by SEQ ID NO: 2 or a complementary sequence thereof exhibited accuracy of 100% in the training cohort and accuracy of 98.0% in the validation cohort.

Specifically, the discriminant accuracy of the measurement using the polynucleotide consisting of the nucleotide sequence represented by SEQ ID NO: 3 or a complementary sequence thereof is shown in Table 8-3. For example, the measurement using the combination of one polynucleotide comprising at least one polynucleotide consisting of the nucleotide sequence represented by SEQ ID NO: 3 or a complementary sequence thereof exhibited accuracy of 85.7% in the training cohort and accuracy of 84.3% in the validation cohort. Also, for example, the measurement using the combinations of two polynucleotides comprising at least one polynucleotide consisting of the nucleotide sequence represented by SEQ ID NO: 3 or a complementary sequence thereof exhibited accuracy of 97.0% in the training cohort and accuracy of 97.0% in the validation cohort. Furthermore, for example, the measurement using the combinations of three polynucleotides comprising at least one polynucleotide consisting of the nucleotide sequence represented by SEQ ID NO: 3 or a complementary sequence thereof exhibited accuracy of 99.0% in the training cohort and accuracy of 98.5% in the validation cohort. Furthermore, for example, the measurement using the combinations of four polynucleotides comprising at least one polynucleotide consisting of the nucleotide sequence represented by SEQ ID NO: 3 or a complementary sequence thereof exhibited accuracy of 99.5% in the training cohort and accuracy of 100% in the validation cohort.

Specifically, the discriminant accuracy of the measurement using the polynucleotide consisting of the nucleotide sequence represented by SEQ ID NO: 10 or a complementary sequence thereof is shown in Table 8-4. For example, the measurement using the combination of one polynucleotide comprising at least one polynucleotide consisting of the nucleotide sequence represented by SEQ ID NO: 10 or a complementary sequence thereof exhibited accuracy of 64.0% in the training cohort and accuracy of 61.6% in the validation cohort. Also, for example, the measurement using the combinations of two polynucleotides comprising at least one polynucleotide consisting of the nucleotide sequence represented by SEQ ID NO: 10 or a complementary sequence thereof exhibited accuracy of 94.0% in the training cohort and accuracy of 92.4% in the validation cohort. Furthermore, for example, the measurement using the combinations of three polynucleotides comprising at least one polynucleotide consisting of the nucleotide sequence represented by SEQ ID NO: 10 or a complementary sequence thereof exhibited accuracy of 99.2% in the training cohort and accuracy of 99.0% in the validation cohort. Furthermore, for example, the measurement using the combinations of four polynucleotides comprising at least one polynucleotide consisting of the nucleotide sequence represented by SEQ ID NO: 10 or a complementary sequence thereof exhibited accuracy of 99.2% in the training cohort and accuracy of 99.5% in the validation cohort.

Specifically, the discriminant accuracy of the measurement using the polynucleotide consisting of the nucleotide sequence represented by SEQ ID NO: 63 or a complementary sequence thereof is shown in Table 8-5. For example, the measurement using the combination of one polynucleotide comprising at least one polynucleotide consisting of the nucleotide sequence represented by SEQ ID NO: 63 or a complementary sequence thereof exhibited accuracy of 79.4% in the training cohort and accuracy of 80.8% in the validation cohort. Also, for example, the measurement using the combinations of two polynucleotides comprising at least one polynucleotide consisting of the nucleotide sequence represented by SEQ ID NO: 63 or a complementary sequence thereof exhibited accuracy of 95.7% in the training cohort and accuracy of 97.5% in the validation cohort. Furthermore, for example, the measurement using the combinations of three polynucleotides comprising at least one polynucleotide consisting of the nucleotide sequence represented by SEQ ID NO: 63 or a complementary sequence thereof exhibited accuracy of 98.2% in the training cohort and accuracy of 98.0% in the validation cohort. Furthermore, for example, the measurement using the combinations of four polynucleotides comprising at least one polynucleotide consisting of the nucleotide sequence represented by SEQ ID NO: 63 or a complementary sequence thereof exhibited accuracy of 99.5% in the training cohort and accuracy of 97.5% in the validation cohort.

Specifically, the discriminant accuracy of the measurement using the polynucleotide consisting of the nucleotide sequence represented by SEQ ID NO: 113 or a complementary sequence thereof is shown in Table 8-6. For example, the measurement using the combination of one polynucleotide comprising at least one polynucleotide consisting of the nucleotide sequence represented by SEQ ID NO: 113 or a complementary sequence thereof exhibited accuracy of 67.8% in the training cohort and accuracy of 69.2% in the validation cohort. Also, for example, the measurement using the combinations of two polynucleotides comprising at least one polynucleotide consisting of the nucleotide sequence represented by SEQ ID NO: 113 or a complementary sequence thereof exhibited accuracy of 97.7% in the training cohort and accuracy of 95.5% in the validation cohort. Furthermore, for example, the measurement using the combinations of three polynucleotides comprising at least one polynucleotide consisting of the nucleotide sequence represented by SEQ ID NO: 113 or a complementary sequence thereof exhibited accuracy of 99.5% in the training cohort and accuracy of 99.0% in the validation cohort. Furthermore, for example, the measurement using the combinations of four polynucleotides comprising at least one polynucleotide consisting of the nucleotide sequence represented by SEQ ID NO: 113 or a complementary sequence thereof exhibited accuracy of 99.5% in the training cohort and accuracy of 99.0% in the validation cohort.

Specifically, the discriminant accuracy of the measurement using the polynucleotide consisting of the nucleotide sequence represented by SEQ ID NO: 124 or a complementary sequence thereof is shown in Table 8-7. For example, the measurement using the combination of one polynucleotide comprising at least one polynucleotide consisting of the nucleotide sequence represented by SEQ ID NO: 124 or a complementary sequence thereof exhibited accuracy of 79.6% in the training cohort and accuracy of 76.8% in the validation cohort. Also, for example, the measurement using the combinations of two polynucleotides comprising at least one polynucleotide consisting of the nucleotide sequence represented by SEQ ID NO: 124 or a complementary sequence thereof exhibited accuracy of 95.0% in the training cohort and accuracy of 91.4% in the validation cohort. Furthermore, for example, the measurement using the combinations of three polynucleotides comprising at least one polynucleotide consisting of the nucleotide sequence represented by SEQ ID NO: 124 or a complementary sequence thereof exhibited accuracy of 98.5% in the training cohort and accuracy of 97.5% in the validation cohort. Furthermore, for example, the measurement using the combinations of four polynucleotides comprising at least one polynucleotide consisting of the nucleotide sequence represented by SEQ ID NO: 124 or a complementary sequence thereof exhibited accuracy of 99.0% in the training cohort and accuracy of 99.0% in the validation cohort.

Specifically, the discriminant accuracy of the measurement using the polynucleotide consisting of the nucleotide sequence represented by SEQ ID NO: 125 or a complementary sequence thereof is shown in Table 8-8. For example, the measurement using the combination of one polynucleotide comprising at least one polynucleotide consisting of the nucleotide sequence represented by SEQ ID NO: 125 or a complementary sequence thereof exhibited accuracy of 77.6% in the training cohort and accuracy of 73.7% in the validation cohort. Also, for example, the measurement using the combinations of two polynucleotides comprising at least one polynucleotide consisting of the nucleotide sequence represented by SEQ ID NO: 125 or a complementary sequence thereof exhibited accuracy of 94.7% in the training cohort and accuracy of 93.4% in the validation cohort. Furthermore, for example, the measurement using the combinations of three polynucleotides comprising at least one polynucleotide consisting of the nucleotide sequence represented by SEQ ID NO: 125 or a complementary sequence thereof exhibited accuracy of 99.0% in the training cohort and accuracy of 96.5% in the validation cohort. Furthermore, for example, the measurement using the combinations of four polynucleotides comprising at least one polynucleotide consisting of the nucleotide sequence represented by SEQ ID NO:125 or a complementary sequence thereof exhibited accuracy of 99.5% in the training cohort and accuracy of 99.0% in the validation cohort.

Specifically, the discriminant accuracy of the measurement using the polynucleotide consisting of the nucleotide sequence represented by SEQ ID NO: 126 or a complementary sequence thereof is shown in Table 8-9. For example, the measurement using the combination of one polynucleotide comprising at least one polynucleotide consisting of the nucleotide sequence represented by SEQ ID NO: 126 or a complementary sequence thereof exhibited accuracy of 90.4% in the training cohort and accuracy of 92.4% in the validation cohort. Also, for example, the measurement using the combinations of two polynucleotides comprising at least one polynucleotide consisting of the nucleotide sequence represented by SEQ ID NO: 126 or a complementary sequence thereof exhibited accuracy of 96.7% in the training cohort and accuracy of 95.5% in the validation cohort. Furthermore, for example, the measurement using the combinations of three polynucleotides comprising at least one polynucleotide consisting of the nucleotide sequence represented by SEQ ID NO: 126 or a complementary sequence thereof exhibited accuracy of 99.7% in the training cohort and accuracy of 98.0% in the validation cohort. Furthermore, for example, the measurement using the combinations of four polynucleotides comprising at least one polynucleotide consisting of the nucleotide sequence represented by SEQ ID NO: 126 or a complementary sequence thereof exhibited accuracy of 99.7% in the training cohort and accuracy of 99.0% in the validation cohort.

Specifically, the discriminant accuracy of the measurement using the polynucleotide consisting of the nucleotide sequence represented by SEQ ID NO: 128 or a complementary sequence thereof is shown in Table 8-10. For example, the measurement using the combination of one polynucleotide comprising at least one polynucleotide consisting of the nucleotide sequence represented by SEQ ID NO: 128 or a complementary sequence thereof exhibited accuracy of 81.4% in the training cohort and accuracy of 81.3% in the validation cohort. Also, for example, the measurement using the combinations of two polynucleotides comprising at least one polynucleotide consisting of the nucleotide sequence represented by SEQ ID NO: 128 or a complementary sequence thereof exhibited accuracy of 96.2% in the training cohort and accuracy of 94.9% in the validation cohort. Furthermore, for example, the measurement using the combinations of three polynucleotides comprising at least one polynucleotide consisting of the nucleotide sequence represented by SEQ ID NO: 128 or a complementary sequence thereof exhibited accuracy of 98.7% in the training cohort and accuracy of 97.5% in the validation cohort. Furthermore, for example, the measurement using the combinations of four polynucleotides comprising at least one polynucleotide consisting of the nucleotide sequence represented by SEQ ID NO: 128 or a complementary sequence thereof exhibited accuracy of 99.2% in the training cohort and accuracy of 99.5% in the validation cohort.

Specifically, the discriminant accuracy of the measurement using the polynucleotide consisting of the nucleotide sequence represented by SEQ ID NO: 130 or a complementary sequence thereof is shown in Table 8-11. For example, the measurement using the combination of one polynucleotide comprising at least one polynucleotide consisting of the nucleotide sequence represented by SEQ ID NO: 130 or a complementary sequence thereof exhibited accuracy of 83.4% in the training cohort and accuracy of 87.4% in the validation cohort. Also, for example, the measurement using the combinations of two polynucleotides comprising at least one polynucleotide consisting of the nucleotide sequence represented by SEQ ID NO: 130 or a complementary sequence thereof exhibited accuracy of 96.2% in the training cohort and accuracy of 94.4% in the validation cohort. Furthermore, for example, the measurement using the combinations of three polynucleotides comprising at least one polynucleotide consisting of the nucleotide sequence represented by SEQ ID NO: 130 or a complementary sequence thereof exhibited accuracy of 99.2% in the training cohort and accuracy of 98.5% in the validation cohort. Furthermore, for example, the measurement using the combinations of four polynucleotides comprising at least one polynucleotide consisting of the nucleotide sequence represented by SEQ ID NO: 130 or a complementary sequence thereof exhibited accuracy of 99.5% in the training cohort and accuracy of 99.5% in the validation cohort.

Specifically, the discriminant accuracy of the measurement using the polynucleotide consisting of the nucleotide sequence represented by SEQ ID NO: 143 or a complementary sequence thereof is shown in Table 8-12. For example, the measurement using the combination of one polynucleotide comprising at least one polynucleotide consisting of the nucleotide sequence represented by SEQ ID NO: 143 or a complementary sequence thereof exhibited accuracy of 64.6% in the training cohort and accuracy of 66.2% in the validation cohort. Also, for example, the measurement using the combinations of two polynucleotides comprising at least one polynucleotide consisting of the nucleotide sequence represented by SEQ ID NO: 143 or a complementary sequence thereof exhibited accuracy of 96.0% in the training cohort and accuracy of 93.9% in the validation cohort. Furthermore, for example, the measurement using the combinations of three polynucleotides comprising at least one polynucleotide consisting of the nucleotide sequence represented by SEQ ID NO: 143 or a complementary sequence thereof exhibited accuracy of 98.7% in the training cohort and accuracy of 98.0% in the validation cohort. Furthermore, for example, the measurement using the combinations of four polynucleotides comprising at least one polynucleotide consisting of the nucleotide sequence represented by SEQ ID NO: 143 or a complementary sequence thereof exhibited accuracy of 99.0% in the training cohort and accuracy of 98.0% in the validation cohort.

Specifically, the discriminant accuracy of the measurement using the polynucleotide consisting of the nucleotide sequence represented by SEQ ID NO: 160 or a complementary sequence thereof is shown in Table 8-13. For example, the measurement using the combination of one polynucleotide comprising at least one polynucleotide consisting of the nucleotide sequence represented by SEQ ID NO: 160 or a complementary sequence thereof exhibited accuracy of 70.9% in the training cohort and accuracy of 67.2% in the validation cohort. Also, for example, the measurement using the combinations of two polynucleotides comprising at least one polynucleotide consisting of the nucleotide sequence represented by SEQ ID NO: 160 or a complementary sequence thereof exhibited accuracy of 96.0% in the training cohort and accuracy of 92.4% in the validation cohort. Furthermore, for example, the measurement using the combinations of three polynucleotides comprising at least one polynucleotide consisting of the nucleotide sequence represented by SEQ ID NO: 160 or a complementary sequence thereof exhibited accuracy of 99.2% in the training cohort and accuracy of 98.5% in the validation cohort. Furthermore, for example, the measurement using the combinations of four polynucleotides comprising at least one polynucleotide consisting of the nucleotide sequence represented by SEQ ID NO: 160 or a complementary sequence thereof exhibited accuracy of 99.5% in the training cohort and accuracy of 99.0% in the validation cohort.

Specifically, the discriminant accuracy of the measurement using the polynucleotide consisting of the nucleotide sequence represented by SEQ ID NO: 561 or a complementary sequence thereof is shown in Table 8-14. For example, the measurement using the combination of one polynucleotide comprising at least one polynucleotide consisting of the nucleotide sequence represented by SEQ ID NO: 561 or a complementary sequence thereof exhibited accuracy of 84.9% in the training cohort and accuracy of 81.8% in the validation cohort. Also, for example, the measurement using the combinations of two polynucleotides comprising at least one polynucleotide consisting of the nucleotide sequence represented by SEQ ID NO: 561 or a complementary sequence thereof exhibited accuracy of 96.5% in the training cohort and accuracy of 97.5% in the validation cohort. Furthermore, for example, the measurement using the combinations of three polynucleotides comprising at least one polynucleotide consisting of the nucleotide sequence represented by SEQ ID NO: 561 or a complementary sequence thereof exhibited accuracy of 98.7% in the training cohort and accuracy of 98.0% in the validation cohort. Furthermore, for example, the measurement using the combinations of four polynucleotides comprising at least one polynucleotide consisting of the nucleotide sequence represented by SEQ ID NO: 561 or a complementary sequence thereof exhibited accuracy of 100% in the training cohort and accuracy of 99.0% in the validation cohort.

Specifically, the discriminant accuracy of the measurement using the polynucleotide consisting of the nucleotide sequence represented by SEQ ID NO: 568 or a complementary sequence thereof is shown in Table 8-15. For example, the measurement using the combination of one polynucleotide comprising at least one polynucleotide consisting of the nucleotide sequence represented by SEQ ID NO: 568 or a complementary sequence thereof exhibited accuracy of 60.2% in the training cohort and accuracy of 67.2% in the validation cohort. Also, for example, the measurement using the combinations of two polynucleotides comprising at least one polynucleotide consisting of the nucleotide sequence represented by SEQ ID NO: 568 or a complementary sequence thereof exhibited accuracy of 97.0% in the training cohort and accuracy of 96.0% in the validation cohort. Furthermore, for example, the measurement using the combinations of three polynucleotides comprising at least one polynucleotide consisting of the nucleotide sequence represented by SEQ ID NO: 568 or a complementary sequence thereof exhibited accuracy of 99.0% in the training cohort and accuracy of 96.0% in the validation cohort. Furthermore, for example, the measurement using the combinations of four polynucleotides comprising at least one polynucleotide consisting of the nucleotide sequence represented by SEQ ID NO: 568 or a complementary sequence thereof exhibited accuracy of 99.5% in the training cohort and accuracy of 98.5% in the validation cohort.

Specifically, the discriminant accuracy of the measurement using the polynucleotide consisting of the nucleotide sequence represented by SEQ ID NO: 573 or a complementary sequence thereof is shown in Table 8-16. For example, the measurement using the combination of one polynucleotide comprising at least one polynucleotide consisting of the nucleotide sequence represented by SEQ ID NO: 573 or a complementary sequence thereof exhibited accuracy of 53.0% in the training cohort and accuracy of 53.5% in the validation cohort. Also, for example, the measurement using the combinations of two polynucleotides comprising at least one polynucleotide consisting of the nucleotide sequence represented by SEQ ID NO: 573 or a complementary sequence thereof exhibited accuracy of 96.5% in the training cohort and accuracy of 95.5% in the validation cohort. Furthermore, for example, the measurement using the combinations of three polynucleotides comprising at least one polynucleotide consisting of the nucleotide sequence represented by SEQ ID NO: 573 or a complementary sequence thereof exhibited accuracy of 98.7% in the training cohort and accuracy of 98.0% in the validation cohort. Furthermore, for example, the measurement using the combinations of four polynucleotides comprising at least one polynucleotide consisting of the nucleotide sequence represented by SEQ ID NO: 573 or a complementary sequence thereof exhibited accuracy of 99.2% in the training cohort and accuracy of 98.5% in the validation cohort.

Specifically, the discriminant accuracy of the measurement using the polynucleotide consisting of the nucleotide sequence represented by SEQ ID NO: 578 or a complementary sequence thereof is shown in Table 8-17. For example, the measurement using the combination of one polynucleotide comprising at least one polynucleotide consisting of the nucleotide sequence represented by SEQ ID NO: 578 or a complementary sequence thereof exhibited accuracy of 52.8% in the training cohort and accuracy of 53.5% in the validation cohort. Also, for example, the measurement using the combinations of two polynucleotides comprising at least one polynucleotide consisting of the nucleotide sequence represented by SEQ ID NO: 578 or a complementary sequence thereof exhibited accuracy of 96.2% in the training cohort and accuracy of 94.9% in the validation cohort. Furthermore, for example, the measurement using the combinations of three polynucleotides comprising at least one polynucleotide consisting of the nucleotide sequence represented by SEQ ID NO: 578 or a complementary sequence thereof exhibited accuracy of 98.5% in the training cohort and accuracy of 96.5% in the validation cohort. Furthermore, for example, the measurement using the combinations of four polynucleotides comprising at least one polynucleotide consisting of the nucleotide sequence represented by SEQ ID NO: 578 or a complementary sequence thereof exhibited accuracy of 99.2% in the training cohort and accuracy of 99.0% in the validation cohort.

Figure 4A:
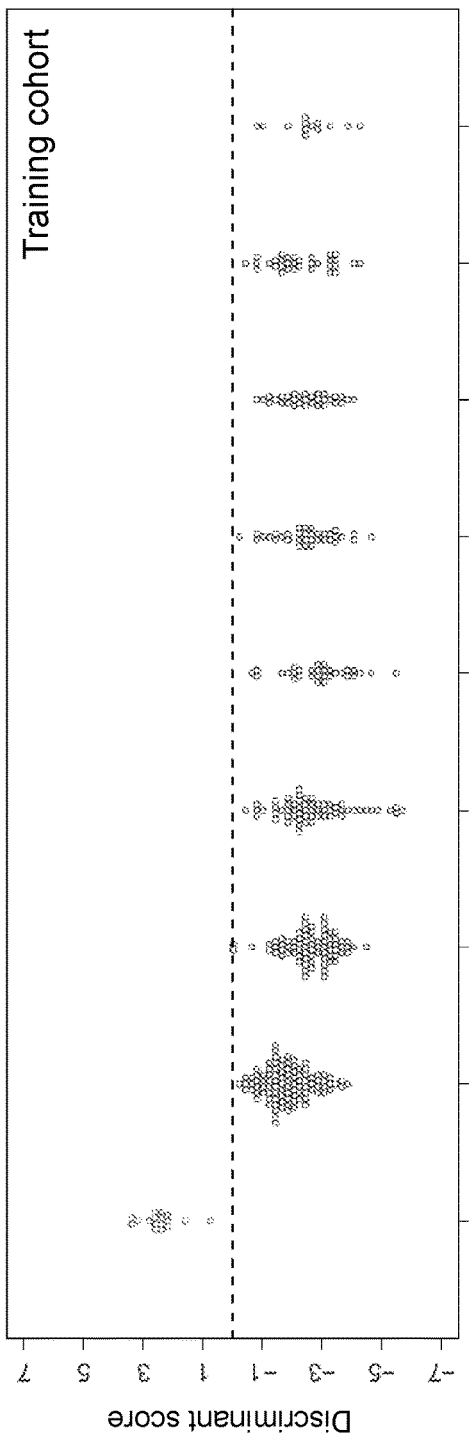
FIGS. 4A and 4B FIG. 4A: a discriminant (−1.86×hsa-miR-6768-5p−0.68×hsa-miR-19b-3p+0.43×hsa-miR-6073−0.87×hsa-miR-6717-5p+25.68) was prepared by use of Fisher's discriminant analysis from the expression level measurement values of hsa-miR-6768-5p (SEQ ID NO: 1), hsa-miR-6717-5p (SEQ ID NO: 113), hsa-miR-19b-3p (SEQ ID NO: 126), and hsa-miR-6073 (SEQ ID NO: 561) in 17 lung cancer patients, 99 healthy subjects, 75 pancreatic cancer patients, 62 biliary tract cancer patients, 32 colorectal cancer patients, 35 stomach cancer patients, 32 esophageal cancer patients, 33 liver cancer patients, and 13 benign pancreaticobiliary disease patients selected as a training cohort, and discriminant scores obtained from the discriminant were plotted on the ordinate against the sample groups on the abscissa. The dotted line in the diagram depicts a discriminant boundary that offered a discriminant score of 0 and discriminated between the two groups.
Figure 4B:
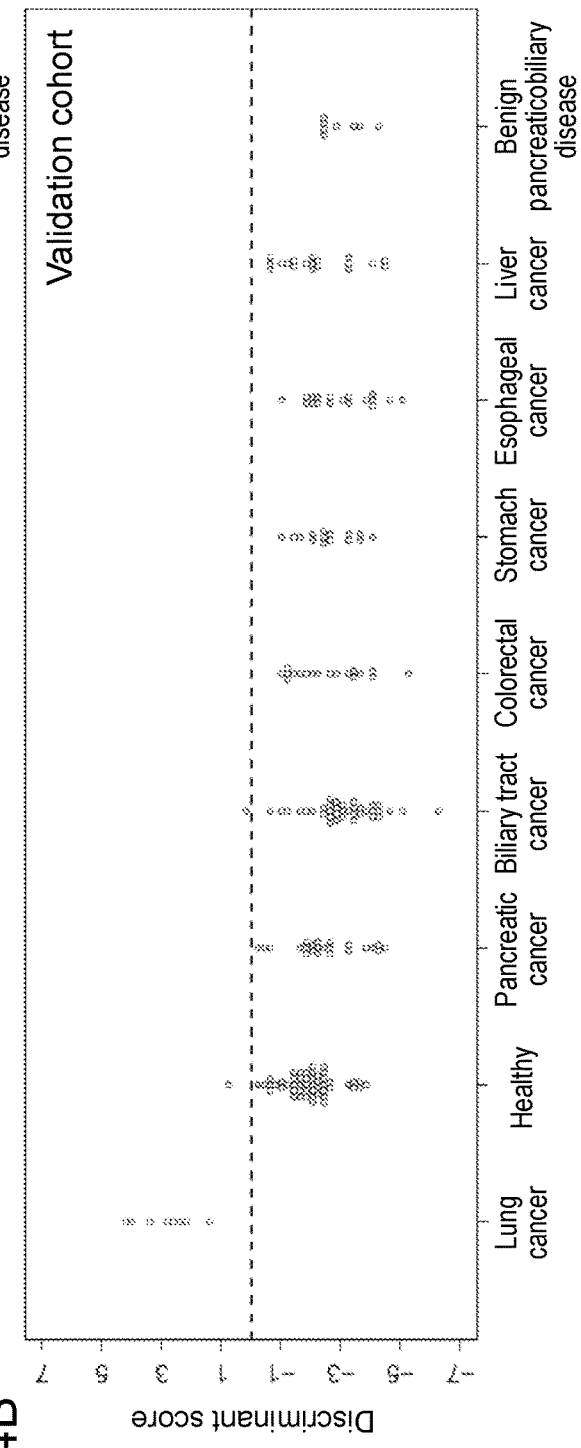

The measurement values of the nucleotide sequences represented by SEQ ID NOs: 1, 113, 126, and 561 were compared among 17 lung cancer patients, 99 healthy subjects, 75 pancreatic cancer patients, 62 biliary tract cancer patients, 32 colorectal cancer patients, 35 stomach cancer patients, 32 esophageal cancer patients, 33 liver cancer patients, and 13 benign pancreaticobiliary disease patients in the training cohort. As a result, a scatter diagram that significantly separated the discriminant score of the lung cancer patient group from the discriminant scores of the other groups was obtained in the training cohort (see FIG. 4A). These results were also reproducible for the validation cohort (see FIG. 4B).

TABLE 8-1

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 1 | 94.2 | 100 | 94.0 | 91.4 | 87.5 | 91.6 |
| 1_113 | 98.7 | 100 | 98.7 | 97.5 | 100 | 97.4 |
| 1_52_126 | 99.2 | 100 | 99.2 | 98.5 | 100 | 98.4 |
| 1_53_113_125 | 99.2 | 100 | 99.2 | 98.5 | 100 | 98.4 |
| 1_10_63_113 | 99.2 | 100 | 99.2 | 98.5 | 100 | 98.4 |
| 1_19_113_143 | 99.2 | 100 | 99.2 | 99.0 | 100 | 98.9 |
| 1_10_113_126 | 99.7 | 100 | 99.7 | 99.0 | 100 | 98.9 |
| 1_2_10_113 | 99.7 | 100 | 99.7 | 98.5 | 100 | 98.4 |

TABLE 8-2

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 2 | 94.0 | 94.1 | 94.0 | 92.4 | 100 | 92.1 |
| 2_126 | 97.2 | 100 | 97.1 | 96.0 | 100 | 95.8 |
| 1_2_113 | 99.5 | 100 | 99.5 | 98.0 | 100 | 97.9 |
| 2_19_53_113 | 99.2 | 100 | 99.2 | 97.5 | 100 | 97.4 |
| 2_72_113_125 | 99.0 | 100 | 99.0 | 96.5 | 100 | 96.3 |
| 2_19_72_113 | 99.0 | 100 | 99.0 | 97.0 | 100 | 96.8 |
| 2_19_113_579 | 98.5 | 100 | 98.4 | 96.5 | 100 | 96.3 |
| 1_2_19_113 | 100 | 100 | 100 | 98.0 | 100 | 97.9 |

TABLE 8-3

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 3 | 85.7 | 94.1 | 85.3 | 84.3 | 100 | 83.7 |
| 3_126 | 97.0 | 94.1 | 97.1 | 97.0 | 100 | 96.8 |
| 1_3_113 | 99.0 | 100 | 99.0 | 98.5 | 100 | 98.4 |
| 3_125_128_568 | 98.5 | 100 | 98.4 | 97.0 | 100 | 96.8 |
| 1_3_10_113 | 99.2 | 100 | 99.2 | 99.0 | 100 | 98.9 |
| 3_113_125_126 | 99.5 | 94.1 | 99.7 | 100 | 100 | 100 |
| 1_3_126_573 | 98.5 | 100 | 98.4 | 98.0 | 100 | 97.9 |
| 3_126_130_561 | 98.2 | 94.1 | 98.4 | 98.0 | 100 | 97.9 |

TABLE 8-4

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 10 | 64.0 | 82.4 | 63.2 | 61.6 | 75.0 | 61.1 |
| 2_10 | 94.0 | 100 | 93.7 | 92.4 | 100 | 92.1 |
| 1_10_113 | 99.2 | 100 | 99.2 | 99.0 | 100 | 98.9 |
| 1_10_113_143 | 99.0 | 100 | 98.9 | 99.5 | 100 | 99.5 |
| 1_10_113_569 | 99.2 | 100 | 99.2 | 99.0 | 100 | 98.9 |
| 1_10_113_562 | 98.7 | 100 | 98.7 | 99.0 | 100 | 98.9 |
| 1_10_113_578 | 99.2 | 100 | 99.2 | 98.5 | 100 | 98.4 |
| 1_7_10_113 | 99.2 | 100 | 99.2 | 99.0 | 100 | 98.9 |

TABLE 8-5

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 63 | 79.4 | 94.1 | 78.7 | 80.8 | 75.0 | 81.1 |
| 63_126 | 95.7 | 94.1 | 95.8 | 97.5 | 100 | 97.4 |
| 1_63_113 | 98.2 | 100 | 98.2 | 98.0 | 100 | 97.9 |
| 1_63_567_578 | 99.5 | 100 | 99.5 | 97.5 | 100 | 97.4 |
| 1_53_63_578 | 98.2 | 100 | 98.2 | 98.0 | 100 | 97.9 |
| 1_63_162_573 | 98.0 | 100 | 97.9 | 97.5 | 87.5 | 97.9 |
| 1_63_162_578 | 98.5 | 100 | 98.4 | 98.0 | 100 | 97.9 |
| 1_63_576_578 | 98.7 | 100 | 98.7 | 98.0 | 100 | 97.9 |

TABLE 8-6

| SEQ ID NO: | Training cohort | | | Validation cohort | | |
| --- | --- | --- | --- | --- | --- | --- |
| | Accuracy (%) | Sensitivity (%) | Specificity (%) | Accuracy (%) | Sensitivity (%) | Specificity (%) |
| 113 | 67.8 | 76.5 | 67.5 | 69.2 | 100 | 67.9 |
| 2_113 | 97.7 | 100 | 97.6 | 95.5 | 100 | 95.3 |
| 1_19_113 | 99.5 | 100 | 99.5 | 99.0 | 100 | 98.9 |
| 1_10_113_567 | 99.5 | 100 | 99.5 | 99.0 | 100 | 98.9 |
| 1_53_63_113 | 99.0 | 100 | 99.0 | 98.0 | 100 | 97.9 |
| 1_53_113_143 | 99.0 | 100 | 99.0 | 98.0 | 100 | 97.9 |
| 2_19_113_125 | 99.0 | 100 | 99.0 | 98.0 | 100 | 97.9 |
| 2_10_113_130 | 99.2 | 100 | 99.2 | 99.5 | 100 | 99.5 |

TABLE 8-7

| SEQ ID NO: | Training cohort | | | Validation cohort | | |
| --- | --- | --- | --- | --- | --- | --- |
| | Accuracy (%) | Sensitivity (%) | Specificity (%) | Accuracy (%) | Sensitivity (%) | Specificity (%) |
| 124 | 79.6 | 94.1 | 79.0 | 76.8 | 100 | 75.8 |
| 2_124 | 95.0 | 100 | 94.8 | 91.4 | 100 | 91.1 |
| 1_113_124 | 98.5 | 100 | 98.4 | 97.5 | 100 | 97.4 |
| 113_124_125_126 | 99.0 | 94.1 | 99.2 | 99.0 | 100 | 98.9 |
| 124_125_128_568 | 98.0 | 100 | 97.9 | 94.9 | 100 | 94.7 |
| 113_124_125_162 | 99.0 | 100 | 99.0 | 98.0 | 100 | 97.9 |
| 52_124_126_561 | 98.0 | 94.1 | 98.2 | 98.0 | 100 | 97.9 |
| 19_113_124_126 | 98.0 | 94.1 | 98.2 | 99.0 | 100 | 98.9 |

TABLE 8-8

| SEQ ID NO: | Training cohort | | | Validation cohort | | |
| --- | --- | --- | --- | --- | --- | --- |
| | Accuracy (%) | Sensitivity (%) | Specificity (%) | Accuracy (%) | Sensitivity (N | Specificity (%) |
| 125 | 77.6 | 82.4 | 77.4 | 73.7 | 87.5 | 73.2 |
| 113_125 | 94.7 | 100 | 94.5 | 93.4 | 100 | 93.2 |
| 2_113_125 | 99.0 | 100 | 99.0 | 96.5 | 100 | 96.3 |
| 1_113_125_160 | 99.5 | 100 | 99.5 | 98.5 | 100 | 98.4 |
| 31_113_125_568 | 99.0 | 100 | 98.9 | 98.0 | 100 | 97.9 |
| 2_53_113_125 | 99.2 | 100 | 99.2 | 98.0 | 100 | 97.9 |
| 1 10_113_125 | 99.5 | 100 | 99.5 | 99.0 | 100 | 98.9 |
| 1_113_125_143 | 99.2 | 100 | 99.2 | 99.0 | 100 | 98.9 |

TABLE 8-9

| SEQ ID NO: | Training cohort | | | Validation cohort | | |
| --- | --- | --- | --- | --- | --- | --- |
| | Accuracy (%) | Sensitivity (%) | Specificity (%) | Accuracy (%) | Sensitivity (%) | Specificity (%) |
| 126 | 90.4 | 94.1 | 90.3 | 92.4 | 100 | 92.1 |
| 1_126 | 96.7 | 100 | 96.6 | 95.5 | 100 | 95.3 |
| 1_113_126 | 99.7 | 100 | 99.7 | 98.0 | 100 | 97.9 |
| 1_126_561_573 | 98.5 | 100 | 98.4 | 97.5 | 100 | 97.4 |
| 113_125_126_568 | 98.5 | 100 | 98.4 | 98.5 | 100 | 98.4 |
| 113_125_126_561 | 99.0 | 94.1 | 99.2 | 98.5 | 100 | 98.4 |
| 1_113_125_126 | 99.7 | 100 | 99.7 | 99.0 | 100 | 98.9 |
| 1_52_126_561 | 99.5 | 100 | 99.5 | 98.0 | 100 | 97.9 |

TABLE 8-10

| SEQ ID NO: | Training cohort | | | Validation cohort | | |
| --- | --- | --- | --- | --- | --- | --- |
| | Accuracy (%) | Sensitivity (%) | Specificity (%) | Accuracy (%) | Sensitivity (%) | Specificity (%) |
| 128 | 81.4 | 82.4 | 81.4 | 81.3 | 87.5 | 81.1 |
| 1_128 | 96.2 | 100 | 96.1 | 94.9 | 100 | 94.7 |
| 1_113_128 | 98.7 | 100 | 98.7 | 97.5 | 100 | 97.4 |
| 26_113_125_128 | 97.7 | 94.1 | 97.9 | 98.5 | 100 | 98.4 |
| 1_113_125_128 | 99.0 | 100 | 99.0 | 99.0 | 100 | 98.9 |
| 1_10_113_128 | 99.2 | 100 | 99.2 | 99.5 | 100 | 99.5 |
| 31_113_125_128 | 97.5 | 94.1 | 97.6 | 99.0 | 100 | 98.9 |
| 2_19_113_128 | 99.0 | 100 | 99.0 | 97.0 | 100 | 96.8 |

TABLE 8-11

| SEQ ID NO: | Training cohort | | | Validation cohort | | |
| --- | --- | --- | --- | --- | --- | --- |
| | Accuracy (%) | Sensitivity (%) | Specificity (%) | Accuracy (%) | Sensitivity (%) | Specificity (%) |
| 130 | 83.4 | 88.2 | 83.2 | 87.4 | 100 | 86.8 |
| 1_130 | 96.2 | 100 | 96.1 | 94.4 | 100 | 94.2 |
| 1_113_130 | 99.2 | 100 | 99.2 | 98.5 | 100 | 98.4 |
| 1_3_130_143 | 97.7 | 100 | 97.6 | 99.0 | 100 | 98.9 |
| 1_10_113_130 | 99.5 | 100 | 99.5 | 99.5 | 100 | 99.5 |
| 1_63_130_578 | 98.7 | 100 | 98.7 | 98.5 | 100 | 98.4 |
| 124_125_130_568 | 98.5 | 100 | 98.4 | 96.5 | 100 | 96.3 |
| 2_19_113_130 | 99.0 | 100 | 99.0 | 98.0 | 100 | 97.9 |

TABLE 8-12

| SEQ ID NO: | Training cohort | | | Validation cohort | | |
| --- | --- | --- | --- | --- | --- | --- |
| | Accuracy (%) | Sensitivity (%) | Specificity (%) | Accuracy (%) | Sensitivity (%) | Specificity (%) |
| 143 | 64.6 | 58.8 | 64.8 | 66.2 | 62.5 | 66.3 |
| 1_143 | 96.0 | 100 | 95.8 | 93.9 | 87.5 | 94.2 |
| 1_113_143 | 98.7 | 100 | 98.7 | 98.0 | 100 | 97.9 |
| 1_3_126_143 | 99.0 | 100 | 98.9 | 98.0 | 100 | 97.9 |
| 1_63_130_143 | 97.7 | 100 | 97.6 | 98.0 | 100 | 97.9 |
| 1_10_52_143 | 98.0 | 100 | 97.9 | 100 | 100 | 100 |
| 2_19_113_143 | 98.5 | 100 | 98.4 | 96.5 | 100 | 96.3 |
| 63_124_130_143 | 96.2 | 94.1 | 96.3 | 96.0 | 100 | 95.8 |

TABLE 8-13

| SEQ ID NO: | Training cohort | | | Validation cohort | | |
| --- | --- | --- | --- | --- | --- | --- |
| | Accuracy (%) | Sensitivity (%) | Specificity (%) | Accuracy (%) | Sensitivity (%) | Specificity (%) |
| 160 | 70.9 | 70.6 | 70.9 | 67.2 | 37.5 | 68.4 |
| 2_160 | 96.0 | 100 | 95.8 | 92.4 | 100 | 92.1 |
| 1_113_160 | 99.2 | 100 | 99.2 | 98.5 | 100 | 98.4 |
| 1_10_113_160 | 99.2 | 100 | 99.2 | 99.0 | 100 | 98.9 |
| 7_113_125_160 | 99.0 | 100 | 99.0 | 97.5 | 100 | 97.4 |
| 1_113_160_567 | 99.5 | 100 | 99.5 | 98.0 | 100 | 97.9 |
| 1_113_160_578 | 98.7 | 100 | 98.7 | 98.0 | 100 | 97.9 |
| 2_19_113_160 | 99.5 | 100 | 99.5 | 98.0 | 100 | 97.9 |

TABLE 8-14

| SEQ ID NO: | Training cohort | | | Validation cohort | | |
|---|---|---|---|---|---|---|
| | Accuracy (%) | Sensitivity (%) | Specificity (%) | Accuracy (%) | Sensitivity (%) | Specificity (%) |
| 561 | 84.9 | 88.2 | 84.8 | 81.8 | 87.5 | 81.6 |
| 126_561 | 96.5 | 94.1 | 96.6 | 97.5 | 100 | 97.4 |
| 1_113_561 | 98.7 | 100 | 98.7 | 98.0 | 100 | 97.9 |
| 113_125_130_561 | 97.7 | 94.1 | 97.9 | 99.5 | 100 | 99.5 |
| 7_126_143_561 | 98.5 | 100 | 98.4 | 98.5 | 100 | 98.4 |
| 1_113_126_561 | 100 | 100 | 100 | 99.0 | 100 | 98.9 |
| 1_126_561_568 | 98.7 | 100 | 98.7 | 98.0 | 100 | 97.9 |
| 7_113_126_561 | 99.2 | 94.1 | 99.5 | 98.5 | 100 | 98.4 |

TABLE 8-15

| SEQ ID NO: | Training cohort | | | Validation cohort | | |
|---|---|---|---|---|---|---|
| | Accuracy (%) | Sensitivity (%) | Specificity (%) | Accuracy (%) | Sensitivity (%) | Specificity (%) |
| 568 | 60.2 | 58.8 | 60.3 | 67.2 | 100 | 65.8 |
| 1_568 | 97.0 | 100 | 96.8 | 96.0 | 100 | 95.8 |
| 1_2_568 | 99.0 | 100 | 98.9 | 96.0 | 100 | 95.8 |
| 7_125_126_568 | 99.2 | 100 | 99.2 | 98.0 | 100 | 97.9 |
| 124_125_126_568 | 98.5 | 100 | 98.4 | 98.0 | 100 | 97.9 |
| 7_113_125_568 | 98.5 | 100 | 98.4 | 98.0 | 100 | 97.9 |
| 1_113_125_568 | 99.5 | 100 | 99.5 | 98.0 | 100 | 97.9 |
| 113_125_128_568 | 97.5 | 100 | 97.4 | 98.5 | 100 | 98.4 |

TABLE 8-16

| SEQ ID NO: | Training cohort | | | Validation cohort | | |
|---|---|---|---|---|---|---|
| | Accuracy (%) | Sensitivity (%) | Specificity (%) | Accuracy (%) | Sensitivity (%) | Specificity (%) |
| 573 | 53.0 | 35.3 | 53.8 | 53.5 | 12.5 | 55.3 |
| 1_573 | 96.5 | 100 | 96.3 | 95.5 | 100 | 95.3 |
| 1_113_573 | 98.7 | 100 | 98.7 | 98.0 | 100 | 97.9 |
| 113_125_126_573 | 98.2 | 94.1 | 98.4 | 99.5 | 100 | 99.5 |
| 1_113_125_573 | 99.2 | 100 | 99.2 | 98.5 | 100 | 98.4 |
| 1_53_113_573 | 98.7 | 100 | 98.7 | 97.5 | 100 | 97.4 |
| 1_124_126_573 | 97.7 | 100 | 97.6 | 96.5 | 100 | 96.3 |
| 1_63_130_573 | 98.7 | 100 | 98.7 | 98.0 | 100 | 97.9 |

TABLE 8-17

| SEQ ID NO: | Training cohort | | | Validation cohort | | |
|---|---|---|---|---|---|---|
| | Accuracy (%) | Sensitivity (%) | Specificity (%) | Accuracy (%) | Sensitivity (%) | Specificity (%) |
| 578 | 52.8 | 52.9 | 52.8 | 53.5 | 50.0 | 53.7 |
| 1_578 | 96.2 | 100 | 96.1 | 94.9 | 100 | 94.7 |
| 1_113_578 | 98.5 | 100 | 98.4 | 96.5 | 100 | 96.3 |
| 1_126_567_578 | 98.5 | 100 | 98.4 | 97.5 | 100 | 97.4 |
| 1_19_113_578 | 99.2 | 100 | 99.2 | 99.0 | 100 | 98.9 |
| 31_126_561_578 | 97.5 | 94.1 | 97.6 | 97.5 | 100 | 97.4 |
| 1_126_160_578 | 98.7 | 100 | 98.7 | 97.0 | 100 | 96.8 |
| 1_113_125_578 | 98.7 | 100 | 98.7 | 98.5 | 100 | 98.4 |

INDUSTRIAL APPLICABILITY

According to the present invention, lung cancer can be effectively detected by a simple and inexpensive method. This permits early detection, diagnosis and treatment of lung cancer. The method of the present invention can detect lung cancer with limited invasiveness using the blood of a patient and therefore allows lung cancer to be detected conveniently and rapidly.

All publications, patents, and patent applications cited herein are incorporated herein by reference in their entirety.

The invention claimed is:

1. A method for detecting lung cancer in a human subject, comprising
measuring an expression level of hsa-miR-4258 in a blood, serum, or plasma sample from the subject;
comparing the measured expression level of hsa-miR-4258 to a control expression level for a healthy subject;
detecting decreased level of hsa-miR-4258 in the sample from the subject as compared to the control expression level from the sample from the healthy subject;
wherein the decreased level of hsa-miR-4258 indicates that the subject has lung cancer; and
wherein the method further comprises treating the subject for the lung cancer or performing a diagnostic procedure on the subject with the lung cancer;
wherein the treatment comprises surgery, radiotherapy, chemotherapy or a combination thereof; and
wherein the diagnostic procedure comprises chest X-ray examination or diagnostic imaging of the lung of the human subject.

2. The method according to claim 1, wherein the expression level of hsa-miR-4258 in the sample is measured by using a kit comprising a nucleic acid(s) that specifically bind to hsa-miR-4258.

3. The method according to claim 2, wherein the kit further comprises at least one nucleic acid capable of specifically binding to at least one polynucleotide selected from the group consist of other lung cancer markers, miR-19b-3p, miR-1228-5p, and miR-1307-3p, miR-4271, miR-642b-3p, miR-6075, miR-6125, miR-887-3p, miR-6851-5p, miR-6763-5p, miR-3928-3p, miR-4443, miR-3648, miR-149-3p, miR-4689, miR-4763-3p, miR-6729-5p, miR-3196, miR-8069, miR-1268a, miR-4739, miR-1268b, miR-5698, miR-6752-5p, miR-4507, miR-564, miR-4497, miR-6877-5p, miR-6087, miR-4731-5p, miR-615-5p, miR-760, miR-6891-5p, miR-6887-5p, miR-4525, miR-1914-3p, miR-619-5p, miR-5001-5p, miR-6722-3p, miR-3621, miR-4298, miR-675-5p, miR-4655-5p, miR-6836-3p, miR-6782-5p, miR-3663-3p, miR-1908-3p, miR-6726-5p, miR-1343-3p, miR-4516, miR-6875-5p, miR-4651, miR-6825-5p, miR-6840-3p, miR-6780b-5p, miR-6749-5p, miR-8063, miR-6784-5p, miR-3184-5p, miR-663b, miR-6880-5p, miR-1908-5p, miR-92a-2-5p, miR-7975, miR-7110-5p, miR-6842-5p, miR-6857-5p, miR-5572, miR-3197, miR-6131, miR-6889-5p, miR-4454, miR-1199-5p, miR-1247-3p, miR-6800-5p, miR-6872-3p, miR-4649-5p, miR-6791-5p, miR-4433b-3p, miR-3135b, miR-128-2-5p, miR-4675, miR-4472, miR-6785-5p, miR-6741-5p, miR-7977, miR-3665, miR-128-1-5p, miR-4286, miR-6765-3p, miR-4632-5p, miR-365a-5p, miR-6088, miR-6816-5p, miR-6885-5p, miR-711, miR-6765-5p, miR-3180, miR-4442, miR-4792, miR-6721-5p, miR-6798-5p, miR-6126, miR-4758-5p, miR-2392, miR-486-3p, miR-6727-5p, miR-4728-5p, miR-6746-5p, miR-4270, miR-3940-5p, miR-4725-3p, miR-7108-5p, miR-3656, miR-6879-5p, miR-6738-5p, miR-1260a, miR-4446-3p, miR-3131, miR-4463, miR-3185, miR-6870-5p, miR-6779-5p, miR-1273g-3p, miR-8059, miR-4697-5p, miR-4674, miR-4433-3p, miR-4257, miR-1915-5p, miR-4417, miR-1343-5p, miR-6781-5p, miR-4695-5p, miR-1237-5p, miR-6775-5p, miR-7845-5p, miR-4746-3p, miR-7641, miR-7847-3p, miR-6806-5p, miR-4467, miR-4726-5p, miR-4648, miR-6089, miR-1260b, miR-4532, miR-5195-3p, miR-3188, miR-6848-5p, miR-1233-5p, miR-6717-5p, miR-3195, miR-6757-5p, miR-8072, miR-4745-5p, miR-6511a-5p, miR-6776-5p, miR-371a-5p, miR-1227-5p, miR-7150, miR-1915-3p, miR-187-5p, miR-614, miR-1225-5p, miR-451a, miR-939-5p, miR-223-3p, miR-125a-3p, miR-92b-5p, miR-22-3p, miR-6073, miR-6845-5p, miR-6769b-5p, miR-4665-3p, miR-1913, miR-1228-3p, miR-940, miR-296-3p, miR-4690-5p, miR-548q, miR-663a, miR-1249, miR-1202, miR-7113-3p, miR-1225-3p, miR-4783-3p, miR-4448 and miR-4534.

4. The method according to claim 1, comprising performing the diagnostic procedure on the subject.

5. The method according to claim 1, wherein the decreased level of hsa-miR-4258 in the sample is measured by using a device comprising a nucleic acid(s) that specifically bind to hsa-miR-4258.

6. The method according to claim 5, wherein the device further comprises at least one nucleic acid capable of specifically binding to at least one polynucleotide selected from the group consist of other lung cancer markers, miR-19b-3p, miR-1228-5p, and miR-1307-3p, miR-4271, miR-642b-3p, miR-6075, miR-6125, miR-887-3p, miR-6851-5p, miR-6763-5p, miR-3928-3p, miR-4443, miR-3648, miR-149-3p, miR-4689, miR-4763-3p, miR-6729-5p, miR-3196, miR-8069, miR-1268a, miR-4739, miR-1268b, miR-5698, miR-6752-5p, miR-4507, miR-564, miR-4497, miR-6877-5p, miR-6087, miR-4731-5p, miR-615-5p, miR-760, miR-6891-5p, miR-6887-5p, miR-4525, miR-1914-3p, miR-619-5p, miR-5001-5p, miR-6722-3p, miR-3621, miR-4298, miR-675-5p, miR-4655-5p, miR-6836-3p, miR-6782-5p, miR-3663-3p, miR-1908-3p, miR-6726-5p, miR-1343-3p, miR-4516, miR-6875-5p, miR-4651, miR-6825-5p, miR-6840-3p, miR-6780b-5p, miR-6749-5p, miR-8063, miR-6784-5p, miR-3184-5p, miR-663b, miR-6880-5p, miR-1908-5p, miR-92a-2-5p, miR-7975, miR-7110-5p, miR-6842-5p, miR-6857-5p, miR-5572, miR-3197, miR-6131, miR-6889-5p, miR-4454, miR-1199-5p, miR-1247-3p, miR-6800-5p, miR-6872-3p, miR-4649-5p, miR-6791-5p, miR-4433b-3p, miR-3135b, miR-128-2-5p, miR-4675, miR-4472, miR-6785-5p, miR-6741-5p, miR-7977, miR-3665, miR-128-1-5p, miR-4286, miR-6765-3p, miR-4632-5p, miR-365a-5p, miR-6088, miR-6816-5p, miR-6885-5p, miR-711, miR-6765-5p, miR-3180, miR-4442, miR-4792, miR-6721-5p, miR-6798-5p, miR-6126, miR-4758-5p, miR-2392, miR-486-3p, miR-6727-5p, miR-4728-5p, miR-6746-5p, miR-4270, miR-3940-5p, miR-4725-3p, miR-7108-5p, miR-3656, miR-6879-5p, miR-6738-5p, miR-1260a, miR-4446-3p, miR-3131, miR-4463, miR-3185, miR-6870-5p, miR-6779-5p, miR-1273g-3p, miR-8059, miR-4697-5p, miR-4674, miR-4433-3p, miR-4257, miR-1915-5p, miR-4417, miR-1343-5p, miR-6781-5p, miR-4695-5p, miR-1237-5p, miR-6775-5p, miR-7845-5p, miR-4746-3p, miR-7641, miR-7847-3p, miR-6806-5p, miR-4467, miR-4726-5p, miR-4648, miR-6089, miR-1260b, miR-4532, miR-5195-3p, miR-3188, miR-6848-5p, miR-1233-5p, miR-6717-5p, miR-3195, miR-6757-5p, miR-8072, miR-4745-5p, miR-6511a-5p, miR-6776-5p, miR-371a-5p, miR-1227-5p, miR-7150, miR-1915-3p, miR-187-

5p, miR-614, miR-1225-5p, miR-451a, miR-939-5p, miR-223-3p, miR-125a-3p, miR-92b-5p, miR-22-3p, miR-6073, miR-6845-5p, miR-6769b-5p, miR-4665-3p, miR-1913, miR-1228-3p, miR-940, miR-296-3p, miR-4690-5p, miR-548q, miR-663a, miR-1249, miR-1202, miR-7113-3p, miR-1225-3p, miR-4783-3p, miR-4448 and miR-4534.

\* \* \* \* \*